US012571047B2

(12) United States Patent
Rabinowitz et al.

(10) Patent No.: US 12,571,047 B2
(45) Date of Patent: Mar. 10, 2026

(54) SYSTEM AND METHOD FOR CLEANING NOISY GENETIC DATA AND DETERMINING CHROMOSOME COPY NUMBER

(71) Applicant: Natera, Inc., San Carlos, CA (US)

(72) Inventors: Matthew Rabinowitz, San Francisco, CA (US); Milena Banjevic, Los Altos Hills, CA (US); Zachary Demko, San Francisco, CA (US); David Johnson, San Francisco, CA (US); Dusan Kijacic, Los Altos Hills, CA (US); Dimitri Petrov, Stanford, CA (US); Joshua Sweetkind-Singer, San Jose, CA (US); Jing Xu, Jersey City, NJ (US)

(73) Assignee: Natera, Inc., San Carlos, CA (US)

( * ) Notice: Subject to any disclaimer, the term of this patent is extended or adjusted under 35 U.S.C. 154(b) by 1139 days.

(21) Appl. No.: 17/503,182

(22) Filed: Oct. 15, 2021

(65) Prior Publication Data

US 2022/0033908 A1 Feb. 3, 2022

Related U.S. Application Data

(63) Continuation of application No. 17/164,599, filed on Feb. 1, 2021, which is a continuation of application No. 16/823,127, filed on Mar. 18, 2020, now Pat. No. 11,111,544, which is a continuation-in-part of application No. 16/411,507, filed on May 14, 2019, now Pat. No. 10,597,724, and a continuation of application No. 16/399,911, filed on Apr. 30, 2019, now abandoned, said application No. 16/411,507 is a continuation of application No. 16/288,690, filed on Feb. 28, 2019, now Pat. No. 11,306,359, said application No. 16/399,911 is a continuation of application No. 15/887,746, filed on Feb. 2, 2018, which is a continuation of application No. 15/446,778, filed on Mar. 1, 2017, now Pat. No. 10,260,096, said application No. 16/288,690 is a continuation of application No. 15/187,555, filed on Jun. 20, 2016, now Pat. No. 10,227,652, which is a continuation of application No. 14/092,457, filed on (Continued)

(51) Int. Cl.

| | |
|---|---|
| *C12Q 1/68* | (2018.01) |
| *C12Q 1/6806* | (2018.01) |
| *C12Q 1/6827* | (2018.01) |
| *C12Q 1/6855* | (2018.01) |
| *C12Q 1/6869* | (2018.01) |
| *C12Q 1/6876* | (2018.01) |
| *C12Q 1/6883* | (2018.01) |
| *C12Q 1/6886* | (2018.01) |
| *G16B 20/00* | (2019.01) |
| *G16B 25/00* | (2019.01) |
| *G16B 30/00* | (2019.01) |
| *G16B 40/00* | (2019.01) |

(52) U.S. Cl.
CPC ......... *C12Q 1/6883* (2013.01); *C12Q 1/6806* (2013.01); *C12Q 1/6827* (2013.01); *C12Q 1/6855* (2013.01); *C12Q 1/6869* (2013.01); *C12Q 1/6876* (2013.01); *C12Q 1/6886* (2013.01); *G16B 20/00* (2019.02); *G16B 25/00* (2019.02); *G16B 30/00* (2019.02); *G16B 40/00* (2019.02); *C12Q 2537/149* (2013.01); *C12Q 2545/114* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 4,040,785 A | 8/1977 | Kim et al. |
|---|---|---|
| 4,683,195 A | 7/1987 | Mullis et al. |

(Continued)

FOREIGN PATENT DOCUMENTS

| CN | 1650032 A | 8/2005 |
|---|---|---|
| CN | 1674028 A | 9/2005 |

(Continued)

OTHER PUBLICATIONS

US 8,501,409 B2, 08/2013, Simen et al. (withdrawn)
Barnby et al. (Am J Hum Genet, 2005, 950-966) (Year: 2005).*
Hao et al. (Hum Molec Genet, 2004, 13(7): 683-691) (Year: 2004).*
Bau, Stephan, et al., "Targeted next-generation sequencing by specific capture of multiple genomic loci using low-volume microfluidic DNA arrays", Anal Bioanal Chem, 2009, 171-175.
Lanman, et al., "Analytical and Clinical Validation of a Digital Sequencing Panel for Quantitative, Highly Accurate Evaluation of Cell-Free Circulating Tumor Dna", Plos One, 2015, 1-27.
Lee, et al., "ERBB2 kinase domain mutation in the lung squamous cell carcinoma", Cancer Letters, 2006, 89-94.

(Continued)

*Primary Examiner* — Stephanie K Mummert

(57) ABSTRACT

Disclosed herein is a system and method for increasing the fidelity of measured genetic data, for making allele calls, and for determining the state of aneuploidy, in one or a small set of cells, or from fragmentary DNA, where a limited quantity of genetic data is available. Poorly or incorrectly measured base pairs, missing alleles and missing regions are reconstructed using expected similarities between the target genome and the genome of genetically related individuals. In accordance with one embodiment, incomplete genetic data from an embryonic cell are reconstructed at a plurality of loci using the more complete genetic data from a larger sample of diploid cells from one or both parents, with or without haploid genetic data from one or both parents. In another embodiment, the chromosome copy number can be determined from the measured genetic data, with or without genetic information from one or both parents.

13 Claims, 13 Drawing Sheets

Related U.S. Application Data

Nov. 27, 2013, now Pat. No. 9,430,611, said application No. 15/446,778 is a continuation of application No. 13/949,212, filed on Jul. 23, 2013, now Pat. No. 10,083,273, said application No. 14/092,457 is a continuation of application No. 13/793,186, filed on Mar. 11, 2013, now Pat. No. 8,682,592, and a continuation of application No. 13/793,133, filed on Mar. 11, 2013, now Pat. No. 9,424,392, said application No. 13/949,212 is a continuation of application No. 12/076,348, filed on Mar. 17, 2008, now Pat. No. 8,515,679, which is a continuation-in-part of application No. 11/634,550, filed on Dec. 6, 2006, now abandoned, said application No. 13/793,133 is a continuation of application No. 11/603,406, filed on Nov. 22, 2006, now Pat. No. 8,532,930, said application No. 12/076,348 is a continuation-in-part of application No. 11/603,406, filed on Nov. 22, 2006, now Pat. No. 8,532,930, said application No. 13/793, 186 is a continuation-in-part of application No. 11/603,406, filed on Nov. 22, 2006, now Pat. No. 8,532,930, said application No. 11/603,406 is a continuation-in-part of application No. 11/496,982, filed on Jul. 31, 2006, now abandoned, said application No. 12/076,348 is a continuation-in-part of application No. 11/496,982, filed on Jul. 31, 2006, now abandoned.

(60) Provisional application No. 61/008,637, filed on Dec. 21, 2007, provisional application No. 61/003,101, filed on Nov. 13, 2007, provisional application No. 60/934,440, filed on Jun. 13, 2007, provisional application No. 60/932,456, filed on May 31, 2007, provisional application No. 60/926,198, filed on Apr. 25, 2007, provisional application No. 60/918,292, filed on Mar. 16, 2007, provisional application No. 60/846,610, filed on Sep. 22, 2006, provisional application No. 60/817,741, filed on Jun. 30, 2006, provisional application No. 60/789,506, filed on Apr. 4, 2006, provisional application No. 60/774,976, filed on Feb. 21, 2006, provisional application No. 60/754,396, filed on Dec. 29, 2005, provisional application No. 60/742,305, filed on Dec. 6, 2005, provisional application No. 60/739,882, filed on Nov. 26, 2005, provisional application No. 60/703,415, filed on Jul. 29, 2005.

(56) References Cited

U.S. PATENT DOCUMENTS

| | | | |
|---|---|---|---|
| 4,942,124 | A | 7/1990 | Church et al. |
| 5,486,477 | A | 1/1996 | Carver |
| 5,635,366 | A | 6/1997 | Cooke et al. |
| 5,648,220 | A | 7/1997 | Bianchi et al. |
| 5,716,776 | A | 2/1998 | Bogart |
| 5,753,467 | A | 5/1998 | Jensen et al. |
| 5,824,467 | A | 10/1998 | Mascarenhas |
| 5,854,033 | A | 12/1998 | Lizardi |
| 5,860,917 | A | 1/1999 | Comanor et al. |
| 5,891,734 | A | 4/1999 | Gill et al. |
| 5,952,170 | A | 9/1999 | Stroun et al. |
| 5,962,223 | A | 10/1999 | Whiteley et al. |
| 5,972,602 | A | 10/1999 | Hyland et al. |
| 5,976,790 | A | 11/1999 | Pinkel et al. |
| 5,994,148 | A | 11/1999 | Stewart et al. |
| 6,001,611 | A | 12/1999 | Will |
| 6,025,128 | A | 2/2000 | Veltri et al. |
| 6,066,454 | A | 5/2000 | Lipshutz et al. |
| 6,100,029 | A | 8/2000 | Lapidus et al. |
| 6,108,635 | A | 8/2000 | Herren et al. |
| 6,124,120 | A | 9/2000 | Lizardi |
| 6,143,496 | A | 11/2000 | Brown et al. |
| 6,156,504 | A | 12/2000 | Gocke et al. |
| 6,180,349 | B1 | 1/2001 | Ginzinger |
| 6,214,558 | B1 | 4/2001 | Shuber et al. |
| 6,221,603 | B1 | 4/2001 | Mahtani |
| 6,235,472 | B1 | 5/2001 | Landegren et al. |
| 6,258,540 | B1 | 7/2001 | Lo et al. |
| 6,300,077 | B1 | 10/2001 | Shuber et al. |
| 6,329,179 | B1 | 12/2001 | Kopreski |
| 6,335,167 | B1 | 1/2002 | Pinkel et al. |
| 6,440,706 | B1 | 8/2002 | Vogelstein et al. |
| 6,479,235 | B1 | 11/2002 | Schumm et al. |
| 6,489,135 | B1 | 12/2002 | Parrott et al. |
| 6,605,451 | B1 | 8/2003 | Marmaro et al. |
| 6,617,137 | B2 | 9/2003 | Dean et al. |
| 6,720,140 | B1 | 4/2004 | Hartley et al. |
| 6,794,140 | B1 | 9/2004 | Goldsborough |
| 6,807,491 | B2 | 10/2004 | Pavlovic et al. |
| 6,852,487 | B1 | 2/2005 | Barany et al. |
| 6,858,412 | B2 | 2/2005 | Willis et al. |
| 6,927,028 | B2 | 8/2005 | Lo et al. |
| 6,958,211 | B2 | 10/2005 | Vingerhoets et al. |
| 6,964,847 | B1 | 11/2005 | Englert |
| 7,035,739 | B2 | 4/2006 | Schadt et al. |
| 7,058,517 | B1 | 6/2006 | Denton et al. |
| 7,058,616 | B1 | 6/2006 | Larder et al. |
| 7,101,663 | B2 | 9/2006 | Godfrey et al. |
| 7,153,656 | B2 | 12/2006 | Nolan et al. |
| 7,218,764 | B2 | 5/2007 | Vaisberg et al. |
| 7,297,485 | B2 | 11/2007 | Bornarth et al. |
| 7,332,277 | B2 | 2/2008 | Dhallan |
| 7,410,764 | B2 | 8/2008 | Gocke et al. |
| 7,414,118 | B1 | 8/2008 | Mullah et al. |
| 7,442,506 | B2 | 10/2008 | Dhallan |
| 7,459,273 | B2 | 12/2008 | Jones et al. |
| 7,537,897 | B2 | 5/2009 | Brenner et al. |
| 7,645,576 | B2 | 1/2010 | Lo et al. |
| 7,655,399 | B2 | 2/2010 | Cantor et al. |
| 7,700,325 | B2 * | 4/2010 | Cantor ................. C12Q 1/6827 536/23.1 |
| 7,718,367 | B2 | 5/2010 | Lo et al. |
| 7,718,370 | B2 | 5/2010 | Dhallan |
| 7,727,720 | B2 | 6/2010 | Dhallan |
| 7,741,463 | B2 | 6/2010 | Gormley et al. |
| 7,785,798 | B2 | 8/2010 | Cantor et al. |
| 7,790,393 | B2 | 9/2010 | Lyamichev et al. |
| 7,790,418 | B2 | 9/2010 | Mayer |
| 7,805,282 | B2 | 9/2010 | Casey et al. |
| 7,838,647 | B2 | 11/2010 | Hahn et al. |
| 7,888,017 | B2 | 2/2011 | Quake |
| 7,981,609 | B2 | 7/2011 | Rubin et al. |
| 8,008,018 | B2 | 8/2011 | Quake et al. |
| 8,024,128 | B2 | 9/2011 | Rabinowitz |
| 8,133,719 | B2 | 3/2012 | Drmanac et al. |
| 8,137,912 | B2 | 3/2012 | Kapur et al. |
| 8,168,389 | B2 | 5/2012 | Shoemaker et al. |
| 8,173,370 | B2 | 5/2012 | Oeth et al. |
| 8,195,415 | B2 | 6/2012 | Fan et al. |
| 8,236,503 | B2 | 8/2012 | Faham et al. |
| 8,296,076 | B2 | 10/2012 | Fan et al. |
| 8,304,187 | B2 | 11/2012 | Fernando |
| 8,318,430 | B2 | 11/2012 | Chuu et al. |
| 8,318,434 | B2 | 11/2012 | Cuppens et al. |
| 8,323,897 | B2 | 12/2012 | Andersen et al. |
| 8,372,584 | B2 | 2/2013 | Shoemaker et al. |
| 8,389,557 | B2 | 3/2013 | Singh et al. |
| 8,389,578 | B2 | 3/2013 | Went et al. |
| 8,450,063 | B2 | 5/2013 | Dube et al. |
| 8,467,976 | B2 | 6/2013 | Lo et al. |
| 8,515,679 | B2 | 8/2013 | Rabinowitz et al. |
| 8,532,930 | B2 | 9/2013 | Rabinowitz et al. |
| 8,609,338 | B2 | 12/2013 | Mitchell et al. |
| 8,679,741 | B2 | 3/2014 | Hoyal-Wrightson et al. |
| 8,682,592 | B2 | 3/2014 | Rabinowitz et al. |
| 8,703,652 | B2 | 4/2014 | Quake et al. |
| 8,706,422 | B2 | 4/2014 | Lo et al. |

(56) References Cited

U.S. PATENT DOCUMENTS

| | | | |
|---|---|---|---|
| 8,748,103 | B2 | 6/2014 | Faham et al. |
| 8,822,153 | B2 | 9/2014 | Hayes et al. |
| 8,825,412 | B2 | 9/2014 | Rabinowitz et al. |
| 9,005,894 | B2 | 4/2015 | Ladner et al. |
| 9,051,602 | B2 | 6/2015 | Oliphant et al. |
| 9,085,798 | B2 | 7/2015 | Chee |
| 9,206,475 | B2 | 12/2015 | Gerdes et al. |
| 9,228,234 | B2 | 1/2016 | Rabinowitz et al. |
| 9,323,888 | B2 | 4/2016 | Rava et al. |
| 9,364,829 | B2 | 6/2016 | Heid et al. |
| 9,404,150 | B2 | 8/2016 | Lee et al. |
| 9,424,392 | B2 | 8/2016 | Rabinowitz et al. |
| 9,453,257 | B2 | 9/2016 | Hoyal-Wrightson et al. |
| 9,476,095 | B2 | 10/2016 | Vogelstein et al. |
| 9,487,829 | B2 | 11/2016 | Vogelstein et al. |
| 9,493,828 | B2 | 11/2016 | Rava et al. |
| 9,506,119 | B2 | 11/2016 | Faham et al. |
| 9,598,731 | B2 | 3/2017 | Talasaz |
| 9,677,118 | B2 | 6/2017 | Zimmermann et al. |
| 10,017,810 | B2 | 7/2018 | Iafrate et al. |
| 10,041,127 | B2 | 8/2018 | Talasaz |
| 10,061,890 | B2 | 8/2018 | Rabinowitz et al. |
| 10,081,839 | B2 | 9/2018 | Rabinowitz et al. |
| 10,083,273 | B2 | 9/2018 | Rabinowitz et al. |
| 10,174,369 | B2 | 1/2019 | Rabinowitz et al. |
| 10,179,937 | B2 | 1/2019 | Babiarz et al. |
| 10,227,652 | B2 | 3/2019 | Rabinowitz et al. |
| 10,229,244 | B2 | 3/2019 | Ghosh |
| 10,240,202 | B2 | 3/2019 | Rabinowitz et al. |
| 10,260,096 | B2 | 4/2019 | Rabinowitz et al. |
| 10,262,755 | B2 | 4/2019 | Babiarz et al. |
| 10,266,893 | B2 | 4/2019 | Rabinowitz et al. |
| 10,308,981 | B2 | 6/2019 | Sparks et al. |
| 10,316,362 | B2 | 6/2019 | Babiarz et al. |
| 10,351,906 | B2 | 7/2019 | Zimmermann et al. |
| 10,360,096 | B2 | 7/2019 | Morris et al. |
| 10,392,664 | B2 | 8/2019 | Rabinowitz et al. |
| 10,450,597 | B2 | 10/2019 | Iafrate et al. |
| 10,522,242 | B2 | 12/2019 | Rabinowitz et al. |
| 10,526,658 | B2 | 1/2020 | Babiarz et al. |
| 10,538,814 | B2 | 1/2020 | Babiarz et al. |
| 10,557,172 | B2 | 2/2020 | Babiarz et al. |
| 10,597,708 | B2 | 3/2020 | Zimmermann et al. |
| 10,597,709 | B2 | 3/2020 | Zimmermann et al. |
| 10,597,723 | B2 | 3/2020 | Babiarz et al. |
| 10,655,180 | B2 | 5/2020 | Babiarz et al. |
| 10,711,309 | B2 | 7/2020 | Rabinowitz et al. |
| 10,731,220 | B2 | 8/2020 | Babiarz et al. |
| 10,774,380 | B2 | 9/2020 | Ryan et al. |
| 10,793,912 | B2 | 10/2020 | Babiarz et al. |
| 10,894,976 | B2 | 1/2021 | Stray et al. |
| 11,111,543 | B2 | 9/2021 | Rabinowitz et al. |
| 11,111,544 | B2 | 9/2021 | Rabinowitz et al. |
| 11,111,545 | B2 | 9/2021 | Babiarz et al. |
| 11,130,995 | B2 | 9/2021 | Quake et al. |
| 11,306,357 | B2 | 4/2022 | Rabinowitz et al. |
| 11,319,596 | B2 | 5/2022 | Babiarz et al. |
| 11,371,100 | B2 | 6/2022 | Babiarz et al. |
| 11,519,035 | B2 | 12/2022 | Rabinowitz et al. |
| 2001/0051341 | A1 | 12/2001 | Lo et al. |
| 2001/0053519 | A1 | 12/2001 | Fodor et al. |
| 2002/0006622 | A1 | 1/2002 | Bradley et al. |
| 2002/0107640 | A1 | 8/2002 | Ideker et al. |
| 2002/0119478 | A1 | 8/2002 | Umansky et al. |
| 2002/0182622 | A1 | 12/2002 | Nakamura et al. |
| 2002/0197630 | A1 | 12/2002 | Knapp et al. |
| 2003/0009295 | A1 | 1/2003 | Markowitz et al. |
| 2003/0040620 | A1 | 2/2003 | Langmore et al. |
| 2003/0044388 | A1 | 3/2003 | Lo et al. |
| 2003/0065535 | A1 | 4/2003 | Karlov et al. |
| 2003/0077586 | A1 | 4/2003 | Pavlovic et al. |
| 2003/0087276 | A1 | 5/2003 | Kopreski et al. |
| 2003/0101000 | A1 | 5/2003 | Bader et al. |
| 2003/0108900 | A1 | 6/2003 | Oliphant et al. |
| 2003/0119004 | A1 | 6/2003 | Wenz et al. |
| 2003/0138780 | A1 | 7/2003 | Gill et al. |
| 2003/0148301 | A1 | 8/2003 | Aono et al. |
| 2003/0211489 | A1 | 11/2003 | Shen et al. |
| 2003/0228613 | A1 | 12/2003 | Bornarth et al. |
| 2003/0232348 | A1 | 12/2003 | Jones et al. |
| 2003/0232353 | A1 | 12/2003 | Kennedy et al. |
| 2003/0235848 | A1 | 12/2003 | Neville et al. |
| 2004/0009518 | A1 | 1/2004 | Lo et al. |
| 2004/0033596 | A1 | 2/2004 | Threadgill et al. |
| 2004/0067493 | A1 | 4/2004 | Matsuzaki et al. |
| 2004/0096874 | A1 | 5/2004 | Neville et al. |
| 2004/0115629 | A1 | 6/2004 | Panzer et al. |
| 2004/0117346 | A1 | 6/2004 | Stoffel et al. |
| 2004/0126760 | A1 | 7/2004 | Broude |
| 2004/0137470 | A1 | 7/2004 | Dhallan et al. |
| 2004/0146866 | A1 | 7/2004 | Fu |
| 2004/0157243 | A1 | 8/2004 | Huang et al. |
| 2004/0185495 | A1 | 9/2004 | Schueler et al. |
| 2004/0197797 | A1 | 10/2004 | Inoko et al. |
| 2004/0209299 | A1 | 10/2004 | Pinter et al. |
| 2004/0229231 | A1 | 11/2004 | Frudakis et al. |
| 2004/0236518 | A1 | 11/2004 | Pavlovic et al. |
| 2004/0259100 | A1 | 12/2004 | Gunderson et al. |
| 2005/0009069 | A1 | 1/2005 | Liu et al. |
| 2005/0043894 | A1 | 2/2005 | Fernandez |
| 2005/0049793 | A1 | 3/2005 | Paterlini-brechot |
| 2005/0053950 | A1 | 3/2005 | Ubani et al. |
| 2005/0064476 | A1 | 3/2005 | Huang et al. |
| 2005/0079521 | A1 | 4/2005 | Beaulieu et al. |
| 2005/0079535 | A1 | 4/2005 | Kirchgesser et al. |
| 2005/0123914 | A1 | 6/2005 | Katz et al. |
| 2005/0130173 | A1 | 6/2005 | Leamon et al. |
| 2005/0142577 | A1 | 6/2005 | Jones et al. |
| 2005/0144664 | A1 | 6/2005 | Smith et al. |
| 2005/0164241 | A1 | 7/2005 | Hahn et al. |
| 2005/0164252 | A1 | 7/2005 | Yeung |
| 2005/0216207 | A1 | 9/2005 | Kermani |
| 2005/0221341 | A1 | 10/2005 | Shimkets et al. |
| 2005/0227263 | A1 | 10/2005 | Green et al. |
| 2005/0250111 | A1 | 11/2005 | Xie et al. |
| 2005/0255508 | A1 | 11/2005 | Casey et al. |
| 2005/0272073 | A1 | 12/2005 | Vaisberg et al. |
| 2005/0282185 | A1 | 12/2005 | Lo et al. |
| 2006/0014179 | A1 | 1/2006 | Roberts |
| 2006/0019278 | A1 | 1/2006 | Lo et al. |
| 2006/0040300 | A1 | 2/2006 | Dapprich et al. |
| 2006/0046258 | A1 | 3/2006 | Lapidus et al. |
| 2006/0051799 | A1 | 3/2006 | Iwaki et al. |
| 2006/0052945 | A1 | 3/2006 | Rabinowitz et al. |
| 2006/0057618 | A1 | 3/2006 | Piper et al. |
| 2006/0068394 | A1 | 3/2006 | Langmore et al. |
| 2006/0088574 | A1 | 4/2006 | Manning et al. |
| 2006/0088871 | A1 | 4/2006 | Finkelstein et al. |
| 2006/0088912 | A1 | 4/2006 | Yan et al. |
| 2006/0094010 | A1 | 5/2006 | Giles et al. |
| 2006/0099614 | A1 | 5/2006 | Gill et al. |
| 2006/0121452 | A1 | 6/2006 | Dhallan |
| 2006/0134662 | A1 | 6/2006 | Pratt et al. |
| 2006/0141499 | A1 | 6/2006 | Sher et al. |
| 2006/0210997 | A1 | 9/2006 | Myerson et al. |
| 2006/0216153 | A1 | 9/2006 | Wobben et al. |
| 2006/0216738 | A1 | 9/2006 | Wada et al. |
| 2006/0228721 | A1 | 10/2006 | Leamon et al. |
| 2006/0229823 | A1 | 10/2006 | Liu |
| 2006/0234264 | A1 | 10/2006 | Hardenbol |
| 2006/0248031 | A1 | 11/2006 | Kates et al. |
| 2006/0281105 | A1 | 12/2006 | Li et al. |
| 2006/0292599 | A1 | 12/2006 | Ritz et al. |
| 2007/0020640 | A1 | 1/2007 | McCloskey et al. |
| 2007/0027636 | A1 | 2/2007 | Rabinowitz |
| 2007/0031857 | A1 | 2/2007 | Makarov et al. |
| 2007/0037166 | A1 | 2/2007 | Wohlgemuth et al. |
| 2007/0042384 | A1 | 2/2007 | Li et al. |
| 2007/0059700 | A1 | 3/2007 | Tao et al. |
| 2007/0059707 | A1 | 3/2007 | Cantor et al. |
| 2007/0122805 | A1 | 5/2007 | Cantor et al. |
| 2007/0128624 | A1 | 6/2007 | Gormley et al. |
| 2007/0134658 | A1 | 6/2007 | Bohmer et al. |
| 2007/0178478 | A1 | 8/2007 | Dhallan |

(56)          References Cited

U.S. PATENT DOCUMENTS

| 2007/0178501 A1 | 8/2007 | Rabinowitz et al. |
| 2007/0184467 A1 | 8/2007 | Rabinowitz et al. |
| 2007/0202525 A1 | 8/2007 | Quake et al. |
| 2007/0202536 A1 | 8/2007 | Yamanishi et al. |
| 2007/0207466 A1 | 9/2007 | Cantor et al. |
| 2007/0212689 A1 | 9/2007 | Bianchi et al. |
| 2007/0231823 A1 | 10/2007 | McKernan et al. |
| 2007/0243549 A1 | 10/2007 | Bischoff |
| 2007/0259351 A1 | 11/2007 | Chinitz |
| 2008/0020390 A1 | 1/2008 | Mitchell |
| 2008/0026390 A1 | 1/2008 | Stoughton et al. |
| 2008/0038733 A1 | 2/2008 | Bischoff et al. |
| 2008/0050739 A1 | 2/2008 | Stoughton et al. |
| 2008/0070792 A1 | 3/2008 | Stoughton |
| 2008/0071076 A1 | 3/2008 | Hahn et al. |
| 2008/0085836 A1 | 4/2008 | Kearns et al. |
| 2008/0090239 A1 | 4/2008 | Shoemaker et al. |
| 2008/0096766 A1 | 4/2008 | Lee |
| 2008/0102455 A1 | 5/2008 | Poetter |
| 2008/0138809 A1 | 6/2008 | Kapur et al. |
| 2008/0161420 A1 | 7/2008 | Shuber |
| 2008/0182244 A1 | 7/2008 | Tafas et al. |
| 2008/0193927 A1 | 8/2008 | Mann et al. |
| 2008/0220422 A1 | 9/2008 | Shoemaker et al. |
| 2008/0234142 A1 | 9/2008 | Lietz |
| 2008/0243398 A1 | 10/2008 | Rabinowitz et al. |
| 2008/0280292 A1 | 11/2008 | Wangh et al. |
| 2008/0286783 A1 | 11/2008 | Hosono et al. |
| 2008/0293589 A1 | 11/2008 | Shapero |
| 2008/0299562 A1 | 12/2008 | Oeth et al. |
| 2008/0305473 A1 | 12/2008 | Chowdary et al. |
| 2009/0023190 A1 | 1/2009 | Lao et al. |
| 2009/0029377 A1 | 1/2009 | Lo et al. |
| 2009/0053719 A1 | 2/2009 | Lo et al. |
| 2009/0087847 A1 | 4/2009 | Lo et al. |
| 2009/0098534 A1 | 4/2009 | Weier et al. |
| 2009/0099041 A1 | 4/2009 | Church et al. |
| 2009/0143570 A1 | 6/2009 | Jiang et al. |
| 2009/0176662 A1 | 7/2009 | Rigatti et al. |
| 2009/0221620 A1 | 9/2009 | Luke et al. |
| 2009/0228299 A1 | 9/2009 | Kangarloo et al. |
| 2009/0233802 A1 | 9/2009 | Bignell et al. |
| 2009/0263800 A1 | 10/2009 | Wohlgemuth et al. |
| 2009/0280479 A1 | 11/2009 | Hoon et al. |
| 2009/0317817 A1 | 12/2009 | Oeth et al. |
| 2010/0035232 A1 | 2/2010 | Ecker et al. |
| 2010/0041048 A1 | 2/2010 | Diehl et al. |
| 2010/0086914 A1 | 4/2010 | bentley et al. |
| 2010/0105049 A1 | 4/2010 | Ehrich et al. |
| 2010/0112575 A1 | 5/2010 | Fan et al. |
| 2010/0112586 A1 | 5/2010 | Stoughton et al. |
| 2010/0112590 A1 | 5/2010 | Lo et al. |
| 2010/0120038 A1 | 5/2010 | Mir et al. |
| 2010/0124751 A1 | 5/2010 | Quake et al. |
| 2010/0129792 A1 | 5/2010 | Makrigiorgos et al. |
| 2010/0129874 A1 | 5/2010 | Mitra et al. |
| 2010/0138165 A1 | 6/2010 | Fan et al. |
| 2010/0171954 A1 | 7/2010 | Quake et al. |
| 2010/0173394 A1 | 7/2010 | Colston et al. |
| 2010/0184043 A1 | 7/2010 | Mitchell et al. |
| 2010/0184069 A1 | 7/2010 | Fernando et al. |
| 2010/0184152 A1 | 7/2010 | Sandler |
| 2010/0196892 A1 | 8/2010 | Quake et al. |
| 2010/0203538 A1 | 8/2010 | Dube et al. |
| 2010/0216145 A1 | 8/2010 | Duvdevani |
| 2010/0216151 A1 | 8/2010 | Lapdus et al. |
| 2010/0216153 A1 | 8/2010 | Lapidus et al. |
| 2010/0227329 A1 | 9/2010 | Cuppens |
| 2010/0248231 A1 | 9/2010 | Wei et al. |
| 2010/0255492 A1 | 10/2010 | Quake et al. |
| 2010/0256013 A1 | 10/2010 | Quake et al. |
| 2010/0273159 A1 | 10/2010 | Melo |
| 2010/0273219 A1 | 10/2010 | May et al. |
| 2010/0273678 A1 | 10/2010 | Alexandre et al. |
| 2010/0285478 A1 | 11/2010 | Chen et al. |
| 2010/0285537 A1 | 11/2010 | Zimmermann |
| 2010/0291572 A1 | 11/2010 | Stoughton et al. |
| 2010/0291635 A1 | 11/2010 | Peleg |
| 2010/0323352 A1 | 12/2010 | Lo et al. |
| 2011/0015096 A1 | 1/2011 | Chiu |
| 2011/0033862 A1 | 2/2011 | Rabinowitz et al. |
| 2011/0039724 A1 | 2/2011 | Lo et al. |
| 2011/0045462 A1 | 2/2011 | Fu et al. |
| 2011/0064824 A1 | 3/2011 | Lascoste et al. |
| 2011/0071031 A1 | 3/2011 | Khripin et al. |
| 2011/0086769 A1 | 4/2011 | Oliphant et al. |
| 2011/0092763 A1 | 4/2011 | Rabinowitz et al. |
| 2011/0105353 A1 | 5/2011 | Lo et al. |
| 2011/0130558 A1 | 6/2011 | Ritt et al. |
| 2011/0151442 A1 | 6/2011 | Fan et al. |
| 2011/0159499 A1 | 6/2011 | Hindson et al. |
| 2011/0160078 A1 | 6/2011 | Fodor et al. |
| 2011/0178719 A1 | 7/2011 | Rabinowitz et al. |
| 2011/0201507 A1 | 8/2011 | Rava et al. |
| 2011/0212446 A1 | 9/2011 | Wang et al. |
| 2011/0212846 A1 | 9/2011 | Spier |
| 2011/0224087 A1 | 9/2011 | Quake et al. |
| 2011/0246083 A1 | 10/2011 | Fan et al. |
| 2011/0251149 A1 | 10/2011 | Perrine et al. |
| 2011/0288780 A1 | 11/2011 | Rabinowitz et al. |
| 2011/0294699 A1 | 12/2011 | Lee et al. |
| 2011/0300608 A1 | 12/2011 | Ryan et al. |
| 2011/0301854 A1 | 12/2011 | Curry et al. |
| 2011/0312503 A1 | 12/2011 | Chuu et al. |
| 2011/0318734 A1 | 12/2011 | Lo et al. |
| 2012/0003635 A1 | 1/2012 | Lo et al. |
| 2012/0003637 A1 | 1/2012 | Lo et al. |
| 2012/0010085 A1 | 1/2012 | Rava et al. |
| 2012/0034603 A1 | 2/2012 | Oliphant et al. |
| 2012/0034685 A1 | 2/2012 | Sparks et al. |
| 2012/0108460 A1 | 5/2012 | Quake et al. |
| 2012/0122701 A1 | 5/2012 | Ryan et al. |
| 2012/0165203 A1 | 6/2012 | Quake et al. |
| 2012/0185176 A1 | 7/2012 | Rabinowitz et al. |
| 2012/0190020 A1 | 7/2012 | Oliphant et al. |
| 2012/0190021 A1 | 7/2012 | Oliphant et al. |
| 2012/0190557 A1 | 7/2012 | Oliphant et al. |
| 2012/0191358 A1 | 7/2012 | Oliphant et al. |
| 2012/0196754 A1 | 8/2012 | Quake et al. |
| 2012/0208706 A1 | 8/2012 | Downing et al. |
| 2012/0214678 A1 | 8/2012 | Rava et al. |
| 2012/0264121 A1 | 10/2012 | Rava et al. |
| 2012/0264618 A1 | 10/2012 | Nygren |
| 2012/0270212 A1 | 10/2012 | Rabinowitz et al. |
| 2012/0270739 A1 | 10/2012 | Rava et al. |
| 2012/0295810 A1 | 11/2012 | Quake et al. |
| 2012/0295819 A1 | 11/2012 | Leamon et al. |
| 2013/0017549 A1 | 1/2013 | Hong |
| 2013/0022973 A1 | 1/2013 | Hansen et al. |
| 2013/0024127 A1 | 1/2013 | Stuelpnagel |
| 2013/0034546 A1 | 2/2013 | Rava et al. |
| 2013/0040375 A1 | 2/2013 | Sparks et al. |
| 2013/0060483 A1 | 3/2013 | Struble et al. |
| 2013/0069869 A1 | 3/2013 | Akao et al. |
| 2013/0085681 A1 | 4/2013 | Deciu et al. |
| 2013/0090250 A1 | 4/2013 | Sparks et al. |
| 2013/0116130 A1 | 5/2013 | Fu et al. |
| 2013/0123120 A1 | 5/2013 | Zimmermann et al. |
| 2013/0130923 A1 | 5/2013 | Ehrich et al. |
| 2013/0172211 A1 | 7/2013 | Oliphant et al. |
| 2013/0178373 A1 | 7/2013 | Rabinowitz et al. |
| 2013/0190653 A1 | 7/2013 | Alvarez Ramos |
| 2013/0196862 A1 | 8/2013 | Rabinowitz et al. |
| 2013/0210644 A1 | 8/2013 | Stoughton et al. |
| 2013/0225422 A1 | 8/2013 | Rabinowitz et al. |
| 2013/0231252 A1 | 9/2013 | Mitchell et al. |
| 2013/0252824 A1 | 9/2013 | Rabinowitz |
| 2013/0253369 A1 | 9/2013 | Rabinowitz et al. |
| 2013/0261004 A1 | 10/2013 | Ryan et al. |
| 2013/0274116 A1 | 10/2013 | Rabinowitz et al. |
| 2013/0303461 A1 | 11/2013 | Iafrate et al. |
| 2013/0323731 A1 | 12/2013 | Lo et al. |
| 2013/0325360 A1 | 12/2013 | Deciu et al. |
| 2014/0032128 A1 | 1/2014 | Rabinowitz et al. |

(56) References Cited

U.S. PATENT DOCUMENTS

| | | |
|---|---|---|
| 2014/0038830 A1 | 2/2014 | Srinivasan et al. |
| 2014/0045181 A1 | 2/2014 | Lo et al. |
| 2014/0051585 A1 | 2/2014 | Prosen et al. |
| 2014/0065621 A1 | 3/2014 | Mhatre et al. |
| 2014/0066317 A1 | 3/2014 | Talasaz |
| 2014/0087385 A1 | 3/2014 | Rabinowitz et al. |
| 2014/0094373 A1 | 4/2014 | Zimmermann et al. |
| 2014/0100126 A1 | 4/2014 | Rabinowitz |
| 2014/0100134 A1 | 4/2014 | Rabinowitz et al. |
| 2014/0106975 A1 | 4/2014 | Stoughton et al. |
| 2014/0141981 A1 | 5/2014 | Zimmermann et al. |
| 2014/0154682 A1 | 6/2014 | Rabinowitz et al. |
| 2014/0155274 A1 | 6/2014 | Xie et al. |
| 2014/0162269 A1 | 6/2014 | Rabinowitz |
| 2014/0193816 A1 | 7/2014 | Rabinowitz et al. |
| 2014/0206552 A1 | 7/2014 | Rabinowitz et al. |
| 2014/0227705 A1 | 8/2014 | Vogelstein et al. |
| 2014/0256558 A1 | 9/2014 | Varley et al. |
| 2014/0256569 A1 | 9/2014 | Rabinowitz et al. |
| 2014/0272956 A1 | 9/2014 | Huang et al. |
| 2014/0274740 A1 | 9/2014 | Srinivasan et al. |
| 2014/0287934 A1 | 9/2014 | Szelinger et al. |
| 2014/0296081 A1 | 10/2014 | Diehn et al. |
| 2014/0329245 A1 | 11/2014 | Spier et al. |
| 2014/0336060 A1 | 11/2014 | Rabinowitz |
| 2015/0051087 A1 | 2/2015 | Rabinowitz et al. |
| 2015/0064695 A1 | 3/2015 | Katz et al. |
| 2015/0086477 A1 | 3/2015 | Mitchell et al. |
| 2015/0087535 A1 | 3/2015 | Patel |
| 2015/0147815 A1 | 5/2015 | Babiarz et al. |
| 2015/0157606 A1 | 6/2015 | Chow Maneval et al. |
| 2015/0197786 A1 | 7/2015 | Osborne et al. |
| 2015/0211050 A1 | 7/2015 | Tafrate et al. |
| 2015/0232938 A1 | 8/2015 | Mhatre |
| 2015/0265995 A1 | 9/2015 | Head et al. |
| 2015/0299812 A1 | 10/2015 | Talasaz |
| 2015/0315657 A1 | 11/2015 | Rhodes et al. |
| 2015/0322507 A1 | 11/2015 | Zimmermann et al. |
| 2015/0329891 A1 | 11/2015 | Tan et al. |
| 2016/0032396 A1 | 2/2016 | Diehn et al. |
| 2016/0046986 A1 | 2/2016 | Eltoukhy et al. |
| 2016/0115541 A1 | 4/2016 | Schutz et al. |
| 2016/0145682 A1 | 5/2016 | Woodward et al. |
| 2016/0186239 A1 | 6/2016 | Sinha |
| 2016/0186253 A1 | 6/2016 | Talasaz et al. |
| 2016/0201124 A1 | 7/2016 | Donahue et al. |
| 2016/0239602 A1 | 8/2016 | Shendure et al. |
| 2016/0244838 A1 | 8/2016 | Babiarz et al. |
| 2016/0257993 A1 | 9/2016 | Fu et al. |
| 2016/0289740 A1 | 10/2016 | Fu et al. |
| 2016/0289753 A1 | 10/2016 | Osborne et al. |
| 2016/0312276 A1 | 10/2016 | Fu et al. |
| 2016/0319345 A1 | 11/2016 | Gnerre et al. |
| 2016/0369333 A1 | 12/2016 | Babiarz et al. |
| 2017/0011166 A1 | 1/2017 | Rabinowitz et al. |
| 2017/0107576 A1 | 4/2017 | Babiarz et al. |
| 2017/0114411 A1 | 4/2017 | Mitchell et al. |
| 2017/0121716 A1 | 5/2017 | Rodi et al. |
| 2017/0152561 A1 | 6/2017 | Hamamah et al. |
| 2017/0218458 A1 | 8/2017 | Fan et al. |
| 2017/0275689 A1 | 9/2017 | Maguire et al. |
| 2017/0283788 A1 | 10/2017 | Khoja et al. |
| 2017/0314014 A1 | 11/2017 | Green et al. |
| 2017/0342477 A1 | 11/2017 | Jensen et al. |
| 2017/0362649 A1 | 12/2017 | Lieberman-Aiden et al. |
| 2018/0023128 A1 | 1/2018 | Yanai et al. |
| 2018/0025109 A1 | 1/2018 | Rabinowitz et al. |
| 2018/0127744 A1 | 5/2018 | Hu et al. |
| 2018/0148777 A1 | 5/2018 | Kirkizlar et al. |
| 2018/0155775 A1 | 6/2018 | Zimmermann et al. |
| 2018/0155776 A1 | 6/2018 | Zimmermann et al. |
| 2018/0155779 A1 | 6/2018 | Zimmermann et al. |
| 2018/0155785 A1 | 6/2018 | Rabinowitz et al. |
| 2018/0155786 A1 | 6/2018 | Rabinowitz et al. |
| 2018/0155792 A1 | 6/2018 | Rabinowitz et al. |
| 2018/0171409 A1 | 6/2018 | Rabinowitz et al. |
| 2018/0171420 A1 | 6/2018 | Babiarz et al. |
| 2018/0173845 A1 | 6/2018 | Sigurjonsson et al. |
| 2018/0173846 A1 | 6/2018 | Sigurjonsson et al. |
| 2018/0187241 A1 | 7/2018 | Selvaraj et al. |
| 2018/0201995 A1 | 7/2018 | Rabinowitz et al. |
| 2018/0237841 A1 | 8/2018 | Stray et al. |
| 2018/0251553 A1 | 9/2018 | Mcgranahan et al. |
| 2018/0265917 A1 | 9/2018 | Barany et al. |
| 2018/0288982 A1 | 10/2018 | Sinha |
| 2018/0298439 A1 | 10/2018 | Ryan et al. |
| 2018/0300448 A1 | 10/2018 | Rabinowitz et al. |
| 2018/0320239 A1 | 11/2018 | Babiarz et al. |
| 2019/0010543 A1 | 1/2019 | Babiarz et al. |
| 2019/0106737 A1 | 4/2019 | Underhill |
| 2019/0106751 A1 | 4/2019 | Zimmermann et al. |
| 2019/0185913 A1 | 6/2019 | Zimmermann et al. |
| 2019/0185936 A1 | 6/2019 | Babiarz et al. |
| 2019/0194743 A1 | 6/2019 | Ryan et al. |
| 2019/0194758 A1 | 6/2019 | Babiarz et al. |
| 2019/0194759 A1 | 6/2019 | Babiarz et al. |
| 2019/0203290 A1 | 7/2019 | Rabinowitz et al. |
| 2019/0203294 A1 | 7/2019 | Babiarz et al. |
| 2019/0211391 A1 | 7/2019 | Rabinowitz et al. |
| 2019/0211392 A1 | 7/2019 | Rabinowitz et al. |
| 2019/0211393 A1 | 7/2019 | Rabinowitz et al. |
| 2019/0211399 A1 | 7/2019 | Rabinowitz et al. |
| 2019/0211402 A1 | 7/2019 | Babiarz et al. |
| 2019/0211406 A1 | 7/2019 | Babiarz et al. |
| 2019/0249241 A1 | 8/2019 | Rabinowitz et al. |
| 2019/0256894 A1 | 8/2019 | Zimmermann et al. |
| 2019/0256906 A1 | 8/2019 | Rabinowitz et al. |
| 2019/0256907 A1 | 8/2019 | Ryan et al. |
| 2019/0256908 A1 | 8/2019 | Rabinowitz et al. |
| 2019/0256909 A1 | 8/2019 | Rabinowitz et al. |
| 2019/0256912 A1 | 8/2019 | Rabinowitz et al. |
| 2019/0256916 A1 | 8/2019 | Babiarz et al. |
| 2019/0256917 A1 | 8/2019 | Babiarz et al. |
| 2019/0256919 A1 | 8/2019 | Babiarz et al. |
| 2019/0256924 A1 | 8/2019 | Vogelstein et al. |
| 2019/0256931 A1 | 8/2019 | Babiarz et al. |
| 2019/0264277 A1 | 8/2019 | Rabinowitz et al. |
| 2019/0264280 A1 | 8/2019 | Rabinowitz et al. |
| 2019/0264288 A1 | 8/2019 | Rabinowitz et al. |
| 2019/0271043 A1 | 9/2019 | Babiarz et al. |
| 2019/0276888 A1 | 9/2019 | Rabinowitz et al. |
| 2019/0284623 A1 | 9/2019 | Rabinowitz et al. |
| 2019/0300950 A1 | 10/2019 | Rabinowitz et al. |
| 2019/0309358 A1 | 10/2019 | Rabinowitz et al. |
| 2019/0309359 A1 | 10/2019 | Zimmermann et al. |
| 2019/0309365 A1 | 10/2019 | Babiarz et al. |
| 2019/0316177 A1 | 10/2019 | Zimmermann et al. |
| 2019/0316184 A1 | 10/2019 | Zimmermann et al. |
| 2019/0316200 A1 | 10/2019 | Rabinowitz et al. |
| 2019/0323076 A1 | 10/2019 | Rabinowitz et al. |
| 2019/0360036 A1 | 11/2019 | Rabinowitz et al. |
| 2020/0024653 A1 | 1/2020 | Bethke |
| 2020/0032323 A1 | 1/2020 | Talasaz et al. |
| 2020/0109449 A1 | 4/2020 | Stamm et al. |
| 2020/0123612 A1 | 4/2020 | Babiarz et al. |
| 2020/0126634 A1 | 4/2020 | Sigurjonsson et al. |
| 2020/0140950 A1 | 5/2020 | Babiarz et al. |
| 2020/0149111 A1 | 5/2020 | Babiarz et al. |
| 2020/0157629 A1 | 5/2020 | Babiarz et al. |
| 2020/0172977 A1 | 6/2020 | Rabinowitz et al. |
| 2020/0181697 A1 | 6/2020 | Rabinowitz et al. |
| 2020/0190570 A1 | 6/2020 | Ryan et al. |
| 2020/0190573 A1 | 6/2020 | Rabinowitz et al. |
| 2020/0190591 A1 | 6/2020 | Rabinowitz et al. |
| 2020/0208196 A1 | 7/2020 | Zimmermann et al. |
| 2020/0208221 A1 | 7/2020 | Babiarz et al. |
| 2020/0224273 A1 | 7/2020 | Rabinowitz et al. |
| 2020/0232036 A1 | 7/2020 | Rabinowitz et al. |
| 2020/0232037 A1 | 7/2020 | Babiarz et al. |
| 2020/0248264 A1 | 8/2020 | Rabinowitz et al. |
| 2020/0248266 A1 | 8/2020 | Swanton et al. |
| 2020/0316498 A1 | 10/2020 | Mitchell |
| 2020/0318191 A1 | 10/2020 | Babiarz et al. |
| 2020/0347454 A1 | 11/2020 | Babiarz et al. |

(56) References Cited

U.S. PATENT DOCUMENTS

| | | | |
|---|---|---|---|
| 2020/0350034 | A1 | 11/2020 | Rabinowitz et al. |
| 2020/0362415 | A1 | 11/2020 | Rabinowitz et al. |
| 2020/0407788 | A1 | 12/2020 | Ryan et al. |
| 2020/0407798 | A1 | 12/2020 | Babiarz et al. |
| 2021/0009990 | A1 | 1/2021 | Stray et al. |
| 2021/0025005 | A1 | 1/2021 | Babiarz et al. |
| 2021/0054459 | A1 | 2/2021 | Rabinowitz et al. |
| 2021/0071246 | A1 | 3/2021 | Zimmermann et al. |
| 2021/0139969 | A1 | 5/2021 | Mitchell et al. |
| 2021/0139983 | A1 | 5/2021 | Mitchell et al. |
| 2021/0139988 | A1 | 5/2021 | Mitchell et al. |
| 2021/0155988 | A1 | 5/2021 | Rabinowitz et al. |
| 2021/0189498 | A1 | 6/2021 | Babiarz et al. |
| 2021/0198733 | A1 | 7/2021 | Moshkevich et al. |
| 2021/0198742 | A1 | 7/2021 | Rabinowitz et al. |
| 2021/0198743 | A1 | 7/2021 | Rabinowitz et al. |
| 2021/0222230 | A1 | 7/2021 | Zimmermann et al. |
| 2021/0222240 | A1 | 7/2021 | Moshkevich et al. |
| 2021/0257048 | A1 | 8/2021 | Zimmermann et al. |
| 2021/0269879 | A1 | 9/2021 | Mitchell et al. |
| 2021/0324463 | A1 | 10/2021 | Rabinowitz et al. |
| 2021/0327538 | A1 | 10/2021 | Egilsson et al. |
| 2021/0327542 | A1 | 10/2021 | Ryan et al. |
| 2021/0355536 | A1 | 11/2021 | Rabinowitz et al. |
| 2022/0025455 | A1 | 1/2022 | Zimmermann et al. |
| 2022/0025456 | A1 | 1/2022 | Rabinowitz et al. |
| 2022/0033909 | A1 | 2/2022 | Babiarz et al. |
| 2022/0042103 | A1 | 2/2022 | Rabinowitz et al. |
| 2022/0056509 | A1 | 2/2022 | Zimmermann |
| 2022/0056534 | A1 | 2/2022 | Rivers |
| 2022/0073978 | A1 | 3/2022 | Rabinowitz et al. |
| 2022/0073979 | A1 | 3/2022 | Rabinowitz et al. |
| 2022/0098667 | A1 | 3/2022 | Rabinowitz et al. |

FOREIGN PATENT DOCUMENTS

| | | | | |
|---|---|---|---|---|
| CN | 101675169 A | 3/2010 | | |
| CN | 104736722 A | 6/2015 | | |
| CN | 105229175 A | 1/2016 | | |
| EP | 0270017 A2 | 6/1988 | | |
| EP | 1325963 A1 | 7/2003 | | |
| EP | 1524321 A1 * | 4/2005 | ........... | C12Q 1/6806 |
| EP | 1325963 B1 | 9/2006 | | |
| EP | 1524321 B1 | 7/2009 | | |
| EP | 2163622 A1 | 3/2010 | | |
| EP | 2128169 A1 | 12/2010 | | |
| EP | 2902500 A1 | 8/2015 | | |
| EP | 3026124 A1 | 6/2016 | | |
| EP | 3285193 A1 | 2/2018 | | |
| EP | 2877594 B1 | 12/2019 | | |
| EP | 3187597 B1 | 6/2020 | | |
| EP | 3134541 B1 | 8/2020 | | |
| EP | 3760730 A1 | 1/2021 | | |
| EP | 3760731 A1 | 1/2021 | | |
| EP | 3760732 A1 | 1/2021 | | |
| EP | 3824470 | 5/2021 | | |
| EP | 3443119 B1 | 2/2022 | | |
| GB | 2488358 | 8/2012 | | |
| JP | 2965699 | 8/1999 | | |
| JP | 2002-530121 A | 9/2002 | | |
| JP | 2002-300894 A | 10/2002 | | |
| JP | 2003/521252 A | 7/2003 | | |
| JP | 2004502466 A | 1/2004 | | |
| JP | 2004121087 A | 4/2004 | | |
| JP | 2004533243 A | 11/2004 | | |
| JP | 2005514956 A | 5/2005 | | |
| JP | 2005160470 A | 6/2005 | | |
| JP | 2006-254912 A | 9/2006 | | |
| JP | 2008-263974 A | 11/2008 | | |
| JP | 2008/271980 A | 11/2008 | | |
| JP | 2010-509922 A | 4/2010 | | |
| JP | 2011/508662 A | 3/2011 | | |
| JP | 2011/516069 A | 5/2011 | | |
| JP | 2015-535681 | 12/2015 | | |
| RU | 2290078 C1 | 12/2006 | | |

| | | |
|---|---|---|
| WO | 95/01796 | 1/1995 |
| WO | 1996036736 A2 | 11/1996 |
| WO | 98/39474 | 9/1998 |
| WO | 98/44151 | 10/1998 |
| WO | 00/18957 | 4/2000 |
| WO | 2001007640 A2 | 2/2001 |
| WO | 0134844 A1 | 5/2001 |
| WO | 01/57269 A2 | 8/2001 |
| WO | 2001/079851 A1 | 10/2001 |
| WO | 200190419 A2 | 11/2001 |
| WO | 2002004672 A2 | 1/2002 |
| WO | 02/44411 A1 | 6/2002 |
| WO | 2002055985 A2 | 7/2002 |
| WO | 02/070751 A1 | 9/2002 |
| WO | 2002076377 | 10/2002 |
| WO | 02/090505 A2 | 11/2002 |
| WO | 03/000919 A2 | 1/2003 |
| WO | 03/018757 A3 | 3/2003 |
| WO | 03/020974 A3 | 3/2003 |
| WO | 2003031646 A1 | 4/2003 |
| WO | 2003/050532 A1 | 6/2003 |
| WO | 2003062441 A1 | 7/2003 |
| WO | 2003/102595 A1 | 12/2003 |
| WO | 2003/106623 A2 | 12/2003 |
| WO | 2004/051218 A2 | 6/2004 |
| WO | 2004069849 A2 | 8/2004 |
| WO | 2004070005 A2 | 8/2004 |
| WO | 2004070007 A2 | 8/2004 |
| WO | WO-2004078999 A1 | 9/2004 |
| WO | WO-2004081183 A2 | 9/2004 |
| WO | 2004087863 A2 | 10/2004 |
| WO | 2005003375 A2 | 1/2005 |
| WO | 2005021793 A1 | 3/2005 |
| WO | 2005023091 A2 | 3/2005 |
| WO | 2005030999 A1 | 4/2005 |
| WO | 2005035725 A2 | 4/2005 |
| WO | 2005/039389 A3 | 5/2005 |
| WO | WO-2005090607 A1 | 9/2005 |
| WO | 2005100401 A2 | 10/2005 |
| WO | 2005123779 A2 | 12/2005 |
| WO | 2007145612 A1 | 6/2006 |
| WO | 2006110855 A2 | 10/2006 |
| WO | 2006/128192 A2 | 11/2006 |
| WO | 2007/011903 A3 | 1/2007 |
| WO | 2007/052006 A1 | 5/2007 |
| WO | 2007057647 A1 | 5/2007 |
| WO | 2007062164 A3 | 5/2007 |
| WO | 2007/073171 A2 | 6/2007 |
| WO | 2007070280 A2 | 6/2007 |
| WO | 2007070482 A2 | 6/2007 |
| WO | 2007075836 A2 | 7/2007 |
| WO | 2007/092473 A2 | 8/2007 |
| WO | 2007086935 A2 | 8/2007 |
| WO | 2007/117256 A1 | 10/2007 |
| WO | 2007117039 A1 | 10/2007 |
| WO | 2007132167 A2 | 11/2007 |
| WO | 2007/147073 A2 | 12/2007 |
| WO | 2007/147076 A2 | 12/2007 |
| WO | 2007140417 A2 | 12/2007 |
| WO | 2007147074 A2 | 12/2007 |
| WO | 2007147079 A2 | 12/2007 |
| WO | 2008024473 A2 | 2/2008 |
| WO | 2008048931 A1 | 4/2008 |
| WO | 2008/061213 A2 | 5/2008 |
| WO | 2008051928 A2 | 5/2008 |
| WO | 2008056937 A1 | 5/2008 |
| WO | 2008059578 A2 | 5/2008 |
| WO | 2008079374 A2 | 7/2008 |
| WO | 2008081451 A2 | 7/2008 |
| WO | 2008084405 A2 | 7/2008 |
| WO | 2008115427 A2 | 9/2008 |
| WO | 2008115497 A2 | 9/2008 |
| WO | 2008118988 A1 | 10/2008 |
| WO | 2008135837 A2 | 11/2008 |
| WO | 2008157264 A2 | 12/2008 |
| WO | 2009009769 A2 | 1/2009 |
| WO | 2009013492 A1 | 1/2009 |
| WO | 2009013496 A1 | 1/2009 |
| WO | 2009019215 A1 | 2/2009 |

(56) References Cited

FOREIGN PATENT DOCUMENTS

| | | | |
|---|---|---|---|
| WO | 2009019455 | A2 | 2/2009 |
| WO | 2009/032779 | A2 | 3/2009 |
| WO | 2009/036525 | A2 | 3/2009 |
| WO | 2009030100 | A1 | 3/2009 |
| WO | 2009032781 | A2 | 3/2009 |
| WO | 2009033178 | A1 | 3/2009 |
| WO | 2009049889 | A1 | 4/2009 |
| WO | 2009017784 | A2 | 5/2009 |
| WO | 2009064897 | A2 | 5/2009 |
| WO | 2009091934 | A1 | 7/2009 |
| WO | 2009092035 | A2 | 7/2009 |
| WO | 2009/105531 | A1 | 8/2009 |
| WO | 2009099602 | A1 | 8/2009 |
| WO | 2009100029 | A1 | 8/2009 |
| WO | 2009117122 | A2 | 9/2009 |
| WO | 2009120808 | A2 | 10/2009 |
| WO | 2009145828 | A2 | 12/2009 |
| WO | 2009146335 | A1 | 12/2009 |
| WO | 2010014920 | A1 | 2/2010 |
| WO | 2010017214 | A1 | 2/2010 |
| WO | 2010/033639 | A2 | 3/2010 |
| WO | 2010/033652 | A1 | 3/2010 |
| WO | 2010033578 | A2 | 3/2010 |
| WO | 2010042831 | A2 | 4/2010 |
| WO | 2010045617 | A2 | 4/2010 |
| WO | 2010075459 | | 7/2010 |
| WO | 2010/088288 | A2 | 8/2010 |
| WO | 2010115016 | A2 | 10/2010 |
| WO | 2010115154 | A1 | 10/2010 |
| WO | 2010118016 | A2 | 10/2010 |
| WO | 2010/127186 | A1 | 11/2010 |
| WO | 2011/023078 | A1 | 3/2011 |
| WO | 2011/032078 | A1 | 3/2011 |
| WO | 2011041485 | A1 | 4/2011 |
| WO | 2011/051283 | A1 | 5/2011 |
| WO | 2011/057061 | A1 | 5/2011 |
| WO | 2011057094 | | 5/2011 |
| WO | 2011/090556 | A1 | 7/2011 |
| WO | 2011087760 | | 7/2011 |
| WO | 2011102998 | A2 | 8/2011 |
| WO | 2011109440 | A1 | 9/2011 |
| WO | 2011140433 | A2 | 11/2011 |
| WO | 2011146632 | A1 | 11/2011 |
| WO | 2012/019200 | A2 | 2/2012 |
| WO | 2012/028746 | A1 | 3/2012 |
| WO | 2012042374 | A2 | 4/2012 |
| WO | 2012/058488 | A1 | 5/2012 |
| WO | 201283250 | | 6/2012 |
| WO | 2012088456 | A2 | 6/2012 |
| WO | 20120071621 | | 6/2012 |
| WO | 2012108920 | A1 | 8/2012 |
| WO | 2012/142531 | A2 | 10/2012 |
| WO | 2007/149791 | A2 | 12/2012 |
| WO | 2013050577 | | 3/2013 |
| WO | 2013/045432 | A1 | 4/2013 |
| WO | 2013/049892 | A1 | 4/2013 |
| WO | 2013052557 | A2 | 4/2013 |
| WO | 2013/078470 | A2 | 5/2013 |
| WO | 2013/086464 | A1 | 6/2013 |
| WO | 2013/123220 | A1 | 8/2013 |
| WO | 2013/138510 | A1 | 9/2013 |
| WO | 2013/138510 | A9 | 9/2013 |
| WO | 20130130848 | | 9/2013 |
| WO | 2013/159035 | A2 | 10/2013 |
| WO | 2013/169339 | A1 | 11/2013 |
| WO | 2013/177220 | A1 | 11/2013 |
| WO | 2013/181651 | A1 | 12/2013 |
| WO | 2014/004726 | A1 | 1/2014 |
| WO | 2014/014497 | A1 | 1/2014 |
| WO | 20140018080 | | 1/2014 |
| WO | 2014/035986 | A1 | 3/2014 |
| WO | 2014/122288 | A1 | 8/2014 |
| WO | 2014/145078 | A1 | 9/2014 |
| WO | 2014/145232 | A2 | 9/2014 |
| WO | 2014/149134 | A2 | 9/2014 |
| WO | 2014/150300 | A2 | 9/2014 |
| WO | 2014/151117 | A1 | 9/2014 |
| WO | 2014/194113 | A2 | 12/2014 |
| WO | 2015134552 | A1 | 3/2015 |
| WO | 2015/048535 | A1 | 4/2015 |
| WO | 2015/100427 | A1 | 7/2015 |
| WO | 2015/148494 | A1 | 10/2015 |
| WO | 2015/164432 | A1 | 10/2015 |
| WO | 2016/009059 | A1 | 1/2016 |
| WO | 2016009224 | A1 | 1/2016 |
| WO | 2016/063122 | A1 | 4/2016 |
| WO | 2016/065295 | A1 | 4/2016 |
| WO | 2016/077313 | A1 | 5/2016 |
| WO | 2016/123698 | A1 | 8/2016 |
| WO | 2016/138080 | A1 | 9/2016 |
| WO | 2016/176662 | A1 | 11/2016 |
| WO | 2016/183106 | A1 | 11/2016 |
| WO | 2016/193490 | A1 | 12/2016 |
| WO | 2017/058784 | A1 | 4/2017 |
| WO | 2017/181146 | A1 | 10/2017 |
| WO | 2017/181202 | A2 | 10/2017 |
| WO | 2017/190106 | A1 | 11/2017 |
| WO | 2017205540 | A1 | 11/2017 |
| WO | 2018/009723 | A1 | 1/2018 |
| WO | 2018/083467 | A1 | 5/2018 |
| WO | 2018/085603 | A1 | 5/2018 |
| WO | 2018/106798 | A1 | 6/2018 |
| WO | 2018/136562 | A2 | 7/2018 |
| WO | 2018/156418 | A1 | 8/2018 |
| WO | 2018/237081 | A1 | 12/2018 |
| WO | 2019/046817 | A1 | 3/2019 |
| WO | 2019/118926 | A1 | 6/2019 |
| WO | 2019/140298 | A1 | 7/2019 |
| WO | 2019/161244 | A1 | 8/2019 |
| WO | 2019/200228 | A1 | 10/2019 |
| WO | 2019/241349 | A1 | 12/2019 |
| WO | 2020/010255 | A1 | 1/2020 |
| WO | 2020/018522 | A1 | 1/2020 |
| WO | 2020/041449 | A1 | 2/2020 |
| WO | 2020/076957 | A1 | 4/2020 |
| WO | 2020/106987 | A1 | 5/2020 |
| WO | 2020/131699 | A2 | 6/2020 |
| WO | 2020/214547 | A1 | 10/2020 |
| WO | 2020/247263 | A1 | 12/2020 |
| WO | 2021/055968 | A1 | 3/2021 |
| WO | 2007100911 | A2 | 9/2021 |
| WO | 2021/243045 | A1 | 12/2021 |
| WO | 2022/015676 | A1 | 1/2022 |

OTHER PUBLICATIONS

Park, et al., "First-Line Erlotinib Therapy Until and Beyond Response Evaluation Criteria in Solid Tumors Progression in Asian Patients With Epidermal Growth Factor Receptor Mutation-Positive Non-Small-Cell Lung Cancer", JAMA Oncol., 2015, 305-312.

Tseng, Jeng-Sen, et al., "Dynamic Plasma EGFR Mutation Status as a Predictor of EGFR-TKI Efficacy in Patients with fGFR-Mutant Lung Adenocarcinoma", Thorac Oncol., 2015, 603-610.

"European Application No. 014198110, European Search Report Mailed Apr. 28, 2015, 3 pages."

PRNewswire (Research Suggests Daily Consumption of Orange Juice Can Reduce Blood Pressure and May Provide Beneficial Effects to Blood Vessel Function: New Study Identified Health Benefits in Orange Juice, Dec. 8, 2010), 3 pages.

"Abstracts for CNAPS III Circulating Nucleic Acids in Plasma and Serum and Serum Proteomics", Clinical Chemistry, vol. 49, No. 11, 2003, 33 pages.

"Abstracts for CNAPS IV Circulating Nucleic Acids in Plasma/Serum", Fourth International Conference on Circulating Nucleic Acids in Plasma/Serum (CNAPS-IV), 2005, 40 pages.

"How Many Carbs in a Potato?, [Online]", New Health Guide, Nov. 1, 2014, 3 pages.

"Random variable", The Penguin Dictionary of Mathematics, 2008, 1 page.

Abaan, O. D et al., "The Exomes of the NCI-60 Panel: A Genomic Resource for Cancer Biology and Systems Pharmacology", Cancer Res., vol. 73, No. 14, Jul. 15, 2013, 4372-4382.

(56) References Cited

OTHER PUBLICATIONS

Abbosh, C. et al., "Phylogenetic ctDNA analysis depicts early-stage lung cancer evolution", Nature, vol. 545, May 25, 2017, 446-451.
Abd-Elsalam, Kamel A. , "Bioinformatic Tools And Guideline for PCR Primer Design", African Journal of Biotechnology, vol. 2, 2003, pp. 91-95.
Abidi, S. et al., "Leveraging XML-based electronic medical records to extract experiential clinical knowledge: An automated approach to generate cases for medical case-based reasoning systems", International Journal of Medical Informatics, 68(1-3), 2002, 187-203.
Academic Press, "Fixed Medium", 1996, 1 pg.
Adalsteinsson, V. A. et al., "Scalable whole-exome sequencing of cell-free DNA reveals high concordance with metastatic tumors", Nature Communications, vol. 18, No. 1324, 2017, 13 pages.
Adinolfi, M. et al., "Rapid Detection of Aneuploidies by Microsatellite and the Quantitative Fluorescent Polymerase Chain Reaction", Prenatal Diagnosis, vol. 17, No. 13, 1997, 1299-1311.
Agarwal, Ashwin et al., "Commercial Landscape of Noninvasive Prenatal Testing in the United States", Prenatal Diagnosis, 33, 2013, 521-531.
Agbor-Enoh, S. et al., "Donor-derived cell-free DNA predicts allograft failure and mortality after lung transplantation", EBioMedicine, vol. 40, 2019, 541-553.
Alaeddini, R. et al., "Forensic implications of genetic analyses from degraded DNA—A review", Forensic Science International: Genetics, vol. 4, 2010, 148-157.
Alberts, B. et al., "Chapter 20: Germ Cells and Fertilization", Molecular Biology of the Cell, Fourth Edition, 2002, 1127-1156.
Alberts, B. et al., "Chapter 4: DNA and Chromosomes", Molecular Biology of the Cell, Fourth Edition, 2002, 191-234.
Alizadeh, Mehdi et al., "Quantitative Assessment of Hematopoietic Chimerism after Bone Marrow Transplantation by Real-time Quantitative Polymerase Chain Reaction", Blood, vol. 99, No. 12, Jun. 15, 2002, 4618-4625.
Alkan, Can et al., "Personalized Copy Number and Segmental Duplication Maps Using Next-Generation Sequencing", Nature Genetics, 41, 10, 2009, 1061-1068.
Allaire, F R. , "Mate selection by selection index theory", Theoretical Applied Genetics, 57(6), 1980, 267-272.
Allan, J. et al., "Micrococcal Nuclease Does Not Substantially Bias Nucleosome Mapping", Journal of Molecular Biology, vol. 417, Jan. 30, 2012, 152-164.
Allawi, Hatim T. et al., "Thermodynamics of internal C•T Mismatches in DNA", Nucleic Acids Research, 26 (11), 1998, 2694-2701.
Ambardar, S. et al., "High Throughput Sequencing: An Overview of Sequencing Chemistry", Indian J. Microbiol., vol. 56, No. 4, 2016, 394-404.
Amicucci, P. et al., "Prenatal Diagnosis of Myotonic Dystrophy Using Fetal DNA Obtained from Maternal Plasma", Clinical Chemistry, vol. 46, No. 2, 2000, 301-302.
Andras, S. C. et al., "Strategies for Signal Amplification in Nucleic Acid Detection", Molecular Biotechnology, vol. 19, 2001, 29-44.
Anker, P. et al., "Circulating DNA in Plasma or Serum", Medicina, vol. 60, 2000, 699-702.
Anker, P. et al., "Detection of circulating tumour DNA in the blood (plasma/serum) of cancer patients", Cancer and Metastasis Reviews, vol. 18, 1999, 65-73.
Anker, P. et al., "The Second International Symposium on Circulating Nucleic Acids in Plasma and Serum (CNAPS-2) held in conjunction with the 6th Annual Scientific Symposium of the Hong Kong Cancer Institute", Clinical Chemistry, vol. 47, No. 2, 2001, 361-370.
Ansorge, Wilhelm J. , "Next-generation DNA Sequencing Techniques", New Biotechnology, vol. 25, No. 4, Feb. 2, 2009, 195-203.
Antonarakis, S. E. et al., "Chromosome 21 and Down Syndrome: From Genomics to Pathophysiology", Nature Reviews Genetics, vol. 5, Oct. 2004, 725-738.

Aoki, Yasuhiro , "Statistical and Probabilistic Bases of Forensic DNA Testing", The Journal of the Iwate Medical Association, 2002, vol. 54, p. 81-94.
Arandjelovic, M. et al., "Two-Step Multiplex Polymerase Chain Reaction improves the Speed and Accuracy of Genotyping Using DNA from Noninvasive and Museum Samples", Molecular Ecology Resources, vol. 9, 2009, pp. 28-36.
Ashoor, G. et al., "Fetal fraction in maternal plasma cell-free DNA at 11-13 weeks' gestation: relation to maternal and fetal characteristics", Ultrasound in Obstetrics and Gynecology, vol. 41, 2013, 26-32.
Ashoor, Ghalia et al., "Chromosome-Selective Sequencing of Maternal Plasma Cell-Free DNA for First-Trimester Detection of Trisomy 21 and Trisomy 18", American Journal of Obstetrics & Gynecology, 206, 2012, 322.e1-322.e5.
Ashoor, Ghalia et al., "Fetal Fraction in Maternal Plasma Cell-Free DNA at 11-13 Weeks' Gestation: Effect of Maternal and Fetal Factors", Fetal Diagnosis Therapy, 2012, 1-7.
Auld, D. S. , "Use of Chelating Agents to Inhibit Enzymes", Methods in Enzymology, vol. 158, 1988, 110-114.
Avent, Neil D. et al., "Cell-free Fetal DNA in The Maternal Serum And Plasma: Current And Evolving Applications", Current Opinion in Obstretrics and Gynecology, vol. 21, No. 2, Apr. 1, 2009, 175-179.
Avgidou, K. et al., "Prospective first-trimester screening for trisomy 21 in 30,564 pregnancies", American Journal of Obstetrics and Gynecology, vol. 192, 2005, 1761-1767.
Ayala, et al., "Long-Term Follow-Up of Donor Chimerism Tolerance After Human Liver Transplantation", Liver Transplantation, vol. 15, No. 6,, May 28, 2009, 581-591.
Bada, Michael A. et al., "Computational Modeling of Structural Experimental Data", Methods in Enzymology,317, 2000, 470-491.
Bai, H. et al., "Detection and Clinical Significance of Intratumoral EGFR Mutational Heterogeneity in Chinese Patients with Advanced Non-Small Cell Lung Cancer", PLOS One, vol. 8, No. 2, Feb. 2013, 7 pages.
Balavoine, Guillaume , "Identification of Members of Several Homeobox Genes in a Planarian Using a Ligation-Mediated Polymerase Chain Reaction Technique", Nucleic Acids Research, vol. 24, 1996, pp. 1547-1553.
Balduini, et al., "Utility of Biochemical Markers in The Follow-up Heart Transplant Recipients", Transplantation Proceedings, vol. 35, No. 8, Dec. 1, 2003, 3075-3078.
Bale, J. R. et al., "Reducing Birth Defects: Meeting the Challenge in the Developing World", Institute of Medicine of the National Academies, 2003, 270 pgs.
Ballif, B. C. et al., "Detection of Low-Level Mosaicism by Array CGH in Routine Diagnostic Specimens", American Journal of Medical Genetics Part A, vol. 140A, 2006, 2757-2767.
Banfi, G. et al., "The role of ethylenediamine tetraacetic acid (EDTA) as in vitro anticoagulant for diagnostic purposes", Clin. Chem., vol. 45, No. 5, 2007, 565-576.
Barbazuk, et al., "SNP Discovery via 454 Transcriptome Sequencing", The Plant Journal, vol. 51, Jul. 27, 2007, 910-918.
Barra, G. B. et al., "EDTA-mediated inhibition of DNases protects circulating cell-free DNA from ex vivo degradation in blood samples", Clinical Biochemistry, vol. 48, 2015, 976-981.
Barski, A. et al., "High-Resolution Profiling of Histone Methylations in the Human Genome", Cell, vol. 129, May 18, 2007, 823-837.
Bartlett, John M. et al., "PCR Protocols", PCR Protocols, vol. 226, 2003, 519 pages.
Bashashati, A. et al., "Distinct evolutionary trajectories of primary high-grade serous ovarian cancers revealed through spatial mutational profiling", Journal of Pathology, vol. 231, 2013, 21-34.
Bauer, M. et al., "A prospective analysis of cell-free fetal DNA concentration in maternal plasma as an indicator for adverse pregnancy outcome", Prenatal Diagnosis, vol. 26, 2006, 831-836.
Baxter, L. L. et al., "Discovery and genetic localization of Down syndrome cerebellar phenotypes using the Ts65Dn mouse", Human Molecular Genetics, vol. 9, No. 2, Jan. 2000, 195-202.
Baxter-Lowe, et al., "Tracking Microchimeric DNA in Plasma to Diagnose and Manage Organ Transplant Rejection", Clinical Chemistry, vol. 52, No. 4, Apr. 1, 2006, 559-561.

(56) References Cited

OTHER PUBLICATIONS

Beaumont, Mark A. et al., "The Bayesian Revolution in Genetics", Nature Reviews Genetics, 5, 2004, 251-261.

Beck, et al., "Next Generation Sequencing of Serum Circulating Nucleic Acids from Patients with Invasive Ductal Breast Cancer Reveals Differences to Healthy and Nonmalignant Controls", Molecular Cancer Research, vol. 8, No. 3, Mar. 1, 2010, 335-342.

Beck, J. et al., "Digital Droplet PCR for Rapid Quantification of Donor DNA in the Circulation of Transplant Recipients as a Potential Universal Biomarker of Graft Injury", Clinical Chemistry, vol. 59, No. 12, 2013, 1732-1741.

Beck, J. et al., "Profile of the Circulating DNA in Apparently Healthy Individuals", Clinical Chemistry, vol. 55, No. 4, 2009, 730-738.

Beer, Alan E. et al., "The Biological Basis of Passage of Fetal Cellular Material into the Maternal Circulation", Annals New York Academy of Sciences, 731, 1994, 21-35.

Beerenwinkel, et al., "Methods for Optimizing Antiviral Combination Therapies", Bioinformatics, 19(1), 2003, i16-i25.

Beerenwinkel, N. et al., "Geno2pheno: estimating phenotypic drug resistance from HIV-1 genotypes", Nucleic Acids Research, 31(13), 2003, 3850-3855.

Belostotsky, Dmitry A. et al., "Plant Systems Biology", Methods in Molecular Biology, vol. 553, Aug. 25, 2009, 3-408.

Bender, et al., "A Multiplex SNP Typing Approach for the DNA Pyrosequencing Technology", International Congress Series, vol. 1288, Apr. 20, 2006, 73-75.

Benjamini, Y. et al., "Controlling the False Discovery Rate: A Practical and Powerful Approach to Multiple Testing", Journal of the Royal Statistical Society, Series B (Methodological), vol. 57, No. 1, 1995, 289-300.

Benn, P. et al., "Non-Invasive Prenatal Testing for Aneuploidy: Current Status and Future Prospects", Ultrasound Obstet Gynecol, 42, 2013, 15-33.

Benn, P et al., "Non-Invasive prenatal Diagnosis for Down Syndrome: the Paradigm Will Shift, but Slowly", Ultrasound Obstet. Gynecol., 39, 2012, 127-130.

Bennett, S. T. et al., "Toward the $1000 human genome". Pharmacogenomics, vol. 6, No. 4, 2005, 373-382.

Bentley, et al., "High-resolution, High-throughput HLA Genotyping by Next-generation Sequencing", Tissue Antigens, vol. 74, No. 5, Nov. 1, 2009, 393-403.

Bentley, David R. et al., "Accurate Whole Human Genome Sequencing Using Reversible Terminator Chemistry", Nature, 456, 6, 2008, 53-59.

Bergen, A. W. et al., "Effects of DNA mass on multiple displacement whole genome amplification and genotyping performance", BMC Biotechnology, vol. 5, No. 24, Sep. 16, 2005, 11 pgs.

Bermudez, M. et al., "Single-cell sequencing and mini-sequencing for preimplantation genetic diagnosis", Prenatal Diagnosis, 23, 2003, 669-677.

Beroud, C. et al., "Prenatal diagnosis of spinal muscular atrophy by genetic analysis of circulating fetal cells", The Lancet, vol. 361, Mar. 22, 2003, 1013-1014.

Bevinetto, Gina , Bevinetto (5 Foods All Pregnant Women Need, American Baby, available at http://www.parents.com/pregnancy/mybody/nutrition/5greatpregnancyfoods/, Apr. 15, 2008), 8 pgs.

Bianchi, D W. et al., "Fetal gender and aneuploidy detection using fetal cells maternal blood: analysis of NIFTY I data", Prenat Diagn 2002; 22, 2002, 609-615.

Bianchi, D W. et al., "Insights Into Fetal and Neonatal Development Through Analysis of Cell-Free RNA in Body Fluids", Early Human Development, vol. 86, No. 11, Nov. 2010, 747-752.

Bianchi, D. W. , "Circulating Fetal DNA: Its Origin and Diagnostic Potential—A Review", Placenta, vol. 25, Supplemental A, May 2004, S93-S101.

Bianchi, D. W. et al., "Genome-Wide Fetal Aneuploidy Detection by Maternal Plasma DNA Sequencing", Obstetrics & Gynecology, vol. 119, No. 5, May 2012, 890-901.

Bianchi, D. W. , "Review: Fetal Cells in the Maternal Circulation: Feasibility for Prenatal Diagnosis", British Journal of Haematology, vol. 105, 1999, 574-583.

Binladen, J. et al., "The Use of Coded PCR Primers Enables High-Throughput Sequencing of Multiple Homolog Amplification Products by 454 Parallel Sequencing", PLOS One, Issue 2, Feb. 2007, 9 pages.

Birch, Lyndsey et al., "Accurate and Robust Quantification of Circulating Fetal and Total DNA in Maternal Plasma from 5 to 41 Weeks of Gestation", Clinical Chemistry, 51(2), 2005, 312-320.

Birkenkamp-Demtroder, K. et al., "Abstract 3653: Sequencing of plasma cfDNA from patients with locally advanced bladder cancer for surveillance and therapeutic efficacy monitoring", Cancer Research, vol. 78, No. 13 Supplement, Jul. 2019, 1 page.

Bischoff, F. Z. et al., "Cell-free fetal DNA in maternal blood: kinetics, source and structure", Human Reproduction Update, vol. 11, No. 1, 2005, 59-67.

Bischoff, F. Z. et al., "Intact fetal cells in maternal plasma: are they really there?", Lancet, vol. 361, 2003, 139-140.

Bisignano, et al., "PGD and Aneuploidy Screening for 24 Chromosomes: Advantages and Disadvantages of Competing Platforms", Reproductive BioMedicine Online, 23, 2011, 677-685.

Blomquist, T M. et al., "Targeted RNA-Sequencing with Competitive Multiplex-PCR Amplicon Libraries", Plos One, vol. 8, Issue 11, Nov. 2013, 14 pages.

Blow, N. , "The personal side of genomics", Nature, vol. 449, Oct. 4, 2007, 627-630.

Board, R.E. et al., "Detection of BRAF mutations in the tumour and serum of patients enrolled in the AZD6244 (ARRY-142886) advanced melanoma phase II study", British Journal of Cancer, vol. 101, 2009, 1724-1730.

Bodenreider, O. , "The Unified Medical Language System (UMLS): Integrating Biomedical Terminology", Nucleic Acids Research, 32, (Database issue), 2004, D267-D270.

Bordoni, et al., "Evaluation of Human Gene Variant Detection in Amplicon Pools by the GS-FLX Parallel Pyrosequencer", BMC Genomics, vol. 9, Oct. 8, 2008, 1-8.

Boudsocq, F. et al., "Sulfolobus solfataricus P2 DNA polymerase IV (Dpo4): an archael DinB-like DNA polymerase with lesion-bypass properties akin to eukaryotic poln", Nucleic Acids Research, vol. 29, No. 22, 2001, 4607-4616.

Bouma, B. N. et al., "Human Blood Coagulation Factor", The Journal of Biological Chemistry, vol. 252, No. 18, 1977, 6432-6437.

Brastianos, P. K. et al., "Genomic Characterization of Brain Metastases Reveals Branched Evolution and Potential Therapeutic Targets", Cancer Discovery, vol. 5, Sep. 26, 2015, 1164-1177.

Breithaupt, Holger , "The Future of Medicine", EMBO Reports, 21(61), 2001, 465-467.

Brinza, D. et al., "2SNP: scalable phasing based on 2-SNP haplotypes", Bioinformatics, vol. 22, No. 3, 2006, 371-373.

Brockman, et al., "Quality Scores and SNP Detection In Sequencing-by-synthesis Systems", Genome Research, vol. 18, No. 5, May 1, 2008, 763-770.

Broude, N E. et al., "High-Level Multiplex DNA Amplification", Antisense & Nucleic Acid Drug Development, vol. 11, 2001, 327-332.

Broude, N. E. et al., "High Multiplexity PCR Based on PCR Suppression", DNA Amplification Current Technologies and Applications, 2004, 61-76.

Broude, N. E. et al., "Multiplex Allele-specific Target Amplification based on PCR Suppression", PNAS, vol. 98, No. 1, Jan. 2, 2001, 206-211.

Brownie, Jannine et al., "The Elimination of Primer-Dimer Accumulation in PCR", Nucleic Acids Research, 25(16), 1997, 3235-3241.

Browning, S. R. et al., "Rapid and Accurate Haplotype Phasing and Missing-Data Inference for Whole-Genome Association Studies By Use of Localized Haplotype Clustering", The American Journal of Human Genetics, vol. 81, Nov. 2007, 1084-1097.

Bryant, A. P. , "Terminology of Sugars", Ind. Eng. Chem., vol. 26, No. 2, 1933, 231.

Burkey, B. F. et al., "Hepatic apolipoprotein J is secreted as a lipoprotein", Journal of Lipid Research, vol. 33, 1992, 1517-1526.

(56) References Cited

OTHER PUBLICATIONS

Burkova, E. E. et al., "Extremely Stable Soluble High Molecular Mass Multi-Protein Complex with DNase Activity in Human Placental Tissue", PLOS One, vol. 9, No. 11: e011234, Nov. 26, 2014, 26 pages.

Burnham, P. et al., "Myriad Applications of Circulating Cell-Free DNA in Precision Organ Transplant Monitoring", Annals of the American Thoracic Society, vol. 14, Supplement 3, Sep. 2017, S237-S241.

Bustamante-Aragones, Ana et al., "New Strategy for The Prenatal Detection/Exclusion of Paternal Cystic Fibrosis Mutations in Maternal Plasma", Journal of Cystic Fibrosis, vol. 7, Issue 6, Nov. 1, 2008, 505-510.

Butler, et al., "Cardiovascular Magnetic Resonance in the Diagnosis of Acute Heart Transplant Rejection: A Review", Journal of Cardiovascular Magnetic Resonance, vol. 11, No. 1, Mar. 12, 2009, 1-11.

Butler, J. et al., "The Development of Reduced Size STR Amplicons as Tools for Analysis of Degraded DNA*", Journal of Forensic Sciences, vol. 48, No. 5, 2003, 1054-1064.

Butt, A. N. et al., "Overview of Circulating Nucleic Acids in Plasma/Serum: Update on Potential Prognostic and Diagnostic Value in Diseases Excluding Fetal Medicine and Oncology", Ann. N.Y. Acad. Sci., vol. 1137, 2008, 236-242.

Cairns, Paul et al., "Homozygous Deletions of 9p21 in Primary Human Bladder Tumors Detected by Comparative Multiplex Polymerase Chain Reaction", Cancer Research, 54, 1994, 1422-1424.

Caliendo, Angela , "Multiplex PCR and Emerging Technologies for the Detection of Respiratory Pathogens", Clinical Infectious Diseases, 52(4), 2011, S326-S330.

Calin, G. A. et al., "A MicroRNA Signature Associated with Prognosis and Progression in Chronic Lymphocytic Leukemia", N Engl J Med, vol. 353, 2005, 1793-1801.

Campbell, P. J. et al., "Subclonal phylogenetic structures in cancer revealed by ultra-deep sequencing", PNAS, vol. 105, No. 35, Sep. 2, 2008, 13081-13086.

Canick, J. A. et al., "The impact of maternal plasma DNA fetal fraction on next generation sequencing tests for common fetal aneuploidies", Prenatal Diagnosis, vol. 33, 2013, 667-674.

Cansar, , "Hs-578-T—Copy Number Variation—Cell Line Synopsis", ICR Cancer Research UK, Retrieved on Mar. 26, 2018 from https://cansar.icr.ac.uk/cansar/cell-lines/Hs-578-T/copy_number_variation/chromosome_8/, Mar. 26, 2018, 50 pgs.

Cao, Y. et al., "Clinical Evaluation of Branched DNA Signal Amplification for Quantifying HIV Type 1 in Human Plasma", AIDS Research and Human Retroviruses, vol. 11, No. 3, 1995, 353-361.

Carnevale, Alessandra et al., "Attitudes of Mexican Geneticists Towards Prenatal Diagnosis and Selective Abortion", American Journal of Medical Genetics, 75, 1998, 426-431.

Carvalho, B. et al., "Exploration, normalization, and genotype calls of high-density oligonucleotide SNP array data", Biostatistics, vol. 8, No. 2, 2007, 485-499.

Casbon, J. A. et al., "A method for counting PCR template molecules with application to next-generation sequencing", Nucleic Acids Research, vol. 39, No. 12, Apr. 13, 2011, 1-8.

Castleberry, C. D et al., "Quantification of Circulating Cell—Free DNA in Pediatric Heart Transplant Recipients", Journal of Heart and Lung Transplantation, vol. 30, No. 4, Apr. 1, 2011, S139.

Chakraborty, R. et al., "Paternity Exclusion by DNA Markers: Effects of Paternal Mutations", Journal of Forensic Sciences, vol. 41, No. 4, Jul. 1996, 671-677.

Chan, Allen K. et al., "Cell-free Nucleic Acids In Plasma, Serum And Urine: A New Tool in Molecular Diagnosis", Annals of Clinical Biochemistry, vol. 40, Issue 2, Mar. 1, 2003, 122-130.

Chan, K.C. et al., "Size Distributions of Maternal and Fetal DNA in Maternal Plasma", Clinical Chemistry, vol. 50, No. 1, 2004, 88-92.

Chang, H.W. et al., "Assessment of Plasma DNA Levels, Allelic Imbalance, and CA 125 as Diagnostic Tests for Cancer", Journal of the National Cancer Institute, vol. 94, No. 22, Nov. 20, 2002, 1697-1703.

Chavali, Sreenivas et al., "Oligonucleotide Properties Determination and Primer Designing: A Critical Examination of Predictions", Bioinformatics, vol. 21, 2005, pp. 3918-3925.

Chen, E. et al., "Noninvasive Prenatal Diagnosis of Fetal Trisomy 18 and Trisomy 13 by Maternal Plasma DNA Sequencing", PLoS One, 6 (7), e21791, 2011, 7 pgs.

Chen, Bing-Yuan et al., "PCR Cloning Protocols", PCR Cloning Protocols, vol. 192, 2002, 434 pages.

Chen, C. P. et al., "Fetal DNA in maternal plasma: the prenatal detection of a paternally inherited fetal aneuploidy", Prenatal Diagnosis, vol. 20, 2000, 353-357.

Chen, X. Q. et al., "Microsatallite alterations in plasma DNA of small cell lung cancer patients", Nature Medicine, vol. 2, No. 9, Sep. 1996, 1033-1035.

Chetty, Shilpa et al., "Uptake of Noninvasive Prenatal Testing (NIPT) in Women Following Positive Aneuploidy Screening", Prenatal Diagnosis,33, 2013, 542-546.

Cheung, S. W. et al., "Rapid Publication: Microarray-Based CGH Detects Chromosomal Mosaicism Not Revealed by Conventional Cytogenetics", American Journal of Medical Genetics Part A, vol. 143A, 2007, 1679-1686.

Cheung, V. G. et al., "Whole genome amplification using a degenerate oligonucleotide primer allows hundreds of genotypes to be performed on less than one nanogram of genomic DNA", Proceedings of the National Academy of Sciences, USA, vol. 93, Dec. 1996, 14676-14679.

Chim, S. S. et al., "Detection and Characterization of Placental MicroRNAs in Maternal Plasma", Clinical Chemistry, vol. 54, No. 3, 2008, 482-490.

Chinnapapagari, S. K. et al., "Treatment of Maternal Blood Samples with Formaldehyde Does Not Alter the Proportion of Circulatory Fetal Nucleic Acids (DNA and mRNA) in Maternal Plasma", Clinical Chemistry, vol. 51, No. 3, 2005, 653-655.

Chitty, L. S. et al., "Noninvasive Prenatal Screening for Genetic Diseases Using Massively Parallel Sequencing of Maternal Plasma DNA", Cold Spring Harbor Perspectives in Medicine, vol. 5, No. 9, 2015, 20 pages.

Chiu, R. et al., "Non-Invasive Prenatal Assessment of Trisomy 21 by Multiplexed Maternal Plasma DNA Sequencing: Large Scale Validity Study", BMJ, 342, c7401, 2011, 9 pgs.

Chiu, R.W.K. et al., "Hypermethylation of RASSF1A in Human and Rhesus Placentas", The American Journal of Pathology, vol. 170, No. 3, Mar. 2007, 941-950.

Chiu, Rossa W. et al., "Effects of Blood-Processing Protocols on Fetal and Total DNA Quantification in Maternal Plasma", Clinical Chemistry, 47(9), 2001, 1607-1613.

Chiu, Rossa W.K. et al., "Maternal Plasma DNA Analysis with Massively Parallel Sequencing by Litigation for Noninvasive Prenatal Diagnosis of Trisomy 21", Clinical Chemistry, 56, 3, 2010, 459-463.

Chiu, Rossa W.K. et al., "Non-Invasive Prenatal Diagnosis by Single Molecule Counting Technologies", Trends in Genetics, 25 (7), 2009, 324-331.

Chiu, Rossa W.K. et al., "Noninvasive Prenatal Diagnosis of Fetal Chromosomal Aneuploidy by Massively Parallel Genomic Sequencing of DNA in Maternal Plasma (with Supporting Information)", PNAS, vol. 105, No. 51, 2008, 20458-20463.

Choi, M. et al., "Genetic diagnosis by whole exome capture and massively parallel DNA sequencing", PNAS, vol. 106, No. 45, Nov. 10, 2009, 19096-19101.

Choi, Y. et al., "Comparison of phasing strategies for whole human genomes", PLOS Genetics, Apr. 5, 2018, 26 pages.

Chu, T. et al., "Statistical Considerations for Digital Approaches to Non-Invasive Fetal Genotyping", Bioinformatics (Advance Access publication), 26 (22), 2010, 2863-2866.

Chu, Tianjiao et al., "Statistical Model for Whole Genome Sequencing and its Application to Minimally Invasive Diagnosis of Fetal Genetic Disease", Bioinformatics, 25(10), 2009, 1244-1250.

(56) References Cited

OTHER PUBLICATIONS

Chu, Tianjiao et al., "A Novel Approach Toward the Challenge of Accurately Quantifying Fetal DNA in Maternal Plasma", Prenatal Diagnosis,30, 2010, 1226-1229.

Chung, G. T. et al., "Lack of Dramatic Enrichment of Fetal DNA in Maternal Plasma by Formaldehyde Treatment", Clinical Chemistry, vol. 51, No. 3, 2005, 655-658.

Church, et al., "Multiplex DNA Sequencing", Science, vol. 240, No. 4849, Apr. 8, 1988, 185-188.

Ciriello, G. et al., "Emerging landscape of oncogenic signatures across human cancers", Nature Genetics, vol. 45, No. 10, Oct. 2013, 1127-1135.

Clausen, F. B. et al., "Improvement in fetal DNA extraction from maternal plasma. Evaluation of the NucliSens Magnetic Extraction system and the QIAamp DSP Virus Kit in comparison with the QIAamp DNA Blood Mini Kit", Prenatal Diagnosis, vol. 27, 2007, 6-10.

Cole, Neal W. et al., "Hyperglycemia-Induced Membrane Lipid Peroxidation and Elevated Homocysteine Levels Are Poorly Attenuated by Exogenous Folate in Embryonic Chick Brains", Comparative Biochemistry and Physiology, Part B, 150, 2008, 338-343.

Colella, S. et al., "QuantiSNP: an Objectives Bayes Hidden-Markov Model to Detect and Accurately Map Copy Number Variation Using SNP Genotyping Data", Nucleic Acids Research, 35 (6), 2007, 2013-2025.

Conlin, L. K. et al., "Mechanisms of mosaicism, chimerism and uniparental disomy identified by single nucleotide polymorphism array analysis", Human Molecular Genetics, vol. 19, No. 7, Jan. 6, 2010, 1263-1275.

Coombes, R. C. , "Abstract P4-01-02: Early detection of residual breast cancer through a robust, scalable and personalized analysis of circulating tumour DNA (ctDNA) antedates overt metastatic recurrence", Cancer Research, vol. 79, No. 4 Supplement, Feb. 15, 2019.

Cossu, Gianfranco et al., "Rh D/d Genotyping by Quantitative Polymerase Chain Reaction and Capillary Zone Electrophoresis", Electrophoresis, 17, 1996, 1911-1915.

Couraud, S. et al., "Noninvasive Diagnosis of Actionable Mutations by Deep Sequencing of Circulating Free DNA in lung Cancer from Never-Smokers: A Proof-of-Concept Study from BioCAST / IFCT-1002", Clinical Cancer Research, vol. 20, No. 17, Jul. 10, 2014, 4613-4624.

Couraud, S. et al., "Supplementary Data for Noninvasive Diagnosis of Actionable Mutations by Deep Sequencing of Circulating Free DNA in lung Cancer from Never-Smokers: A Proof-of-Concept Study from BioCAST / IFCT-1002", 2014, 13 pages.

Coyle, J. F. et al., "Standards for detailed clinical models as the basis for medical data exchange and decision support", International Journal of Medical Informatics, 69(2-3), 2003, 157-174.

Craig, D. W. et al., "Identification of genetic variants using barcoded multiplexed sequencing", Nature Methods, vol. 5, Oct. 2008, 887-893.

Crespo-Leiro, et al., "Gene Expression Profiling for Monitoring Graft Rejection in Heart Transplant Recipients", Transplantation Proceedings, vol. 41, No. 6, Jul. 1, 2009, 2240-2243.

Cronn, R. et al., "Multiplex sequencing of plant chloroplast genomes using Solexa sequencing-by-synthesis technology", Nucleic Acids Research, vol. 36, No. 19, Aug. 27, 2008, 11 pgs.

Cross, Jillian et al., "Resolution of trisomic mosaicism in prenatal diagnosis: estimated performance of a 50K SNP microarray", Prenat Diagn 2007; 27, 2007, 1197-1204.

Cunningham, K. S. et al., "An approach to endomyocardial biopsy interpretation", Journal of Clinical Pathology, vol. 59, No. 2, Mar. 2006, 121-129.

Dahl, et al., "Multigene Amplification and Massively Parallel Sequencing for Cancer Mutation Discovery", Proceedings of the National Academy of Sciences, vol. 104, No. 22, May 29, 2007, 9387-9392.

Dambrin, et al., "A New Rejection Criteria in the Heterotopically Placed Rat Heart by Non-invasive Measurement of Dp/Dtmax", The Journal of Heart and Lung Transplantation, vol. 18, No. 6, Jun. 18, 1999, 524-531.

D'Aquila, Richard et al., "Maximizing sensitivity and specificity of PCR by pre-amplification heating", Nucleic Acids Research, 19(13), 1991, p. 3749.

Daruwala, Raoul-Sam et al., "A Versatile Statistical Analysis Algorithm to Detect Genome Copy Number Variation", PNAS, 101(46), 2004, 16292-16297.

Dawson, S.J. et al., "Analysis of Circulating Tumor DNA to Monitor Metastatic Breast Cancer", The New England Journal of Medicine, vol. 368, No. 13, Mar. 28, 2013, 1199-1209.

De Bruin, E. et al., "Spatial and temporal diversity in genomic instability processes defines lung cancer evolution", Science, vol. 346, No. 6206, Oct. 10, 2014, 251-256.

De Jong, M. M. et al., "Genes other than BRCA 1 and BRCA2 involved in breast cancer susceptibility", J. Med. Genet., vol. 39, 2009, 225-242.

De Vries, et al., "Diagnostic genome profiling in mental retardation", Am J Hum Genet, 77, published online Aug. 30, 2005, 2005, 606-616.

Deangelis, M. et al., "Solid-phase Reversible Immobilization for the Isolation of PCR Products", Nucleic Acids Research, 23 (22), 1995, 4742-4743.

Deb, Mahua et al., "Development of a Multiplexed PCR Detection Method for Barley and Cereal Yellow Dwarf Viruses, Wheat Spindle Streak Virus, Wheat Streak Mosaic Virus and Soil-Borne Wheat Mosaic Virus", Journal of Virological Methods, vol. 148, 2008, pp. 17-24.

Delaneau, O. et al., "Shape-IT: new rapid and accurate algorithm for haplotype inference", BMC Bioinformatics, vol. 9, No. 540, Dec. 16, 2008, 14 pages.

Delgado, P. O. et al., "Characterization of cell-free circulating DNA in plasma in patients with prostate cancer", Tumor Biol., vol. 34, 983-986, 2013.

Deng, S. et al., "TNER: A Novel Background Error Suppression Method for Mutation Detection in Circulating Tumor DNA", bioRxiv, http://dx.doi.org/10.1101/214379, Nov. 5, 2017, 12 pgs.

Deutsch, S. et al., "Detection of aneuploidies by paralogous sequence quantification", J Med Genet, vol. 41, 2004, 908-915.

Devaney, S. et al., "Noninvasive Fetal Sex Determination Using Cell-Free Fetal DNA: A Systematic Review and Meta-analysis", JAMA, 306(6), 2011, 627-636.

Dhallan, et al., "Methods to Increase the Percentage of Free Fetal DNA Recovered from the Maternal Circulation", JAMA, 291(9), 2004, 1114-1119.

Dhallan, Ravinder et al., "A non-invasive test for prenatal diagnosis based on fetal DNA present in maternal blood: a preliminary study", The Lancet, 369, 2007, 474-481.

Di, X. et al., "Dynamic model based algorithms for screening and genotyping", Bioinformatics, vol. 21, No. 9, 2005, 1958-1963.

Dias-Santagata, D. et al., "BRAF V600E Mutations Are Common in Pleomorphic Xanthoastrocytoma: Diagnostic and Therapeutic Implications", PLoS One, vol. 6, No. 3, Mar. 2011, 9 pages.

Dickover, R. E. et al., "Optimization of Specimen-Handling Procedures for Accurate Quantitation of Levels of Human Immunodeficiency Virus RNA in Plasma by Reverse Transcriptase PCR", Journal of Clinical Microbiology, vol. 36, No. 4, 1998, 1070-1073.

Dieffenbach, C W. et al., "General concepts for PCR primer design", Genome Research. PCR methods and Applications vol. 3, 1993, S30-S37.

Diehl, F. et al., "Circulating mutant DNA to assess tumor dynamics", Nature Medicine, vol. 14, No. 9, Jul. 31, 2008, 985-990.

Diehl, F. et al., "Detection and quantification of mutations in the plasma of patients with colorectal tumors", PNAS, vol. 102, No. 45, Nov. 8, 2005, 16368-16373.

Dietmaier, W. et al., "Multiple Mutation Analyses in Single Tumor Cells with Improved Whole Genome Amplification", American Journal of Pathology, vol. 154, No. 1, Jan. 1999, 83-95.

Ding, C et al., "Direct molecular haplotyping of long-range genomic DNA with M1-PCR", PNAS 100(13), 2003, 7449-7453.

Ding, C. et al., "MS analysis of single-nucleotide differences in circulating nucleic acids: Application to noninvasive prenatal diagnosis", PNAS, vol. 101, No. 29, Jul. 20, 2004, 10762-10767.

Dodge, Y. , "Bayes' Theorem", The Concise Encyclopedia of Statistics, 2008, 30-31.

(56)         References Cited

OTHER PUBLICATIONS

Dohm, J. et al., "Substantial Biases in Ultra-Short Read Data Sets From High-Throughput DNA Sequencing", Nucleic Acids Research, 36 (16), e105, 2008, 10 pgs.

Dolganov, Gregory et al., "A Novel Method of Gene Transcript Profiling in Airway Biopsy Homogenates Reveals Increased Expression of a Na—K+—Cl-Cotransporter (NKCC1) in Asthmatic Subjects", Genome Res., 11, 2001, 1473-1483.

Donaghue, C. et al., "Detection of mosaicism for primary trisomies in prenatal samples by QF-PCR and karyotype analysis", Prenatal Diagnosis, vol. 25, 2005, 65-72.

Donohoe, Gerard G et al., "Rapid Single-Tube Screening of the C282Y Hemochromatosis Mutation by Real-Time Multiplex Allele-specific PCR without Fluorescent Probes", Clinical Chemistry, 46, 10, 2000, 1540-1547.

Donoso, P. et al., "Current Value of Preimplantation Genetic Aneuploidy Screening in IVF", Human Reproduction Update, 13(1), 2007, 15-25.

Doostzadeh, et al., "High Throughput Automated Allele Frequency Estimation by Pyrosequencing", PLoS One, vol. 3, No. 7, Jul. 16, 2008, 1-4.

Dorit, D. L. , "cDNA Amplification Using One-sided (Anchored) Pcr", Current Protocols in Molecular Biology, vol. 17, 1992, pp. 15.6.1-15.6.10.

Dorit, Robert L. et al., "One-sided Anchored Polymerase Chain Reaction for Amplification and Sequencing of Complementary DNA", Methods in Enzymology, vol. 218 1993, pp. 36-47.

Dowd, P. et al., "On the mechanism of the anticlotting action of vitamin R quinone", Proc. Natl. Acad. Sci. USA, vol. 92, 1995, 8171-8175.

Downward, J. , "Targeting Ras Signalling Pathways in Cancer Therapy", Nature Reviews, vol. 3, Jan. 2003, 11-22.

Dressman, D. et al., "Transforming single DNA molecules into fluorescent magnetic particles for detection and enumeration of genetic variations", PNAS, vol. 100, No. 15, Jul. 22, 2003, 8817-8822.

Echeverri, et al., "Caffeine's Vascular Mechanisms of Action", International Journal of Vascular Medicine vol. 2010(2010), 10 pages, Aug. 25, 2010.

Edwards, M. C. et al., "Multiplex PCR: Advantages, Development, and Applications", Genome Research, vol. 3, 1994, S65-S75.

Efron, B. et al., "Bootstrap Methods for Standard Errors, Confidence Intervals, and Other Measures of Statistical Accuracy", Statistical Science, vol. 1, No. 1, 1986, 54-77.

Ehrich, Mathias et al., "Noninvasive Detection of Fetal Trisomy 21 by Sequencing of DNA in Maternal Blood: A Study in a Clinical Setting", American Journal of Obstetrics & Gynecology, 204, 2011, 205.e1-205.e11.

Eichler, H , "Mild Course of Fetal Rh D Haemolytic Disease due to Maternal Alloimmunisation to Paternal HLA Class I and II Antigens", Vox Sang, 68, 1995, 243-247.

Ellison, Aaron M. , "Bayesian Inference in Ecology", Ecology Letters, vol. 7, 2004, 509-520.

Ellonen, P. et al., "Development of SNP Microarray for Supplementary Paternity Testing", International Congress Series, 1261, 2004, 12-14.

Elnifro, Elfath M. "Multiplex PCR: Optimization and Application in Diagnostic Virology", Clinical Microbiology Reviews, vol. 13, 2000, pp. 559-570.

Eltoukhy, H. et al., "Modeling and Base-Calling for DNA Sequencing-by-Synthesis", IEEE, 2006, II-1032-II-1035.

EP06838311.6, "European Communication and Extended European Search Report", mailed Dec. 30, 2008, 8 pgs.

EP08742125.1, "European Communication pursuant to Article 94(3) EPC and Examination Report", mailed Feb. 12, 2010, 5 pgs.

Erijman, Ariel et al., "Transfer-PCR (TPCR): A Highway for DNA Cloning and Protein Engineering", Journal of Structural Biology, vol. 175, 2011, pp. 171-177.

Erlich, R. L. et al., "Next-generation sequencing for HLA typing of class II loci", BMC Genomics, vol. 12, No. 42, 2011, 13 pages.

Eronen, L. et al., "HaploRec: efficient and accurate large-scale reconstruction of haplotypes", BMC Bioinformatics, vol. 7, No. 542, Dec. 22, 2006, 18 pages.

European Commission, "The 7th International Conference on Circulating Nucleic Acids in Plasma and Serum (CNAPS VII) in Madrid—Spain", The International Conference on Circulating Nucleic Acids in Plasma and Serum, Oct. 24, 2011, 2 pgs.

Everitt, B. S. , "Medical Statistics From A to Z", 2003, 3 pages.

Fackenthal, J. D. et al., "Aberrant RNA splicing and its functional consequences in cancer cells", Disease Models & Mechanisms, vol. 1, 2008, 37-42.

Faham, M. et al., "Deep-sequencing approach for minimal residual disease detection in acute lymphoblastic leukemia", Blood Journal, vol. 120, No. 26, Dec. 20, 2012, 5173-5180.

Falcon, O. , "Screening for trisomy 21 by fetal tricuspid regurgitation, nuchal translucency and maternal serum free b-hCG and PAPP-A at 11+0 to 13+6 weeks", Ultrasound Obstet Gynecol, vol. 27, 2006, 151-155.

Fan, et al., "Whole-genome molecular haplotyping of single cells", Nature Biotechnology, vol. 29, No. 1, Jan. 1, 2011, 51-57.

Fan, C H. et al., "Detection of Aneuploidy with Digital Polymerase Chain Reaction", Analytical Chemistry, vol. 79, No. 19, Oct. 1, 2007, 7576-7579.

Fan, Christina H. et al., "Non-Invasive Prenatal Measurement of the Fetal Genome", Nature, doi:10.1038/nature11251, 2012, 26 pgs.

Fan, Christina H. et al., "Noninvasive Diagnosis of Fetal Aneuploidy by Shotgun Sequencing DNA from Maternal Blood", PNAS, 105, 42, 2008, 16266-16271.

Fan, H. C. et al., "In Principle Method for Noninvasive Determination of the Fetal Genome", Nat. Prec., 2010, 16 pgs.

Fan, H. C. et al., "Microfluidic digital PCR enables rapid prenatal diagnosis of fetal aneuploidy", American Journal of Obstetrics & Gynecology, vol. 200, May 2009, 543.e1-543.e7.

Fan, H. Christina et al., "Sensitivity of Noninvasive Prenatal Detection of Fetal Aneuploidy from Maternal Plasma Using Shotgun Sequencing Is Limited Only by Counting Statistics", PLoS One, vol. 5, Issue 5 (e10439), May 3, 2010, 1-6.

Fan, J.-B. et al., "Highly Parallel SNP Genotyping", Cold Spring Harbor Symposia on Quantitative Biology, vol. LXVIII, Feb. 2003, 69-78.

Fan, Jian-Bing et al., "Highly Parallel Genomic Assay", Nature Reviews, 7, 2006, 632-644.

Fat Secret, "5 Foods to Never Eat", https://www.fatsecret.com/calories-nutrition/food/white-bread/carboyhydrate (printed from internet Nov. 1, 14)., 2 pages.

Fazio, Gennaro et al., "Identification of RAPD Markers Linked to Fusarium Crown and Root Rot Resistance (Frl) in Tomato", Euphytica 105, 1999, 205-210.

Fiorentino, F. et al., "Development and Clinical Application of a Strategy for Preimplantation Genetic Diagnosis of Single Gene Disorders Combined with HLA Matching", Molecular Human Reproduction (Advance Access publication), 10 (6), 2004, 445-460.

Fiorentino, F et al., "Strategies and Clinical Outcome of 250 Cycles of Preimplantation Genetic Diagnosis for Single Gene Disorders", Human Reproduction, 21, 3, 2006, 670-684.

Fiorentino, Francesco et al., "Short Tandem Repeats Haplotyping of the HLA Region in Preimplantation HLA Matching", European Journal of Human Genetics, 13, 2005, 953-958.

Fitzgerald, , "Intravascular Ultrasound Imaging of Coronary Arteries: Is Three Layers the Norm?", Circulation, vol. 86, No. 1, Jul. 1, 1992, 154-158.

Ford, E. et al., "A method for generating highly multiplexed ChIP-seq libraries", BMC Research Notes, vol. 7, No. 312, May 22, 2014, 1-5.

Forejt, et al., "Segmental trisomy of mouse chromosome 17: introducing an alternative model of Down's syndrome", Genomics, 4(6), 2003, 647-652.

Forshew, et al., "Noninvasive Identification and Monitoring of Cancer Mutations by Targeted Deep Sequencing of Plasma DNA", Noninvasive identification and monitoring of cancer mutations by targeted deep sequencing of plasma DNA. Sci. Transl. Med. 4, 136 30 (2012)., 1-12.

(56) References Cited

OTHER PUBLICATIONS

Forshew, T. et al., "Supplementary Materials for Noninvasive Identification and Monitoring of Cancer Mutations by Targeted Deep Sequencing of Plasma DNA", Sci. Transl. Med, vol. 4, May 30, 2012, 20 pgs.

Fortina, P. et al., "Detection of the most common mutations causing beta-thalassemia in Mediterraneans using a multiplex amplification refractory mutation system (MARMS)", Genome Res., vol. 2, 1992, 163-166.

Fortina, P. et al., "DOP-PCR Amplification of Whole Genomic DNA and Microchip-Based Capillary Electrophoresis", Methods in Molecular Biology: Capillary Electrophoresis of Nucleic Acids, vol. II Practical Applications of Capillary Electrophoresis, 2001, 211-219.

Fouquet, C. et al., "Rapid and Sensitive p53 Alteration Analysis in Biopsies from Lung Cancer Patients Using a Functional Assay and A Universal Oligonudeotide Array: A Prospective Study", Clinical Cancer Research, vol. 10, May 15, 2004, 3479-3489.

Fournie, et al., "Plasma DNA as a Marker of Cancerous Cell Death. Investigations in Patients Suffering From Lung Cancer and in Nude Mice Bearing Human Tumours", Cancer Letters, vol. 91, No. 2, May 8, 1995, 221-227.

Fredriksson, et al., "Multiplex amplification of all coding sequences within 10 cancer genes by Gene-Collector", Nucleic Acids Research, 2007, vol. 35, No. 7 e47, 1-6.

Fredriksson, M. et al., "Assessing Hematopoietic Chimerism After Allogeneic Stem Cell Transplantation by Multiplexed SNP Genotyping Using Microarrays and Quantitive Analysis of SNP Alleles", Leukemia, vol. 18, Issue 2, Dec. 4, 2003, 255-266.

Freeman, Jennifer L. et al., "Copy Numer Variation: New Insights in Genome Diversity", Genome Research, 16, 2006, 949-961.

Frohman, M A. et al., "On Beyond Classic RACE (Rapid Amplification of cDNA Ends)", Genome Research, vol. 4, 1994, S40-S58.

Frost, Mackenzie S et al., "Differential Effects of Chronic Pulsatile Versus Chronic Constant Maternal Hyperglycemia on Fetal Pancreatic B- Cells", Journal of Pregnancy, 2012,, Article ID 812094, 2012, 8.

Fu, G. K. et al., "Counting individual DNA molecules by the stochastic attachment of diverse labels", PNAS, vol. 108, No. 22, May 31, 2011, 9026-9031.

Fu, G. K. et al., "Digital Encoding of Cellular mRNAs Enabling Precise and Absolute Gene Expression Measurement by Single-Molecule Counting", Analytical Chemistry, vol. 86, Mar. 3, 2014, 2867-2870.

Fu, Yao-Wen et al., "Presence of Donor-and-recipientderived Dna Microchimerism in the Cell-free Blood Samples of Renal Transplantation Recipients Associates With the Acceptance of Transplanted Kidneys", Asian Journal of Andrology, vol. 8, No. 4, Jul. 1, 2006, 477-482.

Gadi, V. K. et al., "Soluble Donor DNA Concentrations in Recipient Serum Correlate with Pancreas-Kidney Rejection", Clinical Chemistry, vol. 52, No. 3, 2006, 379-382.

Ganshirt-Ahlert, D. et al., "Ratio of Fetal to Maternal DNA is Less Than 1 in 5000 at different Gestational Ages in Maternal Blood", Clinical Genetics, 38, 1990, 38-43.

Ganshirt-Ahlert, D. et al., "Fetal DNA in Uterine Vein Blood", Obstetrics & Gynecology, 80 (4), 1992, 601-603.

Ganshirt-Ahlert, Dorothee et al., "Three Cases of 45,X/46,XYnf Mosaicism", Human Genetics, 76, 1987, 153-156.

Gao, et al., "Relation of Donor Age and Preexisting Coronary Artery Disease on Angiography and Intracoronary Ultrasound to Later Development of Accelerated Allograft Coronary Artery Disease", The American Journal of Cardiology, vol. 29, No. 3, Mar. 1, 1997, 623-629.

Gao, F. et al., "Characterizing Immunoglobulin Repertoire from Whole Blood by a Personal Genome Sequencer", PLOS One, vol. 8, No. 9, Sep. 13, 2013, 8 pgs.

Gao, Ming et al., "Characterization of dull1, a Maize Gene Coding for a Novel Starch Synthase", The Plant Cell, vol. 10, 1998, pp. 399-412.

Garcia Moreira, V. et al., "Cell-Free DNA as a Noninvasive Acute Rejection Marker in Renal Transplantation", Clinical Chemistry, vol. 55, No. 11, 2009, 1958-1966.

Garcia-Murillas, I. et al., "Mutation tracking in circulating tumor DNA predicts relapse in early breast cancer", Science Translational Medicine, vol. 7, No. 302, Aug. 26, 2015, 34 pgs.

Gardina, P. et al., "Ploidy Status and Copy Number Aberrations in Primary Glioblastomas Defined by Integrated Analysis of Allelic Ratios, Signal Ratios and Loss of Heterozygosity Using 500K Snp Mapping Arrays", BMC Genomics, 9 (489), (doi: 10.1186/1471-2164-9-489), 2008, 16 pgs.

Gautier, E. et al., "Fetal RhD genotyping by maternal serum analysis: A two-year experience", American Journal of Obstetrics and Gynecology, vol. 192, 2005, 666-669.

Geifman-Holtzman, et al., "Prenatal Diagnosis: Update on Invasive Versus Noninvasive Fetal Diagnostic Testing From Maternal Blood", Expert Review of Molecular Diagnostics, vol. 8, No. 6, Nov. 1, 2008, 727-751.

Geiss, G. K. et al., "Direct multiplexed measurement of gene expression with color-coded probe pairs", Nature Biotechnology, vol. 26, No. 3, Feb. 17, 2008, 317-325.

Ghanta, Sujana et al., "Non-Invasive Prenatal Detection of Trisomy 21 Using Tandem Single Nucleotide Polymorphisms", PLoS One, 5 (10), 2010, 10 pgs.

Gholami, M. et al., "A tailed PCR procedure for cost-effective, two-order multiplex sequencing of candidate genes in polyploid plants", Plant Biotechnology Journal, vol. 10, 2012, 635-645.

Gielis, E. M. et al., "Cell-Free DNA: An Upcoming Biomarker in Transplantation", American Journal of Transplantation, vol. 15, 2015, 2541-2551.

Gielis, E. M. et al., "Plasma donor-derived cell-free DNA kinetics after kidney transplantation using a single tube multiplex PCR assay", PLOS One, vol. 13, No. 12, e0208207, Dec. 6, 2018, 16 pgs.

Gineikiene, Egle et al., "Single Nucleotide Polymorphism-based System Improves the Applicability of Quantitative PCR for Chimerism Monitoring", Journal of Molecular Diagnostics, vol. 11, No. 1, Jan. 1, 2009, 66-74.

Gingeras, et al., "Fifty Years of Molecular (DNA/RNA) Diagnostics", Clinical Chemistry, vol. 51, No. 3, Jan. 13, 2005, 661-671.

Girnita, Diana M. et al., "Disparate Distribution of 16 Candidate Single Nucleotide Polymorphisms Among Racial and Ethnic Groups of Pediatric Heart Transplant Patients", Transplantation, vol. 82, No. 12, Dec. 27, 2006, 1774-1780.

Gjertson, David W. et al., "Assessing Probability of Paternity and the Product Rule in DNA Systems", Genetica, 96, 1995, 89-98.

Gnirke, A. et al., "Solution hybrid selection with ultra-long oligo-nucleotides for massively parallel targeted sequencing", Nature Biotechnology, vol. 27, No. 2, Feb. 2009, 182-189.

Go, A. T. et al., "Non-invasive aneuploidy detection using free fetal DNA and RNA in maternal plasma: recent progress and future possibilities", Human Reproduction Update, vol. 17, No. 3, 2011, 372-382.

Goncalves-Primo, A. et al., "Investigation of Apoptosis-Related Gene Expression Levels in Preimplantation Biopsies as Predictors of Delayed Kidney Graft Function", Transplantation, vol. 97, No. 12, Jun. 27, 2014.

Gordon, et al., "Disease-Specific Motifs Can Be Identified in Circulating Nucleic Acids From Live Elk and Cattle Infected With Transmissible Spongiform Encephalopathies", Nucleic Acids Research, vol. 37. No. 2, Feb. 1, 2009, 550-556.

Gorringe, et al., "Large-scale Genomic Analysis of Ovarian Carcinomas", Molecular oncology, vol. 3, No. 2, Apr. 1, 2009, 157-164.

Gouya, et al., "Coronary Artery Stenosis In High-risk Patients: 64-section Ct and Coronary Angiography-Prospective Study and Analysis of Discordance", Radiology, vol. 252, No. 2, Aug. 1, 2009, 377-385.

Greenwalt, T. et al., "The Quantification of Fetomaternal Hemorrhage by an Enzyme-Linked Antibody Test with Glutaraldehyde Fixation", Vox Sang, 63, 1992, 268-271.

Gregory, et al., "Comparison of Sixty-Four-Slice Multidetector Computed Tomographic Coronary Sngiography to Coronary Angiography With Intravascular Ultrasound for the Detection of

(56) References Cited

OTHER PUBLICATIONS

Transplant Vasculopathy", The American Journal of Cardiology, vol. 98, No. 7, Aug. 4, 2006, 877-884.

Griffiths, A. J. et al., "An Introduction to Genetic Analysis", Sixth Edition, 1996, 5 pages.

Grskovic, M. et al., "Validation of a Clinical-Grade Assay to Measure Donor-Derived Cell-Free DNA in Solid Organ Transplant Recipients", The Journal of Molecular Diagnostics, vol. 18, No. 6 + Supplemental Appendix S1, Nov. 2016, 890-902.

Grunenwald, H. , "Optimization of Polymerase Chain Reactions", Methods in Biology, vol. 226, 2003, 89-99.

Gu, H. et al., "Diagnostic role of microRNA expression profile in the serum of pregnant women with fetuses with neural tube defects", Journal of Neurochemistry, vol. 122, 2012, 641-649.

Guerra, J., "Terminal Contributions for Duplex Oligonucleotide Thermodynamic Properties in the Context of Nearest Neighbor Models", Biopolymers, 95(3), (2010), 2011, 194-201.

Guetta, Esther et al., "Analysis of Fetal Blood Cells in the Maternal Circulation: Challenges, Ongoing Efforts, and Potential Solutions", Stem Cells and Development, 13, 2004, 93-99.

Guichoux, et al., "Current Trends in Microsatellite Genotyping", Molecular Ecology Resources, 11, 2011, 591-911.

Gunderson, K. L. et al., "A genome-wide scalable SNP genotyping assay using microarray technology", Nature Genetics, vol. 37, No. 5, May 2005, 549-554.

Gundry, C. N. et al., "Base-pair neutral homozygotes can be discriminated by calibrated high-resolution melting of small amplicons", Nucleic Acids Research, vol. 36, No. 10, Apr. 29, 2008, 3401-3408.

Guo, H et al., "A Specific and Versatile Genome Walking Technique", Gene, vol. 381, 2006, 18-23.

Gwee, Pai-Chung et al., "Simultaneous Genotyping of Seven Single-nucleotide Polymorphisms in the Mdr1 Gene by Single-tube Multiplex Minisequencing", Pai-Chung Gwee. et al., "Simultaneous Genotyping of Seven Single-nucleotide Polymorphisms in the Mdr1 Gene by Single-tube Multiplex Minisequencing", Clinical chemistry, Apr. 2003, vol. 49, Issue. 3, pp. 672-676., Apr. 1, 2003, 672-676.

Hahn, et al., "Non-invasive Prenatal Diagnostics Using Next Generation Sequencing: Technical, Legal And Social Challenges", Expert Opinion on Medical Diagnostics, vol. 6, No. 6, Nov. 1, 2012, 517-528.

Hahn, S. et al., "Current applications of single-cell PCR", CMLS Cellular and Molecular. Life Sciences, vol. 57, 2000, 96-105.

Hahn, S. et al., "Quantification of Circulating DNA: In the Preparation Lies the Rub", Clinical Chemistry, vol. 47, No. 9, 2001, 1577-1578.

Halford, William P. , "The Essential Prerequisites for Quantitative RT-PCR", Nature Biotechnology, vol. 17, 1999, 1 page.

Hall, M., "Panorama Non-Invasive Prenatal Screening for Microdeletion Syndromes", Apr. 1, 2014 (Apr. 1, 2014), XP055157224, Retrieved from the Internet.

URL:http://www.panoramatest.com/sites/default/files/files/PanoramaMicrodeletionsWhite Paper-2.pdf [retrieved on Dec. 8, 2014].

Han, S-W et al., "Predictive and Prognostic Impact of Epidermal Growth Factor Receptor Mutation in Non-Small-Cell Lung Cancer Patients Treated With Gefitinib", Journal of Clinical Oncology, vol. 23, No. 11, Apr. 10, 2005, 2493-2501.

Handley, D. et al., "Noninvasive prenatal chromosomal aneuploidy detection using plasma cell-free nucleic acid", Expert Rev Obstet. Gynecol, vol. 5, No. 5, 2010, 581-590.

Handyside, et al., "Isothermal whole genome amplification from single and small numbers of cells: a new era for preimplantation genetic diagnosis of inherited disease", Molecular Human Reproduction vol. IO, No. 10 pp. 767-772, 2004.

Hao, T. B. et al., "Circulating cell-free DNA in serum as a biomarker for diagnosis and prognostic prediction of colorectal cancer", British Journal of Cancer, vol. 111, Aug. 26, 2014, 1482-1489.

Hara, Eiji et al., "Subtractive eDNA cloning using oligo(dT)3o-latex and PCR: isolation of eDNA clones specific to undifferentiated human embryonal carcinoma cells", Nucleic Acids Research, 19(25), 1991, 7097-7104.

Hardenbol, P. , "Multiplexed Genotyping With Sequence-Tagged Molecular Inversion Probes", Nature Biotechnology, 21 (6), 2003, 673-678.

Hardenbol, Paul et al., "Highly multiplexed molecular inversion probe genotyping: Over 10,000 targeted SNPs genotyped in a singled tube assay", Genome Research, 15, 2005, 269-275.

Harismendy, O. et al., "Method for Improving Sequence Coverage Uniformity of Targeted Genomic Intervals Amplified by LR-PCR Using Illumina GA Sequencing-by-Synthesis Technology", Bio Techniques, 46(3), 2009, 229-231.

Harper, J. C. et al., "Recent Advances and Future Developments in PGD", Prenatal Diagnosis, 19, 1999, 1193-1199.

Harton, G.L. et al., "Preimplantation Genetic Testing for Marfan Syndrome", Molecular Human Reproduction, 2 (9), 1996, 713-715.

Hartwell, L. H. et al., "Chapter 11: The Direct Detection of Genotype Distinguishes Individual Genomes", Genetics: From Genes to Genomes, Second Edition, 2004, 371-414.

Hartwell, L. H. et al., "Chapter 13: Chromosomal Rearrangements and Changes in Chromosome Number Reshape Eukaryotic Genomes", Genetics: From Genes to Genomes, Second Edition, 2004, 441-486.

Hattori, M. et al., "The DNA sequence of human chromosome 21", Nature, vol. 405, May 18, 2000, 311-319.

Hawkins, T. et al., "Whole genome amplification—applications and advances", Current Opinion in Biotechnology, 13, 2002, 65-67.

Hayden, et al., "Multiplex-Ready PCR: A new method for multiplexed SSR and SNP genotyping", BMC Genomics 2008, 9(80), 1-12.

He, QZ et al., "A method for improving the accuracy of non-invasive prenatal screening by cell-free foetal DNA size selection", British Journal of Biomedical science, vol. 75, No. 3, Jul. 2018, 133-138.

Heaton, Paul R. et al., "Heminested PCR Assay for Detection of Six Genotypes of Rabies and Rabies-related Viruses", Journal of Clinical Microbiology, vol. 35, 1997, pp. 2762-2766.

Heidary, M. et al., "The dynamic range of circulating tumor DNA in metastatic breast cancer", Breast Cancer Research, vol. 16, No. 421, 2014, 10 pages.

Hellani, A. et al., "Clinical Application of Multiple Displacement Amplification in Preimplantation Genetic Diagnosis", Reproductive BioMedicine Online, 10 (3), 2005, 376-380.

Hellani, Ali et al., "Multiple displacement amplification on single cell and possible PGD applications", Molecular Human Reproduction, 10(11), 2004, 847-852.

Henegariu, O. et al., "Multiplex PCR: Critical Parameters and Step-by-Step Protocol", Biotechniques, vol. 23, 1997, pp. 504-511.

Hidestrand, M. et al., "Highly Sensitive Noninvasive Cardiac Transplant Rejection Monitoring Using Targeted Quantification of Donor-Specific Cell-Free Deoxyribonucleic Acid", Journal of the American College of Cardiology, vol. 63, No. 12, 1224-1226, 2014.

Hoberman, Rose et al., "A Probabilistic Approach for SNP Discovery in High-throughput Human Resequencing Data", Genome Research, vol. 19, Jul. 15, 2009, 1542-1552.

Hochberg, et al., "A Novel Rapid Single Nucleotide Polymorphism (SNP)-Based Method for Assessment of Hematopoietic Chimerism After Allogeneic Stem Cell Transplantation", Blood, vol. 101, No. 1, Jan. 1, 2003, 363-369.

Hodges, et al., "Genome-wide In Situ Exon Capture for Selective Resequencing", Nature Genetics, vol. 39, No. 12, Nov. 4, 2007, 1522-1527.

Hodgkinson, C. L. et al., "Tumorigenicity and genetic profiling of circulating tumor cells in small-cell lung cancer", Nature Medicine, vol. 20, No. 8, Aug. 2014, 897-905.

Hoffmann, Steven et al., "Donor Genomics Influence Graft Events: The Effect of Donor Polymorphisms on Acute Rejection and Chronic Allograft Nephropathy", Kidney International, vol. 66, No. 4, Oct. 1, 2004, 1686-1693.

Hojsgaard, S. et al., "BIFROST—Block recursive models induced from relevant knowledge, observations, and statistical techniques", Computational Statistics & Data Analysis, 19(2), 1995, 155-175.

(56)          References Cited

OTHER PUBLICATIONS

Hollas, B. et al., "A stochastic approach to count RN A molecules using DNA sequencing methods", Lecture Notes in Computer Science, vol. 2812, 2003, 55-62.

Holleley, et al., "Multiplex Manager 1.0: a Cross-Platform Computer Program that Plans and Optimizes Multiplex PCR", BioTechniques46:511-517 (Jun. 2009), 511-517.

Hollox, E. et al., "Extensive Normal Copy Number Variation of a β-Defensin Antimicrobial-Gene Cluster", Am. J. Hum. Genet., 73, 2003, 591-600.

Holt, et al., "Detecting SNPS and Estimating Allele Frequencies in Clonal Bacterial Populations by Sequencing Pooled DNA", Bioinformatics, vol. 25, No. 16, Aug. 15, 2009, 2074-2075.

Homer, et al., "Resolving Individuals Contributing Trace Amounts of DNA to Highly Complex Mixtures Using High-Density SNP Genotyping Microarrays", PLOS Genetics, 4(8), 2008, 9 pgs.

Hoogendoorn, Bastiaan et al., "Genotyping Single Nucleotide Polymorphisms by Primer Extension and High Performance Liquid Chromatography", Hum Genet, 104, 1999, 89-93.

Horai, et al., "Novel Implantable Device to Detect Cardiac Allograft Rejection", Circulation, vol. 120, No. Suppl 1, Sep. 15, 2009, 185-190.

Hornak, M. et al., "Aneuploidy Detection in Pigs Using Comparative Genomic Hybridization: From the Oocytes to Blastocysts", PLoS One, vol. 7, No. 1, Jan. 2012, 6 pages.

Hosmillo, Myra D. et al., "Development of Universal SYBR Green Real-time RT-PCR for the Rapid Detection and Quantitation of Bovine and Porcine Toroviruses", Journal of Virological Methods, vol. 168, 2010, pp. 212-217.

Hosono, S. et al., "Unbiased Whole-Genome Amplification Directly From Clinical Samples", Genome Research, vol. 13, 2003, 954-964.

Hospital, F. et al., "A General Algorithm to Compute Multilocus Genotype Frequencies Under Various Mating Systems" vol. 12, No. 6, Jan. 1, 1996 (Jan. 1, 1996), pp. 455-462.

Hou, X. et al., "Analysis of the Repertoire Features of TCR Beta Chain CDR3 in Human by High-Throughput Sequencing", Cellular Physiology and Biochemistry, vol. 39, Jul. 21, 2019, 651-667.

Howie, et al., "Fast and accurate genotype imputation in genome-wide association studies through pre-phasing", Nature Genetics, vol. 44, No. 8, Jul. 22, 2012, 955-959.

Howie, B. N. et al., "A Flexible and Accurate Genotype Imputation Method for the Next Generation of Genome-Wide Association Studies", PLoS Genetics, vol. 5, No. 6, Jun. 2009, 15 pages.

Hu, Dong Gui et al., "Aneuploidy Detection in Single Cells Using DNA Array-Based Comparative Genomic Hybridization", Molecular Human Reproduction, 10(4), 2004, 283-289.

Hu, Hao et al., "Mutation Screening in 86 Known X-linked Mental Retardation Genes by Droplet-based Multiplex Pcr and Massive Parallel Sequencing", Hao Hu et al., "Mutation Screening in 86 Known X-linked Mental Retardation Genes by Droplet-based Multiplex Pcr and Massive Parallel Sequencing", Hugo J, Dec. 2009, vol. 3, pp. 41-49., Dec. 1, 2009, 41-49.

Hu, Y. et al., "Detection of Extrahepatic Hepatitis C Virus Replication by a Novel, Highly Sensitive, Single-Tube Nested Polymerase Chain Reaction", Am. J. Clin Pathol., vol. 119, 2003, 95-100.

Huang, D. J. et al., "Reliable detection of Trisomy 21 using MALDI-TOF mass spectrometry", Genetics in Medicine, vol. 8, Nov. 2006, 728-734.

Huang, D. J. et al., "Use of an Automated Method Improves the Yield and Quality of Cell-Free Fetal DNA Extracted from Maternal Plasma", Clinical Chemistry, vol. 51, No. 12, 2005, 2419-2420.

Huang, J. et al., "Whole genome DNA copy number changes identified by high density oligonucleotide arrays", Human Genomics, vol. 1, No. 4, May 2004, 287-299.

Hubacek, et al., "Detection of Donor DNA After Heart Transplantation: How Far Could It Be Affected by Blood Transfusion and Donor Chimerism?", Transplantation Proceedings, vol. 39, Jun. 1, 2007, 1593-1595.

Hug, H. et al., "Measurement of the number of molecules of a single mRNA species in a complex mRNA preparation", J. Theor. Biol., vol. 221, 2003, 615-624.

Hultin, E. et al., "Competitive enzymatic reaction to control allele-specific extensions", Nucleic Acids Research, vol. 33, No. 5, Mar. 14, 2005, 1-10.

Hung, E.C.W. et al., "Detection of circulating fetal nucleic acids: a review of methods and applications", J. Clin. Pathol., vol. 62, 2009, 308-313.

Hyndman, D L. et al., "PCR Primer Design", Methods in Molecular Biology, vol. 226, Second Edition, 2003, 81-88.

Ido, Yasuo et al., "Hyperglycemia-Induced Apoptosis in Human Umbilical Vein Endothelial Cells: Inhibition by the AMP-Activated Protein Kinase Activation", Diabetes, 51, 2002, 159-167.

Illumina, "Automated GoldenGate™ Genotyping on the BeadStation 500", Pub. No. 970-2004-002, 2004, 2 pages.

Illumina, "Genomic Sequencing", Data Sheet: Sequencing, 2010, 38939-38944.

Illumina, "GoldenGate" Assay Workflow: Illumina's GoldenGate assay protocol provides high-quality, high-multiplex genotyping results with a streamlined workflow, Pub. No. 370-2004-006, 2004, 2 pages.

Illumina, "HiSeq 2500 Sequencing System", System Specification Sheet: Sequencing, available via URL https://www.illumina.com/documents/products/datasheets/datasheet_hiseq2500.pdf, 2015, 4 pgs.

Illumina, "History of Sequencing by Synthesis", https://www.illumina.com/science/technology/next-generation-sequencing/illumina-sequencing-history.html, 2020, 3 pages.

Illumina, "Illumina Extends BeadArray Technology to Address Wider Range of SNP Genotyping Projects; New Microarray Offerings Enable Genotyping at 384 and 786 Multiplex", Businesswire, May 4, 2004, 2 pages.

Illumina, "Illumina® Beadstation 500: A Scalable System That Grows With Your Research Requirements", Pub. No. 970-2005-003, Jul. 1, 2005, 4 pages.

Illumina, "Illumina Announces Benchtop SNP Genotyping System", Press Release, Nov. 5, 2003, 3 pages.

Illumina, "Illumina Begins Shipment of BeadStation 500G Benchtop Genotyping System", Press Release, Apr. 15, 2004, 3 pages.

Illumina, "MiSeq System Information Sheet", 2018, 3 pgs.

Illumina, "Patent Owner Illumina's Preliminary Response to Petition", Oct. 17, 2018, 75 pgs.

Illumina, "Petition for Inter Partes Review of U.S. Pat. No. 8,682,592", Jun. 13, 2019, 91 pages.

Illumina, "Plaintiff/Counterclaim Defendant Illumina, Inc.'s Amended Patent L.R. 3-3 Preliminary Invalidity Contentions for U.S. Pat. No. 8,682,592", Oct. 30, 2018, 22 pages.

Illumina, "Plaintiff/Counterclaim-Defendant Illumina, Inc.'s Patent L.R. 3-3 Contentions for U.S. Patent Preliminary Invalidity Contentions for U.S. Pat. No. 8,682,592", Oct. 9, 2018, 81 pages.

Illumina, "Preparing Samples for Sequencing Genomic DNA", Part # 11251892 Rev. A, 2007, 18 pages.

Illumina, "Preparing Samples for Sequencing Genomic DNA", Part # 1003806 Rev. A, 2007, 20 pages.

Illumina, "Products & Services", Product Literature, Mar. 21, 2007, 3 pages.

Illumina, "Technology: Solexa Sequencing Technology", May 21, 2007, 1 page.

Illumina, "TruSeq™ RNA and DNA Library Preparation Kits v2", Data Sheet: Illumina® Sequencing, 2014, 4.

Illumina Catalog, "Paired-End Sample Preparation Guide, Illumina Catalog# PE-930-1 001, Part# 1005063 Rev. E", 2011, 1-40.

Illumina, Inc., "Declaration of David Peters, Ph.D. in Support of Petition for Inter Partes Review of U.S. Pat. No. 8,682,592", Jun. 13, 2019, 136 pages.

Illumina, Inc. V. Natera, Inc., "Order Re: Claim Construction", Jan. 30, 2019, 16 pgs.

Imielinski, M. et al., "Mapping the Hallmarks of Lung Adenocarcinoma with Massively Parallel Sequencing", Cell, vol. 150, Sep. 14, 2012, 1107-1120.

Ingman, et al., "SNP Frequency Estimation Using Massively Parallel Sequencing of Pooled DNA", European Journal of Human Genetics, vol. 17, No. 3, Oct. 15, 2008, 383-386.

(56)          References Cited

OTHER PUBLICATIONS

Innan, H. et al., "The Pattern of Polymorphism on Human Chromosome 21", Genome Research, vol. 13, 2003, 1158-1168.

Interewicz, B. et al., "DNA Released from Ischemic and Rejecting Organs as an Indicator of Graft Cellular Damage", Annals of Transplantation, vol. 9, No. 2, May 1, 2004, 42-45.

International Human, Genome Sequencing Consortium , "Finishing the Euchromatic Sequence of the Human Genome", Nature, vol. 431, Oct. 21, 2004, 931-945.

Ishii, et al., "Optimization of Annealing Temperature to Reduce Bias Caused by a Primer Mismatch in Multitemplate Pcr", Applied and Environmental Microbiology, Aug. 2001, p. 3753-3755.

Iskow, R. C. et al., "Natural Mutagenesis of Human Genomes by Endogenous Retrotransposons", Cell, vol. 141, Jun. 25, 2010, 1253-1261.

Ivanov, M. et al., "Non-random fragmentation patterns in circulating cell-free DNA reflect epigenetic regulation", BMC Genomics, vol. 16 (Suppl 13):S1, Jun. 2015, 12 pgs.

Jabara, C. B. et al., "Accurate sampling and deep sequencing of the HIV-1 protease gene using a Primer ID", PNAS, vol. 108, No. 50, Dec. 13, 2011, 20166-20171.

Jahr, S. et al., "DNA Fragments in the Blood Plasma of Cancer Patients: Quantitations and Evidence for Their Origin from Apoptotic and Necrotic Cells", Cancer Research, vol. 61, Feb. 15, 2001, 1659-1665.

Jamal-Hanjani, M. et al., "Detection of ubiquitous and heterogeneous mutations in cell-free DNA from patients with early-stage non-small-cell lung cancer", Annals of Oncology, vol. 27, No. 5, Jan. 28, 2016, 862-867.

Jamal-Hanjani, M. et al., "Tracking Genomic Cancer Evolution for Precision Medicine: The Lung TRACERx Study", PLOS Biology, vol. 12, No. 7, Jul. 2014, 1-7.

Jamal-Hanjani, M. et al., "Tracking the Evolution of Non-Small-Cell Lung Cancer", The New England Journal of Medicine, vol. 376, No. 22, Jun. 1, 2017, 2109-2121.

Jarvie, T. , "Next generation sequencing technologies", Drug Discovery Today: Technologies, vol. 2, No. 3, 2005, 255-260.

Jen, J. et al., "An Overview on the Isolation and Analysis of Circulating Tumor DNA in Plasma and Serum", Annals New York Academy of Sciences, 2000, 8-12.

Jenkins, S. et al., "High-throughput SNP genotyping", Comparative and Functional Genomics, vol. 3, Dec. 5, 2001, 57-66.

Jennings, C. et al., "Investigation of Effects of Acid Citrate Dextrose and EDTA on Ability to Quantitatively Culture Human Immunodeficiency Virus", Journal of Clinical Microbiology, vol. 38, No. 9, 2000, 3522.

Jett, K. et al., "Clinical and genetic aspects of neurofibromatosis 1", Genetics In Medicine, vol. 12, No. 1, Jan. 2010, 11 pages.

Jewesbury, E.C.O. , "Reactions after Transfusion of Stored Blood", The British Medical Journal, vol. 1, No. 4191, 1941, 664-665.

Jiang, P. et al., "The Long and Short of Circulating Cell-Free DNA and the Ins and Outs of Molecular Diagnostics", Trends in Genetics, vol. 32, No. 6, Jun. 2016, 360-371.

Johnson, D. S. et al., "Genome-Wide Mapping of in Vivo Protein-DNA Interactions", Science, vol. 316, Jun. 8, 2007, 1497-1502.

Johnson, D.S. et al., "Comprehensive Analysis of Karyotypic Mosaicism Between Trophectoderm and Inner Cell Mass", Molecular Human Reproduction, 16(12), 2010, 944-949.

Johnson, J. B. et al., "Differential mechanisms of complementmediated neutralization of the closely related paramyxoviruses simian virus 5 and mumps virus", Virology, vol. 376, No. 1, 2008, 112-123.

Johnson, K. L. et al., "Interlaboratory Comparison of Fetal Male DNA Detection from Common Maternal Plasma Samples by Real-Time PC", Clinical Chemistry, vol. 50, No. 3, 2004, 516-521.

Johnson D.S, et al., "Preclinical Validation of a Microarray Method for Full Molecular Karyotyping of Blastomeres in a 24-h Protocol", Human Reproduction, 25 (4), 2010, 1066-1075.

Jung, K. et al., "Cell-free DNA in the blood as a solid tu1nor biomarker—A critical appraisal of the literature", Clinica Chimica Acta, vol. 411, 2010, 1611-1624.

Juppner, H. et al., "Functional Properties of the PTH/PTHrP Receptor", Bone, vol. 17, No. 2 Supplement, Aug. 1995, 39S-42S.

Kalendar, Ruslan et al., "Java Web Tools for PCR, in Silico PCR, and Oligonucleotide Assembly and Analysis", Genomics, vol. 98, 2011, pp. 137-144.

Kamat, A. A. et al., "Quantification of total plasma cell-free DNA in ovarian cancer using real-time PCR", Ann N Y Acad Sci., vol. 1075, Sep. 2006, 230-234.

Kamel, A. M. et al., "A simple strategy for breakpoint fragment determination in chronic myeloid leukemia", Cancer Genetics and Cytogenetics, vol. 122, 2000, 110-115.

Kane, M. et al., "Application of Less Primer Method to Commercial Kits", Forensic Science International: Genetics Supplement Series, vol. 1, Issue 1, 2008, 41-43.

Kane, M. , "Application of Less Primer Method to Multiplex PCR", International Congress Series, vol. 1288, 2006, pp. 694-696.

Kanou, et al., "Cell-free DNA in human ex vivo lung perfusate as a potential biomarker to predict the risk of primary graft dysfunction in lung transplantation", The Journal of Heart and Lung Transplantation, vol. 36, No. 45, 2017, S187.

Kapadia, Samir R. et al., "Impact of Intravascular Ultrasound in Understanding Transplant Coronary Artery Disease", Current Opinion In Cardiology, vol. 14, No. 2, Mar. 1, 1999, 1-19.

Kaplinski, Lauris et al., "MultiPLX: Automatic Grouping and Evaluation of PCR Primers", Bioinformatics, 21(8), 2005, 1701-1702.

Karger, et al., "DNA Sequencing by Capillary Electrophoresis", Electrophoresis, vol. 30, Supplement 1, Jun. 1, 2009, 1-11.

Karoui, Noureddine E. et al., "Getting More from Digital SNP Data", Statistics in Medicine, vol. 25, Issue 18, Jan. 5, 2006, 3124-3133.

Kass, et al., "Diagnosis of Graft Coronary Artery Disease", Current Opinion in Cardiology, vol. 22, No. 2, Mar. 1, 2007, 139-145.

Kathiresan, Sekar et al., "Genome-wide Association of Early-onset Myocardial Infarction With Common Single Nucleotide Polymorphisms, Common Copy Number Variants, and Rare Copy Number Variants", Nature Genetics, vol. 41, No. 3, Mar. 1, 2009, 1-23.

Kazakov, V.I. et al., "Extracellular DNA in the Blood of Pregnant Women", Tsitologia, vol. 37, No. 3, 1995, 1-8.

Keith, L. et al., "Clinical Experience With the Prevention of Rh-Isoimmunization: A Historical Comparative Analysis", American Journal of Reproductive Immunology, vol. 5, 1984, 84-89.

Keller, M. C. et al., "Non-Pathological Paternal Isodisomy of Chromosome 2 Detected From a Genome-Wide SNP Scan", American Journal of Medical Genetics, Part A, 2009, 1823-1826.

Kennedy, S. R. et al., "Detecting ultralow-frequency mutations by Duplex Sequencing", Nature Protocols, vol. 9, No. 11, 2014, 2586-2606.

Kibbe, Warren A. , "Oligocalc: An Online Oligonucleotide Properties Calculator", Nucleic Acids Research, vol. 35, 2007, pp. W43-W46.

Kiernan, J. A. , "Formaldehyde, formalin, paraformaldehyde and glutaraldehyde: What they are and what they do.", Microscopy Today, vol. 1, 2000, 8-12.

Kijak, G. et al., "Discrepant Results in the Interpretation of HIV-1 Drug-Resistance Genotypic Data Among Widely Used Algorithms", HIV Medicine, 4, 2003, 72-78.

Kim, H. et al., "Whole-genome and multisector exome sequencing of primary and post-treatment glioblastoma reveals patterns of tumor evolution", Genome Research, vol. 25, No. 3, Feb. 3, 2015, 316-327.

Kimmel, G. et al., "GERBIL: Genotype resolution and block identification using likelihood", PNAS, vol. 102, No. 1, Jan. 4, 2005, 158-162.

Kinde, I. et al., "Detection and quantification of rare mutations with massively parallel sequencing", PNAS, vol. 108, No. 23, Jun. 7, 2011, 9530-9535.

Kinnings, S. L. et al., "Factors affecting levels of circulating cell-free fetal DNA in maternal plasma and their implications for noninvasive prenatal testing", Prenatal Diagnosis, vol. 35, 2015, 816-822.

(56) References Cited

OTHER PUBLICATIONS

Kircher, Martin et al., "Improved Base Calling for the Illumina Genome Analyzer Using Machine Learning Strategies", Genome Biology, vol. 10, Issue 8, Article No. R83, Aug. 14, 2009, 83.2-83.9.

Kirkizlar, E. et al., "Detection of Clonal and Subclonal Copy-Number Variants in Cell-Free DNA from Patients with Breast Cancer Using a Massively Multiplexed PCR Methodology", Translational Oncology, vol. 8, No. 5, Oct. 2015, pp. 407-416.

Kirkness, E. F. et al., "Sequencing of isolated sperm cells for direct haplotyping of a human genome", Genome Research, vol. 23, 2013, 826-832.

Kivioja, T. et al., "Counting absolute number of molecules using unique molecular identifiers", Nature Proceedings, Apr. 14, 2011, 18 pgs.

Kivioja, T. et al., "Counting absolute numbers of molecules using unique molecular identifiers", Nature Methods, Advance Online Publication, Nov. 20, 2011, 1-5.

Kivioja, T. et al., "Counting absolute numbers of molecules using unique molecular identifiers", Nature Methods, vol. 9, No. 1, Jan. 2012, 72-76.

Kobashigawa, et al., "Multicenter Intravascular Ultrasound Validation Study Among Heart Transplant Recipients", Journal of the American College of Cardiology, vol. 45, No. 9, May 3, 2005, 1532-1537.

Koboldt, et al., "VarScan: Variant Detection in Massively Parallel Sequencing of Individual and Pooled Samples", Bioinformatics, vol. 25, No. 17, Jun. 19, 2009, 2283-2285.

Koelman, et al., "Donor-derived Soluble HLA Plasma Levels Can Not Be Used to Monitor Graft Rejection in Heart Transplant Recipients", Transplant Immunology, vol. 8, No. 1, Mar. 1, 2000, 57-64.

Kohler, C. et al., "Levels of plasma circulating cell free nuclear and mitochondrial DNA as potential biomarkers for breast tumors", Molecular Cancer, vol. 8, No. 105, Nov. 17, 2009, 9 pages.

Koide, K. et al., "Fragmentation of cell-free fetal DNA in plasma and urine of pregnant women", Prenatal Diagnosis, vol. 25, 2005, 604-607.

Koldehoff, Michael et al., "Quantitative analysis of chimerism after allogeneic stem cell transplantation by real-time polymerase chain reaction with single nucleotide polymorphisms, standard tandem repeats, and Y-chromosome-specific sequences", American Journal of Hematology, vol. 81, No. 10, Jul. 12, 2006, 735-746.

Konfortov, B A. et al., "A High-Resolution HAPPY Map of Dictyostelium discoideum Chromosome 6", Genome Research, vol. 10, No. 11, Nov. 2000, 1737-1742.

Konfortov, Bernard A. et al., "An Efficient Method for Multi-Locus Molecular Haplotyping", Nucleic Acids Research, 35(1), e6, 2007, 8 pgs.

Kopreski, MS et al., "Detection of mutant K-ras DNA in plasma or serum of patients with colorectal cancer", British Journal of Cancer, vol. 76, No. 10, 1997, 1293-1299.

Koressaar, Triinu et al., "Enhancements and Modifications of Primer Design Program Primer3", Bioinformatics, vol. 23, 2007, pp. 1289-1291.

Korn, et al., "Integrated Genotype Calling and Association Analysis of SNPS, Common Copy Number Polymorphisms and Rare CNVS", Nature Genetics, vol. 40, No. 10, Oct. 1, 2008, 1253-1260.

Krjutskov, K. et al., "Development of a single tube 640-plex genotyping method for detection of nucleic acid variations on microarrays", Nucleic Acids Research, vol. 36, No. 12, May 23, 2008, 7 pages.

Kuhn, H. et al., "Rolling-circle amplification under topological constraints", Nucleic Acids Research, vol. 30, No. 2, 2002, 574-580.

Kukita, Y. et al., "High-fidelity target sequencing of individual molecules identified using barcode sequences: de nova detection and absolute quantitation of mutations in plasma cell-free DNA from cancer patients", DNA Research, vol. 22, No. 4, Jun. 29, 2015, 269-277.

Kuliev, Anver et al., "Thirteen Years' Experience on Preimplantation Diagnosis: Report of the Fifth International Symposium on Preimplantation Genetics", Reproductive BioMedicine Online, 8, 2, 2004, 229-235.

Kumar, P. et al., "Ethylenegycol-Bis-(B-Aminoethylether)Tetraacetate as a Blood Anticoagulant: Preservation of Antigen-Presenting Cell Function and Antigen-Specific Proliferative Response of Peripheral Blood Mononuclear Cells from Stored Blood", Clinical and Diagnostic Laboratory Immunology, vol. 7, No. 4, 2000, 578-583.

Kunishima, S. et al., "First description of somatic mosaicism in MYH9 disorders", British Journal of Haematology, vol. 128, 2005, 360-365.

Kwok, P. Y. , "High-throughput genotyping assay approaches", Pharmacogenomics, vol. 1, No. 1, 2000, 1-5.

Lambert, et al., "Quantification of Maternal Microchimerism by HLA-Specific Real-time Polymerase Chain Reaction", Arthritis and Rheumatism, vol. 50, No. 3, Mar. 1, 2004, 906-914.

Lambert-Messerlian, G. et al., "Adjustment of Serum Markers in First Trimester Screening", Journal of Medical Screening, 16 (2), 2009, 102-103.

Landegren, U. et al., "Padlock and proximity probes for in situ and array-based analyses: tools for the post-genomic era", Comparative and Functional Genomics, vol. 4, 2003, 525-530.

Lander, E. S. et al., "Initial sequencing and analysis of the human genome", Nature, vol. 409, Feb. 15, 2001, 860-921.

Langmore, J. , "Quality Control and Pre-Qualifications of NGS Libraries Made from Clinical Samples", ABRF 2013 Satellite Workshop, Mar. 2, 2013, 35 pages.

Lapaire, O. et al., "Array-CGH analysis of cell-free fetal DNA in 10 mL of amniotic fluid supernatant", Prenatal Diagnosis, vol. 27, May 17, 2007, 616-621.

Lapierre, J.M. et al., "Analysis of uncultured amniocytes by comparative genomic hybridization: a prospective prenatal study", Prenatal Diagnosis, vol. 20, 2000, 123-131.

Lardeux, Frederic et al., "Optimization of a Semi-nested Multiplex PCR to Identify Plasmodium Parasites in Wild-Caught Anopheles in Bolivia, and Its Application to Field Epidemiological Studies", Transactions of the Royal Society of Tropical Medicine and Hygiene, vol. 102, 2008, pp. 485-492.

Larsen, J. B. et al., "Single-step Nested Multiplex PCR to Differentiate Between Various Bivalve Larvae", Marine Biology, vol. 146, 2005, pp. 1119-1129.

Lasken, R. S. et al., "Whole genome amplification: abundant supplies of DNA from precious samples or clinical specimens", TRENDS in Biotechnology, vol. 21, No. 12, Dec. 2003, 531-535.

Lathi, Ruth B. et al., "Informatics Enhanced SNP Microarray Analysis of 30 Miscarriage Samples Compared to Routine Cytogenetics", PLoS One, 7(3), 2012, 5 pgs.

Lavebrat, et al., "Single Nucleotide Polymorphism (SNP) Allele Frequency Estimation in DNA Pools Using Pyrosequencing", Nature Protocols, vol. 1, No. 6, Jan. 11, 2007, 2573-2582.

Lavebratt, Catharina et al., "Pyrosequencing-based SNP Allele Frequency Estimation in DNA Pools", Human Mutation, vol. 23, Issue 1, Dec. 19, 2003, 92-97.

Lavrentieva, I. et al., "High Polymorphism Level of Genomic Sequences Flanking Insertion Sites of Human Endogenous Retroviral Long Terminal Repeats", FEBS Letters, vol. 443, No. 3, Jan. 29, 1999, 341-347.

Leamon, John H. et al., "A massively parallel PicoTiterPlate based platform for discrete picoliter-scale polymerase chain reactions", Electrophoresis, vol. 24, No. 21, Nov. 1, 2003, 3769-3777.

Leary, R. J. et al., "Development of Personalized Tumor Biomarkers Using Massively Parallel Sequencing", Science Translational Medicine, vol. 2, No. 20, Feb. 24, 2010, 1-8.

Leary, Rebecca J et al., "Detection of Chromosomal Alterations in the Circulation of Cancer Patients with Whole-Genome Sequencing", Science Translational Medicine, 4, 162, 2012, 12.

Lecomte, T. et al., "Detection of Free-Circulating Tumor-Associated DNA in Plasma of Colorectal Cancer Patients and Its Association With Prognosis", Int. J. Cancer, vol. 100, 2002, 542-548.

Lee, J et al., "Anchored Multiplex PCR Enables Sensitive and Specific Detection of Variants in Circulating Tumor DNA by

(56)　　References Cited

OTHER PUBLICATIONS

Next-Generation Sequencing", DOI:https://doi.org/10.1016/j.cancergen.2017.04.049, Cancer Genetics 214-215, 2017, 47.

Lee, T. et al., "Down syndrome and cell-free fetal DNA in archived maternal serum", AmJ Obstet Gynecol, vol. 187, No. 5, 1217-1221, Nov. 2002.

Lee, T.H. et al., "Quantitation of genomic DNA in plasma and serum samples: higher concentrations of genomic DNA found in serum than in plasma", Transfusion, vol. 41, Feb. 2001, 276-282.

Levsky, J. M. et al., "Fluorescence in situ hybridization: past, present and future", Journal of Cell Science, vol. 116, No. 14, 2003, 2833-2838.

Levsky, Jeffrey M. et al., "Efficacy of Coronary Ct Angiography: Where We Are, Where We Are Going and Where We Want to Be", Journal of Cardiovascular Computed Tomography, vol. 3, Supplement 2, Nov. 2, 2009, s99-s108.

Li, et al., "Detection of SNPs in the Plasma of Pregnant Women and in the Urine of Kidney Transplant Recipients by Mass Spectrometry", Annals of the New York Academy of Sciences, vol. 1075, Sep. 5, 2006, 144-147.

Li, et al., "Mapping Short DNA Sequencing Reads and Calling Variants Using Mapping Quality Scores", Genome Research, vol. 18, No. 11,, Aug. 19, 2008, 1851-1858.

Li, et al., "Multiplex Padlock Targeted Sequencing Reveals Human Hypermutable CpG Variations", Genome Research, vol. 19, No. 9, Jun. 12, 2009, 1606-1615.

Li, et al., "SOAP2: An Improved Ultrafast Tool for Short Read Alignment", Bioinformatics, vol. 25, No. 15, Aug. 1, 2009, 1966-1967.

Li, B. , "Highly Multiplexed Amplicon Preparation for Targeted Re-Sequencing of Sample Limited Specimens Using the Ion AmpliSeq Technology and Semiconductor Sequencing", Proceedings of the Annual Meeting of the American Society of Human Genetics [retrieved on Oct. 30, 2012]. Retrieved from the Internet: <URL: http://www.ashg.org/2012meeting/abstracts/fulltext/f120121811.htm>, 2012, 1 pg.

Li, R. et al., "SNP detection for massively parallel whole-genome resequencing", Genome Research, vol. 19, 2009, 1124-1132.

Li, Y. et al., "Detection of Paternally Inherited Fetal Point Mutations for b-Thalassemia Using Size-Fractionated Cell-Free DNA in Maternal Plasma", JAMA, vol. 293, No. 7, Apr. 13, 2005, 843-849.

Li, Y. et al., "Non-Invasive Prenatal Diagnosis Using Cell-Free Fetal DNA in Maternal Plasma from PGD Pregnancies", Reproductive BioMedicine Online, 19 (5), 2009, 714-720.

Li, Ying et al., "Detection of Donor-specific DNA Polymorphisms in the Urine of Renal Transplant Recipients", Clinical Chemistry, vol. 49, No. 4, Apr. 1, 2003, 655-658.

Li, Ying et al., "Ready detection of donor-specific single-nucleotide polymorphisms in the urine of renal transplant recipients by matrix-assisted laser desorption/ionization time-of-flight mass spectrometry".

Ying Li. et al., "Ready detection of donor-specific single-nucleotide polymorphisms in the urine of renal transplant recipients by matrix-assisted laser desorption/ionization time-of-flight mass spectrometry",Clin Chem,Oct. 2005,vol. 51,Issue. 10,pp. 1903-1904, Oct. 1, 2005, 1903-1904.

Li, Ying et al., "Size Separation of Circulatory DNA in Maternal Plasma Permits Ready Detection of Fetal DNA Polymorphisms", Clinical Chemistry, 50, 6, 2004, 1002-1011.

Liao, Gary J.W. et al., "Targeted Massively Parallel Sequencing of Maternal Plasma DNA Permits Efficient and Unbiased Detection of Fetal Alleles", Clinical Chemistry, 57 (1), 2011, 92-101.

Liao, J. et al., "An Alternative Linker-Mediated Polymerase Chain Reaction Method Using a Dideoxynucleotide to Reduce Amplification Background", Analytical Biochemistry 253, 137-139 (1997).

Lichtenstein, A. V. et al., "Circulating Nucleic Acids and Apoptosis", Annals New York Academy of Sciences, vol. 945, Aug. 1, 2001, 239-249.

Liew, Michael et al., "Genotyping of Single-Nucleotide Polymorphisms", Clinical Chemistry, 50(7), 2004, 1156-1164.

Life Technologies, "Ion AmpliSeq Comprehensive Cancer Panel", 2012, 2 pgs.

Life Technologies, "Ion AmpliSeq™ Designer provides full flexibility to sequence genes of your choice", 2012, 4 pages.

Liljedahl, Ulrika et al., "Detecting Imbalanced Expression of SNP Alleles by Minisequencing on Microarrays", BMC Biotechnology, vol. 4, Article No. 24, Oct. 22, 2004, 1-10.

Lindberg, J. et al., "Exome Sequencing of Prostate Cancer Supports the Hypothesis of Independent Tumour Origins", European Urology, vol. 63, 2013, 347-353.

Lindroos, Katina et al., "Genotyping SNPs by Minisequencing Primer Extension Using Oligonucleotide Microarrays", Methods in Molecular Biology, 212, Single Nucleotide Polymorphisms: Methods and Protocols, P-K Kwok (ed.), Humana Press, Inc., Totowa, NJ, 2003, 149-165.

Lo, et al., "Digital PCR for the Molecular Detection of Fetal Chromosomal Aneuploidy", PNAS, vol. 104, No. 32, Aug. 7, 2007, 13116-13121.

Lo, et al., "Fetal Nucleic Acids in Maternal Blood: the Promises", Clin. Chem. Lab. Med., 50(6), 2012, 995-998.

Lo, et al., "Free Fetal DNA in Maternal Circulation", JAMA, 292(23), (Letters to the Editor), 2004, 2835-2836.

Lo, et al., "Next-generation Sequencing of Plasma/Serum DNA: An Emerging Research and Molecular Diagnostic Tool", Clinical Chemistry, vol. 55, No. 4, Apr. 1, 2009, 607-608.

Lo, "Non-Invasive Prenatal Diagnosis by Massively parallel Sequencing of Maternal Plasma DNA", Open Biol 2: 120086, 2012, 1-5.

Lo, et al., "Prenatal Sex Determination by DNA Amplification from Maternal Peripheral Blood", The Lancet, 2, 8676, 1989, 1363-1365.

Lo, et al., "Presence of Donor-specific Dna in Plasma of Kidney And Liver-transplant Recipients", Lancet, vol. 351, No. 9112, May 2, 1998, 1329-1330.

Lo, et al., "Rapid Clearance of Fetal DNA from Maternal Plasma", Am. J. Hum. Genet., 64, 1999, 218-224.

Lo, et al., "Strategies for the Detection of Autosomal Fetal DNA Sequence from Maternal Peripheral Blood", Annals New York Academy of Sciences, 731, 1994, 204-213.

Lo, et al., "Two-way cell traffic between mother and fetus: biologic and clinical implications", Blood, 88(11), Dec. 1, 1996, 4390-4395.

Lo, Y M. et al., "Circulating Nucleic Acids in Plasma and Serum: An Overview", Annals of the New York Academy of Sciences, vol. 945, Sep. 1, 2001, 1-7.

Lo, Y. , "Noninvasive prenatal detection of fetal chromosomal aneuploidies by maternal plasma nucleic acid analysis: a review of the current state of the art", BJOG An International Journal of Obstetrics and Gynaecology, vol. 116, 2009, 152-157.

Lo, Y.M. Dennis , "Fetal Nucleic Acids in Maternal Plasma: Toward the Development of Noninvasive Prenatal Diagnosis of Fetal Chromosomal Aneuploidies", Ann. N.Y. Acad. Sci., 1137, 2008, 140-143.

Lo, Y.M. Dennis et al., "Maternal Plasma DNA Sequencing Reveals the Genome-Wide Genetic and Mutational Profile of the Fetus", Science Translational Medicine,, 2 (61), 2010, 13.

Lo, Y.M. Dennis et al., "Plasma placental RNA allelic ratio permits noninvasive prenatal chromosomal aneuploidy detection", Nature Medicine, 13 (2), 2007, 218-223.

Lo, Y.M. Dennis et al., "Presence of Fetal DNA in Maternal Plasma and Serum", The Lancet, 350, 1997, 485-487.

Lo, Y.M. Dennis et al., "Quantitative Analysis of Fetal DNA in Maternal Plasma and Serum: Implications for Noninvasive Prenatal Diagnosis", Am. J. Hum. Genet., 62, 1998, 768-775.

Lo, Y.M.D. , "Fetal DNA in Maternal Plasma: Biology and Diagnostic Applications", Clinical Chemistry, vol. 46, No. 12, 2000, 1903-1906.

Lo, Y.M.D. et al., "Prenatal diagnosis: progress through plasma nucleic acids", Nature Reviews, vol. 8, 2007, 71-77.

Lo, Y-M D. , "Non-invasive prenatal diagnosis using fetal cells in maternal blood", J. Clin. Pathol., vol. 47, 1994, 1060-1065.

Lo, Y-M.D et al., "Detection of Single-Copy Fetal DNA Sequence from Maternal Blood", The Lancet, 335, 1990, 1463-1464.

(56) References Cited

OTHER PUBLICATIONS

Lo, Y-M.D et al., "Prenatal Determination of Fetal Rhesus D Status by DNA Amplification of Peripheral Blood of Rhesus-Negative Mothers", Annals New York Academy of Sciences, 731, 1994, 229-236.

Lo, Y-M.D. et al., "Detection of Fetal RhD Sequence from Peripheral Blood of Sensitized RhD-Negative Pregnant Women", British Journal of Haematology, 87, 1994, 658-660.

Lo, Y-M.D. et al., "Prenatal Determination of Fetal RhD Status by Analysis of Peripheral Blood of Rhesus Negative Mothers", The Lancet, 341, 1993, 1147-1148.

Loh, Elwyn , "Anchored PCR: Amplification with Single-sided Specificity", Methods, vol. 2, 1991, pp. 11-19.

Lovmar, L. et al., "Quantitative evaluation by minisequencing and microarrays reveals accurate multiplexed SNP genotyping of whole genome amplified DN", Nucleic Acids Research, vol. 31, No. 21, 2003,, 9 pgs.

Lu, I. et al., "Establishment of a system based on universal multiplex-PCR for screening genetically modified crops", Anal. Bioanal. Chem, vol. 396, Oct. 24, 2009, 2055-2064.

Lu, S. et al., "Probing Meiotic Recombination and Aneuploidy of Single Sperm Cells by Whole-Genome Sequencing", Science, vol. 338, Dec. 21, 2012, 1627-1630.

Lui, Y. Y. et al., "Predominant Hematopoietic Origin of Cell-Free DNA in Plasma and Serum after Sex-Mismatched Bone Marrow Transplantation", Clinical Chemistry, vol. 48, vol. 3, 2002, 421-427.

Lui, Yanni Y. et al., "Circulating DNA in Plasma and Serum: Biology, Preanalytical Issues and Diagnostic Applications", Clinical Chemistry and Laboratory Medicine, vol. 40, No. 10, Oct. 29, 2002, 962-968.

Lui, Yanni Y. et al., "Origin of Plasma Cell-Free DNA after Solid Organ Transplantation", Clinical Chemistry, vol. 49, No. 3, Mar. 1, 2003, 495-496.

Lun, Fiona M. et al., "Microfluidics Digital PCR Reveals a Higher Than Expected Fraction of Fetal DNA in Maternal Plasma", Clinical Chemistry, vol. 54, No. 10, Aug. 14, 2008, 1664-1672.

Lun, Fiona M. et al., "Noninvasive Prenatal Diagnosis of Monogenic Diseases by Digital Size Selection and Relative Mutation Dosage on DNA in Maternal Plasma", PNAS, 105(50), 2008, 19920-19925.

Ma, Xiaotu et al., "Rise and fall of subclones from diagnosis to relapse in pediatric B-acute lymphoblastic leukaemia", Nature Communications, vol. 6, Mar. 19, 2015, 1-12.

Mackiewicz, D. et al., "Distribution of Recombination Hotspots in the Human Genome—A Comparison of Computer Simulations with Real Data", PLOS One, vol. 8, No. 6, Jun. 2013, 11 pages.

Magbanua, M. J. et al., "Abstract PD2-01: Personalized serial circulating tumor DNA (ctDNA) analysis in high-risk early stage breast cancer patients to monitor and predict response to neoadjuvant therapy and outcome in the I-SPY 2 Trial", Cancer Research, vol. 79, No. 4 Supplement, Feb. 15, 2019.

Mamon, H. et al., "Letters to the Editor: Preferential Amplification of Apoptotic DNA from Plasma: Potential for Enhancing Detection of Minor DNA Alterations in Circulating DNA", Clinical Chemistry, vol. 54, No. 9, 2008, 1582-1584.

Maniatis, T. et al., "In: Molecular Cloning: A Laboratory Manual", Cold Spring Harbor Laboratory, New York, Thirteenth Printing, 1986, 458-459.

Mansfield, Elaine S , "Diagnosis of Down Syndrome and Other Aneuploidies Using Quantitative Polymerase Chain Reaction and Small Tandem Repeat Polymorphisms", Human Molecular Genetics, 2, 1, 1993, 43-50.

Mardis, E. R. , "The impact of next-generation sequencing technology on genetics", Trends in Genetics, vol. 24, No. 3, Feb. 11, 2008, 133-141.

Marguiles, M. et al., "Genome Sequencing in Open Microfabricated High Density Picoliter Reactors", Nature, vol. 437, No. 7057, Sep. 15, 2005, 376-380.

Margulies, M. et al., "Genome sequencing in microfabricated high-density picolitre reactors", Nature, vol. 437, 15 Sep. 2005, 376-380.

Margulies, M. et al., "Genome sequencing in microfabricated high-density picolitre reactors plus Supplemental Methods", Nature, vol. 437, Sep. 15, 2005, 40 pgs.

Marianes, Alexis E. et al., "Targets of Somatic Hypermutation within Immunoglobulin Light Chain Genes in Zebrafish", Immunology, vol. 132, 2010, pp. 240-255.

Markoulatos, P. et al., "Multiplex Polymerase Chain Reaction: A Practical Approach", Journal of Clinical Laboratory Analysis, vol. 16, 2002, 47-51.

Maron, Jill L. et al., "Cell-free Fetal DNA Plasma Extraction and Real-time Polymerase Chain Reaction Quantification", Methods in Molecular Medicine, vol. 132, Aug. 1, 2007, 51-63.

Marshutina, N. V. et al., "Comparative Clinical and Diagnostic Significance of Some Serological Tumor Associated Markers for Different Histological Types of Lung Cancer", Russian Oncological Journal, vol. 3, 2010, 13-16.

Martinez-Lopez, J. et al., "Real-time PCR Quantification of Haematopoietic Chimerism after Transplantation: A Comparison Between TaqMan And Hybridization Probes Technologies", International Journal of Laboratory Hematology, vol. 32, Issue 1, Part 1, May 12, 2009, e17-e25.

Martins, et al., "Quantification of Donor-derived DNA in Serum: A New Approach of Acute Rejection Diagnosis in a Rat Kidney Transplantation Model", Transplantation Proceedings, vol. 37, No. 1,, Jan. 1, 2005, 87-88.

Masuzaki, H. et al., "Detection of cell free placental DNA in maternal plasma: direct evidence from three cases of confined placental mosaicism", J Med Genet, vol. 41, 2004, 289-292.

Matsubara, T. et al., "Pantropic Retroviral Vectors Integrate and Express in Cells of the Malaria Mosquito, Anopheles Gambiae", PNAS, vol. 93, 1996, pp. 6181-6185.

Matsuzaki, H. et al., "Genotyping over 100,000 SNPs on a pair of oligonucleotide arrays", Nature Methods, vol. 1, No. 2, Nov. 2004, 109-111.

May, Robert M. , "How Many Species Are There on Earth?", Science, 241, Sep. 16, 1988, 1441-1449.

Mcbride, D. et al., "Use of Cancer-Specific Genomic Rearrangements to Quantify Disease Burden in Plasma from Patients with Solid Tumors", Genes, Chromosomes & Cancer, vol. 49, Aug. 19, 2010, 1062-1069.

Mccloskey, M. L. et al., "Encoding PCR Products with Batch-stamps and Barcodes", Biochem Genet., vol. 45, Oct. 23, 2007, 761-767.

Mccray, Alexa T. et al., "Aggregating UMLS Semantic Types for Reducing Conceptual Complexity", MEDINFO 2001: Proceedings of the 10th World Congress on Medical Informatics (Studies in Health Technology and Informatics, 84, V. Patel et al. (eds.), IOS Press Amsterdam, 2001, 216-220.

Mcdonald, B. R. et al., "Abstract P4-01-21: Multiplexed targeted digital sequencing of circulating tumor DNA to detect minimal residual disease in early and locally advanced breast cancer", Cancer Research, vol. 79, No. 4 Supplement, Feb. 15, 2019.

Mcdonald, J. P. et al., "Novel thermostable Y-family polymerases: applications for the PCR amplification of damaged or ancient DNAs", Nucleic Acids Research, vol. 34, No. 4, 2006, 1102-1111.

Mennuti, M. et al., "Is It Time to Sound an Alarm About False-Positive Cell-Free DNA Testing for Fetal Aneuploidy?", American Journal of Obstetrics, 2013, 5 pgs.

Merriam-Webster, "Medical Definition of Stimulant", http://www.merriam-webster.com/medical/stimulant, Mar. 14, 2016, 7 pages.

Merriam-Webster, "Universal Definition", Merriam-Webster.com, 3 pages.

Mersy, et al., "Noninvasive Detection of Fetal Trisomy 21: Systematic Review and Report of Quality and Outcomes of Diagnostic Accuracy Studies Performed Between 1997 and 2012", Human Reproduction Update, 19(4), 2013, 318-329.

Mertes, F. et al., "Targeted enrichment of genomic DNA regions for next-generation sequencing", Briefings in Functional Genomics, vol. 10, No. 6, Nov. 26, 2011, 374-386.

Messmer, Trudy O. et al., "Application of a Nested, Multiplex PCR to Psittacosis Outbreaks", Journal of Clinical Microbiology, vol. 35, No. 8, 1997, pp. 2043-2046.

(56) References Cited

OTHER PUBLICATIONS

Metzker, M. L. et al., "Polymerase Chain Reaction", Encyclopedia of Medical Devices and Instrumentation, vol. 5, Second Edition, 2006, 380-387.

Metzker, M. L. et al., "Quantitation of Mixed-Base Populations of HIV-1 Variants by Automated DNA Sequencing with BODIPY* Dye-Labeled Primers", BioTechniques, vol. 25, Sep. 1998, 446-462.

Meuzelaar, Linda S. et al., "Megaplex PCR: A Strategy for Multiplex Amplification", Nature Methods, vol. 4, 2007, pp. 835-837.

Meyer, M et al., "Illumina Sequencing Library Preparation for Highly Multiplexed Target Capture and Sequencing", Cold Spring Harbor Protocols, vol. 2010, Issue 6, Jun. 2010, 1-10.

Meyerson, M. et al., "Advances in understanding cancer genomes through second-generation sequencing", Nature Reviews: Genetics, vol. 11, Oct. 2010, 685-696.

Mikkelsen, T. S. et al., "Genome-wide maps of chromatin state in pluripotent and lineage-committed cells", Nature, vol. 448, No. 2, Aug. 2007, 553-562.

Milani, et al., "Genotyping Single Nucleotide Polymorphisms by Multiplex Minisequencing Using Tag-arrays", DNA Microarrays for Biomedical Research, vol. 529, Jan. 16, 2009, 215-229.

Miller, Robert , "Hyperglycemia-Induced Changes in Hepatic Membrane Fatty Acid Composition Correlate with Increased Caspase-3 Activities and Reduced Chick Embryo Viability", Comparative Biochemistry and Physiology, Part B, 141, 2005, 323-330.

Miller, Robert R. , "Homocysteine-Induced Changes in Brain Membrane Composition Correlate with Increased Brain Caspase-3 Activities and Reduced Chick Embryo Viability", Comparative Biochemistry and Physiology Part B, 136, 2003, 521-532.

Miner, B. E. et al., "Molecular barcodes detect redundancy and contamination in hairpin-bisulfite PCR", Nucleic Acids Research, vol. 32, No. 17, Sep. 30, 2004, 1-4.

Minkoff, E. et al., "Stem Cells, Cell Division, and Cancer", Biology Today Third Edition, Chapter 12, 2004, 10 pages.

Miramontes, Pedro et al., "DNA Dimer Correlations Reflect in Vivo Conditions and Discriminate Among Nearest-neighbor Base Pair Free Energy Parameter Measures", Physica A, vol. 321, 2003, pp. 577-586.

Mitra, S. et al., "Chapter 4 Classification Techniques", Introduction to Machine Learning and Bioinformatics, First Edition, 2008, 101-127.

Morand, et al., "Hesperidin contributes to the vascular protective effects of orange juice: a randomized crossover study in healthy volunteers", Am J Clin Nutr. Jan. 2011;93(1):73-80. Epub Nov. 10, 2010.

Moreau, Valerie et al., "Zip Nucleic Acids: New High Affinity Oligonucleotides as Potent Primers for PCR and Reverse Transcription", Nucleic Acids Research, vol. 37, No. 19, e130, 2009, 14 pages.

Moreira, et al., "Increase in and Clearance of Cell-free Plasma DNA in Hemodialysis Quantified by Real-time PCR", Clinical Chemistry and Laboratory Medicine, vol. 44, No. 12, Dec. 13, 2006, 1410-1415.

Morris, J. K. et al., "Trends in Down's syndrome live births and antenatal diagnoses in England and Wales from 1989 to 2008: analysis of data from the National Down Syndrome Cytogenetic Register", BMJ Online, vol. 339, Oct. 2009, 5 pages.

Munne, S. et al., "Chromosome Abnormalities in Human Embryos", Textbook of Assisted Reproductive Techniques, 2004, pp. 355-377.

Munne, S. et al., "Chromosome abnormalities in human embryos", European Society of Human Reproduction and Embryology: Human Reproduction Update, vol. 4, No. 6, 1998, 842-855.

Munne, S. et al., "Improved implantation after preimplantation genetic diagnosis of aneuploidy", Reproductive BioMedicine Online, vol. 7., No. 1., May 15, 2003, 91-97.

Murali, R. et al., "Crystal structure of Taq DNA polymerase in complex with an inhibitory Fab: The Fab is directed against an intermediate in the helix-coil dynamics of the enzyme", Proc. Natl. Acad. Sci. USA, vol. 95, Oct. 1998, 12562-12567.

Murtaza, M. et al., "Non-Invasive Analysis of Acquired Resistance to Cancer Therapy by Sequencing of Plasma DNA", Nature (doi: 10.1038/nature12065), 2013, 6 pgs.

Muse, Spencer V. , "Examining rates and patterns of nucleotide substitution in plants", Plant Molecular Biology 42: 25-43, 2000.

Myers, Chad L. et al., "Accurate Detection of Aneuploidies in Array CGH and Gene Expression Microarray Data", Bioinformatics, 20(18), 2004, 3533-3543.

Nagalla, S. R. et al., "Proteomic Analysis of Maternal Serum in Down Syndrome: Identification of Novel Protein Biomarkers", Journal of Proteome Research, vol. 6, Mar. 21, 2007, 1245-1257.

Nakamura, N. et al., "Ex Vivo Liver Perfusion with Arterial Blood from a Pig with Ischemic Liver Failure", Artificial Organs, vol. 23, No. 2, 1999, 153-160.

Namlos, H. M. et al., "Noninvasive Detection of ctDNA Reveals Intratumor Heterogeneity and Is Associated with Tumor Burden in Gastrointestinal Stromal Tumor", Molecular Cancer Therapeutics, vol. 17, No. 11, 2018, 2473-2480.

Nannya, Yasuhito et al., "A Robust Algorithm for Copy Number Detection Using High-density Oligonucleotide Single Nucleotide Polymorphism Genotyping Arrays", Cancer Res., 65, 14, 2005, 6071-6079.

Narayan, A. et al., "Ultrasensitive measurement of hotspot mutations in tumor DNA in blood using error-suppressed multiplexed deep sequencing", Cancer Research, vol. 72, No. 14, Jul. 15, 2012, 3492-3498.

Natera, Inc., "Declaration of Sandra L. Haberny", May 16, 2019, 3 pages.

Natera, Inc., "Defendant Natera, Inc.'S Invalidity Contentions Under Patent L.R. 3-3; Document Production Accompanying Invalidity Contentions Under Patent L.R. 3-4", Aug. 20, 2018, 17 pages.

Natera, Inc., "Exhibit 8 EHRICH Invalidity Chart", Aug. 20, 2018, 16 pages.

Natera, Inc., "Exhibits A-H to Haberny Declaration", May 16, 2019, 192 pages.

Natera, Inc., "Motion to Dismiss", May 16, 2019, 2 pages.

Natera, Inc., "Natera Inc.'S First Amended Answer, Affirmative Defenses and Counterclaims", Aug. 16, 2018, 28 pages.

Natera, Inc., "Natera, Inc.'S Supplemental Objections and Response to Plaintiff Illumina, Inc.'s Interrogatory No. 8", Mar. 20, 2019, 29 pages.

Natera, Inc., "Opening Brief in Support of Motion to Dismiss", May 16, 2019, 26 pages.

Natera, Inc., "Petitioner Reply Per Board Order of Nov. 2, 2018 (Paper No. 10)", Nov. 9, 2018, 8 pgs.

National Institutes of Health, , "Genetics Home Reference: Your Guide to Understanding Genetic Conditions", Feb. 28, 2014, 2 pgs.

Nawroz, H et al., "Microsatellite Alterations in Serum DNA of Head and Neck Cancer Patients", Nature Medicine, vol. 2, No. 9, Sep. 1996, 1035-1037.

NCBI, "Blast of AAAAAAAAATTTAAAAAAAAATTT", 2015, 9 pages.

NCBI, "db SNP rs2056688", 2015, 3 pages.

NCBI, "dbSNP record for rs1294331", Retrieved from the Internet: <URL: www.ncbi.nlm.nih.gov/snp/?term=rs 1294331 >, 2019, 2 pgs.

NCBI, "dbSNP record for rs1872575", Retrieved from the Internet: <URL: www.ncbi.nlm.nih.gov/snp/?term=rs1872575, 2019, 2 pgs.

NCBI, "dbSNP record for rs2362450", Retrieved from the Internet: <URL: www.ncbi.nlm.nih.gov/snp/?term=rs2362450>, 2019, 1 pg.

NCBI, "dbSNP record for rs2384571", Retrieved from the Internet: <URL: www.ncbi.nlm.nih.gov/snp/?term=rs2384571>, 2019, 2 pgs.

NCBI, "dbSNP record for rs2498982", Retrieved from the Internet: <URL: www.ncbi.nlm.nih.gov/snp/?term=rs2498982>, 2019, 3 pgs.

NCBI, "dbSNP record for rs3731877", Retrieved from the Internet: <URL: www.ncbi.nlm.nih.gov/snp/?term=rs3731877>, 2019, 2 pgs.

Neve, B. et al., "Rapid SNP Allele Frequency Determination in Genomic DNA Pools by Pyrosequencing", BioTechniques, vol. 32, No. 5, May 1, 2002, 1138-1142.

New England Biolabs, "NucleicAcids, Linkers and Primers: Random Primers", 1998/99Catalog, 1998, 121 and 284.

(56) References Cited

OTHER PUBLICATIONS

Newman, A. M. et al., "Integrated digital error suppression for improved detection of circulating tumor DNA", Nature Biotechnology, vol. 34, No. 5, May 2016, 547-555.

Ng, et al., "Multiplex Sequencing of Paired-end Ditags (MS-PET): A Strategy for the Ultra-high-throughput Analysis of Transcriptomes and Genomes", Nucleic Acids Research, vol. 34, No. 12, Jul. 13, 2006, 1-10.

Ng, S. B. et al., "Individualised multiplexed circulating tumour DNA assays for monitoring of tumour presence in patients after colorectal cancer surgery", Scientific Reports, vol. 7, No. 40737, Jan. 19, 2017, 11 pages.

Nguyen-Dumont, T. , "A high-plex PCR approach for massively parallel sequencing", BioTechniques, vol. 55, No. 2, Aug. 2013, 69-74.

Nicolaides, K. et al., "Noninvasive Prenatal Testing for Fetal Trisomies in a Routinely Screened First-Trimester Population", American Journal of Obstetrics (article in press), 207, 2012, 1.e1-1.e6.

Nicolaides, K.H et al., "Validation of Targeted Sequencing of Single-Nucleotide Polymorphisms for Non-Invasive Prenatal Detection of Aneuploidy of Chromosomes 13, 18, 21, X, and Y", Prenatal Diagnosis, 33, 2013, 575-579.

Nicolaides, Kypros H. et al., "Prenatal Detection of Fetal Triploidy from Cell-Free DNA Testing in Maternal Blood", Fetal Diagnosis and Therapy, 2013, 1-6.

Nilsson, M. et al., "Padlock Probes: Circularizing Oligonucleotides for Localized DNA Detection", Science, vol. 265, Sep. 10, 1994, 2085-2088.

Nishigaki, K. et al., "Random PCR-Based Genome Sequencing: A Non-Divide-and-Conquer Strategy", DNA Research, vol. 7, 2000, 19-26.

Nishiwaki, Morie et al., "Genotyping of Human Papillomaviruses by a Novel One-step Typing Method With Multiplex PCR and Clinical Applications", Journal of Clinical Microbiology, vol. 46, 2008, pp. 1161-1168.

Norton, S. E. et al., "A stabilizing reagent prevents cell-free DNA contamination by cellular DNA in plasma during blood sample storage and shipping as determined by digital PCR", Clin Biochem., vol. 46, No. 15, Oct. 2013, 1561-1565.

Nui, A. et al., "The Functional Integrity of a Normothermic Perfusion System Using Artificial Blood in Pig Liver", Journal of Surgical Research, Vo. 131, 2006, 189-198.

Nygren, et al., "Quantification of Fetal DNA by Use of Methylation-Based DNA Discrimination", Clinical Chemistry 56:10 1627-1635 (2010).

O'Connell, G. C. et al., "High Interspecimen Variability in Nucleic Acid Extraction Efficiency Necessitates the Use of Spike-In Control for Accurate qPCR-based Measurement of Plasma Cell-Free DNA Levels", Lab Medicine, vol. 48, 2017, 332-338.

Oeth, et al., "iPLEX™ Assay: Increased Plexing Efficiency and Flexibility for MassARRAY System Through Single Base Primer Extension with Mass-Modified Terminators", Sequenom Application Note Doc. No. 8876-006, Apr. 28, 2005, 1-12.

Ogino, S. et al., "Bayesian Analysis and Risk Assessment in Genetic Counseling and Testing", Journal of Molecular Diagnostics, 6 (1), 2004, 9 pgs.

Ohara, O et al., "One-sided Polymerase Chain Reaction: The Amplification of cDNA", Proceedings of the National Academy of Sciences, vol. 86, 1989, 5673-5677.

Ohira, T. et al., "Tumor volume determines the feasibility of cell-free DNA sequencing for mutation detection in non-small cell lung cancer", Cancer Science, vol. 107, 2016, 1660-1666.

Ohsawa, M. et al., "Prenatal Diagnosis of Two Pedigrees of Fukuyama Type Congenital Muscular Dystrophy by Polymorphism Analysis", The Health and Welfare Ministry, 1994, 5 pgs.

Okou, et al., "Microarray-based Genomic Selection for High-throughput Resequencing", Nature Methods, vol. 4, No. 11, Oct. 14, 2007, 907-909.

Okou, David T. et al., "Combining Microarray-based Genomic Selection (MGS) with the Illumina Genome Analyzer Platform to Sequence Diploid Target Regions", Annals of Human Genetics, vol. 73, No. 5, Aug. 6, 2009, 502-513.

Olerup, O. et al., "HLA-DR typing by PCR amplification with sequence-specific primers (PCR-SSP) in 2 hours: an alternative to serological DR typing in clinical practice including donor-recipient matching in cadaveric transplantation", Tissue Antigens, vol. 39, No. 5, May 1992, 225-235.

Oliphant, A. et al., "Bead.Array™ Technology: Enabling an Accurate, Cost-Effective Approach to High-Throughput Genotyping", Bio Techniques, vol. 32, Jun. 2002, S56-S6.

Olivarius, S et al., "High-throughput Verification of Transcriptional starting Sites by Deep-RACE", Bio Techniques, vol. 46, No. 2, Feb. 2009, 130-132.

Olive, M. et al., "Characterization of the DiFi Rectal Carcinoma Cell Line Derived from a Familial Adenomatous Polyposis Patient", In Vitro Cellular & Developmental Biology, vol. 29A, No. 3, Part 1, Mar. 1993, 239-248.

Oliver, Dwight H. et al., "Use of Single Nucleotide Polymorphisms (SNP) and Real-time Polymerase Chain Reaction for Bone Marrow Engraftment Analysis", The Journal of Molecular Diagnostics, vol. 2, No. 4, Nov. 1, 2000, 202-208.

Olivier, et al., "The Invader Assay for SNP Genotyping", Mutation Research, vol. 573, No. 1-2, Jun. 3, 2005, 103-110.

Olney, R. S. et al., "Chorionic Villus Sampling and Amniocentesis: Recommendations for Prenatal Counseling", MMWR: Recommendations and Reports, 44(RR-9), Jul. 21, 1995, 1-12.

O'malley, R. et al., "An adapter ligation-mediated PCR method for high-throughput mapping of T-DNA inserts in the Arabidopsis genome", Nat. Protoc., 2, 2007, 2910-2917.

Orozco A.F., et al., "Placental Release of Distinct DNA-Associated Micro-Particles into Maternal Circulation: Reflective of Gestation Time and Preeclampsia", Placenta, 30, 2009, 891-897.

Orsouw, et al., "Complexity Reduction of Polymorphic Sequences (Crops): A Novel Approach for Large-scale Polymorphism Discovery in Complex Genomes", Plos One, vol. 11:e1172, Nov. 14, 2017, 1-10.

Owczarzy, Richard et al., "Melting Temperatures of Nucleic Acids: Discrepancies in Analysis", Biophysical Chemistry, vol. 117, 2005, pp. 207-215.

Ozawa, Makiko et al., "Two Families with Fukuyama Congenital Muscular Dystrophy that Underwent In Utero Diagnosis Based on Polymorphism Analysis", Clinical Muscular Dystrophy: Research in Immunology and Genetic Counseling—FY 1994 Research Report, (including copy of text in Japanese), 1994, 8.

Paez, Guillermo J. et al., "Genome coverage and sequence fidelity of Φ29 polymerase-based multiple strand displacement whole genome amplification", Nucleic Acids Research, 32(9), 2004, 1-11.

Page, S. L. et al., "Chromosome Choreography: The Meiotic Ballet", Science, 301, 2003, 785-789.

Paik, P. K. et al., "Next-Generation Sequencing of Stage IV Squamous Cell Lung Cancers Reveals an Association of P13K Aberrations and Evidence of Clonal Heterogeneity in Patients with Brain Metastases", Cancer Discovery, vol. 5, Apr. 30, 2015, 610-621.

Pakstis, et al., "Candidate SNPs for a Universal Individual Identification Panel", Human Genetics, vol. 121, No. 3-4,, Feb. 27, 2007, 305-317.

Pakstis, et al., "SNPS for Individual Identification", Forensic Science International, vol. 1, May 22, 2008, 479-481.

Palka-Santini, Maria et al., "Large Scale Multiplex PCR Improves Pathogen Detection by DNA Microarrays", BMC Microbiology, vol. 9, No. 1, 2009, 14 pages.

Palomaki, G. E. et al., "DNA sequencing of maternal plasma to detect Down syndrome: An international clinical validation study", Genetics In Medicine, vol. 13, No. 1, Nov. 2011, 913-920.

Palomaki, Glenn et al., "DNA Sequencing of Maternal Plasma Reliably Identifies Trisomy 18 and Trisomy 13 as Well as Down Syndrome: an International Collaborative Study", Genetics in Medicine, 2012, 10.

Palomaki, Glenn E. et al., "DNA Sequencing of Maternal Plasma to Detect Down Syndrome: An International Clinical Validation Study", Genetics in Medicine (pre-print version), 13, 2011, 8 pgs.

(56)        References Cited

OTHER PUBLICATIONS

Panjkovich, Alejandro et al., "Comparison of Different Melting Temperature Calculation Methods for Short DNA Sequences", Bioinformatics, vol. 21, 2005, pp. 711-722.

Papadopoulou, E. et al., "Cell-Free DNA and RNA in Plasma as a New Molecular Marker for Prostate Cancer", Oncology Research, vol. 14, 2004, 439-445.

Papageorgiou, Elisavet A. et al., "Fetal-Specific DNA Methylation Ratio Permits Noninvasive Prenatal Diagnosis of Trisomy 21", Nature Medicine (advance online publication), 17, 2011, 5 pgs.

Parameswaran, P. et al., "A pyrosequencing-tailored nucleotide barcode design unveils opportunities for large-scale sample multiplexing", Nucleic Acids Research, vol. 35, No. 19, Oct. 11, 2007, 9 pages.

Parker, A. V. et al., "The Effect of Sodium Citrate on the Stimulation of Polymorphonuclear Leukocytes", Investigative Ophthalmology & Visual Science, vol. 26, 1985, 1257-1261.

Paruzynski, A. et al., "Genome-wide high-throughput integrome analyses by nrLAM-PCR and next-generation sequencing", Nature Protocols, vol. 5, No. 8, Jul. 8, 2010, 1379-1395.

Pask, R. et al., "Investigating the utility of combining 29 whole genome amplification and highly multiplexed single nucleotide polymorphism BeadArray TM genotyping", BMC Biotechnology, vol. 4, No. 15, Jul. 27, 2004, 8 pages.

Pastinen, T. et al., "Minisequencing: A Specific Tool for DNA Analysis and Diagnostics on Oligonucleotide Arrays", Genome Research, vol. 7, 1997, 606-614.

Pathak, A. et al., "Circulating Cell-Free DNA in Plasma/Serum of Lung Cancer Patients as a Potential Screening and Prognostic Tool", Clinical Chemistry, 52, 2006, 1833-1842.

Patil, N. et al., "Blocks of Limited Haplotype Diversity Revealed by High-Resolution Scanning of Human Chromosome 21", Science, vol. 294, Nov. 23, 2001, 1719-1723.

Paunio, T. et al., "Preimplantation diagnosis by whole-genome amplification, PCR amplification, and solid-phase minisequencing of blastomere DNA", Clinical Chemistry, vol. 42, No. 9, 1996, 1382-1390.

PCT/US2006/045281, "International Preliminary Report on Patentability", mailed May 27, 2008, 1 pg.

PCT/US2006/045281, "International Search Report and Written Opinion", mailed Sep. 28, 2007, 7 pgs.

PCT/US2008/003547, "International Search Report", mailed Apr. 15, 2009, 5 pgs.

PCT/US2009/034506, "International Search Report", mailed Jul. 8, 2009, 2 pgs.

PCT/US2009/045335, "International Search Report", mailed Jul. 27, 2009, 1 pg.

PCT/US2009/052730, "International Search Report", mailed Sep. 28, 2009, 1 pg.

PCT/US2010/050824, "International Search Report", mailed Nov. 15, 2010, 2 pgs.

PCT/US2011/037018, , "International Search Report", mailed Sep. 27, 2011, 2 pgs.

PCT/US2011/061506, "International Search Report", mailed Mar. 16, 2012, 1 pgs.

PCT/US2011/066938, "International Search Report", mailed Jun. 20, 2012, 1 pg.

PCT/US2012066339, , "International Search Report", mailed Mar. 5, 2013, 1 pg.

PCT/US2013/028378, "International Search Report and Written Opinion", mailed May 28, 2013, 11 pgs.

PCT/US2013/57924, "International Search Report and Written Opinion", mailed Feb. 18, 2014, 8 pgs.

PCT/US2014/051926, "International Search Report and Written Opinion", Dec. 9, 2014, 3 pgs.

Pearson, K. , "On the criterion that a given system of deviations from the probable in the case of a correlated system of variables is such that it can be reasonably supposed to have arisen from random sampling", Philosophical Magazine Series 5, vol. 50, Issue 302, 1900, 157-175.

Pelizzari, C. A. et al., "Quantitative analysis of DNA array autoradiographs", Nucleic Acids Research, vol. 28, No. 22, 2000, 4577-4581.

Pena, Sergio D.J et al., "Paternity Testing in the DNA Era", Trends in Genetics, 10, 6, 1994, 204-209.

Perakis, S. et al., "Advances in Circulating Tumor DNA Analysis", Advances in Clinical Chemistry, vol. 80, 2017, 73-153.

Pergament, E. et al., "Single-Nucleotide Polymorphism-Based Non-invasive Prenatal Screening in a High-Risk and Low-Risk Cohort", Obstetrics & Gynecology, vol. 124, No. 2, Part 1, Aug. 2014, 210-218 + Appendices.

Perkel, Jeffrey M. , "Overcoming the Challenges of Multiplex PCR", Biocompare Editorial Article, 2012, 1-5.

Perry, George H. et al., "The Fine-Scale and Complex Architecture of Human Copy-Number Variation", The American Journal of Human Genetics, 82, 2008, 685-695.

Pertl, B. et al., "Detection of Male and Female Fetal DNA in Maternal Plasma by Multiplex Fluorescent Polymerase Chain Reaction Amplification of Short Tandem Repeats", Hum. Genet., 106, 2000, 45-49.

Peters, D. , "List of Materials Considered By David Peters, Ph.D.", Jun. 13, 2019, 2 pages.

Peters, David P. et al., "Noninvasive Prenatal Diagnosis of a Fetal Microdeletion Syndrome", New England Journal of Medicine, 365(19), 2011, 1847-1848.

Pfaffl, Michael W. , "Quantification Strategies in Real-time PCR", A-Z of quantitative PCR, 2004, pp. 87-112.

Pfaffl, Michael W. , "Relative Expression Software Tool (REST©) for Group-Wise Comparison and Statistical Analysis of Relative Expression Results in real-Time PCR", Nucleic Acids Research, 30(9), 2002, 10 pgs.

Philip, J. et al., "Late First-Trimester Invasive Prenatal Diagnosis: Results of an International Randomized Trial", American College of Obstetricians and Gynecologists, vol. 103, No. 6, Jun. 2004, 1164-1173.

Phillips, C. et al., "Resolving Relationship Tests that Show Ambiguous STR Results Using Autosomal SNPs as Supplementary Markers", Forensic Science International: Genetics 2, 2008, 198-204.

Pinard, et al., "Assessment of Whole Genome Amplification-induced Bias Through High-throughput, Massively Parallel Whole Genome Sequencing", BMC Genomics, vol. 7:216, Aug. 23, 2006, 1-21.

Pirker, C. et al., "Whole Genome Amplification for CGH Analysis: Linker-Adapter PCR as the Method of Choice for Difficult and Limited Samples", Cytometry Part A, vol. 61A, 2004, 26-34.

Podder, Mohua et al., "Robust Sn P genotyping by multiplex PCR and arrayed primer", BMC Medical Genomics, 1(5), 2008, 1-15.

Poirier, K. et al., "Maternal mosaicism for mutations in the ARX gene in a family with X linked mental retardation", Human Genetics, vol. 118, Aug. 3, 2005, 45-48.

Pont-Kingdon, G. et al., "Rapid Detection of Aneuploidy (Trisomy 21) by Allele Quantification Combined with Melting Curves Analysis of Single-Nucleotide Polymorphism Loci", Clinical Chemistry, vol. 49, No. 7, 2003, 1087-1094.

Poon, L. L. et al., "Differential DNA Methylation between Fetus and Mother as a Strategy for Detecting Fetal DNA in Maternal Plasma", Clinical Chemistry, vol. 48, No. 1, 2002, 35-41.

Popova, T. et al., "Genome Alteration Print (GAP): a tool to visualize and mine complex cancer genomic profiles obtained by SNP arrays", Genome Biology, vol. 10, R128, Nov. 11, 2009, 1-14.

Porreca, Gregory J et al., "Multiplex Amplification of Large Sets of Human Exons", Nature Methods, 4, (advance online publication), 2007, 6.

Pourmand, et al., "Multiplex Pyrosequencing", Nucleic Acid Research, vol. 30, No. 7, Apr. 1, 2002, 1-5.

Prabhu, et al., "Overlapping Pools for High-throughput Targeted Resequencing", Genome Research, vol. 19, May 15, 2009, 1254-1261.

Price, T.S. et al., "SW-ARRAY: a dynamic programming solution for the identification of copy-number changes in genomic DNA using array comparative genome hybridization data", Nucleic Acids Research, vol. 33, No. 11, Jun. 16, 2005, 3455-3464.

(56)　　　　　References Cited

OTHER PUBLICATIONS

Primdahl, H. et al., "Allelic Imbalances in Human Bladder Cancer: Genome-Wide Detection With High-Density Single-Nucleotide Polymorphism Arrays", Journal of the National Cancer Institute, vol. 94, No. 3, Feb. 6, 2002, 216-223.

Profitt, J et al., "Isolation and Characterisation of Recombination Events Involving Immunoglobulin Heavy Chain Switch Regions in Multiple Myeloma Using Long Distance Vectorette PCR (Ldv-pcr)", Leukemia, vol. 13, No. 7, Jul. 1999, 1100-1107.

Puszyk, William M. et al., "Noninvasive Prenatal Diagnosis of Aneuploidy Using Cell-free Nucleic Acids in Maternal Blood: Promises and Unanswered Questions", Prenatal Diagnosis, vol. 28, No. 1, Nov. 16, 2007, 1-6.

Qiagen, "QIAamp DNA Mini Kit and QIAamp DNA Blood Mini Kit Handbook", QIAamp DNA Mini Kit and QIAamp DNA Blood Mini Kit Handbook, Feb. 2003 ("Qiagen (2003)"), 2003, 68 pages.

Qin, Z. S. et al., "Partition-Ligation-Expectation-Maximization Algorithm for Haplotype Inference with Single-Nucleotide Polymorphisms", Am. J. Hum Genet., vol. 71, 2002, 1242-1247.

Quan, P. C. et al., "Studies on the mechanism of NK cell lysis", The Journal of Immunology, vol. 128, 1982, 1786-1791.

Quinlan, M. P. , "Amniocentesis: Indications and Risks", American Medical Association Journal of Ethics: Virtual Mentor, vol. 10, No. 5, May 2008, 304-306.

Quinn, G. P. et al., "Experimental Design and Data Analysis for Biologists", Graphical Exploration of Data, 2002, 64-67.

Rabinowitz, et al., "Accurate Prediction of HIV-1 Drug Response from the Reverse Transcriptase and Protease Amino Acid Sequences Using Sparse Models Created by Convex Optimization", Bioinformatics, 22, 5, 2006, 541-549.

Rabinowitz, M. , "A System and Method for Integrating, Validating and Applying Genetic and Clinical Data to Enhance Medical Decisions", Nov. 29, 2005, 155 pgs.

Rabinowitz, Matthew et al., "Origins and rates of aneuploidy inhuman blastomeres", Fertility and Sterility, vol. 97, No. 2, Feb. 2012, 395-401.

Rabinowitz, Matthew et al., "Non-Invasive Prenatal Aneuploidy Testing of Chromosomes 13, 18, 21, X, and Y Using Targeted Sequencing of Polymorphic Loci", The American Society of Human Genetics, meeting poster, 2012, 1 pg.

Rachlin, J. et al., "Computational tradeoffs in multiplex PCR assay design for SNP genotyping", BMC Genomics, vol. 6, No. 102, Jul. 25, 2005, 11 pages.

Ragoussis, J. , "Genotyping Technologies for Genetic Research", Annual Review of Genomics and Human Genetics, vol. 10 (1), Sep. 1, 2009, 117-133.

Rahmann, Sven et al., "Mean and variance of the Gibbs free energy of oligonucleotides in the nearest neighbor model under varying conditions", Bioinformatics, 20(17), 2004, 2928-2933.

Raindance Technologies, "Multiplexing with RainDrop Digital PCR", Application Note, 2013, 2 pgs.

Raindance Technologies, et al., "RainDance Technologies Introduces the RDT 1000", RainDance Technologies, Nov. 12, 2008.

Rava, Richard P. et al., "Circulating Fetal Cell-Free DNA Fraction Differ in Autosomal Aneuploidies and Monosomy X", Clinical Chemistry, 60(1), (papers in press), 2013, 8 pgs.

Ravipati, Goutham et al., "Comparison of Sensitivity, Specificity, Positive Predictive Value, and Negative Predictive Value of Stress Testing Versus 64-Multislice Coronary Computed Tomography Angiography in Predicting Obstructive Coronary Artery Disease Diagnosed by Coronary Angiogr", The American Journal of Cardiology, Coronary Artery Disease. Vol. 101, Issue 6, Mar. 15, 2008, 774-775.

Rechitsky, Svetlana et al., "Preimplantation Genetic Diagnosis with HLA Matching", Reproductive Bio Medicine Online, 9, 2, 2004, 210-221.

Reeves, R. H. et al., "Too much of a good thing: mechanisms of gene action in Down syndrome", Trends in Genetics, vol. 17, No. 2, Feb. 2, 2001, 83-88.

Reinert, T. et al., "Analysis of circulating tumour DNA to monitor disease burden following colorectal cancer surgery", Gut, vol. 65, 2016, 625-634.

Renwick, P. et al., "Proof of Principle and First Cases Using Preimplantation Genetic Haplotyping—A Paradigm Shift for Embryo Diagnosis", Reproductive BioMedicine Online, 13 (1), 2006, 110-119.

Rhoads, A. et al., "PacBio Sequencing and Its Applications", Genomics Proteomics Bioinformatics, vol. 13, Nov. 2, 2015, 278-289.

Ricciotti, Hope, "Eating by Trimester", Online]. Retrieved from Internet:<http://www.youandyourfamily.com/article.php?story=Eating+by+Trimester>, 2014, 3.

Riley, D. E. , "DNA Testing: An Introduction for Non-Scientists an Illustrated Explanation", Scientific Testimony: An Online Journal, http://www.scientific.org/tutorials/articles/riley/riley.html, Apr. 6, 2005, 22 pages.

Riva, F., "Patient-Specific Circulating Tumor DNA Detection during Neoadjuvant Chemotherapy in Triple-Negative Breast Cancer", Clinical Chemistry, vol. 63, No. 3, 2017, 691-699.

Robertson, G. et al., "Genome-wide profiles of STAT1 DNA association using chromatin immunoprecipitation and massively parallel sequencing", Nature Methods, vol. 4, No. 8, Aug. 2007, 651-657.

Roche Diagnostics, et al., "Versatile Nucleic Acid Purification", MagnaPure Manual, Feb. 3, 2012.

Rogaeva, E. et al., "The Solved and Unsolved Mysteries of the Genetics of Early-Onset Alzheimer's Disease", NeuroMolecular Medicine, vol. 2, 2002, 1-10.

Roman, B. L. et al., "Non-Radioisotopic AFLP Method Using PCR Primers Fluorescently Labeled with CyA 5", BioTechniques, vol. 26, Feb. 1999, 236-238.

Roper, Stephen M. et al., "Forensic Aspects of DNA-Based Human Identity Testing", Journal of Forensic Nursing, 4, 2008, 150-156.

Rosado, J. A. et al., "Tyrosine kinases activate store-mediated Ca2+ entry in human platelets through the reorganization of the actin cytoskeleton", Biochem. J., vol. 351, 2000, 429-437.

Rosen, D. R. et al., "Mutations in Cu/Zn superoxide dismutase gene are associated with familial amyotrophic lateral sclerosis", Nature, vol. 362, Mar. 4, 1993, 59-62.

Ross, P. et al., "Quantitative Approach to Single-Nucleotide Polymorphism Analysis Using MALDI-TOF Mass Spectrometry", BioTechniques, vol. 29, Sep. 2000, 620-629.

Rothberg, et al., "The Development and Impact of 454 Sequencing", Nature Biotechnology, vol. 26, No. 10, Oct. 9, 2008, 1117-1124.

Roux, K., "Optimization and Troubleshooting in PCR", PCR Methods Appl. 4, 1995, 185-194.

Rozen, Steve et al., "Primer3 on the WWW for General Users and for Biologis Programmers", Methods in Molecular Biology, 132: Bioinformatics Methods and Protocols, 1999, 365-386.

Ruano, G. et al., "Haplotype of multiple polymorphisms resolved by enzymatic amplification of single DNA molecules", Proc. Nati. Acad. Sci. USA, vol. 87, Aug. 1990, 6296-6300.

Rubio, J. M. et al., "Semi-nested, Multiplex Polymerase Chain Reaction for Detection of Human Malaria Parasites and Evidence of Plasmodium Vivax Infection in Equatorial Guinea", The American Journal of Tropical Medicine and Hygiene, vol. 60, 1999, pp. 183-187.

Ruschendorf, et al., "Alohomora: A Tool For Linkage Analysis Using 10K SNP Array Data", Bioinformatics Applications Notes, vol. 21, No. 9, Jan. 12, 2005, 2123-2125.

Russell, L. M., "X Chromosome Loss and Ageing", Cytogenetic and Genome Res., 116, 2007, 181-185.

Ryan, A. et al., "Informatics-Based, Highly Accurate, Noninvasive Prenatal Paternity Testing", Genetics in Medicine (advance online publication), 2012, 5 pgs.

Ryan, B. M. et al., "A prospective study of circulating mutant KRAS2 in the serum of patients with colorectal neoplasia: strong prognostic indicator in postoperative follow up", Gut, vol. 52, 2003, 101-108.

Rychlik, et al., "Optimization of the annealing temperature for DNA amplification in vitro", Nucleic Acids Research, 18(21), 1990, 6409-6412.

(56)    References Cited

OTHER PUBLICATIONS

Sahota, A., "Evaluation of Seven PCR-Based Assays for the Analysis of Microchimerism", Clinical Biochemistry, vol. 31, No. 8., 1998, 641-645.

Sahukhal, G. S. et al., "msaABCR operon positively regulates biofilm development by repressing proteases and autolysis in Staphylococcus aureus", FEMS Microbiology Letters, vol. 362, No. 4, 2015, 1-10.

Saito, H. et al., "Prenatal DNA diagnosis of a single-gene disorder from maternal plasma", The Lancet, vol. 356, Sep. 30, 2000, 1170.

Saker, A. et al., "Genetic characterisation of circulating fetal cells allows non-invasive prenatal diagnosis of cystic fibrosis", Prenatal Diagnosis, vol. 26, Jul. 11, 2006, 906-916.

Samango-Sprouse, C. et al., "SNP-Based Non-Invasive Prenatal Testing Detects Sex Chromosome Aneuploidies with High Accuracy", Prenatal Diagnosis, 33, 2013, 1-7.

Samura, O. et al., "Diagnosis of Trisomy 21 in Fetal Nucleated Erythrocytes from Maternal Blood by Use of Short Tandem Repeat Sequences", Clinical Chemistry, vol. 47, No. 9, 2001, 1622-1626.

Sanchez, C. et al., "New insights into structural features and optimal detection of circulating tumor DNA determined by single-strand DNA analysis", Nature Partner Journals, vol. 3, No. 31, Nov. 23, 2018, 12 pgs.

Sander, Chris, "Genetic Medicine and the Future of Health Care", Science, 287(5460), 2000, 1977-1978.

Sanger, et al., "Nucleotide Sequence of Bacteriophage Lambda DNA", Journal of Molecular Biology, vol. 162, No. 4, Dec. 25, 1982, 729-773.

Santalucia, J. et al., "The Thermodynamics of DNA Structural Motifs", Annu. Rev. Biophys. Biomol. Struct., 33, 2004, 415-440.

Santalucia, John J.R et al., "Improved Nearest-Neighbor Parameters for Predicting DNA Duplex Stability", Biochemistry, 35, 1996, 3555-3562.

Santalucia, Jr., J. , "Physical Principles and Visual-OMP Software for Optimal PCR Design", Methods in Molecular Biology, vol. 402, 2007, 3-33.

Sasabe, Yutaka, "Genetic Diagnosis of Gametes and Embryos Resulting from ART", Japanese Journal of Fertility and Sterility, vol. 46, No. 1, 2001, 43-46.

Scarpa, A. et al., "Molecular Typing of Lung Adenocarcinoma on Cytological Samples Using a Multigene Next Generation Sequencing Panel", PLOS One, vol. 8, No. 11, Nov. 13, 2013, 6 pgs.

Schaaf, C. P. et al., "Copy Number and SNP Arrays In Clinical Diagnostics", Annu. Rev. Genomics Hum. Genet., vol. 12, 2011, 25-51.

Scheet, P. et al., "A Fast and Flexible Statistical Model for Large-Scale Population Genotype Data: Applications to Inferring Missing Genotypes and Haplotypic Phase", The American Journal of Human Genetics, vol. 78, Apr. 2006, 629-644.

Schmitt, M. W. et al., "Detection of ultra-rare mutations by next-generation sequencing", PNAS, vol. 109, No. 36, Sep. 4, 2012, 14508-14513.

Schoske, R et al., "Multiplex PCR Design Strategy used for the Simultaneous Amplification of 10 Y Chromosome Short Tandem Repeat (STR) Loci", Analytical and Bioanalytical Chemistry, vol. 375, 2003, 333-343.

Schoumans, J et al., "Detection of chromosomal imbalances in children with idiopathic mental retardation by array based comparative genomic hybridisation (array—CGH)", JMed Genet, 42, 2005, 699-705.

Schubert, "Picking out prenatal DNA", Nature Medicine, vol. 10, No. 785, Aug. 2004, 1 page.

Schwarzenbach, H. et al., "Cell~free nucleic acids as biomarkers in cancer patients", Nature Reviews: Cancer, vol. 11, Jun. 2011, 426-437.

Schwarzenbach, H. et al., "Detection and Characterization of Circulating Microsatellite-DNA in Blood of Patients with Breast Cancer", Ann. N.Y. Acad. Sci., vol. 1022, 2004, 25-32.

Schwarzenbach, H. et al., "Evaluation of cell-free tumour DNA and RNA in patients with breast cancer and benign breast disease", Molecular BioSystems, vol. 7, 2011, 2848-2854.

Sebat, Jonathan et al., "Strong Association of De Novo Copy Number Mutations with Autism", Science, 316, 2007, 445-449.

Sehnert, A. et al., "Optimal Detection of Fetal Chromosomal Abnormalities by Massively Parallel DNA Sequencing of Cell-Free Fetal DNA from Maternal Blood", Clinical Chemistry (papers in press), 57 (7), 2011, 8 pgs.

Seppo, A. et al., "Detection of circulating fetal cells utilizing automated microscopy: potential for noninvasive prenatal diagnosis of chromosomal aneuploidies", Prenatal Diagnosis, vol. 28, Jul. 22, 2008, 815-821.

Sermon, Karen et al., "Preimplantation genetic diagnosis", The Lancet, Lancet Limited. 363(9421), 2000, 1633-1641.

Servin, B et al., "MOM: A Program to Compute Fully Informative Genotype Frequencies in Complex Breeding Schemes", Journal of Heredity, vol. 93, No. 3, Jan. 1, 2002 (Jan. 1, 2002), pp. 227-228.

Sham, P. et al., "DNA Pooling: A Tool for Large-Scale Association Studies", Nature Reviews Genetics, vol. 3, Nov. 2002, 862-871.

Shapero, M. H. et al., "Mara: A Novel Approach for Highly Multiplexed Locus-specific SNP Genotyping Using High-density DNA Oligonucleotide Arrays", Nucleic Acids Research, vol. 32, No. 22, 2004, 1-9.

Sharples, et al., "Diagnostic Accuracy of Coronary Angiography and Risk Factors for Post-heart-transplant Cardiac Allograft Vasculopathy", Transplantation, vol. 76, No. 4, Aug. 27, 2003, 679-682.

Shaw-Smith, et al., "Microarray Based Comparative Genomic Hybridisation (array—CGH) Detects Submicroscopic Chromosomal Deletions and Duplications in Patients with Learning Disability/Mental Retardation and Dysmorphic Features", J. Med. Genet., 41, 2004, 241-248.

Shen, et al., "High-quality DNA sequence capture of 524 disease candidate genes", High-quality DNA sequence capture of 524 disease candidate genes, Proceedings of the National Academy of Sciences, vol. 108, No. 16, Apr. 5, 2011 (Apr. 5, 2011), pp. 6549-6554.

Shen, R. et al., "High-throughput SNP genotyping on universal bead arrays", Mutation Research, vol. 573, Feb. 11, 2005, 70-82.

Shen, Zhiyong, "MPprimer: a program for reliable multiplex PCR primer design", BMC Bioinformatics 2010, 11:143, 1-7.

Shendure, J. et al., "Accurate Multiplex Polony Sequencing of an Evolved Bacterial Genome", Science, Nov. 30, 2007, 18-24.

Shendure, J. et al., "Next-generation DNA sequencing", Nature Biotechnology, vol. 26, No. 10, Oct. 2008, 1135-1145.

Sherlock, J et al., "Assessment of Diagnostic Quantitative Fluorescent Multiplex Polymerase Chain Reaction Assays Performed on Single Cells", Annals of Human Genetics, 62, 1, 1998, 9-23.

Shi, H. et al., "Melanoma whole-exome sequencing identifies V600E B-RAF amplification-mediated acquired B-RAF inhibitor resistance", Nature Communications, vol. 3, No. 724, Mar. 6, 2012, 8 pages.

Shinozaki, M. et al., "Utility of Circulating B-RAF DNA Mutation in Serum for Monitoring Melanoma Patients Receiving Biochemotherapy", Clin Cancer Res, vol. 13, No. 7, Apr. 1, 2007, 2068-2074.

Shiroguchi, K. et al., "Digital RNA sequencing minimizes sequence-dependent bias and amplification noise with optimized single-molecule barcodes", PNAS, vol. 109, No. 4, Jan. 24, 2012, 1347-1352.

Shokralla, S. et al., "Next-generation DNA barcoding: using next-generation sequencing to enhance and accelerate DNA barcode capture from single specimens", Molecular Ecology Resources, vol. 14, 2014, 892-901.

Short, N. J. et al., "Targeted next-generation sequencing of circulating cell-free DNA vs bone marrow in patients with acute myeloid leukemia", Blood Advances, vol. 4, No. 8, Apr. 23, 2020, 1670-1677.

Shyamala, Venkatakrishna et al., "Genome Walking by Single-Specific-Primer Polymerase Chain Reaction: SSP-PCR", Gene, vol. 84, 1989, pp. 1-8.

(56)        References Cited

OTHER PUBLICATIONS

Siebert, P. D. et al., "An improved PCR method for walking in uncloned genomic DNA", Nucleic Acids Research, vol. 23, No. 6, 1995, 1087-1088.

Sigdel, T. et al., "Plasma Donor-Derived Cell-Free DNA Quantification by massively multiplex PCR Distinguishes Kidney Transplant Acute Rejection", Transplantation, vol. 102, No. 7S, Jul. 2018, S178-S179.

Sigdel, T. K. et al., "Optimizing Detection of Kidney Transplant Injury by Assessment of Donor-Derived Cell-Free DNA via Massively Multiplex PCR", Journal of Clinical Medicine, vol. 8, No. 19, Dec. 23, 2018, 17 pages.

Simpson, J. et al., "Fetal Cells in Maternal Blood: Overview and Historical Perspective", Annals New York Academy of Sciences, 731, 1994, 1-8.

Singh, Vinayak K. et al., "PCR Primer Design", Molecular Biology Today, vol. 2, 2001, pp. 27-32.

Sint, Daniela et al., "Advances in Multiplex PCR: Balancing Primer Efficiencies and Improving Detection Success", Methods in Ecology and Evolution, 3, 2012, 898-905.

Sivertsson, A. et al., "Pyrosequencing as an Alternative to Single-Strand Conformation Polymorphism Analysis for Detection of N-ras Mutations in Human Melanoma Metastases", Clinical Chemistry, vol. 48, No. 12, 2002, 2164-2170.

Slater, Howard et al., "High-Resolution Identification of Chromosomal Abnormalities Using Oligonucleotide Arrays Containing 116,204 SNPs", Am. J. Hum. Genet., 77, 5, 2005, 709-726.

Smith, et al., "Rapid Whole-genome Mutational Profiling using Next-generation Sequencing Technologies", Genome Research, vol. 18, Sep. 4, 2008, 1638-1642.

Smith, James F. et al., "Cell-free Fetal DNA in Maternal Plasma", Neo Reviews, vol. 9, No. 8, Aug. 1, 2008, e332-e337.

Snijders, Antoine et al., "Assembly of Microarrays for Genome-Wide Measurement of DNA Copy Number", Nature Genetic, 29, 2001, 263-264.

Snyder, T. M. et al., "Universal noninvasive detection of solid organ transplant rejection", PNAS, vol. 108, No. 15, Apr. 12, 2011, 6229-6234.

Societies Related to Genetic Med, , "Guideline related to genetic examination", Japanese Society for Genetic Counseling, Japanese Society for Gene Diagnosis and Therapy, Japan Society of Obstetrics and Gynecology, 2003, 2-15.

Solexa, "Application Note: DNA Sequencing", 2006, 1-2.

Solomon, M. J. et al., "Formaldehyde-mediated DNA-protein crosslinking: A probe for in vivo chromatin structures", Proc. Natl. Acad. Sci. USA, vol. 82, 1985, 6470-6474.

Sorenson, G. D. et al., "Soluble Normal and Mutated DNA Sequences from Single-Copy Genes in Human Blood", Cancer Epdemiology, Biomarkers & Prevention, vol. 3, Jan./Feb. 1994, 67-71.

Sourceforge.net, "Primer3", 2009, 1 pg.

Sparks, A. et al., "Non-Invasive Prenatal Detection and Selective Analysis of Cell-Free DNA Obtained from Maternal Blood: Evaluation for Trisomy 21 and Trisomy 18", American Journal of Obstetrics & Gynecology 206, 2012, 319.e1-319.e9.

Sparks, Andrew B. et al., "Selective Analysis of Cell-Free DNA in Maternal Blood for Evaluation of Fetal Trisomy", Prenatal Diagnosis, 32, 2012, 1-7.

Spencer, K. et al., "Maternal serum levels of dimeric inhibin A in pregnancies affected by trisomy 21 in the first trimester", Prenatal Diagnosis, vol. 21, 2001, 441-444.

Spencer, K. et al., "Maternal serum levels of total activin-A in first-trimester trisomy 21 pregnancies", Prenatal Diagnosis, vol. 21, 2001, 270-273.

Spertini, D. et al., "Screening of Transgenic Plants by Amplification of Unknown Genomic DNA Flanking T-DNA", BioTechniques, vol. 27, Aug. 1999, 308-314.

Spes, et al., "Diagnostic And Prognostic Value of Serial Dobutamine Stress Echocardiography for Noninvasive Assessment of Cardiac Allograft Vasculopathy: A Comparison With Coronary Angiography and Intravascular Ultrasound", Circulation, vol. 100, No. 5, Aug. 3, 1999, 509-515.

Spindler, K.L. G. et al., "Cell-free DNA in healthy individuals, noncancerous disease and strong prognostic value in colorectal cancer", International Journal of Cancer, vol. 135, 2014, 2984-2991.

Spindler, K.-L. G. et al., "Cell-Free DNA in Metastatic Colorectal Cancer: A Systematic Review and Meta-Analysis", The Oncologist, vol. 22, 2017, 1049-1055.

Spiro, Alexander et al., "A Bead-Based Method for Multiplexed Identification and Quantitation of DNA Sequences Using Flow Cytometry", Applied and Environmental Microbiology, 66, 10, 2000, 4258-4265.

Spits, C et al., "Optimization and Evaluation of Single-Cell Whole Genome Multiple Displacement Amplification", Human Mutation, 27(5), 496-503, 2006.

Srinivasan, et al., "Noninvasive Detection of Fetal Subchromosome Abnormalities via Deep Sequencing of Maternal Plasma", The American Journal of Human Genetics 92, 167-176, Feb. 7, 2013.

Stephens, M. et al., "Accounting for Decay of Linkage Disequilibrium in Haplotype Inference and Missing-Data Imputation", Am. J. Hum. Genet., vol. 76, 2005, 449-462.

Stephens, Mathews et al., "A Comparison of Bayesian Methods for Haplotype Reconstruction from Population Genotype Data", Am. J. Hum. Genet.,73, 2003, 1162-1169.

Stevens, Robert et al., "Ontology-Based Knowledge Representation for Bioinformatics", Briefings in Bioinformatics, 1, 4, 2000, 398-414.

Stewart, C. M. et al., "Circulating cell-free DNA for non-invasive cancer management", Cancer Genetics, vol. 228-229, 2018, 169-179.

Stewart, S. et al., "Revision of the 1990 Working Formulation for the Standardization of Nomenclature in the Diagnosis of Heart Rejection", The Journal of Heart and Lung Transplantation, vol. 24, No. 11, Nov. 2005, 1710-1720.

Steyerberg, E.W et al., "Application of Shrinkage Techniques in Logistic Regression Analysis: A Case Study", Statistica Neerlandica, 55(1), 2001, 76-88.

Stiller, et al., "Direct Multiplex Sequencing (DMPS)—A Novel Method For Targeted High-thoroughput Sequencing of Ancient and Highly Degraded DNA", Genome Research, vol. 19, No. 10, Jul. 27, 2009, 1843-1848.

Stolerman, Elliot S. et al., "Haplotype structure of the ENPP1 Gene and Nominal Association of the K121Q missense single nucleotide polymorphism with glycemic traits in the Framingham Heart Study", Diabetes, vol. 57, Issue 7, Jul. 1, 2008, 1971-1977.

Stone, J. P. et al., "Ex Vivo Normothermic Perfusion Induces Donor-Derived Leukocyte Mobilization and Removal Prior to Renal Transplantation", Kidney Int Rep., vol. 1, No. 4, Aug. 6, 2016, 230-239.

Strom, C. et al., "Three births after preimplantation genetic diagnosis for cystic fibrosis with sequential first and second polar body analysis", American Journal of Obstetrics and Gynecology, 178 (6), 1998, 1298-1306.

Strom, Charles M. et al., "Neonatal Outcome of Preimplantation Genetic Diagnosis by Polar Body Removal: The First 109 Infants", Pediatrics, 106( 4), 2000, 650-653.

Stroun, Maurice et al., "Prehistory of the Notion of Circulating Nucleic Acids in Plasma/Serum (CNAPS): Birth of a Hypothesis", Ann. N.Y. Acad. Sci., 1075, 2006, 10-20.

Su, S.Y. et al., ""Inferring combined CNV/SNP haplotypes from genotype data"", Bioinformatics, vol. 26, No. 11,1, Jun. 1, 2010, 1437-1445.

Su, Z. et al., "A Platform for Rapid Detection of Multiple Oncogenic Mutations With Relevance to Targeted Therapy in Non-Small-Cell Lung Cancer", The Journal of Molecular Diagnostics,, vol. 13, No. 1, Jan. 2011, 74-84.

Sun, Guihua et al., "SNPs in human miRNA genes affect biogenesis and function", RNA, 15(9), 2009, 1640-1651.

Swarup, V. et al., "Circulating (cell-free) nucleic acids—A promising, non-invasive tool for early detection of several human diseases", FEBS Letters, vol. 581, 2007, 795-799.

(56) References Cited

OTHER PUBLICATIONS

Sweet-Kind Singer, J. A. et al., "Log-penalized linear regression", IEEE International Symposium on Information Theory, 2003. Proceedings, 2003, 286.

Swinkels, D. W. et al., "Effects of Blood-Processing Protocols on Cell-free DNA Quantification in Plasma", Clinical Chemistry, vol. 49, No. 3, 2003, 525-526.

Syvanen, A.C. , "Toward genome-wide SNP genotyping", Nature Genetics Supplement, vol. 37, Jun. 2005, S5-S10.

Taback, B. et al., "Quantification of Circulating DNA in the Plasma and Serum of Cancer Patients", Ann. N.Y. Acad. Sci, vol. 1022, 2004, 17-24.

Takala, et al., "A High-throughput Method for Quantifying Alleles and Haplotypes of the Malaria Vaccine Candidate Plasmodium Falciparum Merozoite Surface Protein-1 19 kDa", Malaria Journal, vol. 5:31, Apr. 20, 2006, 1-10.

Takano, T. et al., "Epidermal Growth Factor Receptor Gene Mutations and Increased Copy Numbers Predict Gefitinib Sensitivity in Patients With Recurrent Non-Small-Cell Lung Cancer", Journal of Clinical Oncology, vol. 23, No. 28, Oct. 1, 2005, 6829-6837.

Takara Biomedicals, , "Competitive PCR Guide", Lit. # L0126, Aug. 1999, 9 pages.

Takashima, Y. et al., "Expansion-contraction of photoresponsive artificial muscle regulated by host-guest interactions", Nature Communications, vol. 3, No. 1270, Dec. 11, 2012, 8 pages.

Taliun, D. et al., "Efficient haplotype block recognition of very long and dense genetic sequences", BMC Bioinformatics, vol. 15 (10), 2014, 1-18.

Tamura, et al., "Sibling Incest and formulation of paternity probability: case report", Legal Medicine, 2000, vol. 2, p. 189-196.

Tang, et al., , Multiplex fluorescent PCR for noninvasive prenatal detection of fetal-derived paternally inherited diseases using circulatory fetal DNA in maternal plasma, Eur J Obstet Gynecol Reprod Biol, 2009, v.144, No. 1, p. 35-39.

Tang, N. et al., "Detection of Fetal-Derived Paternally Inherited X-Chromosome Polymorphisms in Maternal Plasma", Clinical Chemistry, 45 (11), 1999, 2033-2035.

Tebbutt, S. J. et al., "Microarray genotyping resource to determine population stratification in genetic association studies of complex disease", BioTechniques, vol. 37, Dec. 2004, 977-985.

Ten Bosch, J. , "Keeping Up With the Next Generation Massively Parallel Sequencing in Clinical Diagnostics", Journal of Molecular Diagnostics, vol. 10, No. 6, 2008, 484-492.

Tewhey, R. et al., "Microdroplet-based PCR enrichment for large-scale targeted sequencing", Nature Biotechnology, vol. 27, No. 11, Nov. 2009, 1025-1031.

Tewhey, R. et al., "The importance of phase information for human genomics", Nature Reviews Genetics, vol. 12, No. 3, Mar. 1, 2011, 215-223.

Thavarajah, R. et al., "Chemical and physical basics of routine formaldehyde fixation", Journal of Oral and Maxillofacial Pathology, vol. 16, No. 3, 2012, 400-405.

The Bump Message Boards, , The Bump (Panorama Test, attached), Jul. 1, 2013, 8 pages.

The International Hapmap Consort, , "The International HapMap Project", Nature, vol. 426, Dec. 18, 2003, 789-796.

Thermofisher Scientific, , "Ion AmpliSeq Cancer Hotspot Panel v2", Retrieved from the Internet: https://tools.thermofisher.com/content/sfs/brochures/Ion-AmpliSeq-Cancer-Hotspot-Panel-Flyer.pdf, 2015, 2 pages.

Thomas, M.R et al., "The Time of Appearance and Disappearance of Fetal DNA from the Maternal Circulation", Prenatal Diagnosis, 15, 1995, 641-646.

Thompson, J. C. et al., "Detection of Therapeutically Targetable Driver and Resistance Mutations in Lung Cancer Patients by Next-Generation Sequencing of Cell-Free Circulating Tumor DNA", Clin Cancer Res, vol. 22, No. 23, Dec. 1, 2016, 5772-5782.

Thornton, Brenda et al., "Real-time Pcr (qPCR) Primer Design Using Free Online Software", Biochemistry and Molecular Biology Education, vol. 39, 2011, pp. 145-154.

Tiersch, T. R. et al., "Reference Standards for Flow Cytometry and Application in Comparative Studies of Nuclear DNA Content", Cytometry, vol. 10, Mar. 21, 1989, 706-710.

Tong, et al., "Diagnostic Developments Involving Cell-free (Circulating) Nucleic Acids", Clinica Chimica Acta, vol. 363, No. (1-2), Aug. 26, 2005, 187-196.

Tong, Yu et al., "Noninvasive Prenatal Detection of Fetal Trisomy 18 by Epigenetic Allelic Ratio Analysis in Maternal Plasma: Theoretical and Empirical Considerations", Clinical Chemistry, 52(12), 2006, 2194-2202.

Tong, Yu K. et al., "Noninvasive Prenatal Detection of Trisomy 21 by Epigenetic-Genetic Chromosome-Dosage Approach", Clinical Chemistry, 56(1), 2010, 90-98.

Toshikazu, et al., "Estimation of Haplotype Frequencies, Linkage-disequilibrium Measures, and Combination of Haplotype Copies in Each Pool by Use of Pooled DNA Data", American Journal of Human Genetics, vol. 72, Jan. 17, 2003, 384-398.

Tounta, G. et al., "Non-invasive prenatal diagnosis using cell-free fetal nucleic acids in maternal plasma: Progress overview beyond predictive and personalized diagnosis", EPMA Journal, vol. 2, Issue 2, 2011, 163-171.

Tounta, G. et al., "A Multiplex PCR for Non-invasive Fetal RHD Genotyping Using Cell-free Fetal DNA", in vivo, vol. 25, 2011, 411-418.

Treff, N. R. et al., "Single Cell Whole Genome Amplification Technique Significantly Impacts the Accuracy and Precision of Microarray Based 23 Chromosome Aneuploidy Screening", Poster Presentations Preimplantation Genetic Diagnosis, vol. 88, Supplement 1, Sep. 1, 2007, S231.

Troeger, C. et al., "Approximately Half of the Erythroblasts in Maternal Blood are of Fetal Origin", Molecular Human Reproduction, vol. 5, No. 12, Dec. 1, 1999, 1162-1165.

Troutt, et al., "Ligation-anchored PCR: A Simple Amplification Technique with Single-sided Specificity", Proceedings of the National Academy of Sciences, vol. 89, Oct. 1992, 9823-9825.

Troyanskaya, Olga G. et al., "A Bayesian Framework for Combining Heterogeneous Data Sources for Gene Function Prediction (in Saccharomyces cerevisiae)", PNAS, 100(14), 2003, 8348-8353.

Tsang, Jason C. et al., "Circulating Nucleic Acids in Plasma/Serum", Pathology, vol. 39, No. 2, Apr. 1, 2007, 197-207.

Tsangaris, G. T. et al., "Proteomic analysis of amniotic fluid in pregnancies with Down syndrome", Proteomics, vol. 6, 2006, 4410-4419.

Tsui, N. B. et al., "Systematic micro-array based identification of placental mRNA in maternal plasma: towards non-invasive prenatal gene expression profiling", J. Med. Genet, vol. 41, 2004, 461-467.

Tsui, Nancy B.Y et al., "Non-Invasive Prenatal Detection of Fetal Trisomy 18 by RNA-SNP Allelic Ratio Analysis Using Maternal Plasma SERPINB2 mRNA: A Feasibility Study", Prenatal Diagnosis, 29, 2009, 1031-1037.

Tu, J. et al., "Pair-barcode high-throughput sequencing for large-scale multiplexed sample analysis", BMC Genomics, vol. 13, No. 43, Jan. 25, 2012, 1-9.

Tufan, N L. et al., "Analysis of Cell-Free Fetal DNA from Maternal Plasma and Serum Using a Conventional Multiplex PCR: Factors Influencing Success", The Turkish Journal of Medical Sciences, vol. 35, 2005, 85-92.

Turner, E. et al., "Massively Parallel Exon Capture and Library-Free Resequencing Across 16 Genomes", Nature Methods, 6 (5), 2009, 315-316.

Tuzcu, et al., "Intravascular Ultrasound Evidence of Angiographically Silent Progression in Coronary Atherosclerosis Predicts Long-term Morbidity and Mortality After Cardiac Transplantation", The American Journal of Cardiology, vol. 45, No. 9, May 3, 2005, 1538-1542.

Tynan, J. A. et al., "Restriction Enzyme-Mediated Enhanced Detection of Circulating Cell-Free Fetal DNA in Maternal Plasma", The Journal of Molecular Diagnostics, vol. 13, No. 4, Jul. 2011, 382-389.

Tzimagiorgis, G. et al., "Recovering circulating extracellular or cell-free RNA from bodily fluids", Cancer Epidemiology, vol. 35, 2011, 580-589.

(56)　　　　　References Cited

OTHER PUBLICATIONS

Umetani, N. et al., "Increased Integrity of Free Circulating DNA in Sera of Patients with Colorectal or Periampullary Cancer: Direct Quantitative PCR for ALU Repeats", Clinical Chemistry, vol. 52, No. 6, 2006, 1062-1069.

Urbaniak, S. J. et al., "RhD haemolytic disease of the fetus and the newborn", Blood Reviews, vol. 14, 2000, 44-61.

Urbanova, M. et al., "Circulating Nucleic Acids as a New Diagnostic Tool", Cellular & Molecular Biology Letters, vol. 15, 2010, 242-259.

Vallone, P. M. et al., "A multiplex allele-specific primer extension assay for forensically informative SNPs distributed throughout the mitochondrial genome", Int J Legal Medicine, vol. 118, Feb. 4, 2004, 147-157.

Vallone, Peter , "AutoDimer: a Screening Tool for Primer-Dimer and Hairpin Structures", Bio Techniques, 37, 2004, 226-231.

Vallone, Peter M. et al., "Demonstration of Rapid Multiplex PCR Amplification Involving 16 Genetic Loci", Forensic Science International: Genetics, vol. 3, 2008, pp. 42-45.

Van Den Oever, J. M. et al., "Single Molecule Sequencing of Free DNA from Maternal Plasma for Noninvasive Trisomy 21 Detection", Clinical Chemistry, vol. 58, No. 4, 2012, 699-706.

Van Uitert, I. et al., "The influence of different membrane components on the electrical stability of bilayer lipid membranes", Biochimica et Biophysica Acta, vol. 1798, 2010, 21-31.

Vanneste, Marion et al., "Functional Genomic Screening Independently Identifies CUL3 as a Mediator of Vemurafenib Resistance via Src-RAC1 Signaling Axis", Frontiers in Oncology, vol. 10, 2020, 16 pages.

Varley, Katherine Elena et al., "Nested Patch PCR Enables Highly Multiplexed Mutation Discovery in Candidate Genes", Genome Res., 18(11), 2008, 1844-1850.

Verlaan, et al., "Allele-specific Chromatin Remodeling in the ZPBP22/GSDMB/ORMDL3 Locus Associated with the Risk of Asthma and Autoimmune Disease", The American Journal of Human Genetics, vol. 85, No. 3, Sep. 11, 2009, 377-393.

Verlaan, et al., "Targeted Screening of Cis-Regulatory Variation in Human Haplotypes", Genome Research, vol. 19, No. 1, Jan. 1, 2009, 118-127.

Verlinsky, Y. et al., "Over a Decade of Experience with Preimplantation Genetic Diagnosis", Fertility and Sterility, 82 (2), 2004, 302-303.

Vlaminck, I. D. et al., "Circulating Cell-Free DNA Enables Noninvasive Diagnosis of Heart Transplant Rejection", Sci Transl Med., vol. 6, No. 241, Jun. 18, 2018, 26 pages.

Voelkerding, et al., "Next-generation Sequencing: From Basic Research to Diagnostics", Clinical Chemistry, vol. 55, No. 4, Apr. 1, 2009, 641-658.

Vogelstein, B. et al., "Digital PCR", Proc. Natl. Acad. Sci. USA, vol. 96, Aug. 1999, 9236-9241.

Von Ahsen, Nicolas et al., "Oligonucleotide Melting Temperatures under PCR Conditions: Nearest-Neighbor Corrections for Mg2+, Deoxynucleotide Triphosphate, and Dimethyl Sulfoxide Concentrations with Comparison to Alternative Empirical Formulas", Clinical Chemistry, vol. 47, 2001, pp. 1956-1961.

Von Eggeling, F. et al., "Applications of Random PCR", Cellular and Molecular Biology, vol. 41, No. 5, 1995, 653-670.

Wagner, Jasenka et al., "Non-Invasive Prenatal Paternity Testing from Maternal Blood", Int. J. Legal Med., 123, 2009, 75-79.

Wang, D. G. et al., "Large-Scale Identification, Mapping, and Genotyping of Single-Nucleotide Polymorphisms in the Human Genome", Science, vol. 280, May 15, 1998, 1077-1082.

Wang, Eric et al., "Gestational Age and Maternal Weight Effects on Fetal Cell-Free DNA in Maternal Plasma", Prenatal Diagnosis, 33, 2013, 662-666.

Wang, Hui-Yun et al., "A genotyping system capable of simultaneously analyzing >1000 single nucleotide polymorphisms in a haploid genome", Genome Res., 15, 2005, 276-283.

Wang, J. et al., "Genome-wide Single-Cell Analysis of Recombination Activity and De Novo Mutation Rates in Human Sperm", Cell, vol. 150, Jul. 20, 2012, 402-412.

Wang, S. et al., "Potential Clinical Significance of a Plasma-Based KRAS Mutation Analysis in Patients with Advanced Non-Small Cell Lung Cancer", Clin Cancer Res, vol. 16, No. 4, Feb. 15, 2010, 1324-1330.

Wang, T.L. et al., "Digital karyotyping", PNAS, vol. 99, No. 25, Dec. 10, 2002, 16156-16161.

Wang, W.-P. et al., "Multiplex single nucleotide polymorphism genotyping by adapter ligation-mediated allele-specific amplification", Analytical Biochemistry, vol. 355, May 5, 2006, 240-248.

Wang, Yuker et al., "Allele quantification using molecular inversion probes (MIP)", Nucleic Acids Research, vol. 33, No. 21, Nov. 28, 2005, 14 pgs.

Wapner, R. et al., "Chromosomal Microarray Versus Karyotyping for Prenatal Diagnosis", The New England Journal of Medicine, 367 (23), 2012, 2175-2184.

Wapner, R. et al., "First-Trimester Screening for Trisomies 21 and 18", The New England Journal of Medicine, vol. 349, No. 15, Oct. 9, 2003, 1405-1413.

Wapner, R. J. et al., "Expanding the scope of noninvasive prenatal testing: detection of fetal microdeletion syndromes", American Journal of Obstetrics & Gynecology, vol. 212, Dec. 17, 2014, 1.e1-1.e9.

Wartell, Roger M. et al., "Thermal Denaturation of DNA Molecules: A Comparison of Theory with Experiment", Physics Reports, vol. 126, 1985, pp. 67-107.

Wasson, Jon et al., "Assessing Allele Frequencies of Single Nucleotide Polymorphisms in DNA Pools by Pyrosequencing Technology", BioTechniques, vol. 32, No. 5, May 1, 2002, 1144-1152.

Watkins, N. et al., "Thermodynamic contributions of single internal rA •dA, rC • dC, rG • dG and rU • dT mismatches in RNA/DNA duplexes", Nucleic Acids Research, 9 (5),, 2010, 1894-1902.

Watt, Heather L. , "Sex Diagnosis of Preimplantation Porcine Embryos through PCR Amplification of the Sry Gene", Sex Diagnosis of Preimplantation Porcine Embryos Through PCR Amplification of the SRY Gene (1998) ("Watt (1998)"), 1998, 151 pages.

Wei, C. et al., "Detection and Quantification by Homogeneous PCR of Cell-free Fetal DNA in Maternal Plasma", Clinical Chemistry, vol. 47, No. 2, 2001, 336-338.

Wei, Ting et al., "Novel Approaches to Mitigate Primer Interaction and Eliminate Inhibitors in Multiplex PCR, Demonstrated Using an Assay for Detection of three Strawberry Viruses", Journal of Virological Methods, vol. 151, 2008, pp. 132-139.

Weiss, C. A. , "Chapter 8: Confidence Intervals for One Population Mean", Introductory Statistics, Sixth Edition, 2002, 340-381.

Wellnhofer, et al., "Angiographic Assessment of Cardiac Allograft Vasculopathy: Results of a Consensus Conference of the Task Force for Thoracic Organ Transplantation of the German Cardiac Society", Transplant International, vol. 23, No. 11, Aug. 19, 2010, 1094-1104.

Wells, D , "Microarray for Analysis and Diagnosis of Human Embryos", 12th International Congress on Prenatal Diagnosis and Therapy, Budapest, Hungary, 2004, 9-17.

Wells, Dagan , "Advances in Preimplantation Genetic Diagnosis", European Journal of Obstetrics and Gynecology and Reproductive Biology, 115S, 2004, S97-S101.

Wells, Dagan , "Detailed Chromosomal and Molecular Genetic Analysis of Single Cells by Whole Genome Amplification and Comparative Genomic Hybridisation", Nucleic Acids Research, 27, 4, 1999, 1214-1218.

Wen, Daxing et al., "Universal Multiples PCR: A Novel Method of Simultaneous Amplification of Multiple DNA Fragments", Plant Methods, 8(32), Null, 2012, 1-9.

What to Expect Message Boards, , What to Expect (Weird Harmony results), May 1, 2015, 7 pages.

Widlak, P. et al., "Cleavage Preferences of the Apoptotic Endonuclease DFF 40 (Caspase~activated DNase or Nuclease) on Naked DNA and Chromatin Substrates", The Journal of Biological Chemistry, vol. 275, No. 11, Mar. 17, 2000, 8228-8232.

(56)                    References Cited

OTHER PUBLICATIONS

Wiedmann, Ralph T. et al., "SNP Discovery in Swine by Reduced Representation and High Throughput Pyrosequencing", BMC Genetics, vol. 9, Article No. 81, Dec. 4, 2008, 1-7.

Wikipedia, , "Buffy coat", Retrieved from "https://en.wikipedia.orgJw/index.php?title=Buffy_coat&oldid=900992886" Jun. 9, 2019, 2 pgs.

Wikipedia, , "Maximum a posteriori estimation", https://en.wikipedia.org/w/index.php?title=Maximum_a_posteriori_estimat ion&oldid=26878808, [retrieved on Aug. 1, 2017], Oct. 30, 2005, 2 pages.

Wikipedia, "Stimulant", 17 pages.

Wilkening, Stefan et al., "Determination of Allele Frequency in Pooled DNA: Comparison of Three PCR-based Methods", Bio Techniques, vol. 39, No. 6, May 30, 2005, 853-857.

Wilkinson, Sarah T. et al., "Decreased MHC Class II Expression in Diffuse Large B-Cell Lymphoma does not Correlate with CPG Methylation of Ciita Promoters III and IV", Leuk Lymphoma, vol. 50, 2009, pp. 1875-1878.

Wilton, et al., "Birth of a Healthy Infant After Preimplantation Confirmation of Euploidy by Comparative Genomic Hybridization", N. Engl. J. Med., 345(21), 2001, 1537-1541.

Wilton, L. , "Preimplantation Genetic Diagnosis and Chromosome Analysis of Blastomeres Using Comparative Genomic Hybridization", Human Reproduction Update, 11 (1), 2005, 33-41.

Winsor, E. J. et al., "Maternal Cell Contamination in Uncultured Amniotic Fluid", Prenatal Diagnosis, vol. 16, 1996, 49-54.

Witherspoon, David J. et al., "Mobile Element Scanning (Me-scan) by Targeted High-throughput Sequencing", BMC Genomics, vol. 410, 2010, 15 pages.

Wittwer, C. T. et al., "Real-Time Multiplex PCR Assays", Methods, vol. 25, 2001, 430-448.

Wong, K. H. et al., "Multiplex Illumina Sequencing Using DNA Barcoding", Current Protocols in Molecular Biology, vol. 101, Jan. 2013, 7.11.1-7.11.11.

Wong, K. K. et al., "Allelic imbalance analysis by high-density single nucleotide polymorphic allele (SNP) array with whole genome amplified DNA", Nucleic Acids Research, vol. 32, No. 9, May 17, 2004, 8 pages.

Wright, C. et al., "The use of cell-free fetal nucleic acids in maternal blood for non-invasive prenatal diagnosis", Human Reproduction Update, vol. 15, No. 1, 2009, 139-151.

Wright, C. F. et al., "Cell-free fetal DNA and RNA in maternal blood: implications for safer antenatal testing", BMJ, vol. 39, Jul. 18, 2009, 161-165.

Wright, Caroline et al., "Cell-free Fetal Nucleic Acids for Noninvasive Prenatal Diagnosis", PHG Foundation, Jan. 1, 2009, 1-64.

Wu, T.L. et al., "Cell-free DNA: measurement in various carcinomas and establishment of normal reference range", Clinica Chimica Acta, vol. 321, 2002, 77-87.

Wu, Y. Y. et al., "Rapid and/or high-throughput genotyping for human red blood cell, platelet and leukocyte antigens, and forensic applications", Clinica Chimica Acta, vol. 363, 2006, 165-176.

Xia, et al., "Simultaneous Quantitative Assessment of Circulating Cell-free Mitochondrial and Nuclear DNA by Multiplex Real-time PCR", Genetics and Molecular Biology, vol. 32, No. 1, Mar. 1, 2009, 20-24.

Xia, Tianbing et al., "Thermodynamic Parameters for an Expanded Nearest-Neighbor Model for Formation of RNA Duplexes with Watson-Crick Base Pairs", Biochemistry, 37, 1998, 14719-14735.

Xian, et al., "Advances on Circulating Fetal DNA in Maternal Plasma", Chinese Medical Journal, vol. 120, No. 14, Jul. 2, 2007, 1256-1259.

Xie, et al., "CNV-SEQ, A New Method to Detect Copy Number Variation Using Highthroughput Sequencing", BMC Bioinformatics, vol. 10:80, Mar. 6, 2009, 1-9.

Xu, N. et al., "A Mutation in the Fibroblast Growth Factor Receptor 1 Gene Causes Fully Penetrant Normosmic Isolated Hypogonadotropic Hypogonadism", The Journal of Clinical Endocrinology & Metabolism, vol. 92, No. 3, 2007, 1155-1158.

Xu, S. et al., "Circulating tumor DNA identified by targeted sequencing in advanced-stage non-small cell lung cancer patients", Cancer Letters, vol. 370, 2016, 324-331.

Xu, W. et al., "A Novel Universal Primer-Multiplex-PCR Method with Sequencing Gel Electrophoresis Analysis", PLOS One, vol. 7, No. 1, Jan. 17, 2012, 10 pgs.

Xue, et al., "Optimizing the Yield and Utility of Circulating Cell-free DNA From Plasma and Serum", Clinica Chimica Acta, vol. 404, No. 2, Jun. 27, 2009, 100-104.

Yamada, T. et al., "Detection of K-ras Gene Mutations in Plasma DNA of Patients with Pancreatic Adenocarcinoma: Correlation with Clinicopathological Features", Clinical Cancer Research, vol. 4, Jun. 1998, 1527-1532.

Yamada, T. et al., "PrimerStation: a highly specific multiplex genomic PCR primer design server for the human genome", Nucleic Acids Research, vol. 34, 2006, W665-W669.

Yang, Lin et al., "64-MDCT Coronary Angiography of Patients With Atrial Fibrillation: Influence of Heart Rate on Image Quality and Efficacy in Evalution of Coronary Artery Disease", AJR, vol. 193, No. 3, Sep. 1, 2009, 795-801.

Yaron, Y. , "The implications of non-invasive prenatal testing failures: a review of an under-discussed phenomenon", Prenatal Diagnosis, vol. 36, 2016, 391-396.

Yeh, Iwei et al., "Knowledge Acquisition, Consistency Checking and Concurrency Control for Gene Ontology (GO)", Bioinformatics, 19, 2, 2003, 241-248.

Yijen, et al., "Noninvasive Evaluation of Cardiac Allograft Rejection by Cellular and Functional Cardiac Magnetic Resonance", JACC: Cardiovacular Imaging, vol. 2, No. 6, Jun. 1, 2009, 731-741.

Yilmaz, A. et al., "Comparative Evaluation of Left and Right Ventricular Endomyocardial Biopsy", Circulation, vol. 122, No. 9, Aug. 31, 2010, 900-909.

You, Frank M. et al., "BatchPrimer3: A high throughput web application for PCR and sequencing primer design", BMC Bioinformatics, Biomed Central, London, GB, vol. 9, No. 1, May 29, 2008 (May 29, 2008), p. 253.

Yuan, X. et al., "Probability Theory-based SNP Association Study Method for Identifying Susceptibility Loci and Genetic Disease Models in Human Case-Control Data", IEEE Trans Nanobioscience, vol. 9, No. 4, Dec. 2010, 232-241.

Yuanxin, Yan et al., "T-linker-specific Ligation PCR (T-linker Pcr): An Advanced PCR Technique for Chromosome Walking or for Isolation of Tagged DNA Ends", Nucleic Acids Research, vol. 31, No. 12, e68, 2003, 7 pages.

Yung, T. K. et al., "Single-Molecule Detection of Epidermal Growth Factor Receptor Mutations in Plasma by Microfluidics Digital PCR in Non-Small Cell Lung Cancer Patients", Clinical Cancer Research, vol. 15, Mar. 10, 2009, 2076-2084.

Zachariah, R. et al., "Circulating cell-free DNA as a potential biomarker for minimal and mild endometriosis", Reproductive BioMedicine Online, vol. 18, No. 3, Jan. 27, 2009, 4007-411.

Zhang, et al., "Diagnosis of Acute Rejection by Analysis of Urinary DNA of Donor Origin in Renal Transplant Recipients", Transplantation Proceedings, vol. 33, No. 1-2, Feb. 2001, 380-381.

Zhang, et al., "Use of PCR and PCR-SSP for Detection of Urinary Donor-Origin Dna in Renal Transplant Recipients With Acute Rejection", Chinese Medical Journal, vol. 116, No. 2, Feb. 2003, 191-194.

Zhang, J. et al., "Presence of Donor- and Recipient-derived DNA in Cell-free Urine Samples of Renal Transplantation Recipients: Urinary DNA Chimerism", Clinical Chemistry, vol. 45, No. 10, 1999, 1741-1746.

Zhang, Kun et al., "Digital RNA Alleotyping Reveals Tissue-specific and Allele-specific Gene Expression in Human", Nature Methods, vol. 6, No. 8, Jul. 20, 2009, 613-618.

Zhang, L. et al., "Whole genome amplification from a single cell: Implications for genetic analysis", Proc. Nat'l. Acad. Sci. USA, vol. 89, Jul. 1992, 5847-5851.

Zhang, Rui et al., "Quantifying RNA allelic ratios by microfluidic multiplex PCR and sequencing", Nature Methods, 11(1), 2014, 51-56.

(56) References Cited

OTHER PUBLICATIONS

Zhao, et al., "Urinary Thromboxane B2 in Cardiac Transplant Patients as a Screening Method of Rejection", Prostaglandins, vol. 54, No. 6, Dec. 1, 1997, 881-889.

Zhao, Xiaojun. et al., "An Integrated View of Copy Number and Allelic Alterations in the Cancer Genome Using Single Nucleotide Polymorphism Arrays", Cancer Research, 64, 2004, 3060-3071.

Zheng, S. et al., "Whole Genome Amplification Increases the Efficiency and Validity of Buccal Cell Genotyping in Pediatric Populations1", Cancer Epidemiology, Biomarkers & Prevention, vol. 10, Jun. 2001, 697-700.

Zheng, Z et al., "Anchored Multiplex PCR for Targeted Next-generation Sequencing", Nature Medicine, vol. 20, No. 12, Dec. 2014, 1479-1486.

Zhong, X Y. et al., "Detection of Fetal Rhesus D and Sex Using Fetal DNA from Maternal Plasma by Multiplex Polymerase Chain Reaction", British Journal of Obstetrics and Gynaecology, vol. 107, Jun. 2000, 766-769.

Zhong, X. et al., "Risk free simultaneous prenatal identification of fetal Rhesus D status and sex by multiplex real-time PCR using cell free fetal DNA in maternal plasma", Swiss Medical Weekly, vol. 131, Mar. 2001, 70-74.

Zhong, Xiao Y. et al., "Cell-free DNA in Urine: A Marker for Kidney Graft Rejection, but Not for Prenatal Diagnosis ?", Annals of the New York Academy of Sciences, vol. 945, Sep. 1, 2001, 250-257.

Zhou, et al., "Pyrosequencing, A High-throughput Method for Detecting Single Nucleotide Polymorphisms in the Dihydrofolate Reductase and Dihydropteroate Synthetase Genes of Plasmodiym Falciparum", Journal of Clinical Microbiology, vol. 44, No. 11, Nov. 1, 2006, 3900-3910.

Zhou, W. et al., "Counting Alleles Reveals a Connection Between Chromosome 18q Loss and Vascular Invasion", Nature Biotechnology, 19, 2001, 78-81.

Zhou, W. et al., "Counting alleles to predict recurrence of early-stage colorectal cancers", The Lancet, vol. 359, Jan. 19, 2002, 219-225.

Zimmer, et al., "Transplant Coronary Artery Disease", JACC: Cardiovascular Interventions, vol. 3, No. 4, Apr. 1, 2010, 367-377.

Zimmermann, et al., "Noninvasive Prenatal Aneuploidy Testing of Chromosomes 13, 18, 21 X, and Y, Using targeted Sequencing of Polymorphic Loci", Prenatal Diagnosis, 32, 2012, 1-9.

Zimmermann, B. , "Declaration Under 37 CFR 1.32", filed in U.S. Appl. No. 14/171,587, filed Feb. 3, 2014, 4 pgs.

Zimmermann, B. et al., "Digital PCR: a powerful new tool for noninvasive prenatal diagnosis?", Prenatal Diagnosis, vol. 28, Nov. 10, 2008, 1087-1093.

Zimmermann, B. , "Noninvasive prenatal aneuploidy testing of chromosomes 13, 18, 21, X, and Y, using targeted sequencing of polymorphic loci, Supplemental Information", Prenatal Diagnosis, vol. 32, 2012, 7 pages.

Zimmermann, B. et al., "Novel Real-Time Quantitative PCR Test for Trisomy 21", Clinical Chemistry, vol. 48, No. 2, 2002, 362-363.

Zimmermann, B. et al., "Optimized Real-Time Quantitative PCR Measurement of Male Fetal DNA in Maternal Plasma", Clinical Chemistry, vol. 51, No. 9, 2005, 1598-1604.

Zimmermann, B. et al., "Real-Time Quantitative Polymerase Chain Reaction Measurement of Male Fetal DNA in Maternal Plasma", Methods in Molecular Medicine, vol. 132, 2007, 43-49.

Zimmermann, B. et al., "Use of Real-Time Polymerase Chain Reaction for the Detection of Fetal Aneuploidies", Methods in Molecular Biology, vol. 336, Feb. 2006, 83-100.

Zlotogora, J. , "Penetrance and expressivity in the molecular age", Genetics in Medicine, vol. 5, No. 5, 2003, 347-352.

Chan K.C.A., et al., "Size Distributions of Maternal and Fetal DNA in Maternal Plasma," Clinical Chemistry, 2004, vol. 50, No. 1, pp. 88-92.

Costa J-M., et al., "Fetal RHD Genotyping in Maternal Serum during the First Trimester of Pregnancy," British Journal of Haematology, 2002, vol. 119, pp. 255-260.

Croft D.T., Jr., et al., "Performance of Whole-Genome Amplified DNA Isolated from Serum and Plasma on High-Density Single Nucleotide Polymorphism Arrays," Journal of Molecular Diagnostics, May 2008, vol. 10, No. 3, pp. 249-257.

Daniels G., et al., "Fetal Blood Group Genotyping from DNA from Maternal Plasma: An Important Advance in the Management and Prevention of Haemolytic disease of the Fetus and Newbornm," Vox Sanguinis, 2004, vol. 87, pp. 225-232.

Goessl C. et al., "DNA Alterations in Body Fluids as Molecular Tumor Markers for Urological Malignancies," European Urology, 2002, vol. 41, pp. 668-676.

Gormally E., et al., "Amount of DNA in Plasma and Cancer Risk: A Prospective Study," International Journal of Cancer, Sep. 20, 2004, vol. 111, No. 5, DOI: 10.1002/ijc.20327, pp. 746-749.

Gormally E., et al., "Circulating Free DNA in Plasma or Serum as Biomaker of Carcinogenesis: Practical Aspects and Biological Significance," Mutation Research, 2007, vol. 635, pp. 105-117.

Jung K., et al., "Increased Cell-free DNA in Plasma of Patients with Metastatic Spread in Prostate Cancer," Cancer Letters, 2004, vol. 205, pp. 173-180.

Kittler R., et al., "A Whole Genome Amplification Method to Generate Long Fragments from Low Quantities of Genomic DNA," Analytical Biochemistry, 2002, vol. 300, pp. 237-244.

Li Y., et al., "Biochemical and Clinical Diagnostic Aspects of Circulating Nucleic Acids," Dissertation, 2005, 103 Pages.

*Natera Inc.* v. *CareDx, Inc.*, Memorandum Opinion: Case 1:20-cv-00038-CFC-CJB, United States District Court for the District of Delaware, Feb. 24, 2025, pp. 1-21.

*Natera Inc.* v. *NeoGenomics Laboratories, Inc.*, Memorandum Opinion and Order: Case 1:23-cv-00629-CCE-JLW, United States District Court for the Middle District of North Carolina, Aug. 28, 2025, pp. 1-16.

Puszyk W.M., "Epigenetics of Cell-free Plasma Dna for Non-invasive Prenatal Diagnosis of Fetal Aneuploidies," Diss. University of Warwick, Sep. 2008, 199 Pages.

Tamkovich S.N., et al., "Circulating Nucleic Acids in Blood of Healthy Male and Female Donors," Clinical Chemistry, Jul. 2005, vol. 51, No. 7, pp. 1317-1319, PubMed PMID: 15976134.

Tungwiwat W., et al., Non-Invasive Fetal Sex Determination using a Conventional Nested PCR Analysis of Fetal DNA in Maternal Plasma, Clinica Chimica Acta, 2003, vol. 334, No. 1-2, pp. 173-177.

Wagner F.F., et al., "RHD Gene Deletion Occurred in the Rhesus box," Blood, Jun. 15, 2000, vol. 95, No. 12, pp. 3662-3668.

* cited by examiner

Sample 1: 20 Loci; 2 Runs per locus. 0.3ng per well. Ave Std Dev 0.597

Difference in Ct Crossover of Taqman Assay per SNP measured in Cycle Number

Sample 0: Mean 26.640 and Std 1.148

Ct Crossover of qPCR Assay Measured in Cycle Number

SYSTEM AND METHOD FOR CLEANING NOISY GENETIC DATA AND DETERMINING CHROMOSOME COPY NUMBER

CROSS-REFERENCES TO RELATED APPLICATIONS

This application is a continuation of U.S. application Ser. No. 17/164,599, filed Feb. 1, 2021. U.S. application Ser. No. 17/164,599 is a continuation of U.S. application Ser. No. 16/823,127 filed Mar. 18, 2020, now U.S. Pat. No. 11,111, 544. U.S. application Ser. No. 16/823,127 (now U.S. Pat. No. 11,111,544) is a continuation-in-part of U.S. application Ser. No. 16/411,507 filed May 14, 2019, now U.S. Pat. No. 10,597,724, and a continuation-in-part of U.S. application Ser. No. 16/399,911 filed Apr. 30, 2019, now abandoned. U.S. application Ser. No. 16/411,507, now U.S. Pat. No. 10,597,724, is a continuation of U.S. application Ser. No. 16/288,690 filed Feb. 28, 2019, which is a continuation of U.S. application Ser. No. 15/187,555 filed Jun. 20, 2016, now U.S. Pat. No. 10,227,652, which is a continuation of U.S. application Ser. No. 14/092,457 filed Nov. 27, 2013, now U.S. Pat. No. 9,430,611. U.S. application Ser. No. 14/092,457 is a continuation of U.S. application Ser. No. 13/793,133 filed Mar. 11, 2013, now U.S. Pat. No. 9,424, 392, and a continuation of U.S. application Ser. No. 13/793, 186 filed Mar. 11, 2013, now U.S. Pat. No. 8,682,592. Each of U.S. application Ser. No. 13/793,133 and U.S. application Ser. No. 13/793,186 is a continuation of U.S. application Ser. No. 11/603,406 filed Nov. 22, 2006, now U.S. Pat. No. 8,532,930, which claims the benefit of U.S. Prov. Appl. No. 60/739,882 filed Nov. 26, 2005; U.S. Prov. Appl. No. 60/742,305 filed Dec. 6, 2005; U.S. Prov. Appl. No. 60/754, 396 filed Dec. 29, 2005; U.S. Prov. Appl. No. 60/774,976 filed Feb. 21, 2006; U.S. Prov. Appl. No. 60/789,506 filed Apr. 4, 2006; U.S. Prov. Appl. No. 60/817,741 filed Jun. 30, 2006; and U.S. Prov. Appl. No. 60/846,610 filed Sep. 22, 2006. U.S. application Ser. No. 16/399,911 (now abandoned) is a continuation of U.S. application Ser. No. 15/887, 746 filed Feb. 2, 2018, which is a continuation of U.S. application Ser. No. 15/446,778 filed Mar. 1, 2017, now U.S. Pat. No. 10,260,096, which is a continuation of U.S. application Ser. No. 13/949,212 filed Jul. 23, 2013, now U.S. Pat. No. 10,083,273, which is a continuation of U.S. application Ser. No. 12/076,348 filed Mar. 17, 2008, now U.S. Pat. No. 8,515,679. U.S. application Ser. No. 12/076,348 is a continuation-in-part of U.S. application Ser. No. 11/496,982 filed Jul. 31, 2006, now abandoned; a continuation-in-part of U.S. application Ser. No. 11/603,406 filed Nov. 22, 2006, now U.S. Pat. No. 8,532,930; and a continuation-in-part of U.S. application Ser. No. 11/634,550 filed Dec. 6, 2006, now abandoned; and claims the benefit of U.S. Prov. Appl. No. 60/918,292 filed Mar. 16, 2007; U.S. Prov. Appl. No. 60/926,198 filed Apr. 25, 2007; U.S. Prov. Appl. No. 60/932, 456 filed May 31, 2007; U.S. Prov. Appl. No. 60/934,440 filed Jun. 13, 2007; U.S. Prov. Appl. No. 61/003,101 filed Nov. 13, 2007; and U.S. Prov. Appl. No. 61/008,637 filed Dec. 21, 2007. U.S. application Ser. No. 11/634,550 claims the benefit of U.S. Prov. Appl. No. 60/742,305 filed Dec. 6, 2005; U.S. Prov. Appl. No. 60/754,396 filed Dec. 29, 2005; U.S. Prov. Appl. No. 60/774,976 filed Feb. 21, 2006; U.S. Prov. Appl. No. 60/789,506 filed Apr. 4, 2006; U.S. Prov. Appl. No. 60/817,741 filed Jun. 30, 2006; and U.S. Prov. Appl. No. 60/846,610 filed Sep. 22, 2006. U.S. application Ser. No. 11/603,406 is a continuation-in-part of U.S. application Ser. No. 11/496,982 filed Jul. 31, 2006; and also claims the benefit of U.S. Prov. Appl. No. 60/739,882 filed Nov. 26, 2005; U.S. Prov. Appl. No. 60/742,305 filed Dec. 6, 2005; U.S. Prov. Appl. No. 60/754,396 filed Dec. 29, 2005; U.S. Prov. Appl. No. 60/774,976 filed Feb. 21, 2006; U.S. Prov. Appl. No. 60/789,506 filed Apr. 4, 2006; U.S. Prov. Appl. No. 60/817,741 filed Jun. 30, 2006; and U.S. Prov. Appl. No. 60/846,610 filed Sep. 22, 2006. U.S. application Ser. No. 11/496,982 claims the benefit of U.S. Prov. Appl. No. 60/703,415 filed Jul. 29, 2005; U.S. Prov. Appl. No. 60/742,305 filed Dec. 6, 2005; U.S. Prov. Appl. No. 60/754,396 filed Dec. 29, 2005; U.S. Prov. Appl. No. 60/774,976 filed Feb. 21, 2006; U.S. Prov. Appl. No. 60/789, 506 filed Apr. 4, 2006; and U.S. Prov. Appl. No. 60/817,741 filed Jun. 30, 2006. Each of the applications cited above is hereby incorporated by reference in its entirety.

GOVERNMENT LICENSING RIGHTS

This invention was made with government support under Grant No. R44HD054958-02A2 awarded by the National Institutes of Health. The government has certain rights in the invention.

BACKGROUND OF THE INVENTION

Field of the Invention

The invention relates generally to the field of acquiring, manipulating and using genetic data for medically predictive purposes, and specifically to a system in which imperfectly measured genetic data of a target individual are made more accurate by using known genetic data of genetically related individuals, thereby allowing more effective identification of genetic variations, specifically aneuploidy and disease linked genes, that could result in various phenotypic outcomes.

Description of the Related Art

In 2006, across the globe, roughly 800,000 in vitro fertilization (IVF) cycles were run. Of the roughly 150,000 cycles run in the US, about 10,000 involved pre-implantation genetic diagnosis (PGD). Current PGD techniques are unregulated, expensive and highly unreliable: error rates for screening disease-linked loci or aneuploidy are on the order of 10%, each screening test costs roughly $5,000, and a couple is forced to choose between testing aneuploidy, which afflicts roughly 50% of IVF embryos, or screening for disease-linked loci on the single cell. There is a great need for an affordable technology that can reliably determine genetic data from a single cell in order to screen in parallel for aneuploidy, monogenic diseases such as Cystic Fibrosis, and susceptibility to complex disease phenotypes for which the multiple genetic markers are known through whole-genome association studies.

Most PGD today focuses on high-level chromosomal abnormalities such as aneuploidy and balanced transloca-tions with the primary outcomes being successful implantation and a take-home baby. The other main focus of PGD is for genetic disease screening, with the primary outcome being a healthy baby not afflicted with a genetically heritable disease for which one or both parents are carriers. In both cases, the likelihood of the desired outcome is enhanced by excluding genetically suboptimal embryos from transfer and implantation in the mother.

The process of PGD during IVF currently involves extracting a single cell from the roughly eight cells of an early-stage embryo for analysis. Isolation of single cells from human embryos, while highly technical, is now routine in IVF clinics. Both polar bodies and blastomeres have been isolated with success. The most common technique is to remove single blastomeres from day 3 embryos (6 or 8 cell stage). Embryos are transferred to a special cell culture medium (standard culture medium lacking calcium and magnesium), and a hole is introduced into the zona pellucida using an acidic solution, laser, or mechanical techniques. The technician then uses a biopsy pipette to remove a single blastomere with a visible nucleus. Features of the DNA of the single (or occasionally multiple) blastomere are measured using a variety of techniques. Since only a single copy of the DNA is available from one cell, direct measurements of the DNA are highly error-prone, or noisy. There is a great need for a technique that can correct, or make more accurate, these noisy genetic measurements.

Normal humans have two sets of 23 chromosomes in every diploid cell, with one copy coming from each parent. Aneuploidy, the state of a cell with extra or missing chromosome(s), and uniparental disomy, the state of a cell with two of a given chromosome both of which originate from one parent, are believed to be responsible for a large percentage of failed implantations and miscarriages, and some genetic diseases. When only certain cells in an individual are aneuploid, the individual is said to exhibit mosaicism. Detection of chromosomal abnormalities can identify individuals or embryos with conditions such as Down syndrome, Klinefelter's syndrome, and Turner syndrome, among others, in addition to increasing the chances of a successful pregnancy. Testing for chromosomal abnormalities is especially important as the age of a potential mother increases: between the ages of 35 and 40 it is estimated that between 40% and 50% of the embryos are abnormal, and above the age of 40, more than half of the embryos are like to be abnormal. The main cause of aneuploidy is nondisjunction during meiosis. Maternal nondisjunction constitutes 88% of all nondisjunction of which 65% occurs in meiosis 1 and 23% in meiosis II. Common types of human aneuploidy include trisomy from meiosis I nondisjunction, monosomy, and uniparental disomy. In a particular type of trisomy that arises in meiosis II nondisjunction, or M2 trisomy, an extra chromosome is identical to one of the two normal chromosomes. M2 trisomy is particularly difficult to detect. There is a great need for a better method that can detect for many or all types of aneuploidy at most or all of the chromosomes efficiently and with high accuracy.

Karyotyping, the traditional method used for the prediction of aneuploidy and mosaicism is giving way to other more high-throughput, more cost effective methods such as Flow Cytometry (FC) and fluorescent in situ hybridization (FISH). Currently, the vast majority of prenatal diagnoses use FISH, which can determine large chromosomal aberrations and PCR/electrophoresis, and which can determine a handful of SNPs or other allele calls. One advantage of FISH is that it is less expensive than karyotyping, but the technique is complex and expensive enough that generally a small selection of chromosomes are tested (usually chromosomes 13, 18, 21, X, Y; also sometimes 8, 9, 15, 16, 17, 22); in addition, FISH has a low level of specificity. Roughly seventy-five percent of PGD today measures high-level chromosomal abnormalities such as aneuploidy using FISH with error rates on the order of 10-15%. There is a great demand for an aneuploidy screening method that has a higher throughput, lower cost, and greater accuracy.

The number of known disease associated genetic alleles is currently at 389 according to OMIM and steadily climbing. Consequently, it is becoming increasingly relevant to analyze multiple positions on the embryonic DNA, or loci, that are associated with particular phenotypes. A clear advantage of pre-implantation genetic diagnosis over prenatal diagnosis is that it avoids some of the ethical issues regarding possible choices of action once undesirable phenotypes have been detected. A need exists for a method for more extensive genotyping of embryos at the pre-implantation stage.

There are a number of advanced technologies that enable the diagnosis of genetic aberrations at one or a few loci at the single-cell level. These include interphase chromosome conversion, comparative genomic hybridization, fluorescent PCR, mini-sequencing and whole genome amplification. The reliability of the data generated by all of these techniques relies on the quality of the DNA preparation. Better methods for the preparation of single-cell DNA for amplification and PGD are therefore needed and are under study. All genotyping techniques, when used on single cells, small numbers of cells, or fragments of DNA, suffer from integrity issues, most notably allele drop out (ADO). This is exacerbated in the context of in-vitro fertilization since the efficiency of the hybridization reaction is low, and the technique must operate quickly in order to genotype the embryo within the time period of maximal embryo viability. There exists a great need for a method that alleviates the problem of a high ADO rate when measuring genetic data from one or a small number of cells, especially when time constraints exist.

Listed here is a set of prior art which is related to the field of the current invention. None of this prior art contains or in any way refers to the novel elements of the current invention. In U.S. Pat. No. 6,489,135 Parrott et al. provide methods for determining various biological characteristics of in vitro fertilized embryos, including overall embryo health, implantability, and increased likelihood of developing successfully to term by analyzing media specimens of in vitro fertilization cultures for levels of bioactive lipids in order to determine these characteristics. In US Patent Application 20040033596 Threadgill et al. describe a method for preparing homozygous cellular libraries useful for in vitro phenotyping and gene mapping involving site-specific mitotic recombination in a plurality of isolated parent cells. In U.S. Pat. No. 5,635,366 Cooke et al. provide a method for predicting the outcome of IVF by determining the level of 11β-hydroxysteroid dehydrogenase (11β-HSD) in a biological sample from a female patient. In U.S. Pat. No. 7,058,517 Denton et al. describe a method wherein an individual's haplotypes are compared to a known database of haplotypes in the general population to predict clinical response to a treatment. In U.S. Pat. No. 7,035,739 Schadt at al. describe a method is described wherein a genetic marker map is constructed and the individual genes and traits are analyzed to give a gene-trait locus data, which are then clustered as a way to identify genetically interacting pathways, which are validated using multivariate analysis. In US Patent Application US 2004/0137470 A1, Dhallan et al. describe using primers especially selected so as to improve the amplification rate, and detection of, a large number of pertinent disease related loci, and a method of more efficiently quantitating the absence, presence and/or amount of each of those genes. In World Patent Application WO 03/031646, Findlay et al. describe a method to use an improved selection of genetic markers such that amplification of the limited amount of genetic material will give more uniformly amplified material, and it can be genotyped with higher fidelity.

Current methods of prenatal diagnosis can alert physicians and parents to abnormalities in growing fetuses. Without prenatal diagnosis, one in 50 babies is born with serious physical or mental handicap, and as many as one in 30 will have some form of congenital malformation. Unfortunately, standard methods require invasive testing and carry a roughly 1 percent risk of miscarriage. These methods include amniocentesis, chorion villus biopsy and fetal blood sampling. Of these, amniocentesis is the most common procedure; in 2003, it was performed in approximately 3% of all pregnancies, though its frequency of use has been decreasing over the past decade and a half. A major drawback of prenatal diagnosis is that given the limited courses of action once an abnormality has been detected, it is only valuable and ethical to test for very serious defects. As result, prenatal diagnosis is typically only attempted in cases of high-risk pregnancies, where the elevated chance of a defect combined with the seriousness of the potential abnormality outweighs the risks. A need exists for a method of prenatal diagnosis that mitigates these risks.

It has recently been discovered that cell-free fetal DNA and intact fetal cells can enter maternal blood circulation. Consequently, analysis of these cells can allow early Non-Invasive Prenatal Genetic Diagnosis (NIPGD). A key challenge in using NIPGD is the task of identifying and extracting fetal cells or nucleic acids from the mother's blood. The fetal cell concentration in maternal blood depends on the stage of pregnancy and the condition of the fetus, but estimates range from one to forty fetal cells in every milliliter of maternal blood, or less than one fetal cell per 100,000 maternal nucleated cells. Current techniques are able to isolate small quantities of fetal cells from the mother's blood, although it is very difficult to enrich the fetal cells to purity in any quantity. The most effective technique in this context involves the use of monoclonal antibodies, but other techniques used to isolate fetal cells include density centrifugation, selective lysis of adult erythrocytes, and FACS. Fetal DNA isolation has been demonstrated using PCR amplification using primers with fetal-specific DNA sequences. Since only tens of molecules of each embryonic SNP are available through these techniques, the genotyping of the fetal tissue with high fidelity is not currently possible.

Much research has been done towards the use of pre-implantation genetic diagnosis (PGD) as an alternative to classical prenatal diagnosis of inherited disease. Most PGD today focuses on high-level chromosomal abnormalities such as aneuploidy and balanced translocations with the primary outcomes being successful implantation and a take-home baby. A need exists for a method for more extensive genotyping of embryos at the pre-implantation stage. The number of known disease associated genetic alleles is currently at 389 according to OMIM and steadily climbing. Consequently, it is becoming increasingly relevant to analyze multiple embryonic SNPs that are associated with disease phenotypes. A clear advantage of pre-implantation genetic diagnosis over prenatal diagnosis is that it avoids some of the ethical issues regarding possible choices of action once undesirable phenotypes have been detected.

Many techniques exist for isolating single cells. The FACS machine has a variety of applications; one important application is to discriminate between cells based on size, shape and overall DNA content. The FACS machine can be set to sort single cells into any desired container. Many different groups have used single cell DNA analysis for a number of applications, including prenatal genetic diagnosis, recombination studies, and analysis of chromosomal imbalances. Single-sperm genotyping has been used previously for forensic analysis of sperm samples (to decrease problems arising from mixed samples) and for single-cell recombination studies.

Isolation of single cells from human embryos, while highly technical, is now routine in in vitro fertilization clinics. To date, the vast majority of prenatal diagnoses have used fluorescent in situ hybridization (FISH), which can determine large chromosomal aberrations (such as Down syndrome, or trisomy 21) and PCR/electrophoresis, which can determine a handful of SNPs or other allele calls. Both polar bodies and blastomeres have been isolated with success. It is critical to isolate single blastomeres without compromising embryonic integrity. The most common technique is to remove single blastomeres from day 3 embryos (6 or 8 cell stage). Embryos are transferred to a special cell culture medium (standard culture medium lacking calcium and magnesium), and a hole is introduced into the zona pellucida using an acidic solution, laser, or mechanical drilling. The technician then uses a biopsy pipette to remove a single visible nucleus. Clinical studies have demonstrated that this process does not decrease implantation success, since at this stage embryonic cells are undifferentiated.

There are three major methods available for whole genome amplification (WGA): ligation-mediated PCR (LM-PCR), degenerate oligonucleotide primer PCR (DOP-PCR), and multiple displacement amplification (MDA). In LM-PCR, short DNA sequences called adapters are ligated to blunt ends of DNA. These adapters contain universal amplification sequences, which are used to amplify the DNA by PCR. In DOP-PCR, random primers that also contain universal amplification sequences are used in a first round of annealing and PCR. Then, a second round of PCR is used to amplify the sequences further with the universal primer sequences. Finally, MDA uses the phi-29 polymerase, which is a highly processive and non-specific enzyme that replicates DNA and has been used for single-cell analysis. Of the three methods, DOP-PCR reliably produces large quantities of DNA from small quantities of DNA, including single copies of chromosomes. On the other hand, MDA is the fastest method, producing hundred-fold amplification of DNA in a few hours. The major limitations to amplification material from a single cells are (1) necessity of using extremely dilute DNA concentrations or extremely small volume of reaction mixture, and (2) difficulty of reliably dissociating DNA from proteins across the whole genome. Regardless, single-cell whole genome amplification has been used successfully for a variety of applications for a number of years.

There are numerous difficulties in using DNA amplification in these contexts. Amplification of single-cell DNA (or DNA from a small number of cells, or from smaller amounts of DNA) by PCR can fail completely, as reported in 5-10% of the cases. This is often due to contamination of the DNA, the loss of the cell, its DNA, or accessibility of the DNA during the PCR reaction. Other sources of error that may arise in measuring the embryonic DNA by amplification and microarray analysis include transcription errors introduced by the DNA polymerase where a particular nucleotide is incorrectly copied during PCR, and microarray reading errors due to imperfect hybridization on the array. The biggest problem, however, remains allele drop-out (ADO) defined as the failure to amplify one of the two alleles in a heterozygous cell. ADO can affect up to more than 40% of amplifications and has already caused PGD misdiagnoses. ADO becomes a health issue especially in the case of a dominant disease, where the failure to amplify can lead to implantation of an affected embryo. The need for more than one set of primers per each marker (in heterozygotes) complicate the PCR process. Therefore, more reliable PCR assays are being developed based on understanding the ADO origin. Reaction conditions for single-cell amplifications are under study. The amplicon size, the amount of DNA degradation, freezing and thawing, and the PCR program and conditions can each influence the rate of ADO.

All those techniques, however, depend on the minute DNA amount available for amplification in the single cell. This process is often accompanied by contamination. Proper sterile conditions and microsatellite sizing can exclude the chance of contaminant DNA as microsatellite analysis detected only in parental alleles exclude contamination. Studies to reliably transfer molecular diagnostic protocols to the single-cell level have been recently pursued using first-round multiplex PCR of microsatellite markers, followed by real-time PCR and microsatellite sizing to exclude chance contamination. Multiplex PCR allows for the amplification of multiple fragments in a single reaction, a crucial requirement in the single-cell DNA analysis. Although conventional PCR was the first method used in PGD, fluorescence in situ hybridization (FISH) is now common. It is a delicate visual assay that allows the detection of nucleic acid within undisturbed cellular and tissue architecture. It relies firstly on the fixation of the cells to be analyzed. Consequently, optimization of the fixation and storage condition of the sample is needed, especially for single-cell suspensions.

Advanced technologies that enable the diagnosis of a number of diseases at the single-cell level include interphase chromosome conversion, comparative genomic hybridization (CGH), fluorescent PCR, and whole genome amplification. The reliability of the data generated by all of these techniques rely on the quality of the DNA preparation. PGD is also costly, consequently there is a need for less expensive approaches, such as mini-sequencing. Unlike most mutation-detection techniques, mini-sequencing permits analysis of very small DNA fragments with low ADO rate. Better methods for the preparation of single-cell DNA for amplification and PGD are therefore needed and are under study. The more novel microarrays and comparative genomic hybridization techniques, still ultimately rely on the quality of the DNA under analysis.

Several techniques are in development to measure multiple SNPs on the DNA of a small number of cells, a single cell (for example, a blastomere), a small number of chromosomes, or from fragments of DNA. There are techniques that use Polymerase Chain Reaction (PCR), followed by microarray genotyping analysis. Some PCR-based techniques include whole genome amplification (WGA) techniques such as multiple displacement amplification (MDA), and Molecular Inversion Probes (MIPS) that perform genotyping using multiple tagged oligonucleotides that may then be amplified using PCR with a singe pair of primers. An example of a non-PCR based technique is fluorescence in situ hybridization (FISH). It is apparent that the techniques will be severely error-prone due to the limited amount of genetic material which will exacerbate the impact of effects such as allele drop-outs, imperfect hybridization, and contamination.

Many techniques exist which provide genotyping data. Taqman is a unique genotyping technology produced and distributed by Applied Biosystems. Taqman uses polymerase chain reaction (PCR) to amplify sequences of interest. During PCR cycling, an allele specific minor groove binder (MGB) probe hybridizes to amplified sequences. Strand synthesis by the polymerase enzymes releases reporter dyes linked to the MGB probes, and then the Taqman optical readers detect the dyes. In this manner, Taqman achieves quantitative allelic discrimination. Compared with array based genotyping technologies, Taqman is quite expensive per reaction (~$0.40/reaction), and throughput is relatively low (384 genotypes per run). While only 1 ng of DNA per reaction is necessary, thousands of genotypes by Taqman requires microgram quantities of DNA, so Taqman does not necessarily use less DNA than microarrays. However, with respect to the IVF genotyping workflow, Taqman is the most readily applicable technology. This is due to the high reliability of the assays and, most importantly, the speed and ease of the assay (~3 hours per run and minimal molecular biological steps). Also unlike many array technologies (such as 500 k Affymetrix arrays), Taqman is highly customizable, which is important for the IVF market. Further, Taqman is highly quantitative, so aneuploidies could be detected with this technology alone.

Illumina has recently emerged as a leader in high-throughput genotyping. Unlike Affymetrix, Illumina genotyping arrays do not rely exclusively on hybridization. Instead, Illumina technology uses an allele-specific DNA extension step, which is much more sensitive and specific than hybridization alone, for the original sequence detection. Then, all of these alleles are amplified in multiplex by PCR, and then these products hybridized to bead arrays. The beads on these arrays contain unique "address" tags, not native sequence, so this hybridization is highly specific and sensitive. Alleles are then called by quantitative scanning of the bead arrays. The Illumina Golden Gate assay system genotypes up to 1536 loci concurrently, so the throughput is better than Taqman but not as high as Affymetrix 500 k arrays. The cost of Illumina genotypes is lower than Taqman, but higher than Affymetrix arrays. Also, the Illumina platform takes as long to complete as the 500 k Affymetrix arrays (up to 72 hours), which is problematic for IVF genotyping. However, Illumina has a much better call rate, and the assay is quantitative, so aneuploidies are detectable with this technology. Illumina technology is much more flexible in choice of SNPs than 500 k Affymetrix arrays.

One of the highest throughput techniques, which allows for the measurement of up to 250,000 SNPs at a time, is the Affymetrix GeneChip 500K genotyping array. This technique also uses PCR, followed by analysis by hybridization and detection of the amplified DNA sequences to DNA probes, chemically synthesized at different locations on a quartz surface. A disadvantage of these arrays are the low flexibility and the lower sensitivity. There are modified approaches that can increase selectivity, such as the "perfect match" and "mismatch probe" approaches, but these do so at the cost of the number of SNPs calls per array.

Pyrosequencing, or sequencing by synthesis, can also be used for genotyping and SNP analysis. The main advantages to pyrosequencing include an extremely fast turnaround and unambiguous SNP calls, however, the assay is not currently conducive to high-throughput parallel analysis. PCR followed by gel electrophoresis is an exceedingly simple technique that has met the most success in preimplantation diagnosis. In this technique, researchers use nested PCR to amplify short sequences of interest. Then, they run these DNA samples on a special gel to visualize the PCR products. Different bases have different molecular weights, so one can determine base content based on how fast the product runs in the gel. This technique is low-throughput and requires subjective analyses by scientists using current technologies, but has the advantage of speed (1-2 hours of PCR, 1 hour of gel electrophoresis). For this reason, it has been previously used for prenatal genotyping for a myriad of diseases, including: thalassaemia, neurofibromatosis type 2, leukocyte adhesion deficiency type I, Hallopeau-Siemens disease, sickle-cell anemia, retinoblastoma, Pelizaeus-Merzbacher disease, Duchenne muscular dystrophy, and Currarino syndrome.

Another promising technique that has been developed for genotyping small quantities of genetic material with very high fidelity is Molecular Inversion Probes (MIPs), such as Affymetrix's Genflex Arrays. This technique has the capability to measure multiple SNPs in parallel: more than 10,000 SNPS measured in parallel have been verified. For small quantities of genetic material, call rates for this technique have been established at roughly 95%, and accuracy of the calls made has been established to be above 99%. So far, the technique has been implemented for quantities of genomic data as small as 150 molecules for a given SNP. However, the technique has not been verified for genomic data from a single cell, or a single strand of DNA, as would be required for pre-implantation genetic diagnosis.

The MIP technique makes use of padlock probes which are linear oligonucleotides whose two ends can be joined by ligation when they hybridize to immediately adjacent target sequences of DNA. After the probes have hybridized to the genomic DNA, a gap-fill enzyme is added to the assay which can add one of the four nucleotides to the gap. If the added nucleotide (A,C,T,G) is complementary to the SNP under measurement, then it will hybridize to the DNA, and join the ends of the padlock probe by ligation. The circular products, or closed padlock probes, are then differentiated from linear probes by exonucleolysis. The exonuclease, by breaking down the linear probes and leaving the circular probes, will change the relative concentrations of the closed vs. the unclosed probes by a factor of 1000 or more. The probes that remain are then opened at a cleavage site by another enzyme, removed from the DNA, and amplified by PCR. Each probe is tagged with a different tag sequence consisting of 20 base tags (16,000 have been generated), and can be detected, for example, by the Affymetrix GenFlex Tag Array. The presence of the tagged probe from a reaction in which a particular gap-fill enzyme was added indicates the presence of the complimentary amino acid on the relevant SNP.

The molecular biological advantages of MIPS include: (1) multiplexed genotyping in a single reaction, (2) the genotype "call" occurs by gap fill and ligation, not hybridization, and (3) hybridization to an array of universal tags decreases false positives inherent to most array hybridizations. In traditional 500K, TaqMan and other genotyping arrays, the entire genomic sample is hybridized to the array, which contains a variety of perfect match and mismatch probes, and an algorithm calls likely genotypes based on the intensities of the mismatch and perfect match probes. Hybridization, however, is inherently noisy, because of the complexities of the DNA sample and the huge number of probes on the arrays. MIPs, on the other hand, uses multiplex probes (i.e., not on an array) that are longer and therefore more specific, and then uses a robust ligation step to circularize the probe. Background is exceedingly low in this assay (due to specificity), though allele dropout may be high (due to poor performing probes).

When this technique is used on genomic data from a single cell (or small numbers of cells) it will like PCR based approaches suffer from integrity issues. For example, the inability of the padlock probe to hybridize to the genomic DNA will cause allele dropouts. This will be exacerbated in the context of in-vitro fertilization since the efficiency of the hybridization reaction is low, and it needs to proceed relatively quickly in order to genotype the embryo in a limited time period. Note that the hybridization reaction can be reduced well below vendor-recommended levels, and microfluidic techniques may also be used to accelerate the hybridization reaction. These approaches to reducing the time for the hybridization reaction will result in reduced data quality.

Once the genetic data has been measured, the next step is to use the data for predictive purposes. Much research has been done in predictive genomics, which tries to understand the precise functions of proteins, RNA and DNA so that phenotypic predictions can be made based on genotype. Canonical techniques focus on the function of Single-Nucleotide Polymorphisms (SNP); but more advanced methods are being brought to bear on multi-factorial phenotypic features. These methods include techniques, such as linear regression and nonlinear neural networks, which attempt to determine a mathematical relationship between a set of genetic and phenotypic predictors and a set of measured outcomes. There is also a set of regression analysis techniques, such as Ridge regression, log regression and stepwise selection, that are designed to accommodate sparse data sets where there are many potential predictors relative to the number of outcomes, as is typical of genetic data, and which apply additional constraints on the regression parameters so that a meaningful set of parameters can be resolved even when the data is underdetermined. Other techniques apply principal component analysis to extract information from undetermined data sets. Other techniques, such as decision trees and contingency tables, use strategies for subdividing subjects based on their independent variables in order to place subjects in categories or bins for which the phenotypic outcomes are similar. A recent technique, termed logical regression, describes a method to search for different logical interrelationships between categorical independent variables in order to model a variable that depends on interactions between multiple independent variables related to genetic data. Regardless of the method used, the quality of the prediction is naturally highly dependant on the quality of the genetic data used to make the prediction.

Normal humans have two sets of 23 chromosomes in every diploid cell, with one copy coming from each parent. Aneuploidy, a cell with an extra or missing chromosomes, and uniparental disomy, a cell with two of a given chromosome that originate from one parent, are believed to be responsible for a large percentage of failed implantations, miscarriages, and genetic diseases. When only certain cells in an individual are aneuploid, the individual is said to exhibit mosaicism. Detection of chromosomal abnormalities can identify individuals or embryos with conditions such as Down syndrome, Klinefelters syndrome, and Turner syndrome, among others, in addition to increasing the chances of a successful pregnancy. Testing for chromosomal abnormalities is especially important as mothers age: between the ages of 35 and 40 it is estimated that between 40% and 50% of the embryos are abnormal, and above the age of 40, more than half of the embryos are abnormal.

Karyotyping, the traditional method used for the prediction of aneuploidies and mosaicism is giving way to other more high throughput, more cost effective methods. One method that has attracted much attention recently is Flow cytometry (FC) and fluorescence in situ hybridization (FISH) which can be used to detect aneuploidy in any phase of the cell cycle. One advantage of this method is that it is less expensive than karyotyping, but the cost is significant enough that generally a small selection of chromosomes are tested (usually chromosomes 13, 18, 21, X, Y; also sometimes 8, 9, 15, 16, 17, 22); in addition, FISH has a low level of specificity. Using FISH to analyze 15 cells, one can detect mosaicism of 19% with 95% confidence. The reliability of the test becomes much lower as the level of mosaicism gets lower, and as the number of cells to analyze decreases. The test is estimated to have a false negative rate as high as 15% when a single cell is analysed. There is a great demand for a method that has a higher throughput, lower cost, and greater accuracy.

Listed here is a set of prior art which is related to the field of the current invention. None of this prior art contains or in any way refers to the novel elements of the current invention. In U.S. Pat. No. 6,720,140, Hartley et al describe a recombinational cloning method for moving or exchanging segments of DNA molecules using engineered recombination sites and recombination proteins. In U.S. Pat. No. 6,489,135 Parrott et al. provide methods for determining various biological characteristics of in vitro fertilized embryos, including overall embryo health, implantability, and increased likelihood of developing successfully to term by analyzing media specimens of in vitro fertilization cultures for levels of bioactive lipids in order to determine these characteristics. In US Patent Application 20040033596 Threadgill et al. describe a method for preparing homozygous cellular libraries useful for in vitro phenotyping and gene mapping involving site-specific mitotic recombination in a plurality of isolated parent cells. In U.S. Pat. No. 5,994,148 Stewart et al. describe a method of determining the probability of an in vitro fertilization (IVF) being successful by measuring Relaxin directly in the serum or indirectly by culturing granulosa lutein cells extracted from the patient as part of an IVF/ET procedure. In U.S. Pat. No. 5,635,366 Cooke et al. provide a method for predicting the outcome of IVF by determining the level of 11β-hydroxysteroid dehydrogenase (11β-HSD) in a biological sample from a female patient. In U.S. Pat. No. 7,058,616 Larder et al. describe a method for using a neural network to predict the resistance of a disease to a therapeutic agent. In U.S. Pat. No. 6,958,211 Vingerhoets et al. describe a method wherein the integrase genotype of a given HIV strain is simply compared to a known database of HIV integrase genotype with associated phenotypes to find a matching genotype. In U.S. Pat. No. 7,058,517 Denton et al. describe a method wherein an individual's haplotypes are compared to a known database of haplotypes in the general population to predict clinical response to a treatment. In U.S. Pat. No. 7,035,739 Schadt at al. describe a method is described wherein a genetic marker map is constructed and the individual genes and traits are analyzed to give a gene-trait locus data, which are then clustered as a way to identify genetically interacting pathways, which are validated using multivariate analysis. In U.S. Pat. No. 6,025,128 Veltri et al. describe a method involving the use of a neural network utilizing a collection of biomarkers as parameters to evaluate risk of prostate cancer recurrence.

The cost of DNA sequencing is dropping rapidly, and in the near future individual genomic sequencing for personal benefit will become more common. Knowledge of personal genetic data will allow for extensive phenotypic predictions to be made for the individual. In order to make accurate phenotypic predictions high quality genetic data is critical, whatever the context. In the case of prenatal or pre-implantation genetic diagnoses a complicating factor is the relative paucity of genetic material available. Given the inherently noisy nature of the measured genetic data in cases where limited genetic material is used for genotyping, there is a great need for a method which can increase the fidelity of, or clean, the primary data.

SUMMARY OF THE INVENTION

The system disclosed enables the cleaning of incomplete or noisy genetic data using secondary genetic data as a source of information, and also the determination of chromosome copy number using said genetic data. While the disclosure focuses on genetic data from human subjects, and more specifically on as-yet not implanted embryos or developing fetuses, as well as related individuals, it should be noted that the methods disclosed apply to the genetic data of a range of organisms, in a range of contexts. The techniques described for cleaning genetic data are most relevant in the context of pre-implantation diagnosis during in-vitro fertilization, prenatal diagnosis in conjunction with amniocentesis, chorion villus biopsy, fetal tissue sampling, and noninvasive prenatal diagnosis, where a small quantity of fetal genetic material is isolated from maternal blood. The use of this method may facilitate diagnoses focusing on inheritable diseases, chromosome copy number predictions, increased likelihoods of defects or abnormalities, as well as making predictions of susceptibility to various disease- and non-disease phenotypes for individuals to enhance clinical and lifestyle decisions. The invention addresses the shortcomings of prior art that are discussed above.

In one aspect of the invention, methods make use of knowledge of the genetic data of the mother and the father such as diploid tissue samples, sperm from the father, haploid samples from the mother or other embryos derived from the mother's and father's gametes, together with the knowledge of the mechanism of meiosis and the imperfect measurement of the embryonic DNA, in order to reconstruct, in silico, the embryonic DNA at the location of key loci with a high degree of confidence. In one aspect of the invention, genetic data derived from other related individuals, such as other embryos, brothers and sisters, grandparents or other relatives can also be used to increase the fidelity of the reconstructed embryonic DNA. It is important to note that the parental and other secondary genetic data allows the reconstruction not only of SNPs that were measured poorly, but also of insertions, deletions, and of SNPs or whole regions of DNA that were not measured at all.

In one aspect of the invention, the fetal or embryonic genomic data which has been reconstructed, with or without the use of genetic data from related individuals, can be used to detect if the cell is aneuploid, that is, where fewer or more than two of a particular chromosome is present in a cell. The reconstructed data can also be used to detect for uniparental disomy, a condition in which two of a given chromosome are present, both of which originate from one parent. This is done by creating a set of hypotheses about the potential states of the DNA, and testing to see which hypothesis has the highest probability of being true given the measured data. Note that the use of high throughput genotyping data for screening for aneuploidy enables a single blastomere from each embryo to be used both to measure multiple disease-linked loci as well as to screen for aneuploidy.

In another aspect of the invention, the direct measurements of the amount of genetic material, amplified or unamplified, present at a plurality of loci, can be used to detect for monosomy, uniparental disomy, trisomy and other aneuploidy states. The idea behind this method is that measuring the amount of genetic material at multiple loci will give a statistically significant result.

In another aspect of the invention, the measurements, direct or indirect, of a particular subset of SNPs, namely those loci where the parents are both homozygous but with different allele values, can be used to detect for chromosomal abnormalities by looking at the ratios of maternally versus paternally miscalled homozygous loci on the embryo. The idea behind this method is that those loci where each parent is homozygous, but have different alleles, by definition result in a heterozygous loci on the embryo. Allele drop outs at those loci are random, and a shift in the ratio of loci miscalled as homozygous can only be due to incorrect chromosome number.

It will be recognized by a person of ordinary skill in the art, given the benefit of this disclosure, that various aspects and embodiments of this disclosure may implemented in combination or separately.

DETAILED DESCRIPTION OF THE PREFERRED EMBODIMENT

Conceptual Overview of the System

Figure 1:
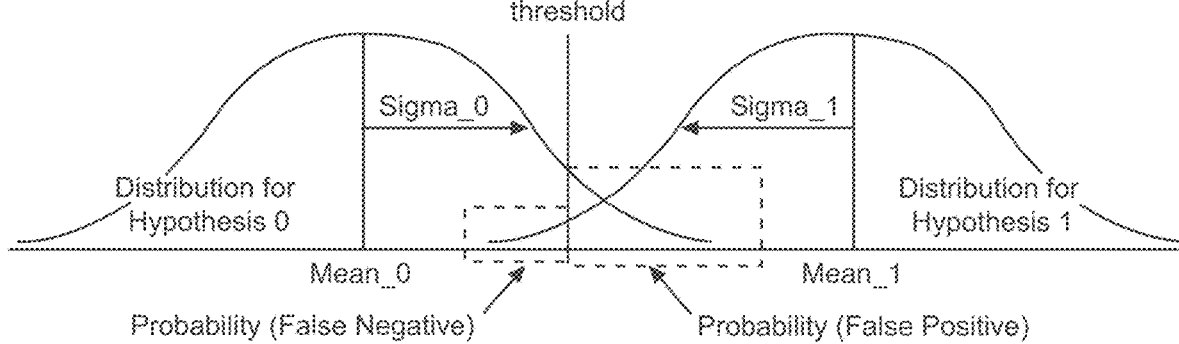
FIG. 1: determining probability of false negatives and false positives for different hypotheses.

The goal of the disclosed system is to provide highly accurate genomic data for the purpose of genetic diagnoses. In cases where the genetic data of an individual contains a significant amount of noise, or errors, the disclosed system makes use of the expected similarities between the genetic data of the target individual and the genetic data of related individuals, to clean the noise in the target genome. This is done by determining which segments of chromosomes of related individuals were involved in gamete formation and, when necessary where crossovers may have occurred during meiosis, and therefore which segments of the genomes of related individuals are expected to be nearly identical to sections of the target genome. In certain situations this method can be used to clean noisy base pair measurements on the target individual, but it also can be used to infer the identity of individual base pairs or whole regions of DNA that were not measured. It can also be used to determine the number of copies of a given chromosome segment in the target individual. In addition, a confidence may be computed for each call made. A highly simplified explanation is presented first, making unrealistic assumptions in order to illustrate the concept of the invention. A detailed statistical approach that can be applied to the technology of today is presented afterward.

In one aspect of the invention, the target individual is an embryo, and the purpose of applying the disclosed method to the genetic data of the embryo is to allow a doctor or other agent to make an informed choice of which embryo(s) should be implanted during IVF. In another aspect of the invention, the target individual is a fetus, and the purpose of applying the disclosed method to genetic data of the fetus is to allow a doctor or other agent to make an informed choice about possible clinical decisions or other actions to be taken with respect to the fetus.

Definitions

SNP (Single Nucleotide Polymorphism): a single nucleotide that may differ between the genomes of two members of the same species. In our usage of the term, we do not set any limit on the frequency with which each variant occurs.

To call a SNP: to make a decision about the true state of a particular base pair, taking into account the direct and indirect evidence.

Locus: a particular region of interest on the DNA of an individual, which may refer to a SNP, the site of a possible insertion or deletion, or the site of some other relevant genetic variation. Disease-linked SNPs may also refer to disease-linked loci.

To call an allele: to determine the state of a particular locus of DNA. This may involve calling a SNP, or determining whether or not an insertion or deletion is present at that locus, or determining the number of insertions that may be present at that locus, or determining whether some other genetic variant is present at that locus.

Correct allele call: An allele call that correctly reflects the true state of the actual genetic material of an individual.

To clean genetic data: to take imperfect genetic data and correct some or all of the errors or fill in missing data at one or more loci. In the context of this disclosure, this involves using genetic data of related individuals and the method described herein.

To increase the fidelity of allele calls: to clean genetic data.

Imperfect genetic data: genetic data with any of the following: allele dropouts, uncertain base pair measurements, incorrect base pair measurements, missing base pair measurements, uncertain measurements of insertions or deletions, uncertain measurements of chromosome segment copy numbers, spurious signals, missing measurements, other errors, or combinations thereof.

Noisy genetic data: imperfect genetic data, also called incomplete genetic data.

Uncleaned genetic data: genetic data as measured, that is, where no method has been used to correct for the presence of noise or errors in the raw genetic data; also called crude genetic data.

Confidence: the statistical likelihood that the called SNP, allele, set of alleles, or determined number of chromosome segment copies correctly represents the real genetic state of the individual.

Parental Support (PS): a name sometimes used for the any of the methods disclosed herein, where the genetic information of related individuals is used to determine the genetic state of target individuals. In some cases, it refers specifically to the allele calling method, sometimes to the method used for cleaning genetic data, sometimes to the method to determine the number of copies of a segment of a chromosome, and sometimes to some or all of these methods used in combination.

Copy Number Calling (CNC): the name given to the method described in this disclosure used to determine the number of chromosome segments in a cell.

Qualitative CNC (also qCNC): the name given to the method in this disclosure used to determine chromosome copy number in a cell that makes use of qualitative measured genetic data of the target individual and of related individuals.

Multigenic: affected by multiple genes, or alleles.

Direct relation: mother, father, son, or daughter.

Chromosomal Region: a segment of a chromosome, or a full chromosome.

Segment of a Chromosome: a section of a chromosome that can range in size from one base pair to the entire chromosome.

Section: a section of a chromosome. Section and segment can be used interchangeably.

Chromosome: may refer to either a full chromosome, or also a segment or section of a chromosome.

Copies: the number of copies of a chromosome segment may refer to identical copies, or it may refer to non-identical copies of a chromosome segment wherein the different copies of the chromosome segment contain a substantially similar set of loci, and where one or more of the alleles are different. Note that in some cases of aneuploidy, such as the M2 copy error, it is possible to have some copies of the given chromosome segment that are identical as well as some copies of the same chromosome segment that are not identical.

Haplotypic Data: also called 'phased data' or 'ordered genetic data;' data from a single chromosome in a diploid or polyploid genome, i.e., either the segregated maternal or paternal copy of a chromosome in a diploid genome.

Unordered Genetic Data: pooled data derived from measurements on two or more chromosomes in a diploid or polyploid genome, i.e., both the maternal and paternal copies of a chromosome in a diploid genome.

Genetic data 'in', 'of', 'at' or 'on' an individual: These phrases all refer to the data describing aspects of the genome of an individual. It may refer to one or a set of loci, partial or entire sequences, partial or entire chromosomes, or the entire genome.

Hypothesis: a set of possible copy numbers of a given set of chromosomes, or a set of possible genotypes at a given set of loci. The set of possibilities may contain one or more elements.

Target Individual: the individual whose genetic data is being determined. Typically, only a limited amount of DNA is available from the target individual. In one context, the target individual is an embryo or a fetus.

Related Individual: any individual who is genetically related, and thus shares haplotype blocks, with the target individual.

Platform response: a mathematical characterization of the input/output characteristics of a genetic measurement platform, such as TAQMAN or INFINIUM. The input to the channel is the true underlying genotypes of the genetic loci being measured. The channel output could be allele calls (qualitative) or raw numerical measurements (quantitative), depending on the context. For example, in the case in which the platform's raw numeric output is reduced to qualitative genotype calls, the platform response consists of an error transition matrix that describes the conditional probability of seeing a particular output genotype call given a particular true genotype input. In the case in which the platform's output is left as raw numeric measurements, the platform response is a conditional probability density function that describes the probability of the numeric outputs given a particular true genotype input.

Copy number hypothesis: a hypothesis about how many copies of a particular chromosome segment are in the embryo. In a preferred embodiment, this hypothesis consists of a set of sub-hypotheses about how many copies of this chromosome segment were contributed by each related individual to the target individual.

Technical Description of the System

A Allele Calling: Preferred Method

Assume here the goal is to estimate the genetic data of an embryo as accurately as possible, and where the estimate is derived from measurements taken from the embryo, father, and mother across the same set of n SNPs. Note that where this description refers to SNPs, it may also refer to a locus where any genetic variation, such as a point mutation, insertion or deletion may be present. This allele calling method is part of the Parental Support (PS) system. One way to increase the fidelity of allele calls in the genetic data of a target individual for the purposes of making clinically actionable predictions is described here. It should be obvious to one skilled in the art how to modify the method for use in contexts where the target individual is not an embryo, where genetic data from only one parent is available, where neither, one or both of the parental haplotypes are known, or where genetic data from other related individuals is known and can be incorporated.

For the purposes of this discussion, only consider SNPs that admit two allele values; without loss of generality it is possible to assume that the allele values on all SNPs belong to the alphabet $A=\{A,C\}$. It is also assumed that the errors on the measurements of each of the SNPs are independent. This assumption is reasonable when the SNPs being measured are from sufficiently distant genic regions. Note that one could incorporate information about haplotype blocks or other techniques to model correlation between measurement errors on SNPs without changing the fundamental concepts of this invention.

Let $e=(e_1,e_2)$ be the true, unknown, ordered SNP information on the embryo, $e_1,e_2 \in A^n$. Define $e_1$ to be the genetic haploid information inherited from the father and $e_2$ to be the genetic haploid information inherited from the mother. Also use $e_i=(e_{1i},e_{2i})$ to denote the ordered pair of alleles at the i-th position of e. In similar fashion, let $f=(f_1,f_2)$ and $m=(m_1,m_2)$ be the true, unknown, ordered SNP information on the father and mother respectively. In addition, let $g_1$ be the true, unknown, haploid information on a single sperm from the father. (One can think of the letter g as standing for gamete. There is no $g_2$. The subscript is used to remind the reader that the information is haploid, in the same way that $f_1$ and $f_2$ are haploid.) It is also convenient to define $r=(f,m)$, so that there is a symbol to represent the complete set of diploid parent information from which e inherits, and also write $r_i=(f_i,m_i)=((f_{1i},f_{2i}),(m_{1i},m_{2i}))$ to denote the complete set of ordered information on father and mother at the i-th SNP. Finally, let $\hat{e}=(\hat{e}_1, \hat{e}_2)$ be the estimate of e that is sought, $\hat{e}_1, \hat{e}_2 \in A^n$.

By a crossover map, it is meant an n-tuple $\theta \in \{1,2\}^n$ that specifies how a haploid pair such as $(f_1,f_2)$ recombines to form a gamete such as $e_1$. Treating $\theta$ as a function whose output is a haploid sequence, define $\theta(f)_i=\theta(f_1,f_2)_i=f_{\theta i,i}$. To make this idea more concrete, let $f_1=$ACAAACCC, let $f_2=$CAACCACA, and let $\theta=$11111222. Then $\theta(f_1,f_2)=$ACAAAACA. In this example, the crossover map $\theta$ implicitly indicates that a crossover occurred between SNPs i=5 and i=6.

Formally, let $\theta$ be the true, unknown crossover map that determines $e_1$ from f, let $\phi$ be the true, unknown crossover map that determines $e_2$ from m, and let $\psi$ be the true, unknown crossover map that determines $g_1$ from f. That is, $e_1=\theta(f)$, $e_2=\phi(m)$, $g_1=\psi(f)$. It is also convenient to define $X=(\theta,\phi,\psi)$ so that there is a symbol to represent the complete set of crossover information associated with the problem. For simplicity sake, write $e=X(r)$ as shorthand for $e=(\theta(f), \phi(m))$; also write $e_i=X(r_i)$ as shorthand for $e_i=X(r)_i$.

In reality, when chromosomes combine, at most a few crossovers occur, making most of the $2^n$ theoretically possible crossover maps distinctly improbable. In practice, these very low probability crossover maps will be treated as though they had probability zero, considering only crossover maps belonging to a comparatively small set $\Omega$. For example, if $\Omega$ is defined to be the set of crossover maps that derive from at most one crossover, then $|\Omega|=2n$.

It is convenient to have an alphabet that can be used to describe unordered diploid measurements. To that end, let $B=\{A,B,C,X\}$. Here A and C represent their respective homozygous locus states and B represents a heterozygous but unordered locus state. Note: this section is the only section of the document that uses the symbol B to stand for a heterozygous but unordered locus state. Most other sections of the document use the symbols A and B to stand for the two different allele values that can occur at a locus. X represents an unmeasured locus, i.e., a locus drop-out. To make this idea more concrete, let $f_1=$ACAAACCC, and let $f_2=$CAACCACA. Then a noiseless unordered diploid measurement off would yield $\tilde{f}=$BBABBBCB.

In the problem at hand, it is only possible to take unordered diploid measurements of e, f, and m, although there may be ordered haploid measurements on $g_1$. This results in noisy measured sequences that are denoted $\tilde{e} \in B^n$, $\tilde{f} \in B^n$, $\tilde{m} \in B^n$, and $\tilde{g}_1 \in A^n$ respectively. It will be convenient to define $\tilde{r}=(\tilde{f}, \tilde{m})$ so that there is a symbol that represents the noisy measurements on the parent data. It will also be convenient to define $\tilde{D}=(\tilde{r}, \tilde{e}, \tilde{g}_1)$ so that there is a symbol to represent the complete set of noisy measurements associated with the problem, and to write $\tilde{D}_i=\tilde{r}_i, \tilde{e}_i, \tilde{g}_{1i})=(\tilde{f}_i, \tilde{m}_i, \tilde{e}_i, \tilde{g}_{1i})$ to denote the complete set of measurements on the i-th SNP. (Please note that, while $f_i$ is an ordered pair such as (A,C), $\tilde{f}_i$ is a single letter such as B.)

Because the diploid measurements are unordered, nothing in the data can distinguish the state $(f_1, f_2)$ from $(f_2, f_1)$ or the state $(m_1, m_2)$ from $(m_2, m_1)$. These indistinguishable symmetric states give rise to multiple optimal solutions of the estimation problem. To eliminate the symmetries, and without loss of generality, assign $\theta_1=\phi_1=1$.

In summary, then, the problem is defined by a true but unknown underlying set of information $\{r, e, g_1, X\}$, with $e=X(r)$. Only noisy measurements $\tilde{D}=(\tilde{r}, \tilde{e}, \tilde{g}_1)$ are available. The goal is to come up with an estimate $\hat{e}$ of e, based on $\tilde{D}$.

Note that this method implicitly assumes euploidy on the embryo. It should be obvious to one skilled in the art how this method could be used in conjunction with the aneuploidy calling methods described elsewhere in this patent. For example, the aneuploidy calling method could be first employed to ensure that the embryo is indeed euploid and only then would the allele calling method be employed, or the aneuploidy calling method could be used to determine how many chromosome copies were derived from each parent and only then would the allele calling method be employed. It should also be obvious to one skilled in the art how this method could be modified in the case of a sex chromosome where there is only one copy of a chromosome present.

Solution Via Maximum a Posteriori Estimation

In one embodiment of the invention, it is possible, for each of the n SNP positions, to use a maximum a posteriori (MAP) estimation to determine the most probable ordered allele pair at that position. The derivation that follows uses a common shorthand notation for probability expressions. For example, $P(e'_i,\tilde{D}|X')$ is written to denote the probability that random variable $e_i$ takes on value $e'_i$ and the random variable $\tilde{D}$ takes on its observed value, conditional on the event that the random variable X takes on the value X'. Using MAP estimation, then, the i-th component of $\hat{e}$, denoted $\hat{e}_i=(\hat{e}_{1i}, \hat{e}_{2i})$ is given by $$\hat{e}_i = \arg\max_{e'_i} P(e'_i \mid \tilde{D})$$

$$= \arg\max_{e'_i} P(e'_i, \tilde{D})$$

$$= \arg\max_{e'_i} \sum_{X' \in \Omega^3} P(X')P(e'_i, \tilde{D} \mid X')$$

$$(a) = \arg\max_{e'_i} \sum_{X' \in \Omega^3 : \theta'_1=\phi'_1=1} P(X')P(e'_i, \tilde{D}_i \mid X')\prod_{j \neq i} P(\tilde{D}_j \mid X')$$

$$(b) = \arg\max_{e'_i} \sum_{X' \in \Omega^3 P: \theta'_1=\phi'_1=1} P(X')$$

$$\sum_{r'_i \in A^A} P(r'_i)P(e'_i, \tilde{D}_i \mid X', r'_i)\prod_{j \neq i} \sum_{r'_j \in A^A} P(r'_j)P(\tilde{D}_j \mid X', r'_j)$$

$$(c) = \arg\max_{e'_i} \sum_{X' \in \Omega^3 : \theta'_1=\phi'_1=1} P(X')$$

$$\sum_{r'_i \in A^A} P(r'_i)P(e'_i \mid X', r'_i)P(\tilde{D}_i \mid X', r'_i)\prod_{j \neq i} \sum_{r'_j \in A^A} P(r'_j)P(\tilde{D}_j \mid X', r'_j)$$

$$(*) = \arg\max_{e'_i} \sum_{X' \in \Omega^3 : \theta'_1=\phi'_1=} P(X')\prod_{j} \sum_{r'_j \in A^A} 1$$

$$(i \neq j \text{ or } X'(r'_j) = e'_i) P(r'_j) P(\tilde{D}_j|X',r'_j)$$

In the preceding set of equations, (a) holds because the assumption of SNP independence means that all of the random variables associated with SNP i are conditionally independent of all of the random variables associated with SNP j, given X; (b) holds because r is independent of X; (c) holds because $e_i$ and $\tilde{D}_i$ are conditionally independent given $r_i$ and X (in particular, $e_i=X(r_i)$); and (*) holds, again, because $e_i = X(r_i)$, which means that $P(e'_i | X', r'_i)$ evaluates to either one or zero and hence effectively filters $r'_i$ to just those values that are consistent with $e'_i$ and $X'$.

The final expression (*) above contains three probability expressions: $P(X')$, $P(r'_j)$, and $P(\tilde{D}_j | X', r'_j)$. The computation of each of these quantities is discussed in the following three sections.

Crossover Map Probabilities

Recent research has enabled the modeling of the probability of recombination between any two SNP loci. Observations from sperm studies and patterns of genetic variation show that recombination rates vary extensively on kilobase scales and that much recombination occurs in recombination hotspots. The NCBI data about recombination rates on the Human Genome is publicly available through the UCSC Genome Annotation Database.

One may use the data set from the Hapmap Project or the Perlegen Human Haplotype Project. The latter is higher density; the former is higher quality. These rates can be estimated using various techniques known to those skilled in the art, such as the reversible-jump Markov Chain Monte Carlo (MCMC) method that is available in the package LDHat.

In one embodiment of the invention, it is possible to calculate the probability of any crossover map given the probability of crossover between any two SNPs. For example, $P(\theta=11111222)$ is one half the probability that a crossover occurred between SNPs five and six. The reason it is only half the probability is that a particular crossover pattern has two crossover maps associated with it: one for each gamete. In this case, the other crossover map is $\theta=22222111$.

Recall that $X=(\theta, \phi, \psi)$, where $e_1=\theta(f)$, $e_2=\phi(m)$, $g_1=\psi(f)$. Obviously $\theta$, $\phi$, and $\psi$ result from independent physical events, so $P(X)=P(\theta)P(\phi)P(\psi)$. Further assume that $P_\theta(\cdot)=P_\phi(\cdot)=P_\psi(\cdot)$, where the actual distribution $P_\theta(\cdot)$ is determined in the obvious way from the Hapmap data.

Allele Probabilities

It is possible to determine $P(r_i)=P(f_i)P(m_i)=P(f_{i1})P(f_{i2})P(m_{i1})P(m_{i2})$ using population frequency information from databases such as dbSNP. Also, as mentioned previously, choose SNPs for which the assumption of intra-haploid independence is a reasonable one. That is, assume that $$P(r) = \prod_i P(r_i)$$

Measurement Errors

Conditional on whether a locus is heterozygous or homozygous, measurement errors may be modeled as independent and identically distributed across all similarly typed loci. Thus:

$$P(\tilde{D} \mid X, r) = \prod_i (\tilde{D}_i \mid X, r_i)$$

$$= \prod_i P(\tilde{f}_i, \tilde{m}_i, \tilde{e}_i, \tilde{g}_{1i} \mid X, f_i, m_i)$$

$$= \prod_i P(\tilde{f}_i \mid f_i)P(\tilde{m}_i \mid m_i)P(\tilde{e}_i \mid \theta(f_i), \phi(m_i))P(\tilde{g}_{1i} \mid \Psi(f_i))$$

where each of the four conditional probability distributions in the final expression is determined empirically, and where the additional assumption is made that the first two distributions are identical. For example, for unordered diploid measurements on a blastomere, empirical values $p_d=0.5$ and $p_a=0.02$ are obtained, which lead to the conditional probability distribution for $P(\tilde{e}_i | e_i)$ shown in Table 1.

Note that the conditional probability distributions mentioned above, $P(\tilde{f}_i | f_i)$, $P(\tilde{m}_i | m_i)$, $P(\tilde{e}_i | e_i)$, can vary widely from experiment to experiment, depending on various factors in the lab such as variations in the quality of genetic samples, or variations in the efficiency of whole genome amplification, or small variations in protocols used. Therefore, in a preferred embodiment, these conditional probability distributions are estimated on a per-experiment basis. We focus in later sections of this disclosure on estimating $P(\tilde{e} | e_i)$, but it will be clear to one skilled in the art after reading this disclosure how similar techniques can be applied to estimating $P(\tilde{f}_i | f_i)$ and $P(m_i | m_i)$. The distributions can each be modeled as belonging to a parametric family of distributions whose particular parameter values vary from experiment to experiment. As one example among many, it is possible to implicitly model the conditional probability distribution $P(\tilde{e}_i | e_i)$ as being parameterized by an allele dropout parameter $p_d$ and an allele dropin parameter $p_a$. The values of these parameters might vary widely from experiment to experiment, and it is possible to use standard techniques such as maximum likelihood estimation, MAP estimation, or Bayesian inference, whose application is illustrated at various places in this document, to estimate the values that these parameters take on in any individual experiment. Regardless of the precise method one uses, the key is to find the set of parameter values that maximizes the joint probability of the parameters and the data, by considering all possible tuples of parameter values within a region of interest in the parameter space. As described elsewhere in the document, this approach can be implemented when one knows the chromosome copy number of the target genome, or when one doesn't know the copy number call but is exploring different hypotheses. In the latter case, one searches for the combination of parameters and hypotheses that best match the data are found, as is described elsewhere in this disclosure.

Note that one can also determine the conditional probability distributions as a function of particular parameters derived from the measurements, such as the magnitude of quantitative genotyping measurements, in order to increase accuracy of the method. This would not change the fundamental concept of the invention.

It is also possible to use non-parametric methods to estimate the above conditional probability distributions on a per-experiment basis. Nearest neighbor methods, smoothing kernels, and similar non-parametric methods familiar to those skilled in the art are some possibilities. Although this disclosure focuses parametric estimation methods, use of non-parametric methods to estimate these conditional probability distributions would not change the fundamental concept of the invention. The usual caveats apply: parametric methods may suffer from model bias, but have lower variance. Non-parametric methods tend to be unbiased, but will have higher variance.

Note that it should be obvious to one skilled in the art, after reading this disclosure, how one could use quantitative information instead of explicit allele calls, in order to apply the PS method to making reliable allele calls, and this would not change the essential concepts of the disclosure.

B Factoring the Allele Calling Equation

In a preferred embodiment of the invention, the algorithm for allele calling can be structured so that it can be executed in a more computationally efficient fashion. In this section the equations are re-derived for allele-calling via the MAP method, this time reformulating the equations so that they reflect such a computationally efficient method of calculating the result.

Notation $X^*, Y^*, Z^* \in \{A,C\}^{n \times 2}$ are the true ordered values on the mother, father, and embryo respectively.

$H^* \in \{A,C\}^{n \times h}$ are true values on h sperm samples.

$B^* \in \{A,C\}^{n \times b \times 2}$ are true ordered values on b blastomeres.

$D=\{x,y,z,B,H\}$ is the set of unordered measurement data on father, mother, embryo, b blastomeres and h sperm samples. $D_i=\{x_i,y_i,z_i,H_i,B_i\}$ is the data set restricted to the i-th SNP.

$r \in \{A,C\}^4$ represents a candidate 4-tuple of ordered values on both the mother and father at a particular locus.

$\hat{Z}_i \in \{A,C\}^2$ is the estimated ordered embryo value at SNP i.

$Q=(2+2b+h)$ is the effective number of haploid chromosomes being measured, excluding the parents. Any hypothesis about the parental origin of all measured data (excluding the parents themselves) requires that Q crossover maps be specified.

$\chi \in \{1,2\}^{n \times Q}$ is a crossover map matrix, representing a hypothesis about the parental origin of all measured data, excluding the parents. Note that there are $2^{nQ}$ different crossover matrices. $\chi_i$ $\chi_{i}$, is the matrix restricted to the i-th row. Note that there are $2^Q$ vector values that the i-th row can take on, from the set $\chi \in \{1,2\}^Q$.

$f(x; y, z)$ is a function of $(x, y, z)$ that is being treated as a function of just x. The values behind the semi-colon are constants in the context in which the function is being evaluated.

PS Equation Factorization $$\hat{Z}_i = \underset{z_i}{\mathrm{argmax}} P(Z_i, D)$$

$$= \underset{z_i}{\mathrm{argmax}} \sum_{\chi} P(\chi)P(Z_i, P \mid \chi)$$

$$= \underset{z_i}{\mathrm{argmax}} \sum_{\chi} P(\chi_1)P(\chi_2 \mid \chi_3) \ldots P(\chi_n, \chi_{n-1})$$

$$\left( \sum_{i \in (A,C)^A} P(r)P(Z_i, D_i \mid X_i, r) \right) \prod_{j \neq 1} \left( \sum_{i \in (A,C)^A} P(r)P(D_j \mid X_j, r) \right)$$

$$= \underset{z_i}{\mathrm{argmax}} \sum_{\chi} P(\chi_1)P(\chi_2 \mid \chi_1) \ldots P(\chi_n, \chi_{n-1})f_1(\chi_i; Z_i, D_i)$$

$$\prod_{j=1} f_2(\chi_j; D_j)$$

$$= \underset{z_i}{\mathrm{argmax}} \sum_{\chi_1 \in \{1,2\}^Q} \ldots \sum_{\chi_2 \in \{1,2\}^Q} P(\chi_1)P(\chi_2 \mid \chi_1) \ldots P(\chi_n, \chi_{n-1})$$

$$f_1(\chi_i Z_i, D_i) \prod_{j=1} f_2(\chi_j; D_j)$$

$$= \underset{z_i}{\mathrm{argmax}} \sum_{\chi_1 \in \{1,2\}^Q} P(\chi_1)f_2(\chi_1; D_1) \times \sum_{\chi_2 \in \{1,2\}^Q} P(\chi_2 \mid \chi_1)$$

$$f_2(\chi_2; D_2) \times \ldots \sum_{\chi_1 \in \{1,2\}^Q} P(\chi_i \mid X_{i-1})f_1(\chi_i; Z_i, D_i) \times$$

$$\sum_{\chi_n \in \{1,2\}^Q} P(\chi_n \mid X_{n-1})f_2(\chi_n; D_n)$$

The number of different crossover matrices $\chi$ is $2^{nQ}$. Thus, a brute-force application of the first line above is $U(n2^{nQ})$.

By exploiting structure via the factorization of $P(\chi)$ and $P(z_i,D|\chi)$, and invoking the previous result, final line gives an expression that can be computed in $O(n2^{2Q})$.

C Quantitative Detection of Aneuploidy

In one embodiment of the invention, aneuploidy can be detected using the quantitative data output from the PS method discussed in this patent. Disclosed herein are multiple methods that make use of the same concept; these methods are termed Copy Number Calling (CNC). The statement of the problem is to determine the copy number of each of 23 chromosome-types in a single cell. The cell is first pre-amplified using a technique such as whole genome amplification using the MDA method. Then the resulting genetic material is selectively amplified with a technique such as PCR at a set of n chosen SNPs at each of m=23 chromosome types.

This yields a data set $[t_{ij}]$, $i=1 \ldots n$, $j=1 \ldots m$ of regularized ct (ct, or CT, is the point during the cycle time of the amplification at which dye measurement exceeds a given threshold) values obtained at SNP i, chromosome j. A regularized ct value implies that, for a given (i,j), the pair of raw ct values on channels FAM and VIC (these are arbitrary channel names denoting different dyes) obtained at that locus are combined to yield a ct value that accurately reflects the ct value that would have been obtained had the locus been homozygous. Thus, rather than having two ct values per locus, there is just one regularized ct value per locus.

The goal is to determine the set $\{n_j\}$ of copy numbers on each chromosome. If the cell is euploid, then $n_j=2$ for all j; one exception is the case of the male X chromosome. If $n_j \neq 2$ for at least one j, then the cell is aneuploid; excepting the case of male X.

Biochemical Model

The relationship between ct values and chromosomal copy number is modeled as follows: $\alpha_{ij}n_jQ2^{\beta_{ij}t_{ij}} = Q_T$ In this expression, $n_j$ is the copy number of chromosome j. Q is an abstract quantity representing a baseline amount of pre-amplified genetic material from which the actual amount of pre-amplified genetic material at SNP i, chromosome j can be calculated as $\alpha_{ij}n_jQ$. $\alpha_{ij}$ is a preferential amplification factor that specifies how much more SNP i on chromosome j will be pre-amplified via MDA than SNP 1 on chromosome 1. By definition, the preferential amplification factors are relative to $$\alpha_{11} \triangleq 1.$$

$\beta_{ij}$ is the doubling rate for SNP i chromosome j under PCR. $t_{ij}$ is the ct value. $Q_T$ is the amount of genetic material at which the ct value is determined. T is a symbol, not an index, and merely stands for threshold.

It is important to realize that $\alpha_{ij}$, $\beta_{ij}$, and $Q_T$ are constants of the model that do not change from experiment to experiment. By contrast, $n_j$ and Q are variables that change from experiment to experiment. Q is the amount of material there would be at SNP 1 of chromosome 1, if chromosome 1 were monosomic.

The original equation above does not contain a noise term. This can be included by rewriting it as follows:

$$(*) \; \beta_{ij} t_{ij} = \log \frac{Q_T}{\alpha_{ij}} - \log n_j, \log Q + Z_{ij}$$

The above equation indicates that the ct value is corrupted by additive Gaussian noise $Z_{ij}$. Let the variance of this noise term be $\sigma_{ij}^2$.

Maximum Likelihood (ML) Estimation of Copy Number

In one embodiment of the method, the maximum likelihood estimation is used, with respect to the model described above, to determine $n_j$. The parameter Q makes this difficult unless another constraint is added:

$$\frac{1}{m}\sum_j \log n_j = 1$$

This indicates that the average copy number is 2, or, equivalently, that the average log copy number is 1. With this additional constraint one can now solve the following ML problem:

$$\hat{Q}, \hat{n}_j = \underset{Q n_j}{\operatorname{argmax}} \prod_{ij} f_z\left(\begin{array}{c}\log n_j + \log Q - \\ \left(\log \frac{Q_T}{\alpha_{ij}} - \beta_{ij} t_{ij}\right)\end{array}\right) \text{ s.t. } \frac{1}{m}\sum_j \log n_j = 1$$

$$= \underset{Q n_j}{\operatorname{argmax}} \sum_{ij} \frac{1}{\sigma_{ij}^2}\left(\begin{array}{c}\log n_j + \log Q - \\ \left(\log \frac{Q_T}{\alpha_{ij}} - \beta_{ij} t_{ij}\right)\end{array}\right)^2 \text{ s.t. } \frac{1}{m}\sum_j \log n_j = 1$$

The last line above is linear in the variables $\log n_j$ and log Q, and is a simple weighted least squares problem with an equality constraint. The solution can be obtained in closed form by forming the Lagrangian $$L(\log n_j, \log Q) = \sum_{ij} \frac{1}{\sigma_{ij}^2}\left(\begin{array}{c}\log n_j + \log Q - \\ \left(\log \frac{Q_T}{\alpha_{ij}} - \beta_{ij} t_{ij}\right)\end{array}\right)^2 + \lambda \sum_j \log n_j$$

and taking partial derivatives.

Solution when Noise Variance is Constant

To avoid unnecessarily complicating the exposition, set $\sigma_{ij}^2 = 1$. This assumption will remain unless explicitly stated otherwise. (In the general case in which each $\sigma_{ij}^2$ is different, the solutions will be weighted averages instead of simple averages, or weighted least squares solutions instead of simple least squares solutions.) In that case, the above linear system has the solution:

$$\log Q_j \triangleq \frac{1}{n}\sum_i \left(\log \frac{Q_T}{\alpha_{ij}} - \beta_{ij} t_{ij}\right)$$

$$\log Q = \frac{1}{m}\sum_j \log Q_j - 1$$

$$\log n_j = \log Q_j - \log Q = \log \frac{Q_j}{Q}$$

The first equation can be interpreted as a log estimate of the quantity of chromosome j. The second equation can be interpreted as saying that the average of the $Q_j$ is the average of a diploid quantity; subtracting one from its log gives the desired monosome quantity. The third equation can be interpreted as saying that the copy number is just the ratio $$\frac{Q_j}{Q}.$$

Note that $n_j$ is a 'double difference', since it is a difference of Q-values, each of which is itself a difference of values.

Simple Solution

The above equations also reveal the solution under simpler modeling assumptions: for example, when making the assumption $\alpha_{ij} = 1$ for all i and j and/or when making the assumption that $\beta_{ij} = \beta$ for all i and j. In the simplest case, when both $\alpha_{ij} = 1$ and $\beta_{ij} = \beta$, the solution reduces to $$(**)\log n_j = 1 + \beta\left(\frac{1}{mn}\sum_{ij} t_{ij} - \frac{1}{n}\sum_i t_{ij}\right)$$

The Double Differencing Method

In one embodiment of the invention, it is possible to detect monosomy using double differencing. It should be obvious to one skilled in the art how to modify this method for detecting other aneuploidy states. Let $\{t_{ij}\}$ be the regularized ct values obtained from MDA pre-amplification followed by PCR on the genetic sample. As always, tau is the ct value on the i-th SNP of the j-th chromosome. Denote by $t_j$ the vector of ct values associated with the j-th chromosome. Make the following definitions:

$$\tilde{t} \triangleq \frac{1}{mn}\sum_{ij} t_{ij}$$

$$\tilde{t}_j \triangleq t_j - \tilde{t} 1$$

Classify chromosome j as monosomic if and only if $f^T \tilde{t}_i$ is higher than a certain threshold value, where f is a vector that represents a monosomy signature. f is the matched filter, whose construction is described next.

The matched filter f is constructed as a double difference of values obtained from two controlled experiments. Begin with known quantities of euploid male genetic data and euploid female genetic material. Assume there are large quantities of this material, and pre-amplification can be omitted. On both the male and female material, use PCR to sequence n SNPs on both the X chromosome (chromosome 23), and chromosome 7. Let $\{t_{ij}^X\}$, i=1 . . . n, j$\in\{7, 23\}$ denote the measurements on the female, and let $\{t_{ij}^Y\}$ similarly denote the measurements on the male. Given this, it is possible to construct the matched filter f from the resulting data as follows:

$$\tilde{t}_7^X \triangleq \frac{1}{n}\sum_i t_{i,7}^X$$

$$\tilde{t}_7^Y \triangleq \frac{1}{n}\sum_i t_{i,7}^Y$$

$$\Delta^X \triangleq t_{23}^X - \tilde{t}_7^X 1$$

$$\Delta^Y \triangleq t_{23}^Y - \tilde{t}_7^Y 1$$

$$f \triangleq \Delta^Y - \Delta^X$$

In the above, equations, $t_7^X$ and $t_7^Y$ are scalars, while $\Delta^X$ and $\Delta^Y$ are vectors. Note that the superscripts X and Y are just symbolic labels, not indices, denoting female and male respectively. Do not to confuse the superscript X with measurements on the X chromosome. The X chromosome measurements are the ones with subscript 23.

The next step is to take noise into account and to see what remnants of noise survive in the construction of the matched filter f as well as in the construction of $\tilde{t}_j$. In this section, consider the simplest possible modeling assumption: that $\beta_{ij}=\beta$ for all i and j, and that $\alpha_{ij}=1$ for all i and j. Under these assumptions, from (*) above: $\beta t_{ij}=\log Q_T-\log n_j-Q+Z_{ij}$ Which can be rewritten as:

$$t_{ij}=\frac{1}{\beta}\log Q_T-\frac{1}{\beta}\log n_j-\frac{1}{\beta}\log Q+Z_{ij}$$

In that case, the i-th component of the matched filter f is given by:

$$f_i\triangleq\Delta_i^Y-\Delta_i^X=$$

$$\{t_{i,23}^Y-\tilde{t}_7^Y\}-\{t_{i,23}^X-\tilde{t}_7^X\}\left\{\left(\frac{1}{\beta}\log Q_T-\frac{1}{\beta}\log n_{23}^Y-\frac{1}{\beta}\log Q^Y+Z_{i,23}^Y\right)-\right.$$

$$\frac{1}{n}\sum_i\left(\frac{1}{\beta}\log Q_T-\frac{1}{\beta}\log n_7^Y-\frac{1}{\beta}Q^Y+Z_{i,7}^Y\right)\bigg\}-$$

$$\left\{\left(\frac{1}{\beta}\log Q_T-\frac{1}{\beta}\log n_{23}^X-\frac{1}{\beta}Q^X+Z_{i,23}^X\right)-\right.$$

$$\frac{1}{n}\sum_i\left(\frac{1}{\beta}\log Q_T-\frac{1}{\beta}\log n_7^X-\frac{1}{\beta}Q^X+Z_{i,7}^X\right)\bigg\}-$$

$$\left\{\left(\frac{1}{\beta}+Z_{i,23}^Y\right)-\frac{1}{n}\sum_i Z_{i,7}^Y\right\}-\left\{Z_{i,23}^X-\frac{1}{n}\sum_i Z_{i,7}^X\right\}$$

Note that the above equations take advantage of the fact that all the copy number variables are known, for example, $n_{23}^Y=1$ and that $n_{23}^X=2$.

Given that all the noise terms are zero mean, the ideal matched filter is $1/\beta 1$. Further, since scaling the filter vector doesn't really change things, the vector 1 can be used as the matched filter. This is equivalent to simply taking the average of the components of $\tilde{t}_j$. In other words, the matched filter paradigm is not necessary if the underlying biochemistry follows the simple model. In addition, one may omit the noise terms above, which can only serve to lower the accuracy of the method. Accordingly, this gives:

$$\tilde{t}_{ij}\triangleq t_j-\tilde{t}=\left\{\frac{1}{\beta}\log Q_T-\frac{1}{\beta}\log n_i-\frac{1}{\beta}\log Q+Z_{ij}\right\}-$$

$$\frac{1}{mn}\sum_{i,j}\left\{\frac{1}{\beta}\log Q_T-\frac{1}{\beta}\log n_i-\frac{1}{\beta}\log Q+Z_{ij}\right\}=$$

$$\frac{1}{\beta}(1-\log n_j)+Z_{ij}-\frac{1}{mn}\sum_{i,j}Z_{ij}$$

In the above, it is assumed that $$\frac{1}{mn}\sum_{i,j}\log n_j=1.$$

that is, that the average copy number is 2.
Each element of the vector is an independent measurement of the log copy number (scaled by $1/\beta$), and then corrupted by noise. The noise term $Z_{ij}$ cannot be gotten rid of: it is inherent in the measurement. The second noise term probably cannot be gotten rid of either, since subtracting out t is necessary to remove the nuisance term $$\frac{1}{\beta}\log Q.$$

Again, note that, given the observation that each element of $\tilde{t}_j$ is an independent measurement of $$\frac{1}{\beta}(1-\log n_j),$$

it is clear that a UMVU (uniform minimum variance unbiased) estimate of $$\frac{1}{\beta}(1-\log n_j)$$

is just the average of the elements of $\tilde{t}_j$. (In the case in which each $\sigma_{ij}^2$ is different, it will be a weighted average.) Thus, performing a little bit of algebra, the UMVU estimator for $\log n_j$ is given by:

$$\frac{1}{n}\sum_i\tilde{t}_{ij}\approx\frac{1}{\beta}(1-\log n_j)\Rightarrow\log n_j\approx 1-\beta\cdot\frac{1}{n}\sum_i\tilde{t}_{ij}=$$

$$1-\beta\left(\frac{1}{n}\sum_i t_{ij}-\frac{1}{mn}\sum_{i,j}t_{ij}\right)$$

Analysis Under the Complicated Model

Now repeat the preceding analysis with respect to a biochemical model in which each $\beta_{ij}$ and $\alpha_{ij}$ is different. Again, take noise into account and to see what remnants of noise survive in the construction of the matched filter f as well as in the construction of $\tilde{t}_j$. Under the complicated model, from (*) above:

$$\beta_{ij}t_{ij}=\log\frac{Q_T}{\alpha_{ij}}-\log n_j-\frac{1}{\beta_{ij}}\log Q+Z_{ij}$$

Which can be rewritten as:

$$(***)t_{ij}=\frac{1}{\beta_{ij}}\log\frac{Q_T}{\alpha_{ij}}-\frac{1}{\beta_{ij}}\log n_j-\frac{1}{\beta_{ij}}\log Q+Z_{ij}$$

The i-th component of the matched filter f is given by:

$$f_i\triangleq\Delta_i^Y-\Delta_i^X-\{t_{i,23}^Y-t_7^Y\}-\{t_{i,23}^X-t_7^X\}=$$

$$\left\{\left(\frac{1}{\beta_{i,23}}\log\frac{Q_T}{\alpha_{i,23}}-\frac{1}{\beta_{i,23}}\log n_{23}^Y-\frac{1}{\beta_{i,23}}\log Q^Y+Z_{i,23}^Y\right)-\right.$$

$$\frac{1}{n}\sum_i\left(\frac{1}{\beta_{i,7}}\log\frac{Q_T}{\alpha_{i,7}}-\frac{1}{\beta_{i,7}}\log n_7^Y-\frac{1}{\beta_{i,7}}\log Q^Y+Z_{i,7}^Y\right)\bigg\}-$$

-continued $$\left\{\left(\frac{1}{\beta_{i,23}}\log\frac{Q_T}{\alpha_{i,23}} - \frac{1}{\beta_{i,23}}\log n_{23}^X - \frac{1}{\beta_{i,23}}\log Q^X + Z_{i,23}^X\right) - \right.$$

$$\frac{1}{n}\sum_i\left(\frac{1}{\beta_{i,7}}\log\frac{Q_T}{\alpha_{i,7}} - \frac{1}{\beta_{i,7}}\log n_7^X - \frac{1}{\beta_{i,7}}\log Q^X + Z_{i,7}^X\right)\right\} = \frac{1}{\beta_{i,23}} +$$

$$\left(\frac{1}{\beta_{i,23}} - \left(\frac{1}{n}\sum_i\frac{1}{\beta_{i,7}}\right)\right)\log\frac{Q^Y}{Q^X} + \left\{Z_{i,23}^Y - Z_{i,23}^X + \frac{1}{n}\sum_i Z_{i,7}^X - \frac{1}{n}\sum_i Z_{i,7}^Y\right\}$$

Under the complicated model, this gives:

$$\tilde{t}_{ij} \triangleq t_j - \tilde{t} = \left\{\frac{1}{B_{ij}}\log\frac{Q_T}{\alpha_{ij}} - \frac{1}{\beta_{ij}}\log n_j - \frac{1}{\beta_{ij}}\log Q + Z_{ij}\right\} -$$

$$\frac{1}{mn}\sum_{i,j}\left\{\frac{1}{\beta_{ij}}\log\frac{Q_T}{\alpha_{ij}} - \frac{1}{\beta_{ij}}\log n_j - \frac{1}{\beta_{ij}}\log Q + Z_{ij}\right\}$$

An Alternate Way to Regularize CT Values

In another embodiment of the method, one can average the CT values rather than transforming to exponential scale and then taking logs, as this distorts the noise so that it is no longer zero mean. First, start with known Q and solve for betas. Then do multiple experiments with known n_j to solve for alphas. Since aneuploidy is a whole set of hypotheses, it is convenient to use ML to determine the most likely n_j and Q values, and then use this as a basis for calculating the most likely aneuploid state, e.g., by taking the n_j value that is most off from 1 and pushing it to its nearest aneuploid neighbor.

Estimation of the Error Rates in the Embryonic Measurements.

In one embodiment of the invention, it is possible to determine the conditional probabilities of particular embryonic measurements given specific underlying true states in embryonic DNA. In certain contexts, the given data consists of (i) the data about the parental SNP states, measured with a high degree of accuracy, and (ii) measurements on all of the SNPs in a specific blastomere, measured poorly.

Use the following notation: U—is any specific homozygote, $\bar{U}$ is the other homozygote at that SNP, H is the heterozygote. The goal is to determine the probabilities $(p_{ij})$ shown in Table 2. For instance $p_{11}$ is the probability of the embryonic DNA being U and the readout being U as well. There are three conditions that these probabilities have to satisfy:

$$p_{11}+p_{12}+p_{13}+p_{14}=1 \tag{1}$$

$$p_{21}+p_{22}+p_{23}+p_{24}=1 \tag{2}$$

$$p_{21}=p_{23} \tag{3}$$

The first two are obvious, and the third is the statement of symmetry of heterozygote dropouts (H should give the same dropout rate on average to either U or $\bar{U}$).

There are 4 possible types of matings: U×U, U×$\bar{U}$, U×H, H×H. Split all of the SNPs into these 4 categories depending on the specific mating type. Table 3 shows the matings, expected embryonic states, and then probabilities of specific readings $(p_{ij})$. Note that the first two rows of this table are the same as the two rows of the Table 2 and the notation $(p_{ij})$ remains the same as in Table 2.

Probabilities $p_{3i}$ and $p_{4i}$ can be written out in terms of $p_{1i}$ and $p_{2i}$.

$$p_{31}=\frac{1}{2}[p_{11}+p_{21}] \tag{4}$$

$$p_{32}=\frac{1}{2}[p_{12}+p_{22}] \tag{5}$$

$$p_{33}=\frac{1}{2}[p_{13}+p_{23}] \tag{6}$$

$$p_{34}=\frac{1}{2}[p_{14}+p_{24}] \tag{7}$$

$$p_{41}=\frac{1}{4}[p_{11}+2p_{21}+p_{13}] \tag{8}$$

$$p_{42}=\frac{1}{2}[p_{12}+p_{22}] \tag{9}$$

$$p_{43}=\frac{1}{4}[p_{11}+2p_{23}+p_{13}] \tag{10}$$

$$p_{44}=\frac{1}{2}[p_{14}+p_{24}] \tag{11}$$

These can be thought of as a set of 8 linear constraints to add to the constraints (1), (2), and (3) listed above. If a vector $P=[p_{11}, p_{12}, p_{13}, p_{14}, p_{21} \ldots, p_{44}]^T$ (16×1 dimension) is defined, then the matrix A (11×16) and a vector C can be defined such that the constraints can be represented as:

$$AP=C \tag{12}$$

$C=[1, 1, 0, 0, 0, 0, 0, 0, 0, 0, 0, 0, 0, 0, 0, 0]^T$. Specifically, A is shown in Table 4, where empty cells have zeroes.

The problem can now be framed as that of finding P that would maximize the likelihood of the observations and that is subject to a set of linear constraints (AP=C). The observations come in the same 16 types as $p_{ij}$. These are shown in Table 5. The likelihood of making a set of these 16 $n_{ij}$ observations is defined by a multinomial distribution with the probabilities $p_{ij}$ and is proportional to:

$$L(P, n_{ij}) \propto \prod_{ij} p_{ij}^{n_{ij}} \tag{13}$$

Note that the full likelihood function contains multinomial coefficients that are not written out given that these coefficients do not depend on P and thus do not change the values within P at which L is maximized. The problem is then to find:

$$\max_P[L(P, n_{ij})] = \max_P[\ln(L(P, n_{ij}))]\max_P\left(\sum_{ij} n_{ij}\ln(p_{ij})\right) \tag{14}$$

subject to the constraints AP=C.

Note that in (14) taking the ln of L makes the problem more tractable (to deal with a sum instead of products). This is standard given that value of x such that f(x) is maximized is the same for which ln(f(x)) is maximized. P(n_j,Q,D)=P(n_j) P(Q)P(D_j|Q,n_j)P(D_{k≠j}|Q).

D MAP Detection of Aneuploidy without Parents

In one embodiment of the invention, the PS method can be applied to determine the number of copies of a given chromosome segment in a target without using parental genetic information. In this section, a maximum a-posteriori (MAP) method is described that enables the classification of genetic allele information as aneuploid or euploid. The method does not require parental data, though when parental data are available the classification power is enhanced. The method does not require regularization of channel values. One way to determine the number of copies of a chromosome segment in the genome of a target individual by incorporating the genetic data of the target individual and related individual(s) into a hypothesis, and calculating the most likely hypothesis is described here. In this description, the method will be applied to ct values from TAQMAN measurements; it should be obvious to one skilled in the art how to apply this method to any kind of measurement from any platform. The description will focus on the case in which there are measurements on just chromosomes X and 7; again, it should be obvious to one skilled in the art how to apply the method to any number of chromosomes and sections of chromosomes.

Setup of the Problem

The given measurements are from triploid blastomeres, on chromosomes X and 7, and the goal is to successfully make aneuploidy calls on these. The only "truth" known about these blastomeres is that there must be three copies of chromosome 7. The number of copies of chromosome X is not known.

The strategy here is to use MAP estimation to classify the copy number $N_7$ of chromosome 7 from among the choices $\{1,2,3\}$ given the measurements D. Formally that looks like this:

$$\hat{n}_7 = \underset{n_7 \in \{1,2,3\}}{\mathrm{argmax}}\, P(n_7, D)$$

Unfortunately, it is not possible to calculate this probability, because the probability depends on the unknown quantity Q. If the distribution f on Q were known, then it would be possible to solve the following:

$$\hat{n}_7 = \underset{n_7 \in \{1,2,3\}}{\mathrm{argmax}} \int f(Q)P(n_7, D \mid Q)dQ$$

In practice, a continuous distribution on Q is not known. However, identifying Q to within a power of two is sufficient, and in practice a probability mass function (pmf) on Q that is uniform on say $\{2^1, 2^2 \ldots, 2^{40}\}$ can be used. In the development that follows, the integral sign will be used as though a probability distribution function (pdf) on Q were known, even though in practice a uniform pmf on a handful of exponential values of Q will be substituted.

This discussion will use the following notation and definitions: $N_7$ is the copy number of chromosome seven. It is a random variable. $n_7$ denotes a potential value for $N_7$. $N_X$ is the copy number of chromosome X. $n_X$ denotes a potential value for $N_X$. $N_j$ is the copy number of chromosome-j, where for the purposes here $j \in \{7,X\}$. $n_j$ denotes a potential value for $N_j$. D is the set of all measurements. In one case, these are TAQMAN measurements on chromosomes X and 7, so this gives $D=\{D_7,D_X\}$, where $D_j=\{t_{ij}{}^A,t_{ij}{}^C\}$ is the set of TAQMAN measurements on this chromosome. $t_{ij}{}^A$ is the ct value on channel-A of locus i of chromosome-j. Similarly, $t_{ij}{}^C$ is the ct value on channel-C of locus i of chromosome-j. (A is just a logical name and denotes the major allele value at the locus, while C denotes the minor allele value at the locus.) Q represents a unit-amount of genetic material such that, if the copy number of chromosome-j is $n_j$, then the total amount of genetic material at any locus of chromosome-j is $n_jQ$. For example, under trisomy, if a locus were AAC, then the amount of A-material at this locus would be 2Q, and the amount of C-material is Q, and the total combined amount of genetic material at this locus is 3Q. $(n^A,n^C)$ denotes an unordered allele patterns at a locus when the copy number for the associate chromosome is n. $n^A$ is the number of times allele A appears on the locus and $n^C$ is the number of times allele C appears on the locus. Each can take on values in $0, \ldots, n$, and it must be the case that $n^A+n^C=n$. For example, under trisomy, the set of allele patterns is $\{(0,3), (1,2), (2,1), (3,0)\}$. The allele pattern $(2,1)$ for example corresponds to a locus value of $A^2C$, i.e., that two chromosomes have allele value A and the third has an allele value of C at the locus. Under disomy, the set of allele patterns is $\{(0,2), (1,1), (2,0)\}$. Under monosomy, the set of allele patterns is $\{(0,1), (1,0)\}$.

$Q_T$ is the (known) threshold value from the fundamental TAQMAN equation $Q_0 2^{\beta t}=Q_T$.

$\beta$ is the (known) doubling-rate from the fundamental TAQMAN equation $Q_0 2^{\beta t}=Q_T$.

$\perp$ (pronounced "bottom") is the ct value that is interpreted as meaning "no signal".

$f_Z(\chi)$ is the standard normal Gaussian pdf evaluated at $\chi$.

$\sigma$ is the (known) standard deviation of the noise on TAQMAN ct values.

MAP Solution

In the solution below, the following assumptions have been made:

$N_7$ and $N_X$ are independent.

Allele values on neighboring loci are independent.

The goal is to classify the copy number of a designated chromosome. In this case, the description will focus on chromosome 7. The MAP solution is given by:

$$\hat{n}_7 = \underset{n_7 \in \{1,2,3\}}{\mathrm{argmax}} \int f(Q)P(n_7, D \mid Q)dQ$$

$$= \underset{n_7 \in \{1,2,3\}}{\mathrm{argmax}} \int f(Q) \sum_{n_X \in \{1,2,3\}} P(n_7, n_X, D \mid Q)dQ$$

$$= \underset{n_7 \in \{1,2,3\}}{\mathrm{argmax}} \int f(Q) \sum_{n_X \in \{1,2,3\}} P(n_7)P(n_X)P(D_7 \mid Q, n_7)$$

$$P(D_X \mid Q, n_X)dQ$$

$$= \underset{n_7 \in \{1,2,3\}}{\mathrm{argmax}} \int f(Q)(P(n_7)P(D_7 \mid Q, n_7))$$

$$\left(\sum_{n_X \in \{1,2,3\}} P(n_X)P(D_X \mid Q, n_X)\right)dQ$$

$$= \underset{n_7 \in \{1,2,3\}}{\mathrm{argmax}} \int f(Q)\left(P(n_7)\prod_i P(t_{i,7}^A, t_{i,7}^C \mid Q, n_7)\right)$$

$$\left(\sum_{n_Z \in \{1,2,3\}} P(n_X)\prod_i P(t_{i,X}^A, t_{i,X}^C \mid Q, n_X)\right)dQ(*)$$

$$= \underset{n_7 \in \{1,2,3\}}{\mathrm{argmax}} \int f(Q)\left(P(n_7)\prod_i \sum_{n^A+n^C=n_7}\right.$$

$$P(n^A, n^C \mid n_7, i)P(t_{i,7}^A \mid Q, n^A)P(t_{i,7}^C \mid Q, n^C)) \times$$

$$\left(\sum_{n_X \in \{1,2,3\}} P(n_X)\prod_i \sum_{n^A+n^C=n_X}\right.$$

$$P(n^A, n^C \mid n_X, i)P(t_{i,X}^A \mid Q, n^A)P(t_{i,X}^C \mid Q, n^C))dQ$$

Allele Distribution Model

Equation (*) depends on being able to calculate values for $P(n^A,n^C | n_7,i)$ and $P(n^A,n^C | n_X,i)$. These values may be calculated by assuming that the allele pattern $(n^A,n^C)$ is drawn i.i.d (independent and identically distributed) according to the allele frequencies for its letters at locus i. An example should suffice to illustrate this. Calculate $P((2,1)$ $\ln_7=3)$ under the assumption that the allele frequency for A is 60%, and the minor allele frequency for C is 40%. (As an aside, note that $P((2,1)\ln_7-2)-0$, since in this case the pair must sum to 2.) This probability is given by $$P((2,1) \mid n_7 = 3) = \binom{3}{2}(.60)^Z(.40)$$

The general equation is $$P(n^A, n^C \mid n_j, i) = \binom{n}{n^A}(1 - p_{ij})^{n^A}(p_{ij})^{n^C}$$

Where $p_{i,j}$ is the minor allele frequency at locus i of chromosome j.

Error Model

Equation (*) depends on being able to calculate values for $P(t^A \mid Q, n^A)$ and $P(t^C \mid Q, n^C)$. For this an error model is needed. One may use the following error model:

$$P(t^A \mid Q, n^A) = \begin{cases} p_d & t^A = \perp \text{ and } n^A > 0 \\ (1 - p_a)fz\left(\frac{1}{\sigma}\left(t^A - \frac{1}{\beta}\log\frac{Q_T}{n^A Q}\right)\right) & t^A \neq \perp \text{ and } n^A > 0 \\ 1 - p_a & t^A = \perp \text{ and } n^A = 0 \\ 2p_a fz\left(\frac{1}{\sigma}(t^A - \perp)\right) & t^A \neq \perp \text{ and } n^A = 0 \end{cases}$$

Each of the four cases mentioned above is described here. In the first case, no signal is received, even though there was A-material on the locus. That is a dropout, and its probability is therefore $p_d$. In the second case, a signal is received, as expected since there was A-material on the locus. The probability of this is the probability that a dropout does not occur, multiplied by the pdf for the distribution on the ct value when there is no dropout. (Note that, to be rigorous, one should divide through by that portion of the probability mass on the Gaussian curve that lies below $\perp$, but this is practically one, and will be ignored here.) In the third case, no signal was received and there was no signal to receive. This is the probability that no drop-in occurred, $1-p_a$. In the final case, a signal is received even through there was no A-material on the locus. This is the probability of a drop-in multiplied by the pdf for the distribution on the ct value when there is a drop-in. Note that the '2' at the beginning of the equation occurs because the Gaussian distribution in the case of a drop-in is modeled as being centered at $\perp$. Thus, only half of the probability mass lies below $\perp$ in the case of a drop-in, and when the equation is normalized by dividing through by one-half, it is equivalent to multiplying by 2. The error model for $P(t^C \mid Q, n^C)$ by symmetry is the same as for $P(t^A \mid Q, n^A)$ above. It should be obvious to one skilled in the art how different error models can be applied to a range of different genotyping platforms, for example the ILLUMINA INFINIUM genotyping platform.

Computational Considerations

In one embodiment of the invention, the MAP estimation mathematics can be carried out by brute-force as specified in the final MAP equation, except for the integration over Q. Since doubling Q only results in a difference in ct value of $1/\beta$, the equations are sensitive to Q only on the log scale. Therefore to do the integration it should be sufficient to try a handful of Q-values at different powers of two and to assume a uniform distribution on these values. For example, one could start at $Q=Q_T 2^{-20\beta}$, which is the quantity of material that would result in a ct value of 20, and then halve it in succession twenty times, yielding a final Q value that would result in a ct value of 40.

What follows is a re-derivation of a derivation described elsewhere in this disclosure, with slightly difference emphasis, for elucidating the programming of the math. Note that the variable D below is not really a variable. It is always a constant set to the value of the data set actually in question, so it does not introduce another array dimension when representing in MATLAB. However, the variables $D_j$ do introduce an array dimension, due to the presence of the index j.

$$\hat{n}_7 = \underset{n_7 \in \{1,2,3\}}{\arg\max} P(n_7, D)$$

$$P(n_7, D) = \sum_Q P(n_7, Q, D)$$

$$P(n_7, Q, D) = P(n_7)P(Q)P(D_7 \mid Q, n_7)P(D_X \mid Q)$$

$$P(D_j \mid Q) - \sum_{n_j \in \{1,2,3\}} P(D_j, n_j \mid Q)$$

$$P(D_j, n_j \mid Q) = P(n_j)P(D_j \mid Q, n_j)$$

$$P(D_j \mid Q, n_j) = \prod_i P(D_{ij} \mid Q, n_j)$$

$$P(D_{ij} \mid Q, n_j) = \sum_{n^A + n^C = n_j} P(D_{ij}, n^A, n^C \mid Q, n_j)$$

$$P\left(\begin{matrix} D_{ij}, n^A, \\ n^C \mid Q, n_j \end{matrix}\right) = P(n^A, n^C \mid n_j, i)P(t_{ij}^A \mid Q, n^A)P(t_{ij}^C \mid Q, n^C)$$

$$P(n^A, n^C \mid n_j, i) = \binom{n}{n^A}(1 - p_{ij})^{n^A}(p_{ij})^{n^C}$$

$$P\left(\begin{matrix} t_{ij}^A \mid Q, \\ n^A \end{matrix}\right) =$$

$$\begin{cases} p_d & t^A = \perp \text{ and } n^A > 0 \\ (1 - p_d)fz\left(\frac{1}{\sigma}\left(t^A - \frac{1}{\beta}\log\frac{Q_T}{n^A Q}\right)\right) & t^A \neq \perp \text{ and } n^A > 0 \\ 1 - p_a & t^A = \perp \text{ and } n^A = 0 \\ 2p_a fz\left(\frac{1}{\sigma}(t^A - \perp)\right) & t^A \neq \perp \text{ and } n^A = 0 \end{cases}$$

E MAP Detection of Aneuploidy with Parental Info

In one embodiment of the invention, the disclosed method enables one to make aneuploidy calls on each chromosome of each blastomere, given multiple blastomeres with measurements at some loci on all chromosomes, where it is not known how many copies of each chromosome there are. In this embodiment, the a MAP estimation is used to classify the copy number $N_j$ of chromosome where $j \in \{1, 2 \dots 22, X, Y\}$, from among the choices $\{0, 1, 2, 3\}$ given the measurements D, which includes both genotyping information of the blastomeres and the parents. To be general, let $j \in \{1, 2 \dots m\}$ where m is the number of chromosomes of interest; m=24 implies that all chromosomes are of interest. Formally, this looks like:

$$\hat{n}_j = \underset{n_j \in \{1,2,3\}}{\arg\max} P(n_j, D)$$

Unfortunately, it is not possible to calculate this probability, because the probability depends on an unknown random variable Q that describes the amplification factor of MDA. If the distribution f on Q were known, then it would be possible to solve the following:

$$\hat{n}_j = \underset{n_j \in \{1,2,3\}}{\operatorname{argmax}} \int f(Q)P(n_j, D \mid Q)dQ$$

In practice, a continuous distribution on Q is not known. However, identifying Q to within a power of two is sufficient, and in practice a probability mass function (pmf) on Q that is uniform on say $\{2^1, 2^2 \ldots, 2^{40}\}$ can be used. In the development that follows, the integral sign will be used as though a probability distribution function (pdf) on Q were known, even though in practice a uniform pmf on a handful of exponential values of Q will be substituted.

This discussion will use the following notation and definitions:

$N_\alpha$ is the copy number of autosomal chromosome $\alpha$, where $\alpha \in \{1, 2 \ldots 22\}$. It is a random variable. $n_\alpha$ denotes a potential value for $N_\alpha$.

$N_X$ is the copy number of chromosome X. $n_X$ denotes a potential value for $N_X$.

$N_j$ is the copy number of chromosome-j, where for the purposes here $j \in \{1, 2 \ldots m\}$. $n_j$ denotes a potential value for $N_j$.

m is the number of chromosomes of interest, m=24 when all chromosomes are of interest.

H is the set of aneuploidy states. $h \in H$. For the purposes of this derivation, let H={paternal monosomy, maternal monosomy, disomy, t1 paternal trisomy, t2 paternal trisomy, t1 maternal trisomy, t2 maternal trisomy}. Paternal monosomy means the only existing chromosome came from the father; paternal trisomy means there is one additional chromosome coming from father. Type 1 (t1) paternal trisomy is such that the two paternal chromosomes are sister chromosomes (exact copy of each other) except in case of crossover, when a section of the two chromosomes are the exact copies. Type 2 (t2) paternal trisomy is such that the two paternal chromosomes are complementary chromosomes (independent chromosomes coming from two grandparents). The same definitions apply to the maternal monosomy and maternal trisomies.

D is the set of all measurements including measurements on embryo $D_E$ and on parents $D_F, D_M$. In the case where these are TAQMAN measurements on all chromosomes, one can say: $D = \{D_1, D_2 \ldots D'_m\}$, $D_E = \{D_{E,1}, D_{E,2} \ldots D_{E,m}\}$, where $D_k = (D_{E,k}, D_{F,k}, D_{M,k})$, $D_{Ej} = \{t_E, ij^A, t_E, ij^C\}$ is the set of TAQMAN measurements on chromosome j.

$t_E, ij^A$ is the ct value on channel-A of locus i of chromosome-j. Similarly, $t_E, ij^C$ is the ct value on channel-C of locus i of chromosome-j. (A is just a logical name and denotes the major allele value at the locus, while C denotes the minor allele value at the locus.)

Q represents a unit-amount of genetic material after MDA of single cell's genomic DNA such that, if the copy number of chromosome-j is $n_j$, then the total amount of genetic material at any locus of chromosome-j is $n_j Q$. For example, under trisomy, if a locus were AAC, then the amount of A-material at this locus is 2Q, the amount of C-material at this locus is Q, and the total combined amount of genetic material at this locus is 3Q.

q is the number of numerical steps that will be considered for the value of Q.

N is the number of SNPs per chromosome that will be measured.

$(n^A, n^C)$ denotes an unordered allele patterns at a locus when the copy number for the associated chromosome is n. $n^A$ is the number of times allele A appears on the locus and $n^C$ is the number of times allele C appears on the locus. Each can take on values in 0, . . . , n, and it must be the case that $n^A + n^C = n$. For example, under trisomy, the set of allele patterns is $\{(0,3),(1,2),(2,1),(3,0)\}$. The allele pattern (2,1) for example corresponds to a locus value of $A^2C$, i.e., that two chromosomes have allele value A and the third has an allele value of C at the locus. Under disomy, the set of allele patterns is $\{(0,2),(1,1),(2,0)\}$. Under monosomy, the set of allele patterns is $\{(0,1),(1,0)\}$.

$Q_T$ is the (known) threshold value from the fundamental TAQMAN equation $Q_0 2^{\beta t} = Q_T$.

$\beta$ is the (known) doubling-rate from the fundamental TAQMAN equation $Q_0 2^{\beta t} = Q_T$.

$\perp$ (pronounced "bottom") is the ct value that is interpreted as meaning "no signal".

$f_Z(x)$ is the standard normal Gaussian pdf evaluated at x.

$\sigma$ is the (known) standard deviation of the noise on TAQMAN ct values.

MAP Solution

In the solution below, the following assumptions are made:

$N_j$s are independent of one another.

Allele values on neighboring loci are independent.

The goal is to classify the copy number of a designated chromosome. For instance, the MAP solution for chromosome a is given by $$\hat{n}_j = \underset{n_j \in \{1,2,3\}}{\operatorname{argmax}} \int f(Q)P(n_j, D \mid Q)dQ$$

$$= \underset{n_j \in \{1,2,3\}}{\operatorname{argmax}} \int f(Q) \sum_{n_1 \in \{1,2,3\}} \cdots \sum_{n_{j-1} \in \{1,2,3\}} \sum_{n_{j+1} \in \{1,2,3\}} \cdots$$

$$\sum_{n_m \in \{1,2,3\}} P(n_1, \ldots n_m, D \mid Q)dQ$$

$$= \underset{n_j \in \{1,2,3\}}{\operatorname{argmax}} \int f(Q) \sum_{n_1 \in \{1,2,3\}} \cdots \sum_{n_{j-1} \in \{1,2,3\}} \sum_{n_{j+1} \in \{1,2,3\}} \cdots$$

$$\sum_{n_m \in \{1,2,3\}} \prod_{k=1}^{m} P(n_k)P(D_k \mid Q, n_k)dQ$$

$$= \underset{n_j \in \{1,2,3\}}{\operatorname{argmax}} \int f(Q)(P(n_j)P(D_j \mid Q, n_j))$$

$$\left( \prod_{k \neq j} \sum_{n_k \in \{1,2,3\}} P(n_k)P(D_k \mid Q, n_k) \right) dQ$$

$$= \underset{n_j \in \{1,2,3\}}{\operatorname{argmax}} \int f(Q) \left( P(n_j) \sum_{h \in H} P(D_j \mid Q, n_j, h)P(h \mid n_j) \right)$$

$$\left( \prod_{k \neq j} \sum_{n_k \in \{1,2,3\}} P(n_k) \sum_{h \in H} P(D_k \mid Q, n_k, h)P(h \mid n_k) \right) dQ$$

$$= \underset{n_j \in \{1,2,3\}}{\operatorname{argmax}} \int f(Q)$$

$$\left( P(n_j) \sum_{h \in H} P(h \mid n_j) \prod_i P(t_{E,ij}^A, t_{E,ij}^C, D_{F,ij}, D_{M,ij} \mid Q, n_j, h) \right) \times$$

$$\left( \prod_{k \neq j} \sum_{n_k \in \{1,2,3\}} P(n_k) \sum_{h \in H} P(h \mid n_k) \right)$$

-continued $$\prod_i P(t_{E,ik}^A, t_{E,ik}^C, D_{F,ik}, D_{M,ik} \mid Q, n_k, h)\bigg)dQ$$

$$= \underset{n_j \in \{1,2,3\}}{\operatorname{argmax}} \int f(Q)$$

$$\left(P(n_j) \sum_{h \in H} P(h \mid n_j) \prod_i \sum_{\substack{n_F^A + n_F^C = 2 \\ n_M^A + n_M^A = 2}} P(n_F^A, n_F^C, n_M^A, n_M^C)\right.$$

$$P(t_{E,ij}^A, t_{E,ij}^C, D_{F,ij}, D_{M,ij} \mid Q, n_j, h, n_F^A, n_F^C, n_M^A, n_M^C)) \times$$

$$\left(\prod_{k \neq j} \sum_{n_k \in \{1,2,3\}} P(n_k) \sum_{h \in H} P(h \mid n_k)\right.$$

$$\prod_i \sum_{\substack{n_F^A + n_F^C = 2 \\ n_M^A + n_M^A = 2}} P(n_F^A, n_F^C, n_M^A, n_M^C)$$

$$P(t_{E,ik}^A, t_{E,ik}^C, D_{F,ik}, D_{M,ik} \mid Q, n_k, h, n_F^A, n_F^C, n_M^A, n_M^C))dQ$$

$$= \underset{n_j \in \{1,2,3\}}{\operatorname{argmax}} \int f(Q) \bigg(P(n_j) \sum_{h \in H} P(h \mid n_j) \prod_i \sum_{\substack{n_F^A + n_F^C = 2 \\ n_M^A + n_M^A = 2}}$$

$$P(n_F^A, n_F^C, n_M^A, n_M^C)P(t_{F,ij}^A \mid n_F^A Q')P(t_{F,ij}^C \mid n_F^C Q')P(t_{M,ij}^A \mid n_M^A Q')$$

$$P(t_{M,ij}^C \mid n_M^C Q') \times \sum_{n^A + n^C = n_j} P(n^A, n^C \mid n_j, h, n_F^A, n_F^C, n_M^A, n_M^C)$$

$$P(t_{E,ij}^A \mid Q, n^A)P(t_{E,ij}^C \mid Q, n^C)) \times (\prod_{k \neq j} \sum_{n_k \in \{1,2,3\}} P(n_k) \sum_{h \in H} P(h \mid n_k)$$

$$\prod_i \sum_{\substack{n_F^A + n_F^C = 2 \\ n_M^A + n_M^A = 2}} P(n_F^A, n_F^C, n_M^A, n_M^C)P(\tau_{F,ik}^A \mid n_F^A Q')$$

$$P(\tau_{F,ik}^C \mid n_F^C Q')P(\tau_{M,ik}^A n_M^A Q')P(\tau_{m,ik}^C n_M^C Q') \times$$

$$\sum_{n^A + n^C = n_1} P(n^A, n^C \mid n_k, h, n_F^A, n_F^C, n_M^A, n_M^C)P(\tau_{E,ik}^A \mid n^A Q)$$

$$P(t_{E,ik}^C \mid n^C Q))dQ(*)$$

Here it is assumed that Q', the Q are known exactly for the parental data.

Copy Number Prior Probability

Equation (*) depends on being able to calculate values for $P(n_\alpha)$ and $P(n_X)$, the distribution of prior probabilities of chromosome copy number, which is different depending on whether it is an autosomal chromosome or chromosome X. If these numbers are readily available for each chromosome, they may be used as is. If they are not available for all chromosomes, or are not reliable, some distributions may be assumed. Let the prior probability $P(n_a=1)=P(n_a=2)=P(n_a=3)=\frac{1}{3}$ for autosomal chromosomes, let the probability of sex chromosomes being XY or XX be $\frac{1}{2}$. $P(n_x=0)=\frac{1}{3} \times \frac{1}{4}=\frac{1}{12}$. $P(n_x=1)=\frac{1}{3} \times \frac{3}{4}+\frac{1}{3} \times \frac{1}{2}+\frac{1}{3} \times \frac{1}{2} \times \frac{1}{4} = \frac{11}{24}=0.458$, where $\frac{3}{4}$ is the probability of the monosomic chromosome being X (as oppose to Y), $\frac{1}{2}$ is the probability of being XX for two chromosomes and $\frac{1}{4}$ is the probability of the third chromosome being Y. $P(n_x=3)=\frac{1}{3} \times \frac{1}{2} \times \frac{3}{4}=\frac{1}{8}=0.125$, where $\frac{1}{2}$ is the probability of being XX for two chromosomes and $\frac{3}{4}$ is the probability of the third chromosome being X. $P(n_x=2)=1-P(n_x=0)-P(n_x=1)-P(n_x=3)=\frac{4}{12}=0.333$.

Aneuploidy State Prior Probability

Equation (*) depends on being able to calculate values for $P(h|n_j)$, and these are shown in Table 6. The symbols used in the Table 6 are explained below

| Symbol | Meaning |
|---|---|
| Ppm | paternal monosomy probability |
| Pmm | maternal monosomy probability |
| Ppt | paternal trisomy probability given trisomy |
| Pmt | maternal trisomy probability given trisomy |
| pt1 | probability of type 1 trisomy for paternal trisomy, or P(type 1\|paternal trisomy) |
| pt2 | probability of type 2 trisomy for paternal trisomy, or P(type 2\|paternal trisomy) |
| mt1 | probability of type 1 trisomy thr maternal txisomy, or P(type 1\|maternal trisomy) |
| mt2 | probability of type 2 trisomy fbr maternal trisomy, or P(type 2\|maternal trisomy) |

Note that there are many other ways that one skilled in the art, after reading this disclosure, could assign or estimate appropriate prior probabilities without changing the essential concept of the patent.

Allele Distribution Model without Parents

Equation (*) depends on being able to calculate values for $p(n^A, n^C \mid n_\alpha, i)$ and $P(n^A, n^C \mid n_X, i)$. These values may be calculated by assuming that the allele pattern $(n^A, n^C)$ is drawn i.i.d according to the allele frequencies for its letters at locus i. An illustrative example is given here. Calculate $P((2,1)\mid n_7=3)$ under the assumption that the allele frequency for A is 60%, and the minor allele frequency for C is 40%. (As an aside, note that $P((2,1)\mid n_7=2)=0$, since in this case the pair must sum to 2.) This probability is given by $$P((2,1) \mid n_7 = 3) = \binom{3}{2}(.60)^2(.40)$$

The general equation is $$P(n^A, n^C \mid n_j, i) = \binom{n}{n^A}(1 - p_{ij})^{n^A}(p_{ij})^{n^C}$$

Where $p_{ij}$ is the minor allele frequency at locus i of chromosome j.

Allele Distribution Model Incorporating Parental Genotypes

Equation (*) depends on being able to calculate values for $p(n^A, n^C \mid n_j, h, T_{P,ij} T_{M,ij})$ which are listed in Table 7. In a real situation, LDO will be known in either one of the parents, and the table would need to be augmented. If LDO are known in both parents, one can use the model described in the Allele Distribution Model without Parents section.

Population Frequency for Parental Truth

Equation (*) depends on being able to calculate $p(T_{FAJ} T_{MAJ})$. The probabilities of the combinations of parental genotypes can be calculated based on the population frequencies. For example, $P(AA,AA)=P(A)^4$, and $P(AC,AC)=P_{heteroz}^2$ where $P_{heteroz}=2P(A)P(C)$ is the probability of a diploid sample to be heterozygous at one locus i.

Error Model

Equation (*) depends on being able to calculate values for $P(t^A|Q,n^A)$ and $P(t^C|Q,n^C)$. For this an error model is needed. One may use the following error model:

$$P(t^A \mid Q, n^A) = \begin{cases} p_d & t^A = \perp \text{ and } n^A > 0 \\ (1 - p_d)fz\left(\frac{1}{\sigma}\left(t^A - \frac{1}{\beta}\log\frac{Q_T}{n^A Q}\right)\right) & t^A \neq \perp \text{ and } n^A > 0 \\ 1 - p_a & t^A = \perp \text{ and } n^A = 0 \\ 2p_a fz\left(\frac{1}{\sigma}(t^A - \perp)\right) & t^A \neq \perp \text{ and } n^A = 0 \end{cases}$$

This error model is used elsewhere in this disclosure, and the four cases mentioned above are described there. The computational considerations of carrying out the MAP estimation mathematics can be carried out by brute-force are also described in the same section.

Computational Complexity Estimation

Rewrite the equation (*) as follows, $$\hat{n}_j = \operatorname*{argmax}_{n_j \in \{1,2,3\}} \int f(Q) \left( p(n_j) \prod_i \sum_{n^A + n^C = n_j} P(n^A, n^C \mid n_j, i) \atop P(t_{i,j}^A \mid Q, n^A)P(t_{i,j}^C \mid Q, n^C) \right) \times$$

$$\left( \prod_{k \neq j} \sum_{n_k \in \{1,2,3\}} P(n_k) \prod_i \sum_{n^A + n^C = n_k} P(n^A, n^C \mid n_k, i)P(t_{i,k}^A \mid Q, n^A)P(t_{i,k}^C \mid Q, n^C) \right) dQ \quad (*)$$

Let the computation time for $P(n^A, n^C \mid n_j, i)$ be $t_x$, that for $P(t_{i,j}^A \mid Q, n^A)$ or $P(t_{i,j}^C \mid Q, n^C)$ be $t_y$. Note that $p(n^A, n^C \mid n_{j,i})$ may be pre-computed, since their values don't vary from experiment to experiment. For the discussion here, call a complete 23-chromosome aneuploidy screen an "experiment". Computation of $\Pi_i \Sigma_{n^A + n^C = n_j} P(n^A, n^C \mid n_{j,i}) P(t_{i,j}^A \mid Q, n^A)P(t_{i,j}^C \mid Q, n^C)$ for 23 chromosomes takes if $n_j=1$, $(2+t_x+2*t_y)*2N*m$ if $n_j=2$, $(2+t_x+2*t_y)*3N*m$ if $n_j=3$, $(2+t_x+2*t_y)*4N*m$ The unit of time here is the time for a multiplication or an addition. In total, it takes $(2+t_x+2*t_y)*9N*m$ Once these building blocks are computed, the overall integral may be calculated, which takes time on the order of $(2+t_x+2*t_y)*9N*m*q$. In the end, it takes $2*m$ comparisons to determine the best estimate for $n_j$. Therefore, overall the computational complexity is $O(N*m*q)$.

What follows is a re-derivation of the original derivation, with a slight difference in emphasis in order to elucidate the programming of the math. Note that the variable D below is not really a variable. It is always a constant set to the value of the data set actually in question, so it does not introduce another array dimension when representing in MATLAB. However, the variables $D_j$ do introduce an array dimension, due to the presence of the index j.

$$\hat{n}_j = \operatorname*{argmax}_{n_j \in \{1,2,3\}} P(n_j, D)$$

$$P(n_j, D) = \sum_Q P(n_j, Q, D)$$

$$P(n_j, Q, D) = P(n_j)P(Q)P(D_j \mid Q, n_j)P(D_{k \neq j} \mid Q)$$

$$P(D_j \mid Q) = \sum_{n_j \in \{1,2,3\}} P(D_j, n_j \mid Q)$$

-continued $$P(D_j, n_j \mid Q) = P(n_j)P(D_j \mid Q, n_j)$$

$$P(D_j \mid Q, n_j) = \prod_i P(D_{ij} \mid Q, n_j)$$

$$P(D_{ij} \mid Q, n_j) = \sum_{n^A + n^C = n_j} P(D_{ij}, n^A, n^C \mid Q, n_j)$$

$$P\left(\begin{matrix} D_{ij}, n^A, \\ n^C \mid Q, n_j \end{matrix}\right) = P(n^A, n^C \mid n_j, i)P(t_{ij}^A \mid Q, n^A)P(t_{ij}^C \mid Q, n^C)$$

$$P(n^A, n^C \mid n_j, i) = \binom{n}{n^A}(1 - p_{ij})^{n^A}(p_{ij})^{n^C}$$

$$P\left(\begin{matrix} t_{ij}^A \mid Q, \\ n^A \end{matrix}\right) = \begin{cases} p_d & t^A = \perp \text{ and } n^A > 0 \\ (1 - p_d)f_z\left(\frac{1}{\sigma}\left(t^A - \frac{1}{\beta}\log\frac{Q_T}{n^A Q}\right)\right) & t^A \neq \perp \text{ and } n^A > 0 \\ 1 - p_a & t^A = \perp \text{ and } n^A = 0 \\ 2p_z f_z\left(\frac{1}{\sigma}(t^A - \perp)\right) & t^A \neq \perp \text{ and } n^A = 0 \end{cases}$$

F Qualitative Chromosome Copy Number Calling

One way to determine the number of copies of a chromosome segment in the genome of a target individual by incorporating the genetic data of the target individual and related individual(s) into a hypothesis, and calculating the most likely hypothesis is described here. In one embodiment of the invention, the aneuploidy calling method may be modified to use purely qualitative data. There are many approaches to solving this problem, and several of them are presented here. It should be obvious to one skilled in the art how to use other methods to accomplish the same end, and these will not change the essence of the disclosure.

Notation for Qualitative CNC

1. N is the total number of SNPs on the chromosome.

2. n is the chromosome copy number.

3. $n^M$ is the number of copies supplied to the embryo by the mother: 0, 1, or 2.

4. $n^F$ is the number of copies supplied to the embryo by the father: 0, 1, or 2.

5. $p_d$ is the dropout rate, and $f(p_d)$ is a prior on this rate.

6. $p_a$ is dropin rate, and $f(p_a)$ is a prior on this rate.

7. c is the cutoff threshold for no-calls.

8. $D=(x_k, y_k)$ is the platform response on channels X and Y for SNP k.

9. $D(c)=\{G(x_k, y_k); c\}=\{\hat{g}_k^{(c)}\}$ is the set of genotype calls on the chromosome. Note that the genotype calls depend on the no-call cutoff threshold c.

10. $\hat{g}_k^{(c)}$ is the genotype call on the k-th SNP (as opposed to the true value): one of AA, AB, BB, or NC (no-call).

11. Given a genotype call $\hat{g}$ at SNP k, the variables ($\hat{g}_X$, $\hat{g}_Y$) are indicator variables (1 or 0), indicating whether the genotype $\hat{g}$ implies that channel X or Y has "lit up". Formally, $\hat{g}_X=1$ just in case $\hat{g}$ contains the allele A, and $\hat{g}_Y=1$ just in case contains the allele B.

12. $M=\{g_k^M\}$ is the known true sequence of genotype calls on the mother. $g^M$ refers to the genotype value at some particular locus.

13. $F=\{g_k^F\}$ is the known true sequence of genotype calls on the father. $g^F$ refers to the genotype value at some particular locus.

14. $n^A, n^B$ are the true number of copies of A and B on the embryo (implicitly at locus k), respectively. Values must be in $\{0,1,2,3,4\}$.

15. $c_M{}^A, c_M{}^B$ are the number of A alleles and B alleles respectively supplied by the mother to the embryo (implicitly at locus k). The values must be in $\{0, 1, 2\}$, and must not sum to more than 2. Similarly, $c_F{}^A, c_F{}^B$ are the number of A alleles and B alleles respectively supplied by the father to the embryo (implicitly at locus k). Altogether, these four values exactly determine the true genotype of the embryo. For example, if the values were (1,0) and (1,1), then the embryo would have type AAB.

Solution 1: Integrate Over Dropout and Dropin Rates.

In the embodiment of the invention described here, the solution applies to just a single chromosome. In reality, there is loose coupling among all chromosomes to help decide on dropout rate $p_d$, but the math is presented here for just a single chromosome. It should be obvious to one skilled in the art how one could perform this integral over fewer, more, or different parameters that vary from one experiment to another. It should also be obvious to one skilled in the art how to apply this method to handle multiple chromosomes at a time, while integrating over ADO and ADI. Further details are given in Solution 3B below.

$$P(n \mid D(c), M, F) = \sum_{(n^M, n^F) \in n} P(n^M, n^F \mid D(c), M, F)$$

$$P\begin{pmatrix} n^M, n^F \mid D(c), \\ M, F \end{pmatrix} = \frac{P(n^M)P(n^F)}{\sum_{(n^M, n^F)} P(n^M)P(n^F)} P(D(c) \mid n^M, n^F, M, F)$$

$$P\begin{pmatrix} D(c) \mid n^M, \\ n^F, M, F \end{pmatrix} = \int \int f(p_d) f(p_a) P\begin{pmatrix} D(c) \mid n^M, n^F, \\ M, F, p_d, p_a \end{pmatrix} dp_d dp_a$$

$$P\begin{pmatrix} D(c) \mid n^M, n^F, \\ M, F, p_d, p_a \end{pmatrix} = \prod_k P(G(x_k, y_k; c) \mid n^M, n^F, g_k^M, g_k^F, p_d, p_a) =$$

$$\prod_{\substack{g^M \in \{AA,AB,BB\} \\ g^F \in \{AA,AB,BB\} \\ \hat{g} \in \{AA,AB,BB,NC\}}} \prod_{\{k: g_k^M = g^M, g_k^F = g^F, \hat{g}_k^{(c)} = \hat{g}\}} P(\hat{g} \mid n^M, n^F g^M, g^F, p_d, p_a) =$$

$$\prod_{\substack{g^M \in \{AA,AB,BB\} \\ g^F \in \{AA,AB,BB\} \\ \hat{g} \in \{AA,AB,BB,NC\}}} P\begin{pmatrix} \hat{g} \mid n^M, n^F, g^M, \\ g^F, p_d, p_a \end{pmatrix}^{\left|\left\{\substack{k: g_k^M = g^M, \\ g_k^F = g^F, \hat{g}_k^{(c)} = \hat{g}}\right\}\right|} =$$

$$\exp\begin{pmatrix} \sum_{\substack{g^M \in \{AA,AB,BB\} \\ g^F \in \{AA,AB,BB\} \\ \hat{g} \in \{AA,AB,BB,NC\}}} \left|\left\{\substack{k: g_k^M = g^M, \\ g_k^F = g^F, \hat{g}_k^{(c)} = \hat{g}}\right\}\right| \times \\ \log P(\hat{g} \mid n^M, n^F, g^M, g^F, p_d, p_a) \end{pmatrix}$$

$$P\begin{pmatrix} \hat{g} \mid n^M, n^F, g^M, \\ g^F, p_d, p_a \end{pmatrix} = \sum_{n^A, n^B} P\begin{pmatrix} n^A, n^B \mid n^M, \\ n^F, g^M, g^F, \end{pmatrix} \overbrace{\begin{pmatrix} P(\hat{g}_X \mid n^A, p_d, p_a) \\ P(\hat{g}_Y \mid n^B, p_d, p_a) \end{pmatrix}}^{platformmodeling} P\begin{pmatrix} \hat{g}_X \mid n^A, \\ p_d, p_a \end{pmatrix} = $$
$$\underbrace{\phantom{\sum}}_{geneticmodeling}$$

-continued $$\left( \hat{g}_X \begin{pmatrix} (1 - p_d^{n^A}) + \\ (n^A = 0) p_a \end{pmatrix} + (1 - \hat{g}_X) \begin{pmatrix} (n^A > 0) p_d^{n^A} + \\ (n^A = 0)(1 - p_a) \end{pmatrix} \right)$$

The derivation other is the same, except applied to channel Y.

$$P\begin{pmatrix} n^A, n^B \mid n^M, \\ n^F, g^M, g^F, \end{pmatrix} =$$

$$\sum_{\substack{c_M^A + c_F^A = n^A \\ c_M^B + c_F^B = n^B}} P\begin{pmatrix} c_M^A, c_M^B \mid \\ n^M, g^M \end{pmatrix} P\begin{pmatrix} c_F^A, c_F^B \mid \\ n^F, g^F \end{pmatrix} P(c_M^A, c_M^B \mid n^M, g^M) =$$

$$(c_M^A + c_M^B = n^M) \begin{cases} (c_M^B = 0), & g^M = AA \\ (c_M^A = 0), & g^M = BB \\ \dfrac{1}{n^M + 1}, & g^M = AB \end{cases}$$

The other derivation is the same, except applied to the father.

Solution 2: Use ML to Estimate Optimal Cutoff Threshold c

Solution 2, Variation A $$\hat{c} = \underset{c \in \langle 0, a]}{\arg\max} \, P(D(c) \mid M, F)$$

$$P(n) = \sum_{(n^M, n^F) \in n} P(n^M, n^F \mid D(\hat{c}), M, F)$$

In this embodiment, one first uses the ML estimation to get the best estimate of the cutoff threshold based on the data, and then use this c to do the standard Bayesian inference as in solution 1. Note that, as written, the estimate of c would still involve integrating over all dropout and dropin rates. However, since it is known that the dropout and dropin parameters tend to peak sharply in probability when they are "tuned" to their proper values with respect to c, one may save computation time by doing the following instead:

Solution 2, Variation B $$\hat{c}, \hat{p}_d, \hat{p}_a = \underset{c, p_d, p_a}{\arg\max} f(p_d) f(p_a) P(D(c) \mid M, F, p_d, p_a)$$

$$P(n) = \sum_{(n^M, n^F) \in n} P(n^M, n^F \mid D(\hat{c}), M, F, \hat{p}_d, \hat{p}_a)$$

In this embodiment, it is not necessary to integrate a second time over the dropout and dropin parameters. The equation goes over all possible triples in the first line. In the second line, it just uses the optimal triple to perform the inference calculation.

Solution 3: Combining Data Across Chromosomes

The data across different chromosomes is conditionally independent given the cutoff and dropout/dropin parameters, so one reason to process them together is to get better resolution on the cutoff and dropout/dropin parameters, assuming that these are actually constant across all chromosomes (and there is good scientific reason to believe that they are roughly constant). In one embodiment of the invention, given this observation, it is possible to use a simple modification of the methods in solution 3 above. Rather than independently estimating the cutoff and dropout/dropin parameters on each chromosome, it is possible to estimate them once using all the chromosomes.

Notation

Since data from all chromosomes is being combined, use the subscript j to denote the j-th chromosome. For example, $D_j(c)$ is the genotype data on chromosome j using c as the no-call threshold. Similarly, $M_j, F_j$ are the genotype data on the parents on chromosome j.

Solution 3, Variation A: Use all Data to Estimate Cutoff Dropout/Dropin $$\hat{c}, \hat{p}_d, \hat{p}_a = \underset{c, p_d, p_a}{\operatorname{argmax}} f(p_d) f(p_a) \prod_j P(D_j(c) \mid M_j, F_j, p_d, p_a)$$

$$P(n_j) = \sum_{(n^M, n^F) \in n_j} P(n^M, n^F \mid D_j(\hat{c}), M_j, F_j, \hat{p}_d, \hat{p}_a)$$

Solution 3, Variation B:

Theoretically, this is the optimal estimate for the copy number on chromosome j.

$$\hat{n}_j = \underset{n}{\operatorname{argmax}} \sum_{(n^M, n^F) \in n} \int \int f(p_d) f(p_a) P(D_j(\hat{c})) \mid n^M, n^F, M_j, F_j, p_d, p_a)$$

$$\prod_{i \neq j} P(D_j(\hat{c})) \mid n^M, n^F, M_i, F_i, p_d, p_a) dp_d dp_a$$

Estimating Dropout/Dropin Rates from Known Samples

For the sake of thoroughness, a brief discussion of dropout and dropin rates is given here. Since dropout and dropin rates are so important for the algorithm, it may be beneficial to analyze data with a known truth model to find out what the true dropout/dropin rates are. Note that there is no single tree dropout rate: it is a function of the cutoff threshold. That said, if highly reliable genomic data exists that can be used as a truth model, then it is possible to plot the dropout/dropin rates of MDA experiments as a function of the cutoff-threshold. Here a maximum likelihood estimation is used.

$$\hat{c}, \hat{p}_d, \hat{p}_a = \underset{c, p_d, p_a}{\operatorname{argmax}} \prod_{jk} P(\hat{g}_{jk}^{(c)} \mid g_{jk}, p_d, p_a)$$

In the above equation, $\hat{g}_{jk}^{(c)}$, is the genotype call on SNP k of chromosome j, using c as the cutoff threshold, while $g_{jk}$, is the true genotype as determined from a genomic sample. The above equation returns the most likely triple of cutoff, dropout, and dropin. It should be obvious to one skilled in the art how one can implement this technique without parent information using prior probabilities associated with the genotypes of each of the SNPs of the target cell that will not undermine the validity of the work, and this will not change the essence of the invention.

G Bayesian Plus Sperm Method

Another way to determine the number of copies of a chromosome segment in the genome of a target individual is described here. In one embodiment of the invention, the genetic data of a sperm from the father and crossover maps can be used to enhance the methods described herein. Throughout this description, it is assumed that there is a chromosome of interest, and all notation is with respect to that chromosome. It is also assumed that there is a fixed cutoff threshold for genotyping. Previous comments about the impact of cutoff threshold choice apply, but will not be made explicit here. In order to best phase the embryonic information, one should combine data from all blastomeres on multiple embryos simultaneously. Here, for ease of explication, it is assumed that there is just one embryo with no additional blastomeres. However, the techniques mentioned in various other sections regarding the use of multiple blastomeres for allele-calling translate in a straightforward manner here.

Notation 1. n is the chromosome copy number.

2. $n^M$ is the number of copies supplied to the embryo by the mother: 0, 1, or 2.

3. $n^F$ is the number of copies supplied to the embryo by the father: 0, 1, or 2.

4. $p_d$ is the dropout rate, and $f(p_d)$ is a prior on this rate.

5. $p_a$ is the dropin rate, and $f(p_a)$ is a prior on this rate.

6. $D=\{\hat{g}_k\}$ is the set of genotype measurements on the chromosome of the embryo. $\hat{g}_k$ is the genotype call on the k-th SNP (as opposed to the true value): one of AA, AB, BB, or NC (no-call). Note that the embryo may be aneuploid, in which case the true genotype at a SNP may be, for example, AAB, or even AAAB, but the genotype measurements will always be one of the four listed. (Note: elsewhere in this disclosure 'B' has been used to indicate a heterozygous locus. That is not the sense in which it is being used here. Here 'A' and 'B' are used to denote the two possible allele values that could occur at a given SNP.)

7. $M=\{g_k^M\}$ is the known true sequence of genotypes on the mother. $g_k^M$ is the genotype value at the k-th SNP.

8. $F=\{g_k^F\}$ is the known true sequence of genotypes on the father. $g_k^F$ is the genotype value at the k-th SNP.

9. $S=\{\hat{g}_k^S\}$ is the set of genotype measurements on a sperm from the father. $\hat{g}_k^S$ is the genotype call at the k-th SNP.

10. $(m_1, m_2)$ is the true but unknown ordered pair of phased haplotype information on the mother. $m_{1k}$ is the allele value at SNP k of the first haploid sequence. $m_{2k}$ is the allele value at SNP k of the second haploid sequence. $(m_1, m_2) \epsilon M$ is used to indicate the set of phased pairs $(m_1, m_2)$ that are consistent with the known genotype M. Similarly, $(m_1, m_2) \epsilon g_k^M$ is used to indicate the set of phased pairs that are consistent with the known genotype of the mother at SNP k.

11. $(f_1, f_2)$ is the true but unknown ordered pair of phased haplotype information on the father. $f_{1k}$ is the allele value at SNP k of the first haploid sequence. $f_{2k}$ is the allele value at SNP k of the second haploid sequence. $(f_1, f_2) \epsilon F$ is used to indicate the set of phased pairs $(f_1, f_2)$ that are consistent with the known genotype F. Similarly, $(f_1, f_2) \epsilon g_k^F$ is used to indicate the set of phased pairs that are consistent with the known genotype of the father at SNP k.

12. $s_1$ is the true but unknown phased haplotype information on the measured sperm from the father. $s_{1k}$ is the allele value at SNP k of this haploid sequence. It can be guaranteed that this sperm is euploid by measuring several sperm and selecting one that is euploid.

13. $\chi^M=\{\phi_1, \ldots, \phi_{nM}\}$ is the multiset of crossover maps that resulted in maternal contribution to the embryo on this chromosome. Similarly, $\chi^F=\{\theta_1, \ldots, \theta_{nF}\}$ is the multiset of crossover maps that results in paternal contribution to the embryo on this chromosome. Here the possibility that the chromosome may be aneuploid is explicitly modeled. Each parent can contribute zero, one, or two copies of the chromosome to the embryo. If the chromosome is an autosome, then euploidy is the case in which each parent contributes exactly one copy, i.e., $\chi^M\{\phi_1\}$ and $\chi^F=\{\theta_1\}$. But euploidy is only one of the $3\times3=9$ possible cases. The remaining eight are all different kinds of aneuploidy. For example, in the case of maternal trisomy resulting from an M2 copy error, one would have $\chi^M=\{\phi_1\phi_1\}$ and $\chi^F=\{\theta_1\}$. In the case of maternal trisomy resulting from an M1 copy error, one would have $\chi^M-\{\phi_1\phi_2\}$ and $\chi^F=\{\theta_1\}$. $(\chi^M,\chi^F)\epsilon n$ will be used to indicate the set of sub-hypothesis pairs $(\chi^N, \chi^F)$ that are consistent with the copy number n. $\chi_k{}^M$ will be used to denote $\{\phi_{1,k}, \ldots, \phi_n M_k\}$, the multiset of crossover map values restricted to the k-th SNP, and similarly for $\chi^F$. $\chi_k{}^M(m_1,m_2)$ is used to mean the multiset of allele values $\{\phi_1,k(m_1, m_2), \ldots, \phi_n M_k(m_1,m_2)\}=\{m_{\phi i,k}, \ldots, m_{\phi n M,k}\}$. Keep in mind that $\phi_{l,k}\epsilon\{1,2\}$.

14. $\psi$ is the crossover map that resulted in the measured sperm from the father. Thus $s_1=\omega(f_1,f_2)$. Note that it is not necessary to consider a crossover multiset because it is assumed that the measured sperm is euploid. $\psi_k$ will be used to denote the value of this crossover map at the k-th SNP.

15. Keeping in mind the previous two definitions, let $\{e_1{}^M, \ldots, e_n{}^MM\}$ be the multiset of true but unknown haploid sequences contributed to the embryo by the mother at this chromosome. Specifically, $e_1{}^M=\phi_1(m_1,m_2)$, where $\phi_l$ is the l-th element of the multiset $\chi^M$, and $e_{lk}{}^M$ is the allele value at the k-th snp. Similarly, let $\{e_1{}^F, \ldots, e_n F^F\}$ be the multiset of true but unknown haploid sequences contributed to the embryo by the father at this chromosome. Then $e_l{}^{F-\theta}{}_l(f_1,f_2)$, where $\theta_l$ is the l-th element of the multiset $\chi^F$, and $f_{1k}{}^M$ is the allele value at the k-th SNP. Also, $\{e_1{}^M, \ldots, e_{nM}{}^M\}=\chi^M(m_1m_2)$, and $\{e_1{}^F, \ldots, e_n F^F\}=\chi^F(f_1,f_2)$ may be written.

16. $P(\hat{g}_k|\chi_k{}^M(m_1,m_2), X_k{}^F(f_1,f_2),p_d,p_c)$ denotes the probability of the genotype measurement on the embryo at SNP k given a hypothesized true underlying genotype on the embryo and given hypothesized underlying dropout and dropin rates. Note that $\chi_k{}^M(m_1,m_2)$ and $\chi_k{}^F(f_1,f_2)$ are both multisets, so are capable of expressing aneuploid genotypes. For example, $\chi_k{}^M(m_1,m_2)=\{A,A\}$ and $\chi_k{}^F(f_1,f_2)=\{B\}$ expresses the maternal trisomic genotype AAB.

Note that in this method, the measurements on the mother and father are treated as known truth, while in other places in this disclosure they are treated simply as measurements. Since the measurements on the parents are very precise, treating them as though they are known truth is a reasonable approximation to reality. They are treated as known truth here in order to demonstrate how such an assumption is handled, although it should be clear to one skilled in the art how the more precise method, used elsewhere in the patent, could equally well be used.

Solution $$\hat{n} = \underset{n}{\mathrm{argmax}}P(n, D, M, F, S)$$

-continued $$P(n, D, M, F, S) = \sum_{(\chi^U,\chi^F)\in n} \sum_{\psi} P(\chi^M, \chi^F, \psi, D, M, F, S)$$

$$= \sum_{(\chi^U,\chi^F)\in n} P(\chi^M)P(\chi^F)\sum_{\psi} P(\psi) \int f(p_d) \int$$

$$f(p_a)\prod_k$$

$$P(\hat{g}_k, g_k^M, g_k^F, \hat{g}_k^S, | \chi_k^M, \chi_k^F, \psi_k, p_d, p_a)$$

$$dp_d dp_a$$

$$= \sum_{(\chi^M,\chi^F)\in n} P(\chi^M)P(\chi^F)\sum_{\psi} P(\psi) \int f(p_d)$$

$$\int f(p_a)\times\prod_k \sum_{(f_1,f_2)=0_k^F} P(f_1)P(f_2)$$

$$P(\hat{g}_k^\Delta | \psi_k(f_1, f_2), p_d, p_a)$$

$$\sum_{(m_1,m_2)=0_k^M} P(m_1)P(m_2)P(\hat{g}_k | \chi_k^M(m_1, m_2),$$

$$\chi_k^F(f_1, f_2),$$

How to calculate each of the probabilities appearing in the last equation above has been described elsewhere in this disclosure. A method to calculate each of the probabilities appearing in the last equation above has also been described elsewhere in this disclosure. Although multiple sperm can be added in order to increase reliability of the copy number call, in practice one sperm is typically sufficient. This solution is computationally tractable for a small number of sperm.

H Simplified Method Using Only Polar Homozygotes

In another embodiment of the invention, a similar method to determine the number of copies of a chromosome can be implemented using a limited subset of SNPs in a simplified approach. The method is purely qualitative, uses parental data, and focuses exclusively on a subset of SNPs, the so-called polar homozygotes (described below). Polar homozygotic denotes the situation in which the mother and father are both homozygous at a SNP, but the homozygotes are opposite, or different allele values. Thus, the mother could be AA and the father BB, or vice versa. Since the actual allele values are not important—only their relationship to each other, i.e. opposites—the mother's alleles will be referred to as MM, and the father's as FF. In such a situation, if the embryo is euploid, it must be heterozygous at that allele. However, due to allele dropouts, a heterozygous SNP in the embryo may not be called as heterozygous. In fact, given the high rate of dropout associated with single cell amplification, it is far more likely to be called as either MM or FF, each with equal probability.

In this method, the focus is solely on those loci on a particular chromosome that are polar homozygotes and for which the embryo, which is therefore known to be heterozygous, but is nonetheless called homozygous. It is possible to form the statistic |MM|/(|MM|+|FF|), where |MM| is the number of these SNPs that are called MM in the embryo and |FF| is the number of these SNPs that are called FF in the embryo.

Under the hypothesis of euploidy, |MM|/(|MM|+|FF|) is Gaussian in nature, with mean $\frac{1}{2}$ and variance $\frac{1}{4}N$, where $N=(|MM|+|FF|)$. Therefore the statistic is completely independent of the dropout rate, or, indeed, of any other factors.

Due to the symmetry of the construction, the distribution of this statistic under the hypothesis of euploidy is known.

Under the hypothesis of trisomy, the statistic will not have a mean of ½. If, for example, the embryo has MMF trisomy, then the homozygous calls in the embryo will lean toward MM and away from FF, and vice versa. Note that because only loci where the parents are homozygous are under consideration, there is no need to distinguish M1 and M2 copy errors. In all cases, if the mother contributes 2 chromosomes instead of 1, they will be MM regardless of the underlying cause, and similarly for the father. The exact mean under trisomy will depend upon the dropout rate, p, but in no case will the mean be greater than ⅓, which is the limit of the mean as p goes to 1. Under monosomy, the mean would be precisely 0, except for noise induced by allele dropins.

In this embodiment, it is not necessary to model the distribution under aneuploidy, but only to reject the null hypothesis of euploidy, whose distribution is completely known. Any embryo for which the null hypothesis cannot be rejected at a predetermined significance level would be deemed normal.

In another embodiment of the invention, of the homozygotic loci, those that result in no-call (NC) on the embryo contain information, and can be included in the calculations, yielding more loci for consideration. In another embodiment, those loci that are not homozygotic, but rather follow the pattern AA|AB, can also be included in the calculations, yielding more loci for consideration. It should be obvious to one skilled in the art how to modify the method to include these additional loci into the calculation.

I Reduction to Practice of the PS Method as Applied to Allele Calling

In order to demonstrate a reduction to practice of the PS method as applied to cleaning the genetic data of a target individual, and its associated allele-call confidences, extensive Monte-Carlo simulations were run. The PS method's confidence numbers match the observed rate of correct calls in simulation. The details of these simulations are given in separate documents whose benefits are claimed by this disclosure. In addition, this aspect of the PS method has been reduced to practice on real triad data (a mother, a father and a born child). Results are shown below in Table 8. The TAQMAN assay was used to measure single cell genotype data consisting of diploid measurements of a large buccal sample from the father (columns $p_1, p_2$), diploid measurements of a buccal sample from the mother ($m_1, m_2$), haploid measurements on three isolated sperm from the father ($h_1$, $h_2, h_3$), and diploid measurements of four single cells from a buccal sample from the born child of the triad. Note that all diploid data are unordered. All SNPs are from chromosome 7 and within 2 megabases of the CFTR gene, in which a defect causes cystic fibrosis.

The goal was to estimate (in E1,E2) the alleles of the child, by running PS on the measured data from a single child buccal cell ($e1, e_2$), which served as a proxy for a cell from the embryo of interest. Since no maternal haplotype sequence was available, the three additional single cells of the child sample—(b11,b12), (b21,b22), (b22,b23), were used in the same way that additional blastomeres from other embryos are used to infer maternal haplotype once the paternal haplotype is determined from sperm. The true allele values (T1,T2) on the child are determined by taking three buccal samples of several thousand cells, genotyping them independently, and only choosing SNPs on which the results were concordant across all three samples. This process yielded 94 concordant SNPs. Those loci that had a valid genotype call, according to the ABI 7900 reader, on the child cell that represented the embryo, were then selected. For each of these 69 SNPs, the disclosed method determined de-noised allele calls on the embryo ($E_1, E_2$), as well as the confidence associated with each genotype call.

Twenty-nine (29%) percent of the 69 raw allele calls in uncleaned genetic data from the child cell were incorrect (marked with a dash "-" in column e1 and e2, Table 8). Columns ($E_1, E_2$) show that PS corrected 18 of these (as indicated by a box in column E1 and E2, but not in column 'conf', Table 8), while two remained miscalled (2.9% error rate; marked with a dash "-" in column 'conf', Table 8). Note that the two SNPs that were miscalled had low confidences of 53.8% and 74.4%. These low confidences indicate that the calls might be incorrect, due either to a lack of data or to inconsistent measurements on multiple sperm or "blastomeres." The confidence in the genotype calls produced is an integral part of the PS report. Note that this demonstration, which sought to call the genotype of 69 SNPs on a chromosome, was more difficult than that encountered in practice, where the genotype at only one or two loci will typically be of interest, based on initial screening of parents' data. In some embodiments, the disclosed method may achieve a higher level of accuracy at loci of interest by: i) continuing to measure single sperm until multiple haploid allele calls have been made at the locus of interest; ii) including additional blastomere measurements; iii) incorporating maternal haploid data from extruded polar bodies, which are commonly biopsied in pre-implantation genetic diagnosis today. It should be obvious to one skilled in the art that there exist other modifications to the method that can also increase the level of accuracy, as well as how to implement these, without changing the essential concept of the disclosure.

J Reduction to Practice of the PS Method as Applied to Calling Aneuploidy

To demonstrate the reduction to practice of certain aspects of the invention disclosed herein, the method was used to call aneuploidy on several sets of single cells. In this case, only selected data from the genotyping platform was used: the genotype information from parents and embryo. A simple genotyping algorithm, called "pie slice", was used, and it showed itself to be about 99.9% accurate on genomic data. It is less accurate on MDA data, due to the noise inherent in MDA. It is more accurate when there is a fairly high "dropout" rate in MDA. It also depends, crucially, on being able to model the probabilities of various genotyping errors in terms of parameters known as dropout rate and dropin rate.

The unknown chromosome copy numbers are inferred because different copy numbers interact differently with the dropout rate, dropin rate, and the genotyping algorithm. By creating a statistical model that specifies how the dropout rate, dropin rate, chromosome copy numbers, and genotype cutoff-threshold all interact, it is possible to use standard statistical inference methods to tease out the unknown chromosome copy numbers.

The method of aneuploidy detection described here is termed qualitative CNC, or qCNC for short, and employs the basic statistical inferencing methods of maximum-likelihood estimation, maximum-a-posteriori estimation, and Bayesian inference. The methods are very similar, with slight differences. The methods described here are similar to those described previously, and are summarized here for the sake of convenience.

Maximum Likelihood (ML)

Let $X_1, \ldots, X_n \sim f(x; \theta)$. Here the $X_i$ are independent, identically distributed random variables, drawn according to a probability distribution that belongs to a family of distributions parameterized by the vector $\theta$. For example, the family of distributions might be the family of all Gaussian distributions, in which case $\theta = (\mu, \sigma)$ would be the mean and variance that determine the specific distribution in question. The problem is as follows: $\theta$ is unknown, and the goal is to get a good estimate of it based solely on the observations of the data $X_1, \ldots, X_n$. The maximum likelihood solution is given by $$\hat{\theta} = \underset{\theta}{\mathrm{argmax}} \prod_i f(X_i; \theta)$$

Maximum A' Posteriori (MAP) Estimation

Posit a prior distribution $f(\theta)$ that determines the prior probability of actually seeing $\theta$ as the parameter, allowing us to write $X_1, \ldots, X_n \sim f(x|\theta)$. The MAP solution is given by $$\hat{\theta} = \underset{\theta}{\mathrm{argmax}} f(\theta) \prod_i (f(X_i \mid \theta)$$

Note that the ML solution is equivalent to the MAP solution with a uniform (possibly improper) prior.

Bayesian Inference

Bayesian inference comes into play when $\theta = (\theta_1, \ldots, \theta_d)$ is multidimensional but it is only necessary to estimate a subset (typically one) of the parameters $\theta_j$. In this case, if there is a prior on the parameters, it is possible to integrate out the other parameters that are not of interest. Without loss of generality, suppose that $\theta_1$ is the parameter for which an estimate is desired. Then the Bayesian solution is given by:

$$\hat{\theta}_1 = \underset{\theta_1}{\mathrm{argmax}} \ f(\theta_1) \int f(\theta_2) \ldots \ f(\theta_d) \prod_i (f(X_i \mid \theta) d\theta_2 \ldots \ d\theta_d$$

Copy Number Classification

Any one or some combination of the above methods may be used to determine the copy number count, as well as when making allele calls such as in the cleaning of embryonic genetic data. In one embodiment, the data may come from INFINIUM platform measurements $\{(x_{jk}, y_{jk})\}$, where $x_{jk}$ is the platform response on channel X to SNP k of chromosome j, and $y_{jk}$ is the platform response on channel Y to SNP k of chromosome j. The key to the usefulness of this method lies in choosing the family of distributions from which it is postulated that these data are drawn. In one embodiment, that distribution is parameterized by many parameters. These parameters are responsible for describing things such as probe efficiency, platform noise. MDA characteristics such as dropout, dropin, and overall amplification mean, and, finally, the genetic parameters: the genotypes of the parents, the true but unknown genotype of the embryo, and, of course, the parameters of interest: the chromosome copy numbers supplied by the mother and father to the embryo.

In one embodiment, a good deal of information is discarded before data processing. The advantage of doing this is that it is possible to model the data that remains in a more robust manner. Instead of using the raw platform data $\{(x_{jk}, y_{jk})\}$, it is possible to pre-process the data by running the genotyping algorithm on the data. This results in a set of genotype calls $(y_{jk})$, where $y_{jk} \in \{NC, AA, AB, BB\}$. NC stands for "no-call". Putting these together into the Bayesian inference paradigm above yields:

$$\hat{n}_j^M, \hat{n}_j^F = \underset{n^M, n^F}{\mathrm{max}} \int \int f(p_d) f(p_a) \prod_i P(g_{jk} \mid n^M, n^F, M_j, F_j, p_d, p_a) dp_d dp_a$$

Explanation of the Notation:

$\hat{n}_j^N, \hat{n}_j^F$ are the estimated number of chromosome copies supplied to the embryo by the mother and father respectively. These should sum to 2 for the autosomes, in the case of euploidy, i.e., each parent should supply exactly 1 chromosome.

$p_d$ and $p_a$ are the dropout and dropin rates for genotyping, respectively. These reflect some of the modeling assumptions. It is known that in single-cell amplification, some SNPs "drop out", which is to say that they are not amplified and, as a consequence, do not show up when the SNP genotyping is attempted on the INFINIUM platform. This phenomenon is modeled by saying that each allele at each SNP "drops out" independently with probability $p_d$ during the MDA phase. Similarly, the platform is not a perfect measurement instrument. Due to measurement noise, the platform sometimes picks up a ghost signal, which can be modeled as a probability of dropin that acts independently at each SNP with probability $p_a$.

$M_j, F_j$ are the true genotypes on the mother and father respectively. The true genotypes are not known perfectly, but because large samples from the parents are genotyped, one may make the assumption that the truth on the parents is essentially known.

Probe Modeling

In one embodiment of the invention, platform response models, or error models, that vary from one probe to another can be used without changing the essential nature of the invention. The amplification efficiency and error rates caused by allele dropouts, allele dropins, or other factors, may vary between different probes. In one embodiment, an error transition matrix can be made that is particular to a given probe. Platform response models, or error models, can be relevant to a particular probe or can be parameterized according to the quantitative measurements that are performed, so that the response model or error model is therefore specific to that particular probe and measurement.

Genotyping

Genotyping also requires an algorithm with some built-in assumptions. Going from a platform response (x,y) to a genotype g requires significant calculation. It is essentially requires that the positive quadrant of the x/y plane be divided into those regions where AA, AB, BB, and NC will be called. Furthermore, in the most general case, it may be useful to have regions where AAA, AAB, etc., could be called for trisomies.

In one embodiment, use is made of a particular genotyping algorithm called the pie-slice algorithm, because it divides the positive quadrant of the x/y plane into three triangles, or "pie slices". Those (x,y) points that fall in the pie slice that hugs the X axis are called AA, those that fall in the slice that hugs the Y axis are called BB, and those in the middle slice are called AB. In addition, a small square is superimposed whose lower-left corner touches the origin. (x,y) points falling in this square are designated NC, because both x and y components have small values and hence are unreliable.

The width of that small square is called the no-call threshold and it is a parameter of the genotyping algorithm. In order for the dropin/dropout model to correctly model the error transition matrix associated with the genotyping algorithm, the cutoff threshold must be tuned properly. The error transition matrix indicates for each true-genotype/called-genotype pair, the probability of seeing the called genotype given the true genotype. This matrix depends on the dropout rate of the MDA and upon the no-call threshold set for the genotyping algorithm.

Note that a wide variety of different allele calling, or genotyping, algorithms may be used without changing the fundamental concept of the invention. For example, the no-call region could be defined by a many different shapes besides a square, such as for example a quarter circle, and the no call thresholds may vary greatly for different genotyping algorithms.

Results of Aneuploidy Calling Experiments

Presented here are experiments that demonstrate the reduction to practice of the method disclosed herein to correctly call ploidy of single cells. The goal of this demonstration was twofold: first, to show that the disclosed method correctly calls the cell's ploidy state with high confidence using samples with known chromosome copy numbers, both euploid and aneuploid, as controls, and second to show that the method disclosed herein calls the cell's ploidy state with high confidence using blastomeres with unknown chromosome copy numbers.

In order to increase confidences, the ILLUMINA INFINIUM II platform, which allows measurement of hundreds of thousands of SNPs was used. In order to run this experiment in the context of PGD, the standard INFINIUM II protocol was reduced from three days to 20 hours. Single cell measurements were compared between the full and accelerated INFINIUM II protocols, and showed ~85% concordance. The accelerated protocol showed an increase in locus drop-out (LDO) rate from <1% to 5-10%; however, because hundreds of thousands of SNPs are measured and because PS accommodates allele dropouts, this increase in LDO rate does not have a significant negative impact on the results.

The entire aneuploidy calling method was performed on eight known-euploid buccal cells isolated from two healthy children from different families, ten known-trisomic cells isolated from a human immortalized trisomic cell line, and six blastomeres with an unknown number of chromosomes isolated from three embryos donated to research. Half of each set of cells was analyzed by the accelerated 20-hour protocol, and the other half by the standard protocol. Note that for the immortalized trisomic cells, no parent data was available. Consequently, for these cells, a pair of pseudo-parental genomes was generated by drawing their genotypes from the conditional distribution induced by observation of a large tissue sample of the trisomic genotype at each locus.

Where truth was known, the method correctly called the ploidy state of each chromosome in each cell with high confidence. The data are summarized below in three tables. Each table shows the chromosome number in the first column, and each pair of color-matched columns represents the analysis of one cell with the copy number call on the left and the confidence with which the call is made on the right. Each row corresponds to one particular chromosome. Note that these tables contain the ploidy information of the chromosomes in a format that could be used for the report that is provided to the doctor to help in the determination of which embryos are to be selected for transfer to the prospective mother. (Note '1' may result from both monosomy and uniparental disomy.) Table 9 shows the results for eight known-euploid buccal cells; all were correctly found to be euploid with high confidences (>0.99). Table 10 shows the results for ten known-trisomic cells (trisomic at chromosome 21); all were correctly found to be trisomic at chromosome 21 and disomic at all other chromosomes with high confidences (>0.92). Table 11 shows the results for six blastomeres isolated from three different embryos. While no truth models exist for donated blastomeres, it is possible to look for concordance between blastomeres originating from a single embryo, however, the frequency and characteristics of mosaicism in human embryos are not currently known, and thus the presence or lack of concordance between blastomeres from a common embryo is not necessarily indicative of correct ploidy determination. The first three blastomeres are from one embryo (e1) and of those, the first two (e1b1 and e1b3) have the same ploidy state at all chromosomes except one. The third cell (e1b6) is complex aneuploid. Both blastomeres from the second embryo were found to be monosomic at all chromosomes. The blastomere from the third embryo was found to be complex aneuploid. Note that some confidences are below 90%, however, if the confidences of all aneuploid hypotheses are combined, all chromosomes are called either euploid or aneuploid with confidence exceeding 92.8%.

K Laboratory Techniques

There are many techniques available allowing the isolation of cells and DNA fragments for genotyping, as well as for the subsequent genotyping of the DNA. The system and method described here can be applied to any of these techniques, specifically those involving the isolation of fetal cells or DNA fragments from maternal blood, or blastomeres from embryos in the context of IVF. It can be equally applied to genomic data in silico, i.e. not directly measured from genetic material. In one embodiment of the system, this data can be acquired as described below. This description of techniques is not meant to be exhaustive, and it should be clear to one skilled in the arts that there are other laboratory techniques that can achieve the same ends.

Isolation of Cells

Adult diploid cells can be obtained from bulk tissue or blood samples. Adult diploid single cells can be obtained from whole blood samples using FACS, or fluorescence activated cell sorting. Adult haploid single sperm cells can also be isolated from a sperm sample using FACS. Adult haploid single egg cells can be isolated in the context of egg harvesting during IVF procedures.

Isolation of the target single cell blastomeres from human embryos can be done using techniques common in in vitro fertilization clinics, such as embryo biopsy. Isolation of target fetal cells in maternal blood can be accomplished using monoclonal antibodies, or other techniques such as FACS or density gradient centrifugation.

DNA extraction also might entail non-standard methods for this application. Literature reports comparing various methods for DNA extraction have found that in some cases novel protocols, such as the using the addition of N-lauroyl-sarcosine, were found to be more efficient and produce the fewest false positives.

Amplification of Genomic DNA

Amplification of the genome can be accomplished by multiple methods including: ligation-mediated PCR (LM-PCR), degenerate oligonucleotide primer PCR (DOP-PCR), and multiple displacement amplification (MDA). Of the three methods, DOP-PCR reliably produces large quantities of DNA from small quantities of DNA, including single copies of chromosomes; this method may be most appropriate for genotyping the parental diploid data, where data fidelity is critical. MDA is the fastest method, producing hundred-fold amplification of DNA in a few hours; this method may be most appropriate for genotyping embryonic cells, or in other situations where time is of the essence.

Background amplification is a problem for each of these methods, since each method would potentially amplify contaminating DNA. Very tiny quantities of contamination can irreversibly poison the assay and give false data. Therefore, it is critical to use clean laboratory conditions, wherein pre- and post-amplification workflows are completely, physically separated. Clean, contamination free workflows for DNA amplification are now routine in industrial molecular biology, and simply require careful attention to detail.

Genotyping Assay and Hybridization

The genotyping of the amplified DNA can be done by many methods including MOLECULAR INVERSION PROBES (MIPs) such as AFFYMETRIX's GENFLEX TAG array, microarrays such as AFFYMETRIX's 500K array or the ILLUMINA BEAD ARRAYS, or SNP genotyping assays such as APPLIEDBIOSCIENCE's TAQMAN assay. The AFFYMETRIX 500K array, MIPs/GENFLEX, TAQMAN and ILLUMINA assay all require microgram quantities of DNA, so genotyping a single cell with either workflow would require some kind of amplification. Each of these techniques has various tradeoffs in terms of cost, quality of data, quantitative vs. qualitative data, customizability, time to complete the assay and the number of measurable SNPs, among others. An advantage of the 500K and ILLUMINA arrays are the large number of SNPs on which it can gather data, roughly 250,000, as opposed to MIPs which can detect on the order of 10,000 SNPs, and the TAQMAN assay which can detect even fewer. An advantage of the MIPs, TAQMAN and ILLUMINA assay over the 500K arrays is that they are inherently customizable, allowing the user to choose SNPs, whereas the 500K arrays do not permit such customization.

In the context of pre-implantation diagnosis during IVF, the inherent time limitations are significant; in this case it may be advantageous to sacrifice data quality for turnaround time. Although it has other clear advantages, the standard MIPs assay protocol is a relatively time-intensive process that typically takes 2.5 to three days to complete. In MIPs, annealing of probes to target DNA and post-amplification hybridization are particularly time-intensive, and any deviation from these times results in degradation in data quality. Probes anneal overnight (12-16 hours) to DNA sample. Post-amplification hybridization anneals to the arrays overnight (12-16 hours). A number of other steps before and after both annealing and amplification bring the total standard timeline of the protocol to 2.5 days. Optimization of the MIPs assay for speed could potentially reduce the process to fewer than 36 hours. Both the 500K arrays and the ILLUMINA assays have a faster turnaround: approximately 1.5 to two days to generate highly reliable data in the standard protocol. Both of these methods are optimizable, and it is estimated that the turn-around time for the genotyping assay for the 500 k array and/or the ILLUMINA assay could be reduced to less than 24 hours. Even faster is the TAQMAN assay which can be run in three hours. For all of these methods, the reduction in assay time will result in a reduction in data quality, however that is exactly what the disclosed invention is designed to address.

Naturally, in situations where the timing is critical, such as genotyping a blastomere during IVF, the faster assays have a clear advantage over the slower assays, whereas in cases that do not have such time pressure, such as when genotyping the parental DNA before IVF has been initiated, other factors will predominate in choosing the appropriate method. For example, another tradeoff that exists from one technique to another is one of price versus data quality. It may make sense to use more expensive techniques that give high quality data for measurements that are more important, and less expensive techniques that give lower quality data for measurements where the fidelity is not as critical. Any techniques which are developed to the point of allowing sufficiently rapid high-throughput genotyping could be used to genotype genetic material for use with this method.

Methods for Simultaneous Targeted Locus Amplification and Whole Genome Amplification.

During whole genome amplification of small quantities of genetic material, whether through ligation-mediated PCR (LM-PCR), multiple displacement amplification (MDA), or other methods, dropouts of loci occur randomly and unavoidably. It is often desirable to amplify the whole genome nonspecifically, but to ensure that a particular locus is amplified with greater certainty. It is possible to perform simultaneous locus targeting and whole genome amplification.

In a preferred embodiment, the basis for this method is to combine standard targeted polymerase chain reaction (PCR) to amplify particular loci of interest with any generalized whole genome amplification method. This may include, but is not limited to: preamplification of particular loci before generalized amplification by MDA or LM-PCR, the addition of targeted PCR primers to universal primers in the generalized PCR step of LM-PCR, and the addition of targeted PCR primers to degenerate primers in MDA.

L Techniques for Screening for Aneuploidy Using High and Medium Throughput Genotyping In one embodiment of the system the measured genetic data can be used to detect for the presence of aneuploidies and/or mosaicism in an individual. Disclosed herein are several methods of using medium or high-throughput genotyping to detect the number of chromosomes or DNA segment copy number from amplified or unamplified DNA from tissue samples. The goal is to estimate the reliability that can be achieved in detecting certain types of aneuploidy and levels of mosaicism using different quantitative and/or qualitative genotyping platforms such as ABI Taqman, MIPS, or Microarrays from Illumina, Agilent and Affymetrix. In many of these cases, the genetic material is amplified by PCR before hybridization to probes on the genotyping array to detect the presence of particular alleles. How these assays are used for genotyping is described elsewhere in this disclosure.

Described below are several methods for screening for abnormal numbers of DNA segments, whether arising from deletions, aneuploidies and/or mosaicism. The methods are grouped as follows: (i) quantitative techniques without making allele calls; (ii) qualitative techniques that leverage allele calls; (iii) quantitative techniques that leverage allele calls; (iv) techniques that use a probability distribution function for the amplification of genetic data at each locus. All methods involve the measurement of multiple loci on a given segment of a given chromosome to determine the number of instances of the given segment in the genome of the target individual. In addition, the methods involve creating a set of one or more hypotheses about the number of instances of the given segment; measuring the amount of genetic data at multiple loci on the given segment; determining the relative probability of each of the hypotheses given the measurements of the target individual's genetic data; and using the relative probabilities associated with each hypothesis to determine the number of instances of the given segment. Furthermore, the methods all involve creating a combined measurement M that is a computed function of the measurements of the amounts of genetic data at multiple loci. In all the methods, thresholds are determined for the selection of each hypothesis $H_i$ based on the measurement M, and the number of loci to be measured is estimated, in order to have a particular level of false detections of each of the hypotheses.

The probability of each hypothesis given the measurement M is $P(H_i|M)$, $P(M|H_i)P(H_i)/P(M)$. Since $P(M)$ is independent of $H_i$, we can determine the relative probability of the hypothesis given M by considering only $P(M|H_i)P(H_i)$. In what follows, in order to simplify the analysis and the comparison of different techniques, we assume that $P(H_i)$ is the same for all $\{H_i\}$, so that we can compute the relative probability of all the $P(H_i|M)$ by considering only $P(M|H_i)$. Consequently, our determination of thresholds and the number of loci to be measured is based on having particular probabilities of selecting false hypotheses under the assumption that $P(H_i)$ is the same for all $\{H_i\}$. It will be clear to one skilled in the art after reading this disclosure how the approach would be modified to accommodate the fact that $P(H_i)$ varies for different hypotheses in the set $\{H_i\}$. In some embodiments, the thresholds are set so that hypothesis $H_{i*}$ is selected which maximizes $P(H_i|M)$ over all i. However, thresholds need not necessarily be set to maximize $P(H_i|M)$, but rather to achieve a particular ratio of the probability of false detections between the different hypotheses in the set $\{H_i\}$.

It is important to note that the techniques referred to herein for detecting aneuploidies can be equally well used to detect for uniparental disomy, unbalanced translocations, and for the sexing of the chromosome (male or female; XY or XX). All of the concepts concern detecting the identity and number of chromosomes (or segments of chromosomes) present in a given sample, and thus are all addressed by the methods described in this document. It should be obvious to one skilled in the art how to extend any of the methods described herein to detect for any of these abnormalities.

The Concept of Matched Filtering

The methods applied here are similar to those applied in optimal detection of digital signals. It can be shown using the Schwartz inequality that the optimal approach to maximizing Signal to Noise Ratio (SNR) in the presence of normally distributed noise is to build an idealized matching signal, or matched filter, corresponding to each of the possible noise-free signals, and to correlate this matched signal with the received noisy signal. This approach requires that the set of possible signals are known as well as the statistical distribution mean and Standard Deviation (SD) of the noise. Herein is described the general approach to detecting whether chromosomes, or segments of DNA, are present or absent in a sample. No differentiation will be made between looking for whole chromosomes or looking for chromosome segments that have been inserted or deleted. Both will be referred to as DNA segments. It should be clear after reading this description how the techniques may be extended to many scenarios of aneuploidy and sex determination, or detecting insertions and deletions in the chromosomes of embryos, fetuses or born children. This approach can be applied to a wide range of quantitative and qualitative genotyping platforms including Taqman, qPCR, Illumina Arrays, Affymetrix Arrays, Agilent Arrays, the MIPS kit etc.

Formulation of the General Problem

Assume that there are probes at SNPs where two allelic variations occur, x and y. At each locus i, i=1 . . . N, data is collected corresponding to the amount of genetic material from the two alleles. In the Taqman assay, these measures would be, for example, the cycle time, Cr, at which the level of each allele-specific dye crosses a threshold. It will be clear how this approach can be extended to different measurements of the amount of genetic material at each locus or corresponding to each allele at a locus. Quantitative measurements of the amount of genetic material may be nonlinear, in which case the change in the measurement of a particular locus caused by the presence of the segment of interest will depend on how many other copies of that locus exist in the sample from other DNA segments. In some cases, a technique may require linear measurements, such that the change in the measurement of a particular locus caused by the presence of the segment of interest will not depend on how many other copies of that locus exist in the sample from other DNA segments. An approach is described for how the measurements from the Taqman or qPCR assays may be linearized, but there are many other techniques for linearizing nonlinear measurements that may be applied for different assays.

The measurements of the amount of genetic material of allele x at loci 1 . . . N is given by data $d_x=[d_{x1} \ldots d_{xN}]$. Similarly for allele y, $d_y=[d_{y1} \ldots d_{yN}]$. Assume that each segment j has alleles $a_j=[a_{j1} \ldots a_{jN}]$ where each element $a_{ji}$ is either x or y. Describe the measurement data of the amount of genetic material of allele x as $d_x=s_x+\upsilon_x$ where $s_x$ is the signal and $\upsilon_x$ is a disturbance. The signal $s_x=[f_x(a_{11}, \ldots, a_{J1}) \ldots f_x(a_{JN}, \ldots, a_{JN})]$ where $f_x$ is the mapping from the set of alleles to the measurement, and J is the number of DNA segment copies. The disturbance vector $\upsilon_x$ is caused by measurement error and, in the case of nonlinear measurements, the presence of other genetic material besides the DNA segment of interest. Assume that measurement errors are normally distributed and that they are large relative to disturbances caused by nonlinearity (see section on linearizing measurements) so that $\upsilon_x \approx n_{xi}$ where $n_{xi}$ has variance $\sigma_{xi}^2$ and vector $n_x$ is normally distributed ~N(0,R), R=E$(n_x n_x^T)$. Now, assume some filter h is applied to this data to perform the measurement $m_x=h^T d_x=h^T s_x+h^T \upsilon_x$. In order to maximize the ratio of signal to noise $(h^T s_x/h^T n_x)$ it can be shown that h is given by the matched filter $h=\mu R^{-1} s_x$ where $\mu$ is a scaling constant. The discussion for allele x can be repeated for allele y.

Method 1a: Measuring Aneuploidy or Sex by Quantitative Techniques that do not Make Allele Calls when the Mean and Standard Deviation for Each Locus is Known Assume for this section that the data relates to the amount of genetic material at a locus irrespective of allele value (e.g. using qPCR), or the data is only for alleles that have 100% penetrance in the population, or that data is combined on multiple alleles at each locus (see section on linearizing measurements)) to measure the amount of genetic material at that locus. Consequently, in this section one may refer to data $d_x$ and ignore $d_y$. Assume also that there are two hypotheses: $h_0$ that there are two copies of the DNA segment (these are typically not identical copies), and $h_1$ that there is only 1 copy. For each hypothesis, the data may be described as $d_{xi}(h_0)=s_{xi}(h_0)+n_{xi}$ and $d_{xi}(h_1)=s_{xi}(h_1)+n_{xi}$ respectively, where $s_{xi}(h_0)$ is the expected measurement of the genetic material at locus i (the expected signal) when two DNA segments are present and $s_{xi}(h_1)$ is the expected data for one segment. Construct the measurement for each locus by differencing out the expected signal for hypothesis $h_0$:

$m_{xi}=d_{xi}-s_{xi}(h_0)$. If $h_1$ is true, then the expected value of the measurement is $E(m_{xi})=s_{xi}(h_1)-s_{xi}(h_0)$. Using the matched filter concept discussed above, set $h=(1/N)R^{-1}(s_{xi}(h_1)-s_{xi}(h_0))$. The measurement is described as $m=h^T d_x = (1/N)\Sigma_{i=1 \ldots N}((s_{xi}(h_1)-s_{xi}(h_0))/\sigma_{xi}^2)m_{xi}$.

If $h_1$ is true, the expected value of $E(m|h_1)=m_1=(1/N)\Sigma_{i=1 \ldots N}(s_{xi}(h_1)-s_{xi}(h_0))^2/\sigma_{xi}^2$ and the standard deviation of m is $\sigma_{m|h1}^2=(1/N^2)\Sigma_{i=1 \ldots N}((s_{xi}(h_1)-s_{xi}(h_0))^2/\sigma_{xi}^4)\sigma_{xi}^2=(1/N^2)\Sigma_{i=1 \ldots N}(s_{xi}(h_1)-s_{xi}(h_0))^2/\sigma_{xi}^2$.

If $h_0$ is true, the expected value of m is $E(m|h_0)=m_0=0$ and the standard deviation of m is again $\sigma_{m|h0}^2=(1/N^2)\Sigma_{i=1 \ldots N}(s_{xi}(h_1)-s_{xi}(h_0))^2/\sigma_{xi}^2$.

FIG. 1 illustrates how to determine the probability of false negatives and false positive detections. Assume that a threshold t is set half-way between $m_1$ and $m_0$ in order to make the probability of false negatives and false positives equal (this need not be the case as is described below). The probability of a false negative is determined by the ratio of $(m_1-t)/\sigma_{m|h1}=(m_1-m_0)/(2\sigma_{m|h1})$. "5-Sigma" statistics may be used so that the probability of false negatives is $1-\text{normcdf}(5,0,1)=2.87e-7$. In this case, the goal is for $(m_1-m_0)/(2\sigma_{m|h0})>5$ or $10\sqrt{((1/N^2)\Sigma_{i=1 \ldots N}(s_{xi}(h_1)-s_{xi}(h_0))^2/\sigma_{xi}^2)}<(1/N)\Sigma_{i=1 \ldots N}(s_{xi}(h_1)-s_{xi}(h_0))^2/\sigma_{xi}^2$ or $\sqrt{(\Sigma_{i=1 \ldots N}(s_{xi}(h_1)-s_{xi}(h_0))^2/\sigma_{xi}^2)}>10$. In order to compute the size of N, Mean Signal to Noise Ratio can be computed from aggregated data: $MSNR=(1/N)\Sigma_{i=1 \ldots N}(s_{xi}(h_1)-s_{xi}(h_0))^2/\sigma_{xi}^2$. N can then be found from the inequality above: $\sqrt{N}\cdot\sqrt{MSNR}>10$ or $N>100/MSNR$.

Figure 2:
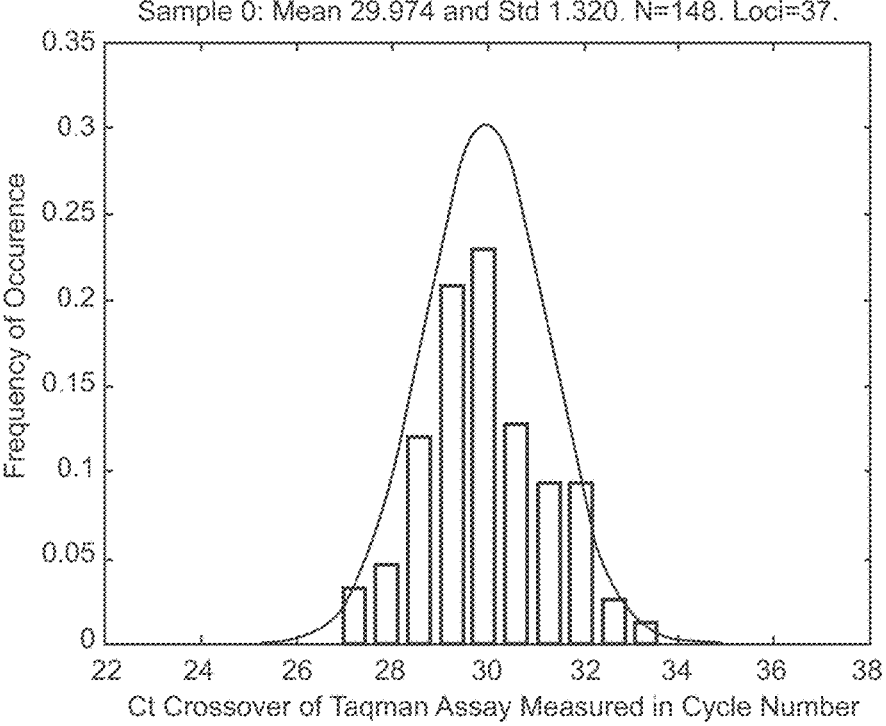
FIG. 2: the results from a mixed female sample, all loci hetero.
Figure 3:
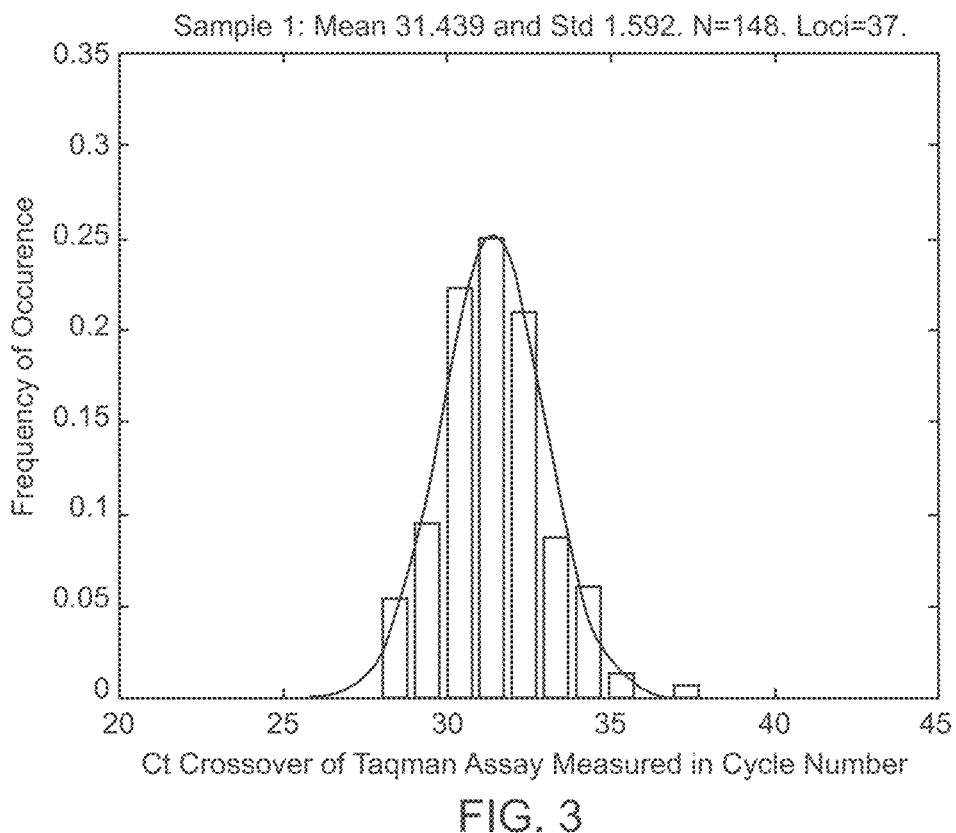
FIG. 3: the results from a mixed male sample, all loci hetero.
Figure 4:
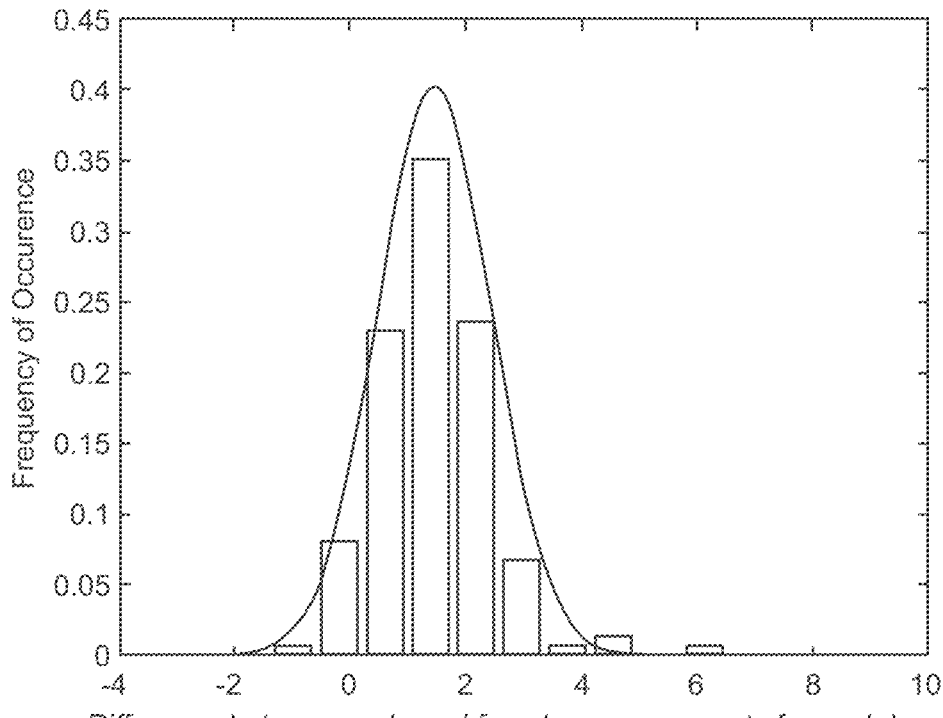
FIG. 4: Ct measurements for male sample differenced from Ct measurements for female sample.

This approach was applied to data measured with the Taqman Assay from Applied BioSystems using 48 SNPs on the X chromosome. The measurement for each locus is the time, $C_t$, that it takes the die released in the well corresponding to this locus to exceed a threshold. Sample 0 consists of roughly 0.3 ng (50 cells) of total DNA per well of mixed female origin where subjects had two X chromosomes; sample 1 consisted of roughly 0.3 ng of DNA per well of mixed male origin where subject had one X chromosome. FIGS. 2 and 3 show the histograms of measurements for samples 1 and 0. The distributions for these samples are characterized by $m_0=29.97$; $S_{D0}=1.32$, $m_1=31.44$, $SD_1=1.592$. Since this data is derived from mixed male and female samples, some of the observed SD is due to the different allele frequencies at each SNP in the mixed samples. In addition, some of the observed SD will be due to the varying efficiency of the different assays at each SNP, and the differing amount of dye pipetted into each well. FIG. 4 provides a histogram of the difference in the measurements at each locus for the male and female sample. The mean difference between the male and female samples is 1.47 and the SD of the difference is 0.99. While this SD will still be subject to the different allele frequencies in the mixed male and female samples, it will no longer be affected the different efficiencies of each assay at each locus. Since the goal is to differentiate two measurements each with a roughly similar SD, the adjusted SD may be approximated for each measurement for all loci as $0.99/\sqrt{2}=0.70$. Two runs were conducted for every locus in order to estimate $\sigma_{xi}$ for the assay at that locus so that a matched filter could be applied. A lower limit of $\sigma_{xi}$ was set at 0.2 in order to avoid statistical anomalies resulting from only two runs to compute $\sigma_{xi}$. Only those loci (numbering 37) for which there were no allele dropouts over both alleles, over both experiment runs and over both male and female samples were used in the plots and calculations. Applying the approach above to this data, it was found that $MSNR=2.26$, hence $N=2^2 5^2/2.26^2=17$ loci. Although applied here only to the X chromosome, and to differentiating 1 copy from 2 copies, this experiment indicates the number of loci necessary to detect M2 copy errors for all chromosomes, where two exact copies of a chromosome occur in a trisomy, using Method 3 described below.

The measurement used for each locus is the cycle number, Ct, that it takes the die released in the well corresponding to a particular allele at the given locus to exceed a threshold that is automatically set by the ABI 7900HT reader based on the noise of the no-template control. Sample 0 consisted of roughly 60 pg (equivalent to genome of 10 cells) of total DNA per well from a female blood sample (XX); sample 1 consisted of roughly 60 pg of DNA per well from a male blood sample (X). As expected, the Ct measurement of female samples is on average lower than that of male samples.

There are several approaches to comparing the Taqman Assay measurements quantitatively between female and male samples. Here illustrated is one approach. To combine information from the FAM and VIC channel for each locus, $C_t$ values of the two channels were converted to the copy numbers of their respective alleles, summed, and then converted back to a composite $C_t$ value for that locus. The conversion between $C_t$ value and the copy number was based on the equation $Nc=10^{(-a^*Ct+b)}$ which is typically used to model the exponential growth of the die measurement during real-time PCR. The coefficients a and b were determined empirically from the $C_t$ values using multiple measurements on quantities of 6 pg and 60 pg of DNA. We determined that $a\approx0.298$, $b\approx10.493$; hence we used the linearizing formula $Nc=10^{(-0.298Ct+10.493)}$.

Figure 14:
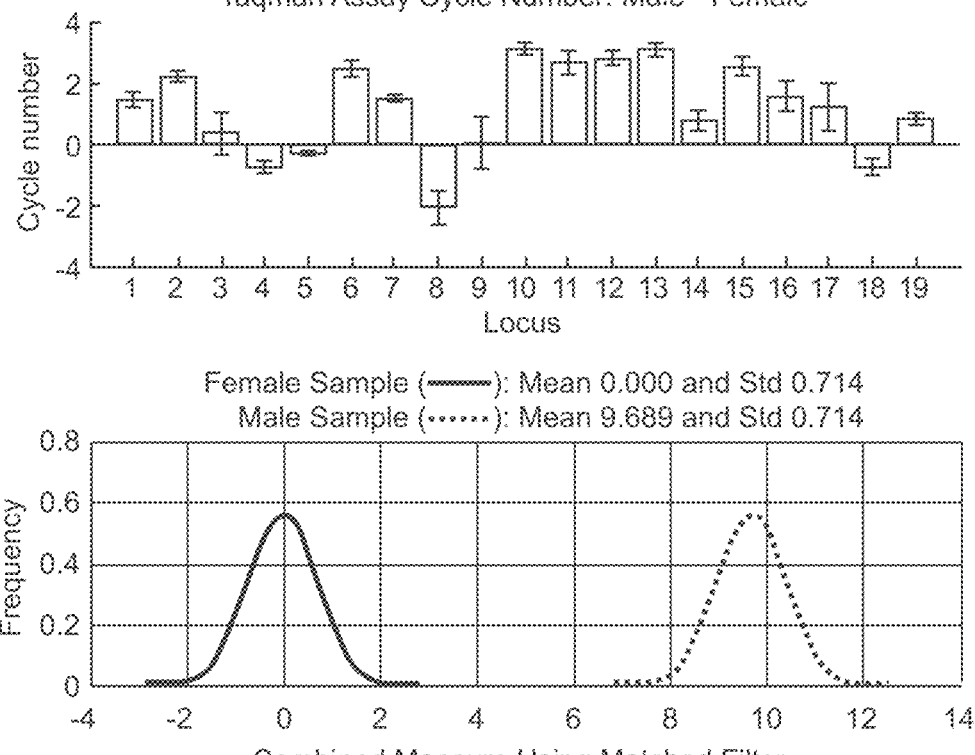
FIG. 14: matched filter and performance for 19 loci measured with Taqman on 60 pg of DNA.

FIG. 14, top panel, shows the means and standard deviations of the differences between the composite $C_t$ values of male and female samples at each of the 19 loci measured. The mean difference between the male and female samples is 1.19 and the SD of the differences is 0.62. Note that this locus-specific SD will not be affected by the different efficiencies of the assay at each locus. Three runs were conducted for every locus in order to estimate $\sigma_{xi}$ for the assay at that locus so that a matched filter could be created and applied. Note that a lower limit of standard deviation at each locus was set at 0.6 in order to avoid statistical anomalies resulting from the small number of runs at each locus. Only those loci for which there were no allele dropouts over at least two experiment runs and over both male and female samples were used in the plots and calculations. Applying the approach above to this data, it was found that $MSNR=9.7$. Hence $N=6$ loci are required in order to have 99.99% confidence of the test, assuming those 6 loci generate the same MSNR (Mean Signal to Noise Ratio) as the 19 loci used in this test. The combined measure m and its expected standard deviation after applying the matched filter for male and female samples is shown in FIG. 14, bottom.

Figure 15:
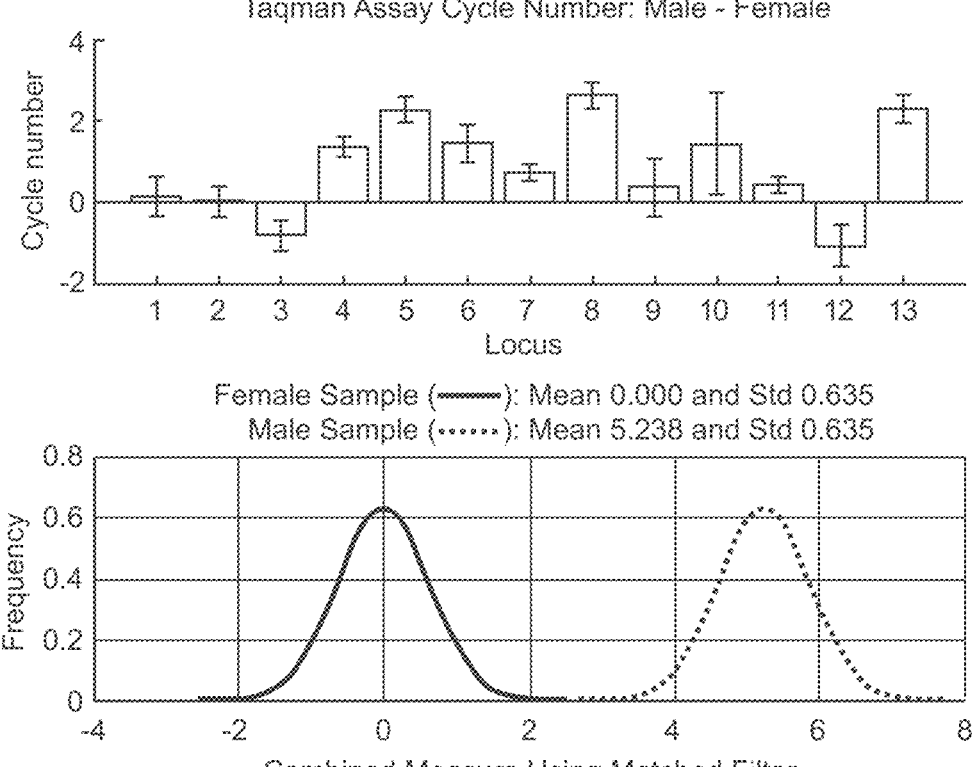
FIG. 15: matched filter and performance for 13 loci measured with Taqman on 6 pg of DNA.

The same approach was applied to samples diluted 10 times from the above mentioned DNA. Now each well consisted of roughly 6 pg (equivalent amount of a single cell genome) of total DNA of female and male blood samples. As is the previous case, three replicates were tested for each locus in order to estimate the mean and standard deviations of the difference in $C_t$ levels between male and female samples, and a lower limit of 0.6 was set on the standard deviation at each locus in order to avoid statistical anomalies resulting from the small number of runs at each locus. Only those loci for which there were no allele dropouts over at least two experiment runs and over both male and female samples were used in the plots and calculations. This resulted in 13 loci that were used in creating the matched filter. FIG. 15, with the same lay out as in FIG. 14, shows how the differences between male and female measurements are combined into a single measure. The estimated number, N, of SNPs that need to be measured in order to assure 99.99% confidence of the test is 11. This assumes that these 11 loci have the same MSNR (Mean Signal to Noise Ration) as the 13 loci tested in this experiment.

Note that this result of 11 loci is significantly lower than we expect to employ in practice. The primary reason is that this experiment performed an allele-specific amplification in each Taqman well, in which 6 pg of DNA is placed. The expected standard deviation for each locus is larger when one initially performs a whole-genome amplification in order to generate a sufficient quantity of genetic material that can be placed in each well. In a later section, we describe the experiment that addresses this issue, using Multiple Displacement Amplification (MDA) whole genome amplification of single cells.

Figure 16:
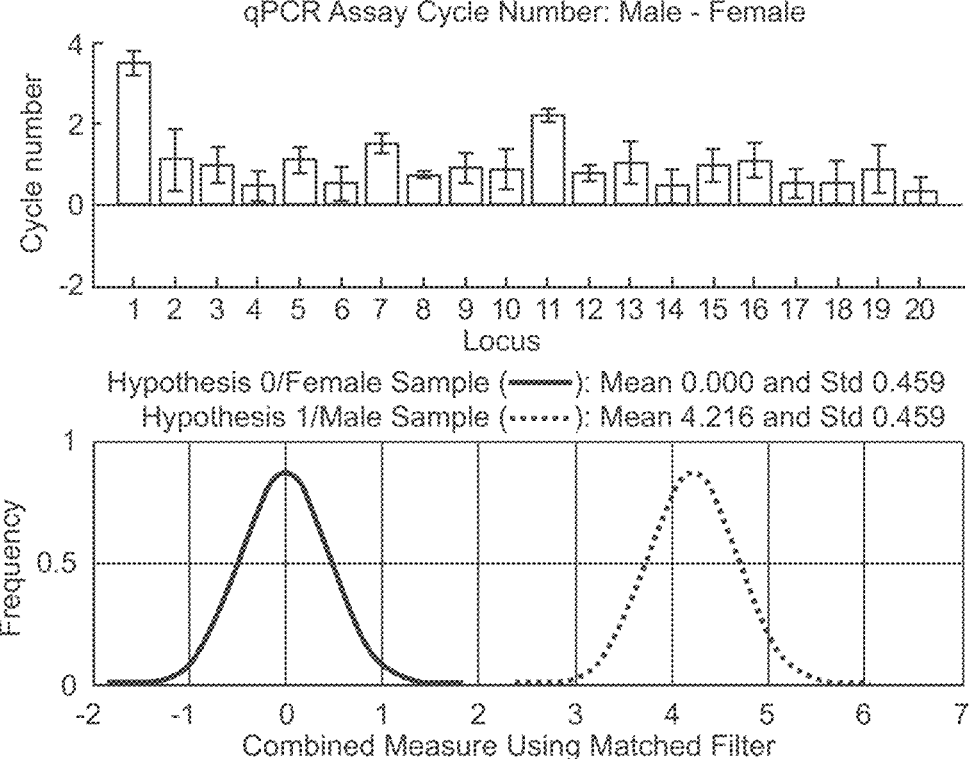
FIG. 16: matched filter and performance for 20 loci measured with qPCR on 60 pg of DNA.

A similar approach to that described above was also applied to data measured with the SYBR qPCR Assay using 20 SNPs on the X chromosome of female and male blood samples. Again, the measurement for each locus is the cycle number, $C_t$, that it takes the die released in the well corresponding to this locus to exceed a threshold. Note that we do not need to combine measurements from different dyes in this case, since only one dye is used to represent the total amount of genetic material at a locus, independent of allele value. Sample 0 and 1 consisted of roughly 60 pg (10 cells) of total DNA per well of female and male samples, respectively. FIG. 16, top show the means and standard deviations of differences of $C_t$ for male and female samples at each of the 20 loci. The mean difference between the male and female samples is 1.03 and the SD of the difference is 0.78. Three runs were conducted for every locus and only those loci for which there were no allele dropouts over at least two experiment runs and over both male and female samples were used. Applying the approach above to this data, it was found that N=14 loci in order to have 99.99% confidence of the test, assuming those 14 loci have the same MSNR as the 20 used in this experiment.

Figure 17:
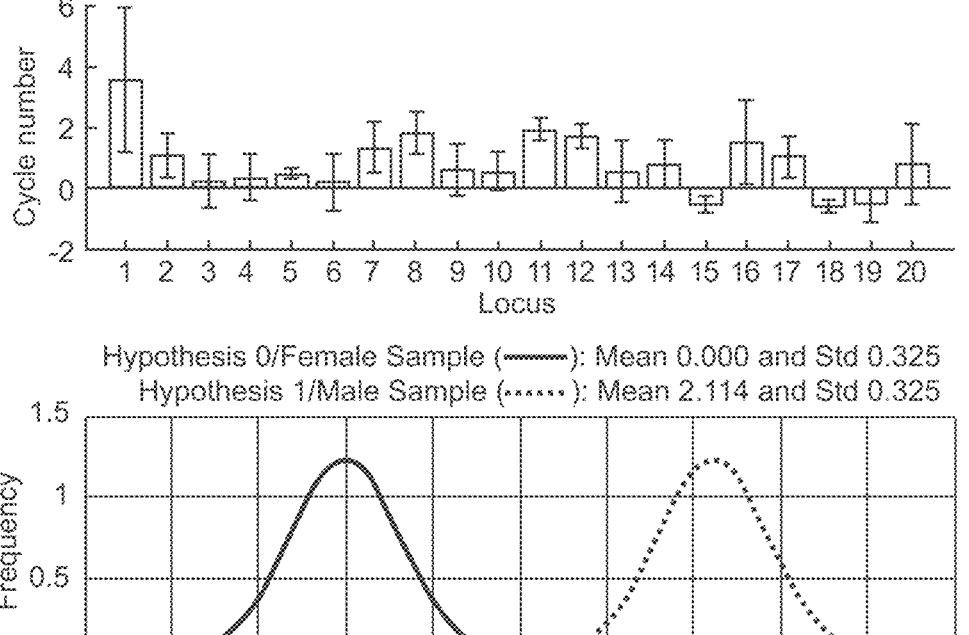
FIG. 17: matched filter and performance for 20 loci measured with qPCR on 6 pg of DNA.

And again, in order to estimate the number of SNPs needed for single cell measurements, this technique was applied to samples that consist of 6 pg of total DNA of female and male origin, see FIG. 17. The estimated number N, of SNPs that need to be measured in order to assure 99.99% confidence in differentiating one chromosome copy from two, is 27, assuming those 27 loci have the same MSNR as the 20 used in this experiment. As described above, this result of 27 loci is lower than we expect to employ in practice, since this experiment uses locus-specific amplification in each qPCR well. We next describe an experiment that addresses this issue. The experiments discussed hitherto were designed to specifically address locus or allele-specific amplification of small DNA quantities, without complicating the experiment by introducing issues of cells lysis and whole genome amplification. The quantitative measurements were done on small quantities of DNA diluted from a large sample, without using whole genome pre-amplification of single cells. Despite the goal to simplify the experiment, separate dilution and pipetting of the two samples affected the amount of DNA used to compare male with female samples at each locus. To ameliorate this effect, the diluted concentrations were measured using spectrometer comparisons to DNA with known concentrations and were calibrated appropriately.

Figure 18A:
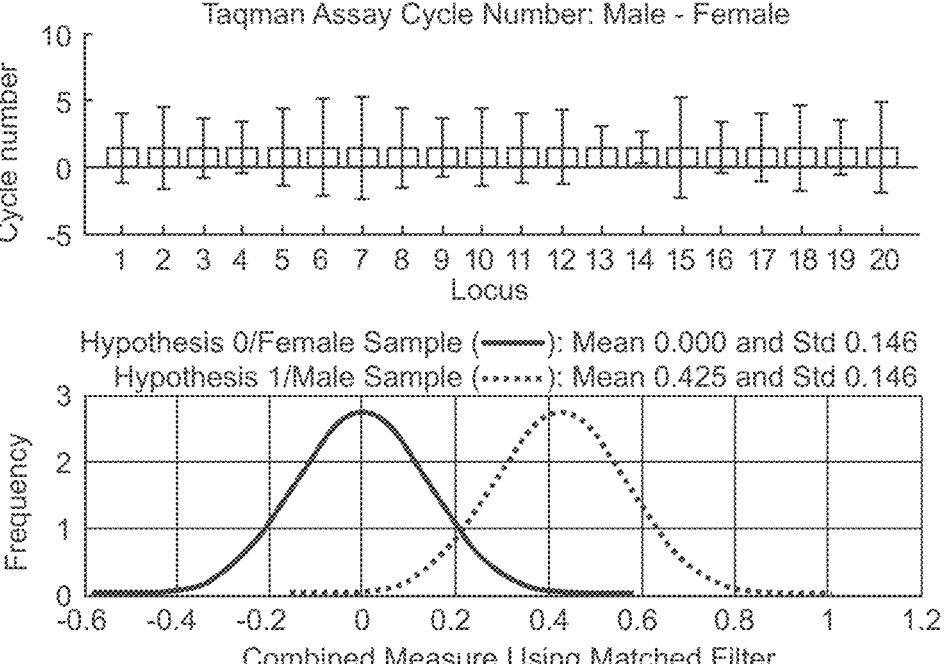
FIG. 18A: matched filter and performance for 20 loci using MDA and Taqman on 16 single cells.

We now describe an experiment that employs the protocol that will be used for real aneuploidy screening, including cell lysis and whole genome amplification. The level of amplification is in excess of 10,000 in order to generate sufficient genetic material to populate roughly 1,000 Taqman wells with 60 pg of DNA from each cell. In order to estimate the standard deviation of single genotyping assays with whole-genome pre-amplifications, multiple experiments were conducted where a single female HeLa cell (XX) was pre-amplified using Multiple Displacement Amplification (MDA) and the amounts of DNA at 20 loci on its X chromosome were measured using quantitative PCR assays. This experiment was repeated for 16 single HeLa Cells in 16 separate MDA pre-amplifications. The results of the experiment are designed to be conservative, since the standard deviation between loci from separate amplifications will be greater than the standard deviation expected between loci used in the same reaction. In actual implementation, we will compare loci of chromosomes that were involved in the same MDA amplification. Furthermore, it is conservative since we assume that the $C_t$ of a cell with one X chromosome will be one cycle more than that of the HeLa cell (XX), i.e. we increased the $C_t$ measurements of a double-X cell by 1 to simulate a single-X cell. This is a conservative estimate because the difference between $C_t$ values are typically greater than 1 due to inefficiencies of the MDA and PCR assays i.e. with a perfectly efficient PCR reaction, the amount of DNA is doubled in each cycle. However, the amplification is typically less than a factor of two in each PCR cycle due to imperfect hybridization and other effects. This experiment was designed to establish an upper limit on the amount of loci that we will need to measure to screen aneuploidy that involve M2 copy errors where quantitative data is necessary. Applying the Matched Filter technique for this data, as shown in FIG. 18A, the minimum number of SNPs to achieve 99.99% is estimated as N=131.

Figure 18B:
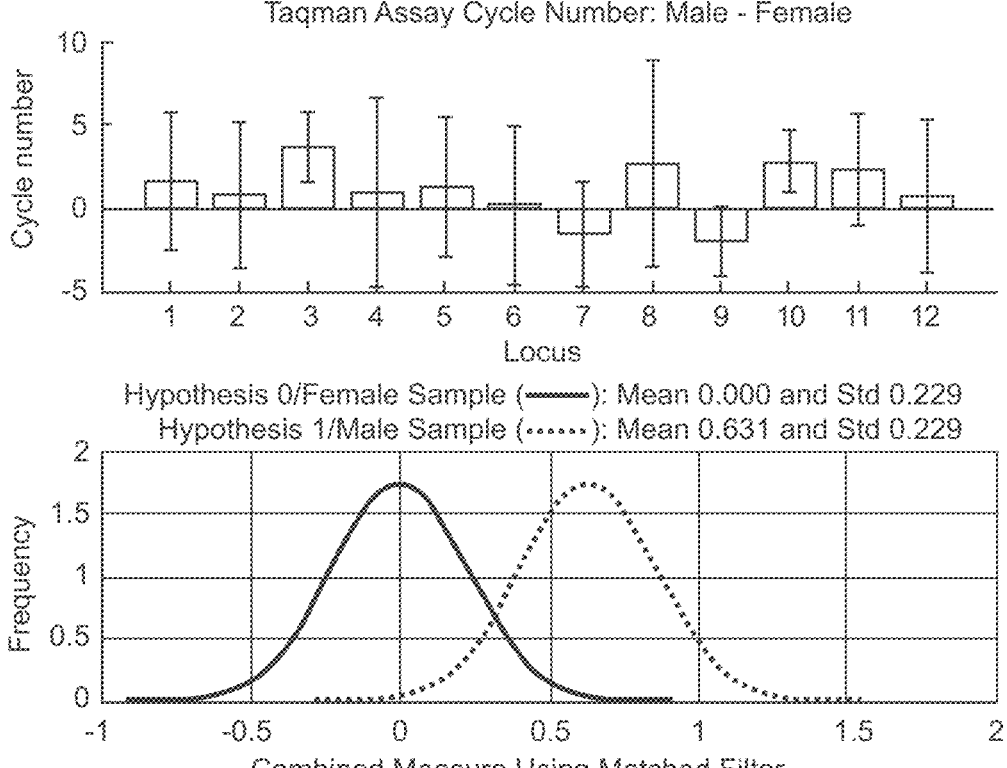
FIG. 18B: Matched filter and performance for 11 loci on Chromosome 7 and 13 loci on Chromosome X using MDA and Taqman on 15 single cells.

To really estimate how many SNPs are required for this approach to differentiate one or two copies of chromosomes in real aneuploidy screening, it is highly desirable to test the system on samples with one sample containing twice the amount of genetic material as in the other. This precise control is not easily achieved by sample handling in separate wells because the dilution, pipetting and/or amplification efficiency vary from well to well. Here an experiment was designed to overcome these issues by using an internal control, namely by comparing the amount of genetic material on Chromosome 7 and Chromosome X of a male sample. Multiple experiments were conducted where a single male MRC-5 cell (X) was pre-amplified using Multiple Displacement Amplification (MDA) and the amounts of DNA at 11 loci on its Chromosome 7 and 13 loci on its Chromosome X were measured using ABI Taqman assays. The difference in numbers of loci on Chromosome 7 and X was chosen because larger standard deviation of measured amount of genetic material is expected for Chromosome X. This experiment was repeated for 15 single MRC-5 Cells in 15 separate MDA pre-amplifications. After combining readouts from both FAM and VIC channels of all loci, we used the averaged composite Ct values on Chromosome 7 as the reference, which corresponds to the "normal" sample referred to in aneuploidy screening. Composite Ct values on Chromosome X were differenced by the reference, and if a significant difference voted by many loci is detected, it then corresponds to the "aneuploidy" condition. To create a matched filter, standard deviation of these differences at each loci was measured using the results of 15 independent single cell experiments. The mean and standard deviation at each loci was shown in FIG. 18B. And MSNR=0.631. So the number of SNPs to be measured to achieve 99.99% confidence, N=88. Note that this is the upper limit because we are still using single cells pre-amplified separately.

Method 1b: Measuring Aneuploidy or Sex by Quantitative Techniques that do not Make Allele Calls when the Mean and Std. Deviation is not Known or is Uniform When the characteristics of each locus are not known well, the simplifying assumptions that all the assays at each locus will behave similarly can be made, namely that $E(m_{xi})$ and $\sigma_{xi}$ are constant across all loci i, so that it is possible to refer instead only to $E(m_x)$ and $\sigma_x$. In this case, the matched filtering approach $m=h^T d_x$ reduces to finding the mean of the distribution of $d_x$. This approach will be referred to as comparison of means, and it will be used to estimate the number of loci required for different kinds of detection using real data.

As above, consider the scenario when there are two chromosomes present in the sample (hypothesis $h_0$) or one chromosome present ($h_1$). For $h_0$, the distribution is $N(\mu_0, \sigma_0^2)$ and for $h_1$ the distribution is $N(\mu_1, \sigma_1^2)$. Measure each of the distributions using $N_0$ and $N_1$ samples respectively, with measured sample means and SDs $m_1$, $m_0$, $s_1$, and $s_0$. The means can be modeled as random variables $M_0$, $M_1$ that are normally distributed as $M_0 \sim N(\mu_0, \sigma_0^2/N_0)$ and $M_1 \sim N(\mu_1, \sigma_1^2/N_1)$. Assume $N_1$ and $N_0$ are large enough (>30) so that one can assume that $M_1 \sim N(m_1, s_1^2/N_1)$ and $M_0 \sim N(m_0, s_0^t/N_0)$. In order to test whether the distributions are different, the difference of the means test may be used, where $d=m_1-m_0$. The variance of the random variable D is $\sigma_d^2=\sigma_1^2/N_1+\sigma_0^2/N_0$ which may be approximated as $\sigma_d^2=s_1^2/N_1+s_0^2/N_0$. Given $h_0$, $E(d)=0$; given $h_1$, $E(d)=\mu_1-\mu_0$. Different techniques for making the call between $h_1$ for $h_0$ will now be discussed.

Figure 5:
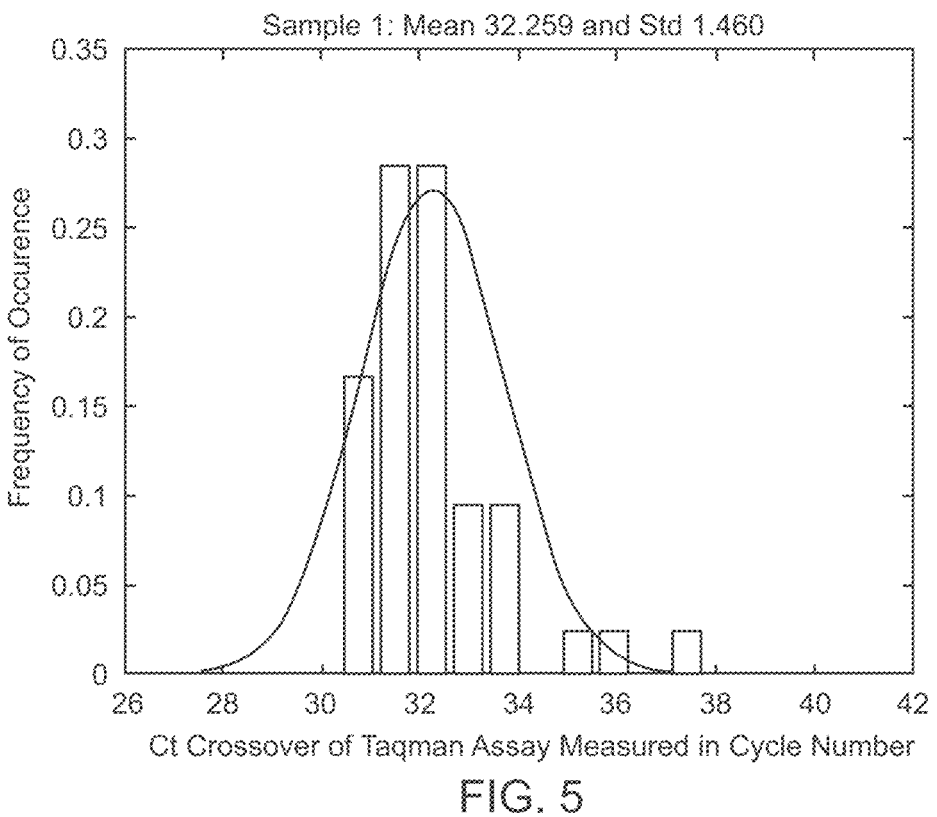
FIG. 5: the results from a mixed female sample; Taqman single dye.
Figure 6:
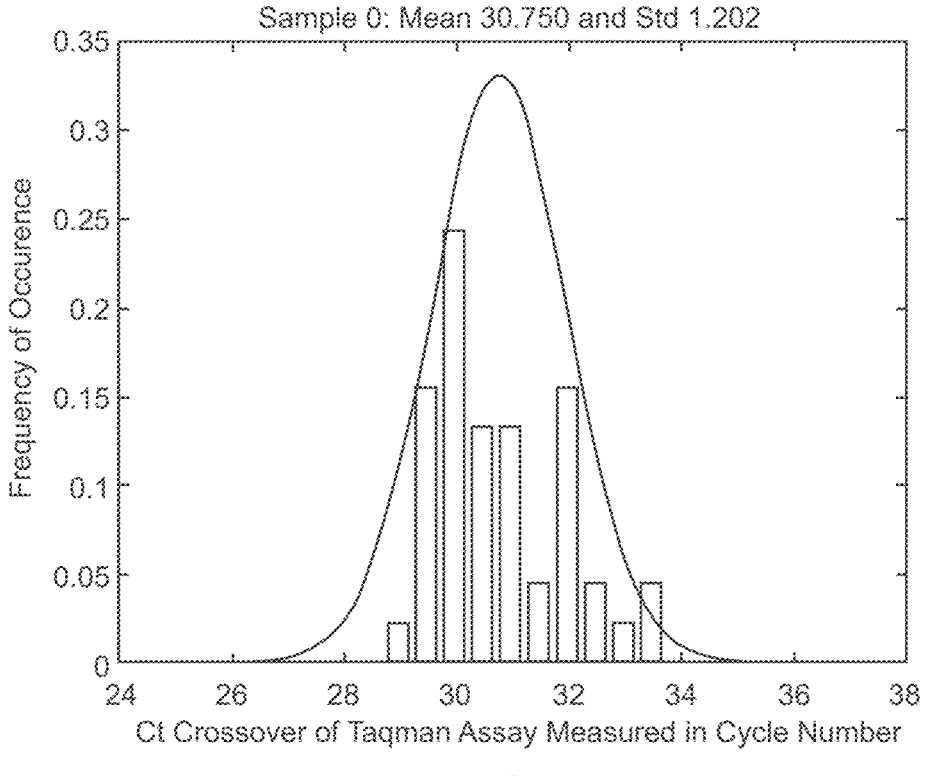
FIG. 6: the results from a mixed male; Taqman single dye.

Data measured with a different run of the Taqman Assay using 48 SNPs on the X chromosome was used to calibrate performance. Sample 1 consists of roughly 0.3 ng of DNA per well of mixed male origin containing one X chromosome; sample 0 consisted of roughly 0.3 ng of DNA per well of mixed female origin containing two X chromosomes. $N_1=42$ and $N_0=45$. FIGS. 5 and 6 show the histograms for samples 1 and 0. The distributions for these samples are characterized by $m_1=32.259$, $s_1=1.460$, $\sigma_{m1}=s_1/\text{sqrt}(N_1)=0.225$; $m_0=30.75$; $s_0=1.202$, $\sigma_{m0}=s_0/\text{sqrt}(N_0)=0.179$. For these samples $d=1.509$ and $\sigma_d=0.2879$.

Figure 7:
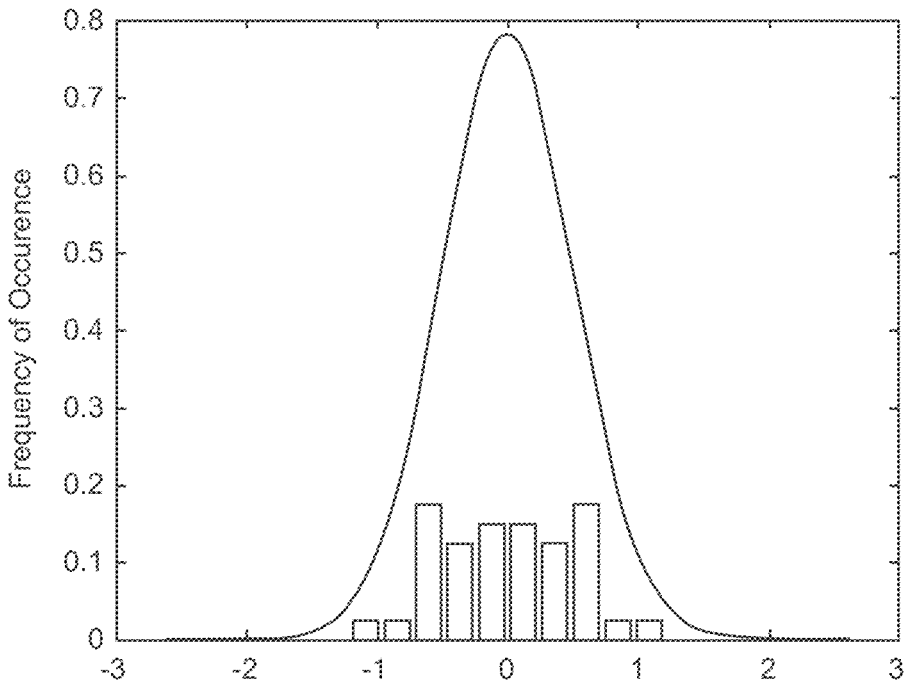
FIG. 7: the distribution of repeated measurements for mixed male sample.

Since this data is derived from mixed male and female samples, much of the standard deviation is due to the different allele frequencies at each SNP in the mixed samples. SD is estimated by considering the variations in $C_t$ for one SNP at a time, over multiple runs. This data is shown in FIG. 7. The histogram is symmetric around 0 since $C_t$ for each SNP is measured in two runs or experiments and the mean value of Ct for each SNP is subtracted out. The average std. dev. across 20 SNPs in the mixed male sample using two runs is s=0.597. This SD will be conservatively used for both male and female samples, since SD for the female sample will be smaller than for the male sample. In addition, note that the measurement from only one dye is being used, since the mixed samples are assumed to be heterozygous for all SNPs. The use of both dyes requires the measurements of each allele at a locus to be combined, which is more complicated (see section on linearizing measurements). Combining measurements on both dyes would double signal amplitude and increase noise amplitude by roughly sqrt(2), resulting in an SNR improvement of roughly sqrt(2) or 3 dB.

Detection Assuming No Mosaicism and No Reference Sample

Assume that $m_0$ is known perfectly from many experiments, and every experiment runs only one sample to compute $m_1$ to compare with $m_0$. $N_1$ is the number of assays and assume that each assay is a different SNP locus. A threshold t can be set half way between $m_0$ and $m_1$ to make the likelihood of false positives equal the number of false negatives, and a sample is labeled abnormal if it is above the threshold. Assume $s_1=s_2=s=0.597$ and use the 5-sigma approach so that the probability of false negatives or positives is $1-\text{normcdf}(5,0,1)=2.87e-7$. The goal is for $5s_1/\text{sqrt}(N_1)<(m_1-m_0)/2$, hence $N_1=100\ s_1^2/(m_1-m_0)^2=16$. Now, an approach where the probability of a false positive is allowed to be higher than the probability of a false negatives, which is the harmful scenario, may also be used. If a positive is measured, the experiment may be rerun. Consequently, it is possible to say that the probability of a false negative should be equal to the square of the probability of a false positive. Consider FIG. 1, let t=threshold, and assume Sigma_0=Sigma_1=s. Thus $(1-\text{normcdf}((t-m_0)/s,0,1))^2=1-\text{normcdf}((m_1-t)/s,0,1)$. Solving this, it can be shown that $t=m_0+0.32(m_1-m_0)$. Hence the goal is for $5s/\text{sqrt}(N_1)<m_1-m_0-0.32(m_1-m_0)=(m_1-m_0)/1.47$, hence $N_1=(5^2)(1.47^2)s^2/(m_1-m_0)^2=9$.

Detection with Mosaicism without Running a Reference Sample

Assume the same situation as above, except that the goal is to detect mosaicism with a probability of 97.7% (i.e. 2-sigma approach). This is better than the standard approach to amniocentesis which extracts roughly 20 cells and photographs them. If one assumes that 1 in 20 cells is aneuploid and this is detected with 100% reliability, the probability of having at least one of the group being aneuploid using the standard approach is $1-0.95^{20}=64\%$. If 0.05% of the cells are aneuploid (call this sample 3) then $m_3=0.95m_0+0.05m_1$ and $\text{var}(m_3)=(0.95s_0^2+0.05s_1^2)/N_1$. Thus, $\text{std}(m_3)2<(m_3-m_0)/2=>\text{sqrt}(0.95s_0^2+0.05s_1^2)/\text{sqrt}(N_1)<0.05(m_1-m_2)/4=>N_1=16(0.95s_2^2+0.05s_1^2)/(0.05^2(m_{16}-m_2)^2)=1001$. Note that using the goal of 1-sigma statistics, which is still better than can be achieved using the conventional approach (i.e. detection with 84.1% probability), it can be shown in a similar manner that $N_1=250$.

Detection with No Mosaicism and Using a Reference Sample

Although this approach may not be necessary, assume that every experiment runs two samples in order to compare $m_1$ with truth sample $m_2$. Assume that $N=N_1=N_0$. Compute $d=m_1-m_0$ and, assuming $\sigma_1=\sigma_0$, set a threshold $t=(m_0+m_1)/2$ so that the probability of false positives and false negatives is equal. To make the probability of false negatives 2.87e-7, it must be the case that $(m1-m2)/2>5\text{sqrt}(s_1^2/N+s_2^2/N)=>N=100(s_1^2+s_2^2)/(m1-m2)^2=32$.

Detection with Mosaicism and Running a Reference Sample

As above, assume the probability of false negatives is 2.3% (i.e. 2-sigma approach). If 0.05% of the cells are aneuploid (call this sample 3) then $m_3=0.95m_0+0.05m_1$ and $\text{var}(m_3)=(0.95s_0^2+0.05s_1^2)/N_1$. $d=m_3-m_2$ and $\sigma_d=(1.95s_0^2+0.05s_1^2)/N$. It must be that $\text{std}(m_3)2<(m_0-m_2)/2=>\text{sqrt}(1.95\ s_2^2+0.05s_1^2)/\text{sqrt}(N)<0.05(m_1-m_2)/4=>N=16(1.95s_2^2+0.05s_1^2)/(0.05^2(m_1-m_2)^2)=2002$. Again using 1-sigma approach, it can be shown in a similar manner that N=500.

Consider the case if the goal is only to detect 5% mosaicism with a probability of 64% as is the current state of the art. Then, the probability of false negative would be 36%. In other words, it would be necssary to find x such that 1−normcdf(x,0,1)=36%. Thus N=4(0.36^2)(1.95$s_2^2$+0.05$s_1^2$)/(0.05$^2$($m_1$−$m_2$)$^2$)=65 for the 2-sigma approach, or N=33 for the 1-sigma approach. Note that this would result in a very high level of false positives, which needs to be addressed, since such a level of false positives is not currently a viable alternative.

Also note that if N is limited to 384 (i.e. one 384 well Taqman plate per chromosome), and the goal is to detect mosaicism with a probability of 97.72%, then it will be possible to detect mosaicism of 8.1% using the 1-sigma approach. In order to detect mosaicism with a probability of 84.1% (or with a 15.9% false negative rate), then it will be possible to detect mosaicism of 5.8% using the 1-sigma approach. To detect mosaicism of 19% with a confidence of 97.72% it would require roughly 70 loci. Thus one could screen for 5 chromosomes on a single plate.

Figure 8:
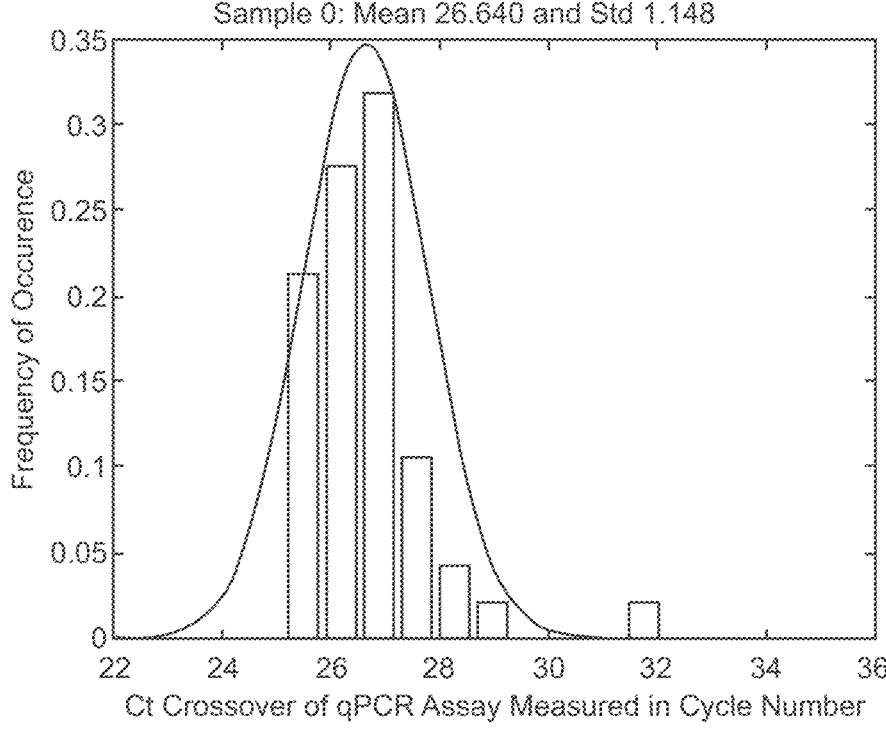
FIG. 8: the results from a mixed female sample; qPCR measures.
Figure 9:
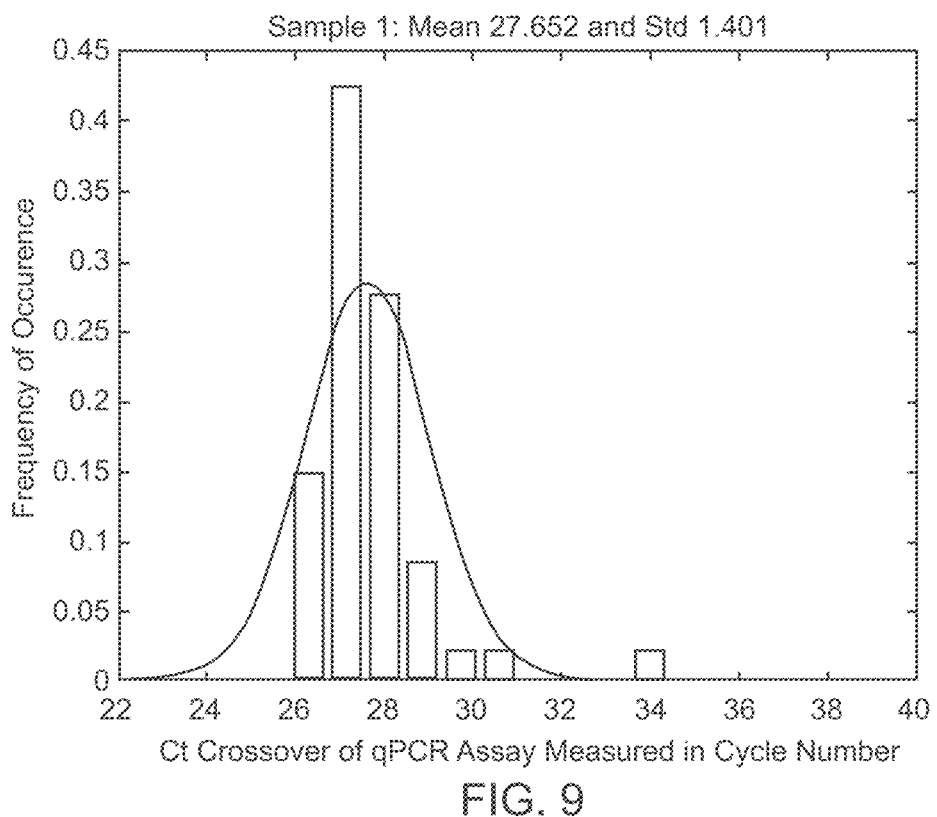
FIG. 9: the results from a mixed male sample; qPCR measures.
Figure 10:
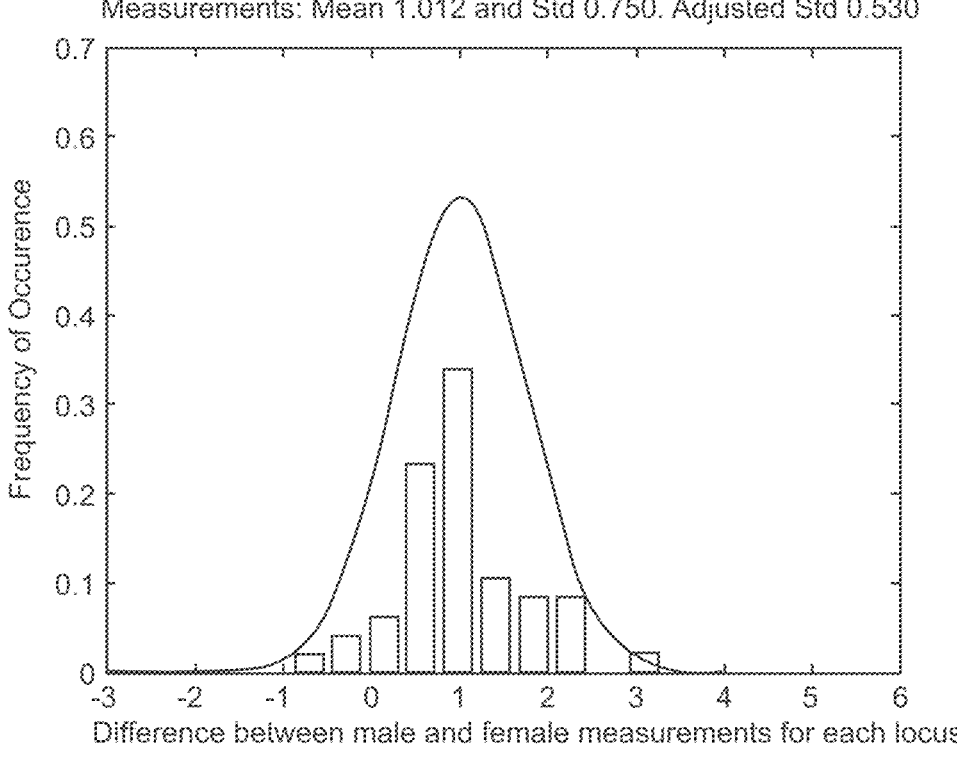
FIG. 10: Ct measurements for male sample differenced from Ct measurements for female sample.

The summary of each of these different scenarios is provided in Table 1. Also included in this table are the results generated from qPCR and the SYBR assays. The methods described above were used and the simplifying assumption was made that the performance of the qPCR assay for each locus is the same. FIGS. 8 and 9 show the histograms for samples 1 and 0, as described above. $N_0$=$N_1$=47. The distributions of the measurements for these samples are characterized by $m_1$=27.65, $s_1$=1.40, $\sigma_{m1}$=$s_1$/sqrt($N_1$)= 0.204; $m_0$=26.64; $s_0$=1.146, $\sigma_{m0}$=$s_0$/sqrt($N_0$)=0.167. For these samples d=1.01 and $\sigma_d$=0.2636. FIG. 10 shows the difference between $C_t$ for the male and female samples for each locus, with a standard deviation of the difference over all loci of 0.75. The SD was approximated for each measurement of each locus on the male or female sample as 0.75/sqrt(2)=0.53.

Method 2: Qualitative Techniques that Use Allele Calls

Figure 11:
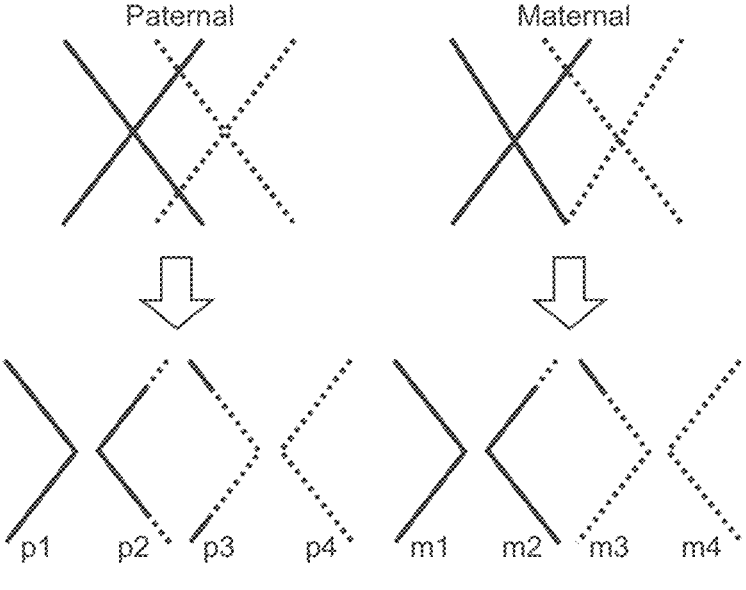
FIG. 11: detecting aneuploidy with a third dissimilar chromosome.

In this section, no assumption is made that the assay is quantitative. Instead, the assumption is that the allele calls are qualitative, and that there is no meaningful quantitative data coming from the assays. This approach is suitable for any assay that makes an allele call. FIG. 11 describes how different haploid gametes form during meiosis, and will be used to describe the different kinds of aneuploidy that are relevant for this section. The best algorithm depends on the type of aneuploidy that is being detected.

Consider a situation where aneuploidy is caused by a third segment that has no section that is a copy of either of the other two segments. From FIG. 11, the situation would arise, for example, if $p_1$ and $p_4$, or $p_2$ and $p_3$, both arose in the child cell in addition to one segment from the other parent. This is very common, given the mechanism which causes aneuploidy. One approach is to start off with a hypothesis $h_0$ that there are two segments in the cell and what these two segments are. Assume, for the purpose of illustration, that $h_0$ is for $p_3$ and $m_4$ from FIG. 11. In a preferred embodiment this hypothesis comes from algorithms described elsewhere in this document. Hypothesis $h_1$ is that there is an additional segment that has no sections that are a copy of the other segments. This would arise, for example, if $p_2$ or $m_1$ was also present. It is possible to identify all loci that are homozygous in $p_3$ and $m_4$. Aneuploidy can be detected by searching for heterozygous genotype calls at loci that are expected to be homozygous.

Assume every locus has two possible alleles, x and y. Let the probability of alleles x and y in general be $p_x$ and $p_y$, respectively, and $p_x$+$p_y$=1. If $h_1$ is true, then for each locus i for which $p_3$ and $m_4$ are homozygous, then the probability of a non-homozygous call is $p_y$ or $p_x$, depending on whether the locus is homozygous in x or y respectively. Note: based on knowledge of the parent data, i.e. $p_1$, $p_2$, $p_4$ and $m_1$, $m_2$, $m_3$, it is possible to further refine the probabilities for having non-homozygous alleles x or y at each locus. This will enable more reliable measurements for each hypothesis with the same number of SNPs, but complicates notation, so this extension will not be explicitly dealt with. It should be clear to someone skilled in the art how to use this information to increase the reliability of the hypothesis.

The probability of allele dropouts is $p_d$. The probability of finding a heterozygous genotype at locus i is $p_{0i}$ given hypothesis $h_0$ and $p_{1i}$ given hypothesis $h_1$.

Given $h_0$: $p_{0i}$=0

Given $h_1$: $p_{1i}$=$p_x$(1−$p_d$) or $p_{1i}$=$p_y$(1−$p_d$) depending on whether the locus is homozygous for x or y.

Create a measurement m=1/$N_h$ $\Sigma_{i=1 \ldots Nh}$ $I_i$ where $I_i$ is an indicator variable, and is 1 if a heterozygous call is made and 0 otherwise. $N_h$ is the number of homozygous loci. One can simplify the explanation by assuming that $p_x$=$p_y$ and $p_{0i}$, $p_{1i}$ for all loci are the same two values $p_0$ and $p_1$. Given $h_0$, E(m)=$p_0$=0 and $\sigma^2_{m|h0}$=$p_0$(1−$p_0$)/$N_h$. Given $h_1$, E(m)=$p_1$ and $\sigma^2_{m|h1}$=$p_1$(1−$p_1$)/$N_h$. Using 5 sigma-statistics, and making the probability of false positives equal the probability of false negatives, it can be shown that ($p_1$−$p_0$)/2>5$\sigma_{m|h1}$ hence $N_h$=100($p_0$(1−$p_0$)+$p_1$(1−$p_1$))/($p_1$−$p_0$)$^2$. For 2-sigma confidence instead of 5-sigma confidence, it can be shown that $N_h$=4.2$^2$($p_0$(1−$p_0$)+$p_1$(1−$p_1$))/($p_1$−$p_0$)$^2$ It is necessary to sample enough loci N that there will be sufficient available homozygous loci $N_{h\text{-}avail}$ such that the confidence is at least 97.7% (2-sigma). Characterize $N_{h\text{-}avail}$=$\Sigma_{i=1 \ldots N}$ $J_i$ where $J_i$ is an indicator variable of value 1 if the locus is homozygous and 0 otherwise. The probability of the locus being homozygous is $p_x^2$+$p_y^2$. Consequently, E($N_{h\text{-}avail}$)=N($p_x^2$+$p_y^2$) and $\sigma_{Nh\text{-}avail}^2$=N($p_x^2$+$p_y^2$)(1−$p_x^2$−$p_y^2$.) To guarantee N is large enough with 97.7% confidence, it must be that E($N_{h\text{-}avail}$)−2$\sigma_{Nh\text{-}avail}$=$N_h$ where $N_h$ is found from above.

For example, if one assumes $p_d$=0.3, $p_x$=$p_y$=0.5, one can find $N_h$=186 and N=391 for 5-sigma confidence. Similarly, it is possible to show that $N_h$=30 and N=68 for 2-sigma confidence i.e. 97.7% confidence in false negatives and false positives.

Note that a similar approach can be applied to looking for deletions of a segment when $h_0$ is the hypothesis that two known chromosome segment are present, and $h_1$ is the hypothesis that one of the chromosome segments is missing. For example, it is possible to look for all of those loci that should be heterozygous but are homozygous, factoring in the effects of allele dropouts as has been done above.

Also note that even though the assay is qualitative, allele dropout rates may be used to provide a type of quantitative measure on the number of DNA segments present.

Method 3: Making Use of Known Alleles of Reference Sequences, and Quantitative Allele Measurements Here, it is assumed that the alleles of the normal or expected set of segments are known. In order to check for three chromosomes, the first step is to clean the data, assuming two of each chromosome. In a preferred embodiment of the invention, the data cleaning in the first step is done using methods described elsewhere in this document. Then the signal associated with the expected two segments is subtracted from the measured data. One can then look for an additional segment in the remaining signal. A matched filtering approach is used, and the signal characterizing the additional segment is based on each of the segments that are believed to be present, as well as their complementary chromosomes. For example, considering FIG. 11, if the results of PS indicate that segments p2 and m1 are present, the technique described here may be used to check for the presence of p2, p3, m1 and m4 on the additional chromosome. If there is an additional segment present, it is guaranteed to have more than 50% of the alleles in common with at least one of these test signals. Note that another approach, not described in detail here, is to use an algorithm described elsewhere in the document to clean the data, assuming an abnormal number of chromosomes, namely 1, 3, 4 and 5 chromosomes, and then to apply the method discussed here. The details of this approach should be clear to someone skilled in the art after having read this document.

Hypothesis $h_0$ is that there are two chromosomes with allele vectors $a_1$, $a_2$. Hypothesis $h_1$ is that there is a third chromosome with allele vector $a_3$. Using a method described in this document to clean the genetic data, or another technique, it is possible to determine the alleles of the two segments expected by $h_0$: $a_1=[a_{11} \ldots a_{1N}]$ and $a_2=[a_{21} \ldots a_{2N}]$ where each element $a_{ji}$ is either x or y. The expected signal is created for hypothesis $h_0$: $s_{0x}=[f_{0x}(a_{11}, a_{21}) \ldots f_{x0}(a_{1N}, \ldots a_{2N})]$, $s_{0y}=[f_y(a_{11}, a_{21}) \ldots f_y(a_{1N}, a_{2N})]$ where $f_x$, $f_y$ describe the mapping from the set of alleles to the measurements of each allele. Given $h_0$, the data may be described as $d_{xi}=s_{0xi}+n_{xi}$, $n_{xi}\sim N(0,\sigma_{xi}^2)$; $d_{yi}=s_{0yi}+n_{yi}$, $n_{yi}\sim N(0,\sigma_{yi}^2)$. Create a measurement by differencing the data and the reference signal: $m_{xi}=d_{xi}-s_{xi}$; $m_{yi}=d_{yi}-s_{yi}$. The full measurement vector is $m=[m_x^T \ m_y^T]^T$.

Now, create the signal for the segment of interest—the segment whose presence is suspected, and will be sought in the residual—based on the assumed alleles of this segment: $a_3=[a_{31} \ldots a_{3N}]$. Describe the signal for the residual as: $s_r=[s_{rx}^T \ s_{ry}^T]^T$ where $s_{rx}=[f_{rx}(a_{31}) \ldots f_{rx}(a_{3N})]$, $s_{ry}=[f_{ry}(a_{31}) \ldots f_{ry}(a_{3N})]$ where $f_{rx}(a_{3i})=\delta_{xi}$ if $a_{3i}=x$ and 0 otherwise, $f_{ry}(a_{3i})=\delta_{yi}$ if $a_{3i}=y$ and 0 otherwise. This analysis assumes that the measurements have been linearized (see section below) so that the presence of one copy of allele x at locus i generates data $\delta_{xi}+n_{xi}$ and the presence of $\kappa_x$ copies of the allele x at locus i generates data $\kappa_x\delta_{xi}+n_{xi}$. Note however that this assumption is not necessary for the general approach described here. Given $h_1$, if allele $a_{3i}=x$ then $m_{xi}=\delta_{xi}+n_{xi}$, $m_{yi}=n_{yi}$ and if $a_{3i}=y$ then $m_{xi}=n_{xi}$, $m_{yi}=\delta_{yi}+n_{yi}$. Consequently, a matched filter $h=(1/N)R^{-1}s_r$ can be created where $R=\text{diag}([\sigma_{x1}^2 \ldots \sigma_{xN}^2 \ \sigma_{y1}^2 \ldots \sigma_{yN}^2])$. The measurement is $m=h^Td$.

$$h_0: \ m=(1/N)\Sigma_{i=1 \ldots N}s_{rxi}n_{xi}/\sigma_{xi}^2+s_{ryi}n_{yi}/\sigma_{yi}^2$$

$$h_1: \ m=(1/N)\Sigma_{i=1 \ldots N}s_{rxi}(\delta_{xi}+n_{xi})/\sigma_{xi}^2+s_{ryi}(\delta_{yi}+n_{yi})/\sigma_{yi}^2$$

In order to estimate the number of SNPs required, make the simplifying assumptions that all assays for all alleles and all loci have similar characteristics, namely that $\delta_{xi}=\delta_{yi}=\delta$ and $\sigma_{xi}=\sigma_{yi}=\sigma$ for i=1 . . . N. Then, the mean and standard deviation may be found as follows:

$$h_0: \ E(m)=m_0=0; \sigma_{m|h0}^2=(1/N^2\sigma^4)(N/2)(\sigma^2\delta^2+\sigma^2\delta^2)$$
$$=\delta^2/(N\sigma^2)$$

$$h_1: \ E(m)=m_1=(1/N)(N/2\sigma^2)(\delta^2+\delta^2)=\delta^2/\sigma^2; \sigma_{m|h1}^2=(1/N^2\sigma^4)(N)(\sigma^2\delta^2)=\delta^2/(N\sigma^2)$$

Now compute a signal-to-noise ratio (SNR) for this test of $h_1$ versus $h_0$. The signal is $m_1-m_0=\delta^2/\sigma^2$, and the noise variance of this measurement is $\sigma_{m|h0}^2+\sigma_{m|h1}^2=2\delta^2/(N\sigma^2)$. Consequently, the SNR for this test is $(\delta^4/\sigma^4)/(2\delta^2/(N\sigma^2))=N\delta^2/(2\sigma^2)$.

Compare this SNR to the scenario where the genetic information is simply summed at each locus without performing a matched filtering based on the allele calls. Assume that $h=(1/N)\bar{1}$ where $\bar{1}$ is the vector of N ones, and make the simplifying assumptions as above that $\delta_{xi}=\delta_{yi}=\delta$ and $\sigma_{xi}=\sigma_{yi}=\sigma$ for i=1 . . . N. For this scenario, it is straightforward to show that if $m=h^Td$:

$$h_0: \ E(m)=m_0=0; \sigma_{m|h0}^2=N\sigma^2/N^2+N\sigma^2/N^2=2\sigma^2/N$$

$$h_1: \ E(m)=m_1=(1/N)(N\delta/2+N\delta/2)=\delta; \sigma_{m|h1}^2=(1/N^2)(N\sigma^2+N\sigma^2)=2\sigma^2/N$$

Consequently, the SNR for this test is $N\delta^2/(4\sigma^2)$. In other words, by using a matched filter that only sums the allele measurements that are expected for segment $a_3$, the number of SNPs required is reduced by a factor of 2. This ignores the SNR gain achieved by using matched filtering to account for the different efficiencies of the assays at each locus.

Note that if we do not correctly characterize the reference signals $s_{xi}$ and $s_{yi}$ then the SD of the noise or disturbance on the resulting measurement signals $m_{xi}$ and $m_{yi}$ will be increased. This will be insignificant if $\delta \ll \sigma$, but otherwise it will increase the probability of false detections. Consequently, this technique is well suited to test the hypothesis where three segments are present and two segments are assumed to be exact copies of each other. In this case, $s_{xi}$ and $s_{yi}$ will be reliably known using techniques of data cleaning based on qualitative allele calls described elsewhere. In one embodiment method 3 is used in combination with method 2 which uses qualitative genotyping and, aside from the quantitative measurements from allele dropouts, is not able to detect the presence of a second exact copy of a segment.

We now describe another quantitative technique that makes use of allele calls. The method involves comparing the relative amount of signal at each of the four registers for a given allele. One can imagine that in the idealized case involving a single, normal cell, where homogenous amplification occurs, (or the relative amounts of amplification are normalized), four possible situations can occur: (i) in the case of a heterozygous allele, the relative intensities of the four registers will be approximately 1:1:0:0, and the absolute intensity of the signal will correspond to one base pair; (ii) in the case of a homozygous allele, the relative intensities will be approximately 1:0:0:0, and the absolute intensity of the signal will correspond to two base pairs; (iii) in the case of an allele where ADO occurs for one of the alleles, the relative intensities will be approximately 1:0:0:0, and the absolute intensity of the signal will correspond to one base pair; and (iv) in the case of an allele where ADO occurs for both of the alleles, the relative intensities will be approximately 0:0:0:0, and the absolute intensity of the signal will correspond to no base pairs.

In the case of aneuploidies, however, different situations will be observed. For example, in the case of trisomy, and there is no ADO, one of three situations will occur: (i) in the case of a triply heterozygous allele, the relative intensities of the four registers will be approximately 1:1:1:0, and the absolute intensity of the signal will correspond to one base pair; (ii) in the case where two of the alleles are homozygous, the relative intensities will be approximately 2:1:0:0, and the absolute intensity of the signal will correspond to two and one base pairs, respectively; (iii) in the case where are alleles are homozygous, the relative intensities will be approximately 1:0:0:0, and the absolute intensity of the signal will correspond to three base pairs. If allele dropout occurs in the case of an allele in a cell with trisomy, one of the situations expected for a normal cell will be observed. In the case of monosomy, the relative intensities of the four registers will be approximately 1:0:0:0, and the absolute intensity of the signal will correspond to one base pair. This situation corresponds to the case of a normal cell where ADO of one of the alleles has occurred, however in the case of the normal cell, this will only be observed at a small percentage of the alleles. In the case of uniparental disomy, where two identical chromosomes are present, the relative intensities of the four registers will be approximately 1:0: 0:0, and the absolute intensity of the signal will correspond to two base pairs. In the case of UPD where two different chromosomes from one parent are present, this method will indicate that the cell is normal, although further analysis of the data using other methods described in this patent will uncover this.

In all of these cases, either in cells that are normal, have aneuploidies or UPD, the data from one SNP will not be adequate to make a decision about the state of the cell. However, if the probabilities of each of the above hypothesis are calculated, and those probabilities are combined for a sufficient number of SNPs on a given chromosome, one hypothesis will predominate, it will be possible to determine the state of the chromosome with high confidence.

Methods for Linearizing Quantitative Measurements

Many approaches may be taken to linearize measurements of the amount of genetic material at a specific locus so that data from different alleles can be easily summed or differenced. We first discuss a generic approach and then discuss an approach that is designed for a particular type of assay.

Assume data $d_{xi}$ refers to a nonlinear measurement of the amount of genetic material of allele x at locus i. Create a training set of data using N measurements, where for each measurement, it is estimated or known that the amount of genetic material corresponding to data $d_{xi}$ is $\beta_{xi}$. The training set $\beta_{xi}$, i=1 . . . N, is chosen to span all the different amounts of genetic material that might be encountered in practice. Standard regression techniques can be used to train a function that maps from the nonlinear measurement, $d_{xi}$, to the expectation of the linear measurement, $E(\beta_{xi})$. For example, a linear regression can be used to train a polynomial function of order P, such that $E(\beta_{xi})=[1\ d_{xi}\ d_{xi}^2\ \ldots\ d_{xi}^P]c$ where c is the vector of coefficients $c=[c_0\ c_1\ \ldots\ c_P]^T$. To train this linearizing function, we create a vector of the amount of genetic material for N measurements $\beta_x=[\beta_{x1}\ \ldots\ \beta_{xN}]^T$ and a matrix of the measured data raised to powers 0 . . . P: $D=[[1\ d_{x1}\ d_{x1}^2\ \ldots\ d_{x1}^P]^T\ [1\ d_{x2}\ d_{x2}^2\ \ldots\ d_{x2}^P]^T\ \ldots\ [1\ d_{xN}\ d_{xN}^2\ \ldots\ d_{xN}^P]^T]^T$. The coefficients can then be found using a least squares fit $c=(D^TD)^{-1}D^T\beta_x$.

Rather than depend on generic functions such as fitted polynomials, we may also create specialized functions for the characteristics of a particular assay. We consider, for example, the Taqman assay or a qPCR assay. The amount of die for allele x and some locus i, as a function of time up to the point where it crosses some threshold, may be described as an exponential curve with a bias offset: $g_{xi}(t)=\alpha_{xi}+\beta_{xi}\exp(\gamma_{xi}t)$ where $\alpha_{xi}$ is the bias offset, $\gamma_{xi}$ is the exponential growth rate, and $\beta_{xi}$ corresponds to the amount of genetic material. To cast the measurements in terms of $\beta_{xi}$, compute the parameter $\alpha_{xi}$ by looking at the asymptotic limit of the curve $g_{xi}(-\infty)$ and then may find $\beta_{xi}$ and $\gamma_{xi}$ by taking the log of the curve to obtain $\log(g_{xi}(t)-\alpha_{xi})=\log(\beta_{xi})+\gamma_{xi}t$ and performing a standard linear regression. Once we have values for $\alpha_{xi}$ and $\gamma_{xi}$, another approach is to compute $\beta_{xi}$ from the time, $t_x$, at which the threshold $g_x$ is exceeded. $\beta_{xi}=(g_x-\alpha_{xi})\exp(-\gamma_{xi}t_x)$. This will be a noisy measurement of the true amount of genetic data of a particular allele.

Whatever techniques is used, we may model the linearized measurement as $\beta_{xi}=\kappa_x\delta_{xi}+n_{xi}$ where $\kappa_x$ is the number of copies of allele x, $\delta_{xi}$ is a constant for allele x and locus i, and $n_{xi} \sim N(0, \sigma_x^2)$ where $\sigma_x^2$ can be measured empirically.

Method 4: Using a Probability Distribution Function for the Amplification of Genetic Data at Each Locus The method described here is relevant for high throughput genotype data either generated by a PCR-based approach, for example using an Affymetrix Genotyping Array, or using the Molecular Inversion Probe (MIPs) technique, with the Affymetrix GenFlex Tag Array. In the former case, the genetic material is amplified by PCR before hybridization to probes on the genotyping array to detect the presence of particular alleles. In the latter case, padlock probes are hybridized to the genomic DNA and a gap-fill enzyme is added which can add one of the four nucleotides. If the added nucleotide (A, C, T, G) is complementary to the SNP under measurement, then it will hybridize to the DNA, and join the ends of the padlock probe by ligation. The closed padlock probes are then differentiated from linear probes by exonucleolysis. The probes that remain are then opened at a cleavage site by another enzyme, amplified by PCR, and detected by the GenFlex Tag Array. Whichever technique is used, the quantity of material for a particular SNP will depend on the number of initial chromosomes in the cell on which that SNP is present. However, due to the random nature of the amplification and hybridization process, the quantity of genetic material from a particular SNP will not be directly proportional to the starting number of chromosomes. Let $q_{s,A}$, $q_{s,G}$, $q_{s,T}$, $q_{s,C}$ represent the amplified quantity of genetic material for a particular SNP s for each of the four nucleic acids (A, C, T, G) constituting the alleles. Note that these quantities are typically measured from the intensity of signals from particular hybridization probes on the array. This intensity measurement can be used instead of a measurement of quantity, or can be converted into a quantity estimate using standard techniques without changing the nature of the invention. Let $q_s$ be the sum of all the genetic material generated from all alleles of a particular SNP: $q_s=q_{s,A}+q_{s,G}+q_{s,T}+q_{s,C}$. Let N be the number of chromosomes in a cell containing the SNP s. N is typically 2, but may be 0, 1 or 3 or more. For either high-throughput genotyping method discussed above, and many other methods, the resulting quantity of genetic material can be represented as $q_s=(A+A_{\theta,s})N+\theta_s$ where A is the total amplification that is either estimated a-priori or easily measured empirically, $A_{\theta,s}$ is the error in the estimate of A for the SNP s, and $\theta_s$ is additive noise introduced in the amplification, hybridization and other process for that SNP. The noise terms $A_{\theta,s}$ and $\theta_s$ are typically large enough that $q_s$ will not be a reliable measurement of N. However, the effects of these noise terms can be mitigated by measuring multiple SNPs on the chromosome. Let S be the number of SNPs that are measured on a particular chromosome, such as chromosome 21. We can then generate the average quantity of genetic material over all SNPs on a particular chromosome $$q = \frac{1}{S}\sum_{s=1}^{S} q_s = NA + \frac{1}{S}\sum_{s=1}^{S} A_{\theta,s}N + \theta_s \tag{15}$$

Assuming that $A_{\theta,s}$ and $\theta_s$ are normally distributed random variables with 0 means and variances $$\sigma_{A_{\theta,s}}^2 \text{ and } \sigma_{\theta_s}^2,$$

we can model q=NA+φ where φ is a normally distributed random variable with 0 mean and variance $$\frac{1}{S}\left(N^2\sigma^2_{A_{\theta,S}} + \sigma^2_{\theta}\right).$$

Consequently, if we measure a sufficient number of SNPs on the chromosome such that $$S \gg \left(N^2\sigma^2_{A_{\theta,S}} + \sigma^2_{\theta}\right),$$

we can accurately estimate N=q/A.

The quantity of material for a particular SNP will depend on the number of initial segments in the cell on which that SNP is present. However, due to the random nature of the amplification and hybridization process, the quantity of genetic material from a particular SNP will not be directly proportional to the starting number of segments. Let $q_{s,A}$, $q_{s,G}$, $q_{s,T}$, $q_{s,C}$ represent the amplified quantity of genetic material for a particular SNP s for each of the four nucleic acids (A,C,T,G) constituting the alleles. Note that these quantities may be exactly zero, depending on the technique used for amplification. Also note that these quantities are typically measured from the intensity of signals from particular hybridization probes. This intensity measurement can be used instead of a measurement of quantity, or can be converted into a quantity estimate using standard techniques without changing the nature of the invention. Let $q_S$ be the sum of all the genetic material generated from all alleles of a particular SNP: $q_s=q_{s,A}+q_{s,G}+q_{s,T}+q_{s,C}$. Let N be the number of segments in a cell containing the SNP s. N is typically 2, but may be 0, 1 or 3 or more. For any high or medium throughput genotyping method discussed, the resulting quantity of genetic material can be represented as $q_s=(A+A_{\theta,s})N+\theta_s$ where A is the total amplification that is either estimated a-priori or easily measured empirically, $A_{\theta,s}$ is the error in the estimate of A for the SNP s, and $\theta_s$ is additive noise introduced in the amplification, hybridization and other process for that SNP. The noise terms $A_{\theta,s}$ and $\theta_s$ are typically large enough that $q_s$ will not be a reliable measurement of N. However, the effects of these noise terms can be mitigated by measuring multiple SNPs on the chromosome. Let S be the number of SNPs that are measured on a particular chromosome, such as chromosome 21. It is possible to generate the average quantity of genetic material over all SNPs on a particular chromosome as follows:

$$q = \frac{1}{S}\sum_{s=1}^{S} q_s = NA + \frac{1}{S}\sum_{s=1}^{S} A_{\theta,s}N + \theta_s \qquad (16)$$

Assuming that $A_{\theta,s}$ and $\theta_s$ are normally distributed random variables with 0 means and variances $$\sigma^2_{A_{\theta,S}} \text{ and } \sigma^2_{\theta_S},$$

one can model q=NA+φ where φ is a normally distributed random variable with 0 mean and variance $$\frac{1}{S}\left(N^2\sigma^2_{A_{\theta,S}} + \sigma^2_{\theta}\right).$$

Consequently, if sufficient number of SNPs are measured on the chromosome such that $$S \gg \left(N^2\sigma^2_{A_{\theta,S}} + \sigma^2_{\theta}\right),$$

then N=q/A can be accurately estimated.

Figures 12A, 12B:
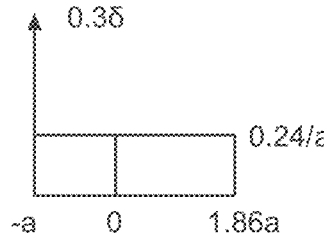
FIGS. 12A and 12B: an illustration of two amplification distributions with constant allele dropout rate.

In another embodiment, assume that the amplification is according to a model where the signal level from one SNP is s=a+α where (a+α) has a distribution that looks like the picture in FIG. 12A, left. The delta function at 0 models the rates of allele dropouts of roughly 30%, the mean is a, and if there is no allele dropout, the amplification has uniform distribution from 0 to $a_0$. In terms of the mean of this distribution $a_0$ is found to be $a_0=2.86a$. Now model the probability density function of α using the picture in FIG. 12B, right. Let $s_c$ be the signal arising from c loci; let n be the number of segments; let $\alpha_i$ be a random variable distributed according to FIGS. 12A and 12B that contributes to the signal from locus i; and let σ be the standard deviation for all $\{\alpha_i\}$. $s_c=anc+\Sigma_{i=1\ldots nc}\alpha_i$; mean($s_c$)=anc; std($s_c$)=sqrt (nc)σ. If σ is computed according to the distribution in FIG. 12B, right, it is found to be $\sigma=0.907a^2$. We can find the number of segments from n=$s_c$/(ac) and for "5-sigma statistics" we require std(n)<0.1 so std($s_c$)/(ac)= 0.1=>0.95a·sqrt(nc)/(ac)=0.1 so c=$0.95^2$ n/$0.1^2$=181.

Another model to estimate the confidence in the call, and how many loci or SNPs must be measured to ensure a given degree of confidence, incorporates the random variable as a multiplier of amplification instead of as an additive noise source, namely s=a(1+α). Taking logs, log(s)=log(a)+log(1+α). Now, create a new random variable γ=log(1+α) and this variable may be assumed to be normally distributed ~N(0, σ). In this model, amplification can range from very small to very large, depending on σ, but never negative. Therefore $\alpha=e^\gamma-1$; and $s_c=\Sigma_{i=1\ldots cn}a(1+\alpha_i)$. For notation, mean($s_c$) and expectation value E($s_c$) are used interchangeably $$E(S_C)=acn+aE(\Sigma_{i=1\ldots cn}\alpha_i)=acn+aE(\Sigma_{i=1\ldots cn}\alpha_i)= acn(1+E(\alpha))$$

To find E(α) the probability density function (pdf) must be found for α which is possible since α is a function of γ which has a known Gaussian pdf. $p_\alpha(\alpha)=p_\gamma(\gamma)(d\gamma/d\alpha)$. So:

$$p_\gamma(\gamma) = \frac{1}{\sqrt{2\pi}\,\sigma}e^{\frac{-\gamma^2}{2\sigma^2}} \text{ and } \frac{d\gamma}{d\alpha} = \frac{d}{d\alpha}(\log(1+\alpha)) = \frac{1}{1+\alpha}e^{-\gamma}$$

and:

$$p_\alpha(\alpha) = \frac{1}{\sqrt{2\pi}\,\sigma}e^{\frac{-\gamma^2}{2\sigma^2}}e^{-\gamma} = \frac{1}{\sqrt{2\pi}\,\sigma}e^{\frac{-(\log(1+\alpha))^2}{2\sigma^2}}\frac{1}{1+\alpha}$$

Figure 13:
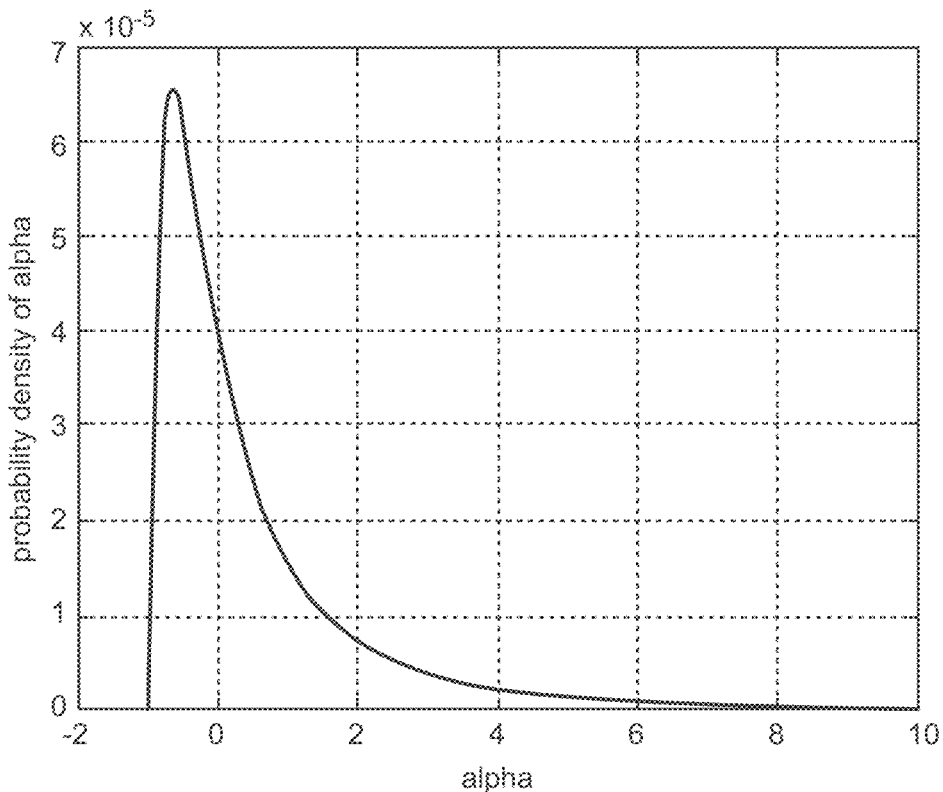
FIG. 13: a graph of the Gaussian probability density function of alpha.

This has the form shown in FIG. 13 for a=1. Now, E(a) can be found by integrating over this pdf $E(\alpha)=\int_{-\infty}^{\infty}\alpha p_\alpha(\alpha) d\alpha$ which can be done numerically for multiple different σ. This gives E($s_c$) or mean($s_c$) as a function of σ. Now, this pdf can also be used to find var($s_c$):

$$\text{var}(S_C) =$$

$$E(S_c - E(S_C))^2 = E\left(\sum_{i=1\ldots cn}\alpha(1+\alpha_i) - acn - aE\left(\sum_{i=1\ldots cn}\alpha_i\right)\right)^2$$

-continued $$= E\left(\sum_{i=1\ldots cn} \alpha\alpha_i - aE\left(\sum_{i=1\ldots cn} \alpha_i\right)\right)^2$$

$$= a^2 E\left(\sum_{i=1\ldots cn} \alpha_i - cnE(\alpha)\right)^2$$

$$= a^2 E\left(\left(\sum_{i=1\ldots cn} \alpha_i\right)^2 - 2cnE(\alpha)\left(\sum_{i=1\ldots cn} \alpha_i\right) + c^2 n^2 E(\alpha)^2\right)$$

$$= a^2 E\left(cn\alpha^2 + cn(cn-1)\alpha_i\alpha_j - 2cnE(\alpha)\left(\sum_{i=1\ldots cn} \alpha_i\right) + c^2 n^2 E(\alpha)^2\right)$$

$$= a^2 c^2 n^2 (E(\alpha^2) + (cn-1)E(\alpha_i\alpha_j) - 2cnE(\alpha)^2 + cnE(\alpha)^2)$$

$$= a^2 c^2 n^2 (E(\alpha^2) + (cn-1)E(\alpha_i\alpha_j) - cnE(\alpha)^2)$$

which can also be solved numerically using $p_\alpha(\alpha)$ for multiple different $\sigma$ to get var($s_c$) as a function of $\sigma$. Then, we may take a series of measurements from a sample with a known number of loci c and a known number of segments n and find std($s_c$)/E($s_c$) from this data. That will enable us to compute a value for $\sigma$. In order to estimate n, E($s_c$)=nac(1+E($\alpha$)) so $$\hat{n} = \frac{S_c}{ac(1+(E(\alpha)))}$$

can be measured so that $$std(\hat{n}) = \frac{std(S_c)}{ac(1+(E(\alpha)))} std(n)$$

When summing a sufficiently large number of independent random variables of 0-mean, the distribution approaches a Gaussian form, and thus $s_c$ (and $\hat{n}$) can be treated as normally distributed and as before we may use 5-sigma statistics:

$$std(\hat{n}) = \frac{std(S_c)}{ac(1+(E(\alpha)))} < 0.1$$

in order to have an error probability of 2normcdf(5,0,1)= 2.7e-7. From this, one can solve for the number of loci c.

Sexing

In one embodiment of the system, the genetic data can be used to determine the sex of the target individual. After the method disclosed herein is used to determine which segments of which chromosomes from the parents have contributed to the genetic material of the target, the sex of the target can be determined by checking to see which of the sex chromosomes have been inherited from the father: X indicates a female, and Y indicates a make. It should be obvious to one skilled in the art how to use this method to determine the sex of the target.

Validation of the Hypotheses

In some embodiments of the system, one drawback is that in order to make a prediction of the correct genetic state with the highest possible confidence, it is necessary to make hypotheses about every possible states. However, as the possible number of genetic states are exceptionally large, and computational time is limited, it may not be reasonable to test every hypothesis. In these cases, an alternative approach is to use the concept of hypothesis validation. This involves estimating limits on certain values, sets of values, properties or patterns that one might expect to observe in the measured data if a certain hypothesis, or class of hypotheses are true. Then, the measured values can tested to see if they fall within those expected limits, and/or certain expected properties or patterns can be tested for, and if the expectations are not met, then the algorithm can flag those measurements for further investigation.

For example, in a case where the end of one arm of a chromosome is broken off in the target DNA, the most likely hypothesis may be calculated to be "normal" (as opposed, for example to "aneuploid"). This is because the particular hypotheses that corresponds to the true state of the genetic material, namely that one end of the chromosome has broken off, has not been tested, since the likelihood of that state is very low. If the concept of validation is used, then the algorithm will note that a high number of values, those that correspond to the alleles that lie on the broken off section of the chromosome, lay outside the expected limits of the measurements. A flag will be raised, inviting further investigation for this case, increasing the likelihood that the true state of the genetic material is uncovered.

It should be obvious to one skilled in the art how to modify the disclosed method to include the validation technique. Note that one anomaly that is expected to be very difficult to detect using the disclosed method is balanced translocations.

M Notes

As noted previously, given the benefit of this disclosure, there are more embodiments that may implement one or more of the systems, methods, and features, disclosed herein.

In all cases concerning the determination of the probability of a particular qualitative measurement on a target individual based on parent data, it should be obvious to one skilled in the art, after reading this disclosure, how to apply a similar method to determine the probability of a quantitative measurement of the target individual rather than qualitative. Wherever genetic data of the target or related individuals is treated qualitatively, it will be clear to one skilled in the art, after reading this disclosure, how to apply the techniques disclosed to quantitative data.

It should be obvious to one skilled in the art that a plurality of parameters may be changed without changing the essence of the invention. For example, the genetic data may be obtained using any high throughput genotyping platform, or it may be obtained from any genotyping method, or it may be simulated, inferred or otherwise known. A variety of computational languages could be used to encode the algorithms described in this disclosure, and a variety of computational platforms could be used to execute the calculations. For example, the calculations could be executed using personal computers, supercomputers, a massively parallel computing platform, or even non-silicon based computational platforms such as a sufficiently large number of people armed with abacuses.

Some of the math in this disclosure makes hypotheses concerning a limited number of states of aneuploidy. In some cases, for example, only monosomy, disomy and trisomy are explicitly treated by the math. It should be obvious to one skilled in the art how these mathematical derivations can be expanded to take into account other forms of aneuploidy, such as nullsomy (no chromosomes present), quadrosomy, etc., without changing the fundamental concepts of the invention.

When this disclosure discusses a chromosome, this may refer to a segment of a chromosome, and when a segment of a chromosome is discussed, this may refer to a full chromosome. It is important to note that the math to handle a segment of a chromosome is the same as that needed to handle a full chromosome. It should be obvious to one skilled in the art how to modify the method accordingly It should be obvious to one skilled in the art that a related individual may refer to any individual who is genetically related, and thus shares haplotype blocks with the target individual. Some examples of related individuals include: biological father, biological mother, son, daughter, brother, sister, half-brother, half-sister, grandfather, grandmother, uncle, aunt, nephew, niece, grandson, granddaughter, cousin, clone, the target individual himself/herself/itself, and other individuals with known genetic relationship to the target. The term 'related individual' also encompasses any embryo, fetus, sperm, egg, blastomere, blastocyst, or polar body derived from a related individual.

It is important to note that the target individual may refer to an adult, a juvenile, a fetus, an embryo, a blastocyst, a blastomere, a cell or set of cells from an individual, or from a cell line, or any set of genetic material. The target individual may be alive, dead, frozen, or in stasis.

It is also important to note that where the target individual refers to a blastomere that is used to diagnose an embryo, there may be cases caused by mosaicism where the genome of the blastomere analyzed does not correspond exactly to the genomes of all other cells in the embryo.

It is important to note that it is possible to use the method disclosed herein in the context of cancer genotyping and/or karyotyping, where one or more cancer cells is considered the target individual, and the non-cancerous tissue of the individual afflicted with cancer is considered to be the related individual. The non-cancerous tissue of the individual afflicted with the target could provide the set of genotype calls of the related individual that would allow chromosome copy number determination of the cancerous cell or cells using the methods disclosed herein.

It is important to note that the method described herein concerns the cleaning of genetic data, and as all living or once living creatures contain genetic data, the methods are equally applicable to any live or dead human, animal, or plant that inherits or inherited chromosomes from other individuals.

It is important to note that in many cases, the algorithms described herein make use of prior probabilities, and/or initial values. In some cases the choice of these prior probabilities may have an impact on the efficiency and/or effectiveness of the algorithm. There are many ways that one skilled in the art, after reading this disclosure, could assign or estimate appropriate prior probabilities without changing the essential concept of the patent.

It is also important to note that the embryonic genetic data that can be generated by measuring the amplified DNA from one blastomere can be used for multiple purposes. For example, it can be used for detecting aneuploidy, uniparental disomy, sexing the individual, as well as for making a plurality of phenotypic predictions based on phenotype-associated alleles. Currently, in IVF laboratories, due to the techniques used, it is often the case that one blastomere can only provide enough genetic material to test for one disorder, such as aneuploidy, or a particular monogenic disease. Since the method disclosed herein has the common first step of measuring a large set of SNPs from a blastomere, regardless of the type of prediction to be made, a physician, parent, or other agent is not forced to choose a limited number of disorders for which to screen. Instead, the option exists to screen for as many genes and/or phenotypes as the state of medical knowledge will allow. With the disclosed method, one advantage to identifying particular conditions to screen for prior to genotyping the blastomere is that if it is decided that certain loci are especially relevant, then a more appropriate set of SNPs which are more likely to cosegregate with the locus of interest, can be selected, thus increasing the confidence of the allele calls of interest.

It is also important to note that it is possible to perform haplotype phasing by molecular haplotyping methods. Because separation of the genetic material into haplotypes is challenging, most genotyping methods are only capable of measuring both haplotypes simultaneously, yielding diploid data. As a result, the sequence of each haploid genome cannot be deciphered. In the context of using the disclosed method to determine allele calls and/or chromosome copy number on a target genome, it is often helpful to know the maternal haplotype; however, it is not always simple to measure the maternal haplotype. One way to solve this problem is to measure haplotypes by sequencing single DNA molecules or clonal populations of DNA molecules. The basis for this method is to use any sequencing method to directly determine haplotype phase by direct sequencing of a single DNA molecule or clonal population of DNA molecules. This may include, but not be limited to: cloning amplified DNA fragments from a genome into a recombinant DNA constructs and sequencing by traditional dye-end terminator methods, isolation and sequencing of single molecules in colonies, and direct single DNA molecule or clonal DNA population sequencing using next-generation sequencing methods.

The systems, methods, and techniques of the present invention may be used to in conjunction with embryo screening or prenatal testing procedures. The systems, methods, and techniques of the present invention may be employed in methods of increasing the probability that the embryos and fetuses obtain by in vitro fertilization are successfully implanted and carried through the full gestation period. Further, the systems, methods, and techniques of the present invention may be employed in methods of decreasing the probability that the embryos and fetuses obtain by in vitro fertilization that are implanted and gestated are not specifically at risk for a congenital disorder.

Thus, according to some embodiments, the present invention extends to the use of the systems, methods, and techniques of the invention in conjunction with pre-implantation diagnosis procedures.

According to some embodiments, the present invention extends to the use of the systems, methods, and techniques of the invention in conjunction with prenatal testing procedures.

According to some embodiments, the systems, methods, and techniques of the invention are used in methods to decrease the probability for the implantation of an embryo specifically at risk for a congenital disorder by testing at least one cell removed from early embryos conceived by in vitro fertilization and transferring to the mother's uterus only those embryos determined not to have inherited the congenital disorder.

According to some embodiments, the systems, methods, and techniques of the invention are used in methods to decrease the probability for the implantation of an embryo specifically at risk for a chromosome abnormality by testing at least one cell removed from early embryos conceived by in vitro fertilization and transferring to the mother's uterus only those embryos determined not to have chromosome abnormalities.

According to some embodiments, the systems, methods, and techniques of the invention are used in methods to increase the probability of implanting an embryo obtained by in vitro fertilization that is at a reduced risk of carrying a congenital disorder.

According to some embodiments, the systems, methods, and techniques of the invention are used in methods to increase the probability of gestating a fetus.

According to preferred embodiments, the congenital disorder is a malformation, neural tube defect, chromosome abnormality, Down's syndrome (or trisomy 21), Trisomy 18, spina bifida, cleft palate, Tay Sachs disease, sickle cell anemia, thalassemia, cystic fibrosis, Huntington's disease, and/or fragile x syndrome. Chromosome abnormalities include, but are not limited to, Down syndrome (extra chromosome 21), Turner Syndrome (45X0) and Klinefelter's syndrome (a male with 2 X chromosomes).

According to preferred embodiments, the malformation is a limb malformation. Limb malformations include, but are not limited to, amelia, ectrodactyly, phocomelia, polymelia, polydactyly, syndactyly, polysyndactyly, oligodactyly, brachydactyly, achondroplasia, congenital aplasia or hypoplasia, amniotic band syndrome, and cleidocranial dysostosis.

According to preferred embodiments, the malformation is a congenital malformation of the heart. Congenital malformations of the heart include, but are not limited to, patent ductus arteriosus, atrial septal defect, ventricular septal defect, and tetralogy of fallot.

According to preferred embodiments, the malformation is a congenital malformation of the nervous system. Congenital malformations of the nervous system include, but are not limited to, neural tube defects (e.g., spina bifida, meningocele, meningomyelocele, encephalocele and anencephaly), Arnold-Chiari malformation, the Dandy-Walker malformation, hydrocephalus, microencephaly, megencephaly, lissencephaly, polymicrogyria, holoprosencephaly, and agenesis of the corpus callosum.

According to preferred embodiments, the malformation is a congenital malformation of the gastrointestinal system. Congenital malformations of the gastrointestinal system include, but are not limited to, stenosis, atresia, and imperforate anus.

According to some embodiments, the systems, methods, and techniques of the invention are used in methods to increase the probability of implanting an embryo obtained by in vitro fertilization that is at a reduced risk of carrying a predisposition for a genetic disease.

According to preferred embodiments, the genetic disease is either monogenic or multigenic. Genetic diseases include, but are not limited to, Bloom Syndrome, Canavan Disease, Cystic fibrosis, Familial Dysautonomia, Riley-Day syndrome, Fanconi Anemia (Group C), Gaucher Disease, Glycogen storage disease 1a, Maple syrup urine disease, Mucolipidosis IV, Niemann-Pick Disease, Tay-Sachs disease, Beta thalessemia, Sickle cell anemia, Alpha thalessemia, Beta thalessemia, Factor XI Deficiency, Friedreich's Ataxia, MCAD, Parkinson disease-juvenile, Connexin26, SMA, Rett syndrome, Phenylketonuria, Becker Muscular Dystrophy, Duchennes Muscular Dystrophy, Fragile X syndrome, Hemophilia A, Alzheimer dementia-early onset, Breast/Ovarian cancer, Colon cancer, Diabetes/MODY, Huntington disease, Myotonic Muscular Dystrophy, Parkinson Disease-early onset, Peutz-Jeghers syndrome, Polycystic Kidney Disease, Torsion Dystonia Combinations of the Aspects of the Invention As noted previously, given the benefit of this disclosure, there are more aspects and embodiments that may implement one or more of the systems, methods, and features, disclosed herein. Below is a short list of examples illustrating situations in which the various aspects of the disclosed invention can be combined in a plurality of ways. It is important to note that this list is not meant to be comprehensive; many other combinations of the aspects, methods, features and embodiments of this invention are possible.

In one embodiment of the invention, it is possible to combine several of the aspect of the invention such that one could perform both allele calling as well as aneuploidy calling in one step, and to use quantitative values instead of qualitative for both parts. It should be obvious to one skilled in the art how to combine the relevant mathematics without changing the essence of the invention.

In a preferred embodiment of the invention, the disclosed method is employed to determine the genetic state of one or more embryos for the purpose of embryo selection in the context of IVF. This may include the harvesting of eggs from the prospective mother and fertilizing those eggs with sperm from the prospective father to create one or more embryos. It may involve performing embryo biopsy to isolate a blastomere from each of the embryos. It may involve amplifying and genotyping the genetic data from each of the blastomeres. It may include obtaining, amplifying and genotyping a sample of diploid genetic material from each of the parents, as well as one or more individual sperm from the father. It may involve incorporating the measured diploid and haploid data of both the mother and the father, along with the measured genetic data of the embryo of interest into a dataset. It may involve using one or more of the statistical methods disclosed in this patent to determine the most likely state of the genetic material in the embryo given the measured or determined genetic data. It may involve the determination of the ploidy state of the embryo of interest. It may involve the determination of the presence of a plurality of known disease-linked alleles in the genome of the embryo. It may involve making phenotypic predictions about the embryo. It may involve generating a report that is sent to the physician of the couple so that they may make an informed decision about which embryo(s) to transfer to the prospective mother.

Another example could be a situation where a 44-year old woman undergoing IVF is having trouble conceiving. The couple arranges to have her eggs harvested and fertilized with sperm from the man, producing nine viable embryos. A blastomere is harvested from each embryo, and the genetic data from the blastomeres are measured using an ILLUMINA INFINIUM BEAD ARRAY. Meanwhile, the diploid data are measured from tissue taken from both parents also using the ILLUMINA INFINIUM BEAD ARRAY. Haploid data from the father's sperm is measured using the same method. The method disclosed herein is applied to the genetic data of the blastomere and the diploid maternal genetic data to phase the maternal genetic data to provide the maternal haplotype. Those data are then incorporated, along with the father's diploid and haploid data, to allow a highly accurate determination of the copy number count for each of the chromosomes in each of the embryos. Eight of the nine embryos are found to be aneuploid, and the one embryo is found to be euploid. A report is generated that discloses these diagnoses, and is sent to the doctor. The report has data similar to the data found in Tables 9, 10 and 11. The doctor, along with the prospective parents, decides to transfer the euploid embryo which implants in the mother's uterus.

Another example may involve a pregnant woman who has been artificially inseminated by a sperm donor, and is pregnant. She is wants to minimize the risk that the fetus she is carrying has a genetic disease. She undergoes amniocentesis and fetal cells are isolated from the withdrawn sample, and a tissue sample is also collected from the mother. Since there are no other embryos, her data are phased using molecular haplotyping methods. The genetic material from the fetus and from the mother are amplified as appropriate and genotyped using the ILLUMINA INFINIUM BEAD ARRAY, and the methods described herein reconstruct the embryonic genotype as accurately as possible. Phenotypic susceptibilities are predicted from the reconstructed fetal genetic data and a report is generated and sent to the mother's physician so that they can decide what actions may be best.

Another example could be a situation where a racehorse breeder wants to increase the likelihood that the foals sired by his champion racehorse become champions themselves. He arranges for the desired mare to be impregnated by IVF, and uses genetic data from the stallion and the mare to clean the genetic data measured from the viable embryos. The cleaned embryonic genetic data allows the breeder to select the embryos for implantation that are most likely to produce a desirable racehorse.

Tables 1-11

Table 1. Probability distribution of measured allele calls given the true genotype.

Table 2. Probabilities of specific allele calls in the embryo using the U and H notation.

Table 3. Conditional probabilities of specific allele calls in the embryo given all possible parental states.

Table 4. Constraint Matrix (A).

Table 5. Notation for the counts of observations of all specific embryonic allelic states given all possible parental states.

Table 6. Aneuploidy states (h) and corresponding $P(h|n_1)$, the conditional probabilities given the copy numbers.

Table 7. Probability of aneuploidy hypothesis (H) conditional on parent genotype.

Table 8. Results of PS algorithm applied to 69 SNPs on chromosome 7.

Table 9. Aneuploidy calls on eight known euploid cells.

Table 10. Aneuploidy calls on ten known trisomic cells.

Table 11. Aneuploidy calls for six blastomeres.

TABLE 1

Probability distribution of measured allele calls given the true genotype.

p(dropout) = 0.5,
p(gain) = 0.02

| | measured | | | |
|---|---|---|---|---|
| true | AA | AB | BB | XX |
| AA | 0.735 | 0.015 | 0.005 | 0.245 |
| AB | 0.250 | 0.250 | 0.250 | 0.250 |
| BB | 0.005 | 0.015 | 0.735 | 0.245 |

TABLE 2

Probabilities of specific allele calls in the embryo using the U and H notation.

| Embryo | Embryo readouts | | | |
|---|---|---|---|---|
| truth state | U | H | U | empty |
| U | $p_{11}$ | $p_{12}$ | $p_{13}$ | $p_{14}$ |
| H | $p_{21}$ | $p_{22}$ | $p_{23}$ | $p_{24}$ |

TABLE 3

Conditional probabilities of specific allele calls in the embryo given all possible parental states.

| Parental matings | Expected truth state in the embryo | Embryo readouts types and conditional probabilities | | | |
|---|---|---|---|---|---|
| | | U | H | $\bar{U}$ | empty |
| U × U | U | $p_{11}$ | $p_{12}$ | $p_{13}$ | $p_{14}$ |
| U × $\bar{U}$ | H | $p_{21}$ | $p_{22}$ | $p_{23}$ | $p_{24}$ |
| U × H | 50% U, 50% H | $p_{31}$ | $p_{32}$ | $p_{33}$ | $p_{34}$ |
| H × H | 25% U, 25% $\bar{U}$, 50% H | $p_{41}$ | $p_{42}$ | $p_{43}$ | $p_{44}$ |

TABLE 4

Constraint Matrix (A).

| | | | | | | | | | | | | | | | | |
|---|---|---|---|---|---|---|---|---|---|---|---|---|---|---|---|---|
| 1 | 1 | 1 | 1 | | | | | | | | | | | | | |
| | | | | 1 | 1 | 1 | 1 | | | | | | | | | |
| | | | | 1 | | −1 | | | | | | | | | | |
| −.5 | | | | −.5 | | | | 1 | | | | | | | | |
| | −.5 | | | | −.5 | | | | 1 | | | | | | | |
| | | −.5 | | | | −.5 | | | | 1 | | | | | | |
| | | | −.5 | | | | −.5 | | | | 1 | | | | | |
| −.25 | | −.25 | | −.5 | | | | | | | | 1 | | | | |
| | −.5 | | | | −.5 | | | | | | | | 1 | | | |
| −.25 | | −.25 | | | | −.5 | | | | | | | | 1 | | |
| | | −.5 | | | | −.5 | | | | | | | | | 1 | |

TABLE 5

Notation for the counts of observations of all specific embryonic allelic states given all possible parental states.

| Parental matings | Expected embryo truth state | Embryo readouts types and observed counts | | | |
|---|---|---|---|---|---|
| | | U | H | $\overline{U}$ | Empty |
| U × U | U | $n_{11}$ | $n_{12}$ | $n_{13}$ | $n_{14}$ |
| U × $\overline{U}$ | H | $n_{21}$ | $n_{22}$ | $n_{23}$ | $n_{24}$ |
| U × H | 50% U, 50% H | $n_{31}$ | $n_{32}$ | $n_{33}$ | $n_{34}$ |
| H × H | 25% U, 25% $\overline{U}$, 50% H | $n_{41}$ | $n_{42}$ | $n_{43}$ | $n_{44}$ |

TABLE 6

Anenpioidy states (h) and corresponding $P(h|n_j)$, the conditional probabilities given the copy numbers.

| N | H | P(h\|n) | In General |
|---|---|---|---|
| 1 | paternal monosomy | 0.5 | Ppm |
| 1 | maternal monosomy | 0.5 | Pmm |
| 2 | Disomy | 1 | 1 |
| 3 | paternal trisomy t1 | 0.5*pt1 | ppt*pt1 |
| 3 | paternal trisomy t2 | 0.5*pt2 | ppt*pt2 |
| 3 | maternal trisomy t1 | 0.5*pm1 | pmt*mt1 |
| 3 | maternal trisomy t2 | 0.5*pm2 | pmt*mt2 |

TABLE 7

Probability of anenploidy hypothesis (H) conditional on parent genotype.

| | embryo allele counts | | hypothesis | (mother, father) genotype | | | | | | | | |
|---|---|---|---|---|---|---|---|---|---|---|---|---|
| copy # | nA | nC | H | AA, AA | AA, AC | AA, CC | AC, AA | AC, AC | AC, CC | CC, AA | CC, AC | CC, CC |
| 1 | 1 | 0 | father only | 1 | 1 | 1 | 0.5 | 0.5 | 1.5 | 0 | 0 | 0 |
| 1 | 1 | 0 | mother only | 1 | 0.5 | 0 | 1 | 0.5 | 0 | 1 | 0.5 | 0 |
| 1 | 0 | 1 | father only | 0 | 0 | 0 | 0 | 0.5 | 0.5 | 1 | 1 | 1 |
| 1 | 0 | 1 | mother only | 0 | 0.5 | 1 | 0.5 | 0.5 | 1 | 0 | 0.5 | 1 |
| 2 | 2 | 0 | disomy | 1 | 0.5 | 0 | 0.5 | 0.25 | 0 | 0 | 0 | 0 |
| 2 | 1 | 1 | disomy | 0 | 0.5 | 1 | 0. | 0.5 | 0.5 | 1 | 0.5 | 0 |
| 3 | 3 | 0 | father t1 | 1 | 0.5 | 0 | 0 | 0 | 0 | 0 | 0 | 0 |
| 3 | 3 | 0 | father t2 | 1 | 0.5 | 0 | 0.5 | 0.25 | 0 | 0 | 0 | 0 |
| 3 | 3 | 0 | mother t1 | 1 | 0 | 0 | 0.5 | 0 | 0 | 0 | 0 | 0 |
| 3 | 3 | 0 | mother t2 | 1 | 0.5 | 0 | 0.5 | 0.25 | 0 | 0 | 0 | 0 |
| 3 | 2 | 1 | father t1 | 0 | 0.5 | 1 | 1 | 0.5 | 0 | 0 | 0 | 0 |
| 3 | 2 | 1 | father t2 | 0 | 0.5 | 1 | 0 | 0.25 | 0.5 | 0 | 0 | 0 |
| 3 | 2 | 1 | mother t1 | 0 | 1 | 0 | 0.5 | 0.5 | 0 | 1 | 0 | 0 |
| 3 | 2 | 1 | mother t2 | 0 | 0 | 0 | 0.5 | 0.25 | 0 | 1 | 0.5 | 0 |
| 3 | 1 | 2 | father t1 | 0 | 0 | 0 | 0 | 0.5 | 1 | 1 | 0.5 | 0 |
| 3 | 1 | 2 | father t2 | 0 | 0 | 0 | 0.5 | 0.25 | 0 | 1 | 0.5 | 0 |
| 3 | 1 | 2 | mother t1 | 0 | 0 | 1 | 0 | 0.5 | 0.5 | 0 | 1 | 0 |
| 3 | 1 | 2 | mother t2 | 0 | 0.5 | 1 | 0 | 0.25 | 0.5 | 0 | 0 | 0 |
| 3 | 0 | 3 | father t1 | 0 | 0 | 0 | 0 | 0 | 0 | 0 | 0.5 | 1 |
| 3 | 0 | 3 | father t2 | 0 | 0 | 0 | 0 | 0.25 | 0.5 | 0 | 0.5 | 1 |
| 3 | 0 | 3 | mother t1 | 0 | 0 | 0 | 0 | 0 | 0.5 | 0 | 0 | 1 |
| 3 | 0 | 3 | mother t2 | 0 | 0 | 0 | 0 | 0.25 | 0.5 | 0 | 0.5 | 1 |

TABLE 8

Results of PS algorithm applied to 69 SNPs on chromosome 7

| probe id | Snp id | p1 | p2 | m1 | m2 | b11 | b12 | b21 | b22 | b31 | b32 | h1 | h2 | h3 | e1 | e2 | T1 | T2 | E1 | E2 | conf |
|---|---|---|---|---|---|---|---|---|---|---|---|---|---|---|---|---|---|---|---|---|---|
| 80 | C__2972977_10 | A | A | A | A | A | A | A | A | X | X | A | A | X | A | A | A | A | A | A | 0.9983 |
| 81 | C__2972981_10 | T | T | T | T | X | X | X | X | X | X | X | T | T | T | T | T | T | T | T | 0.9775 |
| 98 | C_11611980_10 | G | A | A | A | A | A | G | G | X | X | G | X | X | — | — | G | A | A | G | 0.9890 |
| 26 | C__2280961_1_ | G | C | G | C | X | X | X | X | X | X | X | X | X | — | — | G | C | — | — | — |
| 8 | C___341386_1_ | C | C | C | C | X | X | C | C | C | C | C | X | C | C | C | C | C | C | C | 0.9985 |
| 9 | C___341387_1_ | C | C | C | C | C | C | C | C | C | X | C | C | C | C | C | C | C | C | C | 0.9988 |
| 71 | C__2606775_1_ | G | G | G | G | X | X | X | X | X | X | X | X | X | G | G | G | G | G | G | 0.9851 |
| 72 | C__2606779_1_ | G | G | G | G | X | X | G | G | G | G | X | G | X | G | G | G | G | G | G | 0.9972 |
| 27 | C__2280966_10 | T | A | T | A | X | X | X | X | X | X | X | X | X | — | — | T | A | T | A | 0.9211 |
| 73 | C__2606790_10 | T | C | T | C | X | X | T | T | X | X | X | X | X | — | — | T | C | — | — | — |
| 105 | C_22273192_10 | G | G | G | A | X | X | G | G | G | A | G | G | X | — | — | G | A | G | A | 0.9917 |
| 106 | C_25619317_10 | A | A | A | A | X | X | A | A | X | X | X | X | X | A | A | A | A | A | A | 0.9940 |
| 64 | C__2559556_10 | G | G | T | G | X | X | T | T | X | X | G | G | X | — | — | T | G | T | G | 0.9798 |
| 20 | C__2258563_20 | T | T | T | C | C | C | C | X | X | X | X | T | X | T | — | — | T | C | C | T | 0.9324 |
| 49 | C__2546376_1_ | A | A | G | A | G | G | X | X | G | A | A | X | A | — | — | G | A | G | A | 0.9887 |
| 50 | C__2546377_20 | G | A | G | A | G | G | X | X | G | A | X | A | G | A | G | A | G | G | A | 0.9668 |
| 21 | C__2258567_10 | T | C | T | C | X | X | X | X | X | X | C | X | T | C | T | C | T | C | 0.8924 |
| 52 | C__2546385_10 | T | T | T | A | X | X | A | A | X | X | T | X | T | — | — | T | A | A | T | 0.9283 |
| 53 | C__2546435_1_ | C | C | C | C | C | C | C | C | C | C | C | C | C | C | C | C | C | C | C | 0.9994 |
| 104 | C_16163603_10 | T | C | T | C | T | C | X | X | X | X | X | X | X | T | C | T | C | T | C | 0.9840 |
| 92 | C_8966543_10 | A | A | G | A | A | A | G | G | X | X | X | A | X | — | — | G | A | G | A | 0.8622 |

TABLE 8-continued

Results of PS algorithm applied to 69 SNPs on chromosome 7

| probe id | Snp id | p1 | p2 | m1 | m2 | b11 | b12 | b21 | b22 | b31 | b32 | h1 | h2 | h3 | e1 | e2 | T1 | T2 | E1 | E2 | conf |
|---|---|---|---|---|---|---|---|---|---|---|---|---|---|---|---|---|---|---|---|---|---|
| 96 | C_11436986_10 | G | A | G | A | X | X | G | A | G | A | X | G | G | G | A | G | A | G | A | 0.9977 |
| 82 | C__2982699_10 | A | A | G | A | A | A | A | A | X | X | A | A | A | A | A | A | A | A | A | 0.9292 |
| 99 | C_15796183_10 | A | A | C | A | A | A | A | A | A | A | A | A | A | A | A | A | A | A | A | 0.9705 |
| 43 | C__2546319_10 |  | T | T | T | T | T | T | T | T | T | X | T | X | T | T | T | T | T | T | 0.9992 |
| 44 | C__2546335_20 | T | C | T | T | T | T | X | X | X | X | X | T | X | T | T | T | T | T | T | 0.8508 |
| 45 | C__2546344_10 | T | T | T | T | X | X | T | T | T | T | T | T | X | T | T | T | T | T | T | 0.9961 |
| 46 | C__2546353_1_ | T | T | T | C | X | X | T | T | X | X | T | T | T | — | — | T | C | [T] | [C] | 0.9346 |
| 56 | C__2555662_10 | T | C | T | C | X | X | C | C | X | X | C | C | C | — | — | T | C | [C] | [T] | 0.9328 |
| 57 | C__2555670_10 | T | C | T | T | T | T | T | T | T | C | T | X | T | — | — | T | C | [T] | [C] | 0.9604 |
| 58 | C__2555685_10 | T | C | T | T | T | T | T | T | T | T | T | C | C | T | T | T | T | T | T | 0.9982 |
| 59 | C__2555706_10 | A | A | G | A | A | A | X | X | A | A | X | G | G | A | A | A | A | A | A | 0.9345 |
| 15 | C__1843560_10 | T | C | T | C | X | X | X | X | X | X | C | C | C | — | — | T | C | [C] | [T] | 0.9683 |
| 102 | C_16151234_10 | G | A | G | G | X | X | X | X | X | X | A | X | G | — | — | G | A | [A] | [G] | 0.9944 |
| 94 | C_11436903_10 | G | C | C | C | C | C | G | C | G | C | X | C | C | — | — | G | C | [G] | [C] | 0.9991 |
| 18 | C__2256696_20 | G | A | G | G | G | G | G | G | G | G | A | A | X | G | G | G | G | G | G | 0.9638 |
| 7 | C___328336_10 | T | T | T | T | T | T | X | X | X | X | X | X | T | T | T | T | T | T | T | 0.9927 |
| 37 | C__2543108_10 | T | G | G | G | X | X | G | G | G | G | G | X | T | G | G | G | G | G | G | 0.9976 |
| 107 | C_25632606_10 | A | A | A | A | A | A | X | X | A | A | A | X | A | A | A | A | A | A | A | 0.9984 |
| 38 | C__2543111_10 | T | C | C | C | C | C | X | X | C | C | C | X | X | C | C | C | C | C | C | 0.9948 |
| 40 | C__2543116_10 | T | C | T | T | X | X | T | T | T | T | T | C | C | T | T | T | T | T | T | 0.9977 |
| 86 | C__8852708_10 | T | C | C | C | X | X | C | C | C | C | X | X | C | C | C | C | C | C | C | 0.9317 |
| 67 | C__2602203_10 | A | A | C | A | A | A | X | X | A | A | X | X | A | A | A | A | A | A | A | 0.9187 |
| 24 | C__2279233_10 | T | C | C | C | C | C | X | X | C | C | X | T | T | C | C | C | C | C | C | 0.9968 |
| 68 | C__2602208_10 | A | A | A | A | A | A | X | X | X | X | X | X | A | A | A | A | A | A | A | 0.9937 |
| 69 | C__2602221_10 | T | G | T | T | X | X | X | X | X | X | X | X | T | T | T | T | T | T | T | 0.9810 |
| 14 | C___656774_1_ | G | A | A | A | X | X | A | A | X | X | X | X | A | A | A | A | A | A | A | 0.8485 |
| 85 | C__3021372_10 | G | A | G | G | G | G | G | G | X | X | G | A | A | G | G | G | G | G | G | 0.9973 |
| 83 | C__3021345_10 | A | A | A | A | X | X | A | A | X | X | X | X | A | A | A | A | A | A | A | 0.9955 |
| 12 | C___656644_20 | C | C | C | C | C | C | C | C | C | C | X | X | C | C | C | C | C | C | C | 0.9992 |
| 11 | C___656642_1_ | A | A | G | G | G | G | G | G | G | G | X | A | X | G | G | G | G | G | G | 0.7858 |
| 61 | C__2558137_10 | T | C | T | T | T | T | X | X | T | T | C | C | C | T | T | T | T | T | T | 0.9957 |
| 87 | C__8853467_10 | G | G | G | G | X | X | X | X | X | X | X | X | G | G | G | G | G | G | G | 0.9866 |
| 3 | C____17027_10 | T | T | T | T | T | T | T | X | X | T | T | T | T | T | T | T | T | T | T | 0.9959 |
| 28 | C__2540863_10 | T | C | C | C | T | T | T | T | X | X | X | X | X | — | — | T | C | [C] | [T] | 0.9561 |
| 31 | C__2540896_1_ | T | C | T | T | X | X | X | X | X | X | X | X | X | — | — | T | C | [T] | [C] | 0.9058 |
| 35 | C__2540935_10 | C | C | C | C | X | X | X | X | C | C | X | X | X | C | C | C | C | C | C | 0.9944 |
| 36 | C__2540940_10 | T | G | T | G | T | T | X | X | T | G | T | X | T | — | — | T | G | [G] | [T] | 0.9828 |
| 109 | C_25632779_10 | A | A | G | A | X | X | A | A | A | A | A | A | A | A | A | A | A | A | A | 0.9269 |
| 4 | C____75266_10 | T | C | C | C | X | X | X | X | X | X | X | X | X | — | — | T | C | [C] | [T] | 0.9954 |
| 76 | C__2668636_10 | A | A | G | A | A | A | A | A | A | A | A | A | A | A | A | A | A | A | A | 0.9689 |
| 77 | C__2668640_10 | T | T | G | G | T | T | T | T | T | T | X | X | X | T | T | T | T | T | T | 0.6498 |
| 22 | C__2259838_10 | G | C | G | G | G | G | X | X | G | C | G | G | G | G | C | G | C | G | C | 0.9988 |
| 23 | C__2259850_10 | A | A | G | A | X | X | A | A | A | A | X | A | A | A | A | A | A | A | A | 0.9289 |
| 10 | C___349428_10 | A | A | A | A | A | A | A | A | A | A | X | A | X | A | A | A | A | A | A | 0.9974 |
| 5 | C___321446_10 | T | T | T | G | X | X | T | T | X | X | T | T | T | T | T | T | T | T | T | 0.8457 |
| 42 | C__2545620_10 | A | A | A | A | A | A | X | X | A | A | X | X | X | A | A | A | A | A | A | 0.9944 |
| 19 | C__2258307_10 | G | G | G | A | G | G | G | G | G | G | X | X | X | G | G | G | G | G | G | 0.9684 |
| 90 | C__8853956_10 | G | G | G | A | X | X | G | G | X | X | G | X | X | G | G | G | G | G | G | 0.8460 |

TABLE 9

Aneuploidy calls on eight known euploid cells

| Chr # | Cell 1 | | Cell 2 | | Cell 3 | | Cell 4 | | Cell 5 | | Cell 6 | | Cell 7 | | Cell 8 | |
|---|---|---|---|---|---|---|---|---|---|---|---|---|---|---|---|---|
| 1 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 2 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 3 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 4 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 5 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 6 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 7 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 8 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 9 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 10 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 11 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 12 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 13 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 14 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 15 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 16 | 2 | 1.00000 | 2 | 0.99997 | 2 | 1.00000 | 2 | 1.00000 | 2 | 1.00000 | 2 | 1.00000 | 2 | 1.00000 | 2 | 1.00000 |

TABLE 9-continued

Aneuploidy calls on eight known euploid cells

| Chr # | Cell 1 | | Cell 2 | | Cell 3 | | Cell 4 | | Cell 5 | | Cell 6 | | Cell 7 | | Cell 8 | |
|---|---|---|---|---|---|---|---|---|---|---|---|---|---|---|---|---|
| 17 | 2 | 1.00000 | 2 | 0.99995 | 2 | 1.00000 | 2 | 1.00000 | 2 | 1.00000 | 2 | 1.00000 | 2 | 1.00000 | 2 | 1.00000 |
| 18 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 19 | 2 | 1.00000 | 2 | 0.99998 | 2 | 1.00000 | 2 | 1.00000 | 2 | 1.00000 | 2 | 1.00000 | 2 | 1.00000 | 2 | 1.00000 |
| 20 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 21 | 2 | 0.99993 | 2 | 1.00000 | 2 | 1.00000 | 2 | 1.00000 | 2 | 1.00000 | 2 | 1.00000 | 2 | 1.00000 | 2 | 1.00000 |
| 22 | 2 | 1.00000 | 2 | 1.00000 | 2 | 0.99040 | 2 | 1.00000 | 2 | 1.00000 | 2 | 1.00000 | 2 | 1.00000 | 2 | 0.99992 |
| X | 2 | 0.99999 | 2 | 0.99994 | 2 | 1.00000 | 2 | 1.00000 | 2 | 1.00000 | 2 | 1.00000 | 2 | 1.00000 | 2 | 1.00000 |

TABLE 10

Aneuploidy calls on ten known trisomic cells

| Chr # | Cell 1 | | Cell 2 | | Cell 3 | | Cell 4 | | Cell 5 | | Cell 6 | | Cell 7 | | Cell 8 | | Cell 9 | | Cell 10 | |
|---|---|---|---|---|---|---|---|---|---|---|---|---|---|---|---|---|---|---|---|---|
| 1 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 2 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 3 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 4 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 5 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 6 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 7 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 0.92872 | 2 | 1.00000 |
| 8 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 9 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 10 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 11 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 12 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 13 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 14 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 15 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 0.99998 | 2 | 1.00000 |
| 16 | 2 | 1.00000 | 2 | 1.00000 | 2 | 1.00000 | 2 | 1.00000 | 2 | 0.99999 | 2 | 1.00000 | 2 | 1.00000 | 2 | 1.00000 | 2 | 1.00000 | 2 | 1.00000 |
| 17 | 2 | 1.00000 | 2 | 1.00000 | 2 | 1.00000 | 2 | 1.00000 | 2 | 0.96781 | 2 | 1.00000 | 2 | 1.00000 | 2 | 1.00000 | 2 | 1.00000 | 2 | 1.00000 |
| 18 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 19 | 2 | 1.00000 | 2 | 1.00000 | 2 | 0.99999 | 2 | 1.00000 | 2 | 1.00000 | 2 | 1.00000 | 2 | 1.00000 | 2 | 1.00000 | 2 | 1.00000 | 2 | 1.00000 |
| 20 | 2 | 1.00000 | 2 | 1.00000 | 2 | 1.00000 | 2 | 1.00000 | 2 | 0.99997 | 2 | 1.00000 | 2 | 1.00000 | 2 | 1.00000 | 2 | 1.00000 | 2 | 1.00000 |
| 21 | — | 1.00000 | — | 1.00000 | — | 1.00000 | — | 1.00000 | — | 1.00000 | — | 1.00000 | — | 1.00000 | — | 1.00000 | — | 1.00000 | — | 1.00000 |
| 22 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 | 2 | 1.00000 |
| 23 | 2 | 1.00000 | 1 | 1.00000 | 1 | 1.00000 | 1 | 1.00000 | 1 | 1.00000 | 1 | 1.00000 | 1 | 1.00000 | 1 | 1.00000 | 1 | 1.00000 | 1 | 1.00000 |

TABLE 11

Aneuploidy calls for six blastomeres

| Chr # | e1b1 | | e1b3 | | e1b6 | | e2b1 | | e2b2 | | e3b2 | |
|---|---|---|---|---|---|---|---|---|---|---|---|---|
| 1 | 2 | 1.00000 | 2 | 1.00000 | 1 | 1.00000 | 1 | 1.00000 | 1 | 1.00000 | 3 | 1.00000 |
| 2 | 2 | 1.00000 | 2 | 1.00000 | 3 | 1.00000 | 1 | 1.00000 | 1 | 1.00000 | 2 | 0.99994 |
| 3 | 2 | 1.00000 | 2 | 1.00000 | 2 | 1.00000 | 1 | 1.00000 | 1 | 1.00000 | 3 | 1.00000 |
| 4 | 2 | 1.00000 | 2 | 1.00000 | 2 | 1.00000 | 1 | 1.00000 | 1 | 1.00000 | 3 | 1.00000 |
| 5 | 2 | 1.00000 | 2 | 1.00000 | 2 | 1.00000 | 1 | 1.00000 | 1 | 1.00000 | 3 | 0.99964 |
| 6 | 2 | 1.00000 | 2 | 1.00000 | 2 | 1.00000 | 1 | 1.00000 | 1 | 1.00000 | 3 | 1.00000 |
| 7 | 2 | 1.00000 | 2 | 1.00000 | 2 | 1.00000 | 1 | 1.00000 | 1 | 1.00000 | 2 | 0.99866 |
| 8 | 2 | 1.00000 | 2 | 1.00000 | 3 | 0.99966 | 1 | 1.00000 | 1 | 1.00000 | 3 | 1.00000 |
| 9 | 2 | 1.00000 | 2 | 1.00000 | 2 | 1.00000 | 1 | 1.00000 | 1 | 1.00000 | 3 | 0.99999 |
| 10 | 2 | 1.00000 | 2 | 1.00000 | 2 | 1.00000 | 1 | 1.00000 | 1 | 1.00000 | 1 | 1.00000 |
| 11 | 2 | 1.00000 | 2 | 1.00000 | 3 | 1.00000 | 1 | 1.00000 | 1 | 1.00000 | 2 | 0.99931 |
| 12 | 2 | 1.00000 | 2 | 1.00000 | 2 | 1.00000 | 1 | 1.00000 | 1 | 1.00000 | 1 | 1.00000 |
| 13 | 2 | 1.00000 | 2 | 1.00000 | 3 | 0.98902 | 1 | 1.00000 | 1 | 1.00000 | 2 | 0.99969 |
| 14 | 2 | 1.00000 | 2 | 1.00000 | 2 | 0.99991 | 1 | 1.00000 | 1 | 1.00000 | 3 | 1.00000 |
| 15 | 2 | 1.00000 | 2 | 1.00000 | 2 | 0.99986 | 1 | 1.00000 | 1 | 1.00000 | 3 | 0.99999 |
| 16 | 2 | 1.00000 | 3 | 0.98609 | 2 | 0.74890 | 1 | 1.00000 | 1 | 1.00000 | 2 | 0.94126 |
| 17 | 2 | 1.00000 | 2 | 1.00000 | 2 | 0.97983 | 1 | 1.00000 | 1 | 1.00000 | 2 | 1.00000 |
| 18 | 2 | 1.00000 | 2 | 1.00000 | 2 | 0.98367 | 1 | 1.00000 | 1 | 1.00000 | 1 | 1.00000 |
| 19 | 2 | 1.00000 | 2 | 1.00000 | 4 | 0.64546 | 1 | 1.00000 | 1 | 1.00000 | 3 | 1.00000 |
| 20 | 2 | 1.00000 | 2 | 1.00000 | 3 | 0.58327 | 1 | 1.00000 | 1 | 1.00000 | 2 | 0.95078 |
| 21 | 2 | 0.99952 | 2 | 1.00000 | 2 | 0.97594 | 1 | 1.00000 | 1 | 1.00000 | 1 | 0.99776 |
| 22 | 2 | 1.00000 | 2 | 0.98219 | 2 | 0.99217 | 1 | 1.00000 | 1 | 0.99989 | 2 | 1.00000 |
| 23 | 2 | 1.00000 | 3 | 1.00000 | 3 | 1.00000 | 1 | 1.00000 | 1 | 1.00000 | 3 | 0.99998 |
| 24 | 1 | 0.99122 | 1 | 0.99778 | 1 | 0.99999 | | | | | | |

What is claimed is:

1. A method for preparing a non-naturally occurring composition of amplified DNA derived from one or more embryonic or fetal cells of an embryo or unborn fetus useful for reconstructing at least a portion of the genome of the embryo or fetus, comprising:

(a) extracting genomic DNA from the one or more embryonic or fetal cells;

(b) preparing a non-naturally occurring composition of amplified DNA by amplification of a plurality of target loci from the genomic DNA extracted in (a) to obtain amplified DNA;

(c) analyzing the non-naturally occurring composition of amplified DNA obtained in (b) by sequencing-by-synthesis to obtain genetic data of the embryo or fetus for the plurality of target loci, and reconstructing at least a portion of the genome of the embryonic or fetal cells using the genetic data of the embryo or fetus and genetic data of at least one biological parent of the embryo or fetus.

2. The method of claim 1, wherein the extracting comprises extracting genomic DNA from one or more embryonic cells.

3. The method of claim 1, wherein the extracting comprises extracting genomic DNA from a single embryonic cell.

4. The method of claim 1, wherein the extracting comprises extracting genomic DNA from one or more fetal cells.

5. The method of claim 1, wherein the extracting comprises extracting genomic DNA from one or more fetal cells isolated from a maternal blood sample or a fraction thereof.

6. The method of claim 1, wherein the target loci comprise SNP loci.

7. The method of claim 1, wherein the amplification comprises targeted amplification of the target loci.

8. The method of claim 1, wherein the amplification comprises ligation of adaptors to the genomic DNA extracted in (a) followed by universal amplification.

9. The method of claim 1, wherein the sequencing-by-synthesis comprises clonal amplification and measurement of sequences of the clonally amplified DNA.

10. The method of claim 1, wherein the reconstructing comprises reconstructing at least a portion of the genome of the embryo or fetus using the genetic data of the embryo or fetus and genetic data of both biological parents of the embryo or fetus.

11. The method of claim 1, wherein the method further comprises determining haplotypic genetic data of the at least one biological parent of the embryo or fetus.

12. The method of claim 10, wherein the method further comprises determining haplotypic genetic data of both biological parents of the embryo or fetus.

13. A method for preparing a non-naturally occurring composition of amplified DNA derived from one or more embryonic or fetal cells of an embryo or unborn fetus useful for reconstructing at least a portion of the genome of the embryo or fetus, comprising:

(a) extracting genomic DNA from the one or more embryonic or fetal cells;

(b) preparing a non-naturally occurring composition of amplified DNA by amplification of a plurality of SNP loci from the genomic DNA extracted in (a) to obtain amplified DNA;

(c) analyzing the non-naturally occurring composition of amplified DNA obtained in (b) by sequencing-by-synthesis to obtain genetic data of the embryo or fetus for the plurality of SNP loci, and reconstructing at least a portion of the genome of the embryonic or fetal cells using the genetic data of the embryo or fetus and genetic data of both biological parents of the embryo or fetus.

* * * * *